(12) United States Patent
Yuqiu et al.

(10) Patent No.: US 6,579,973 B1
(45) Date of Patent: Jun. 17, 2003

(54) COMPOSITIONS FOR THE TREATMENT AND DIAGNOSIS OF BREAST CANCER AND METHODS FOR THEIR USE

(75) Inventors: Jiang Yuqiu, Kent, WA (US); Davin C. Dillon, Redmond, WA (US); Jennifer L. Mitcham, Redmond, WA (US); Jiangchun Xu, Bellevue, WA (US); Susan L. Harlocker, Seattle, WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/433,826

(22) Filed: Nov. 3, 1999

Related U.S. Application Data

(63) Continuation-in-part of application No. 09/389,681, filed on Sep. 2, 1999, which is a continuation-in-part of application No. 09/339,338, filed on Jun. 23, 1999, which is a continuation-in-part of application No. 09/285,480, filed on Apr. 2, 1999, which is a continuation-in-part of application No. 09/222,575, filed on Dec. 28, 1998, now Pat. No. 6,387,697.

(51) Int. Cl.$^7$ .......................... C07K 1/00; C07K 14/00
(52) U.S. Cl. ........................ 530/806; 530/350
(58) Field of Search ................ 435/69.1; 536/23.1, 536/23.5; 424/277.1, 184.1, 1.11; 514/2–21; 530/350

(56) References Cited

U.S. PATENT DOCUMENTS

| | | | |
|---|---|---|---|
| 5,215,926 A | 6/1993 | Etchells, III et al. | 436/501 |
| 5,240,856 A | 8/1993 | Goffe et al. | 435/286.5 |
| 5,986,170 A | 11/1999 | Subjeck | 800/3 |

FOREIGN PATENT DOCUMENTS

| | | |
|---|---|---|
| WO | WO 89/06280 | 7/1989 |
| WO | WO 91/16116 | 10/1991 |
| WO | WO 92/07243 | 4/1992 |
| WO | WO 96/29430 | 9/1996 |
| WO | WO 98/33915 | 8/1998 |
| WO | WO 98/54963 | 12/1998 |
| WO | WO 99/09155 | 2/1999 |
| WO | WO 00/43420 | 7/2000 |

OTHER PUBLICATIONS

L Anderson et al.,Electrophoresis, "A comparison of selected mRNA and protein abundances in human liver," 1997, 18:533–537.*
Gura (Science, vol. 278, Nov. 1997, pp. 1041–1042).*
Hartwell et al. (Science, vol. 278, Nov. 1997, pp. 1064–1068).*
GenBank Accession No. AL157387, Feb. 18, 2000.
GenBank Accession No. AC036170, Apr. 9, 2000.
Jäger, D. et al, "Identification of a Tissue–specific Putative Transcription Factor in Breast Tissue by Serological Screening of a Breast Cancer Library," *Cancer Research* 61(5):2055–2061, Mar. 1, 2001.
Chang and Shu, "Current status of adoptive immunotherapy of cancer," *Critical Reviews in Oncology/Hematology* 22(3):213–228, Apr. 1996.
Cheever and Chen, "Therapy with cultured T cells: principles revisited," *Immunological Reviews,* 157:177–194, 1997.
Cheever et al., "Potential uses of interleukin 2 in cancer therapy," *Immunobiol,* 172:365–382, 1986.
Cole et al., "Characterization of the functional specificity of a cloned T–cell receptor heterodimer recognizing the MART–1 melanoma antigent," *Cancer Research,* 55:748–752, Feb. 15, 1995.
Durrant L., "Cancer vaccines," *Anti–Cancer Drugs,* 8:727–733, 1997.
Eshhar Z., "Tumor–specific T–bodies: toward clinical application," *Cancer Immunol Immunother,* 45:131–136, 1997.
Hwu et al., "In vivo antitumor activity of T cells redirected with chimeric antibody/T–cell receptor genes," *Cancer Research,* 55:3369–3373, Aug. 1, 1995.
Porter–Jordan and Lippman, "Overview of the biologic markers of breast cancer," *Breast Cancer* 8:(1):73–100, Feb. 1994.
Wei et al., "Protection against mammary tumor growth by vaccination with full–length, modified human ErbB–2 DNA," *Int. J. Cancer,* 81:748–754, 1999.
GenBank Accession No. AA864891, Feb. 20, 1998.
GenBank Accession No. AA398925, Apr. 25, 1997.
Geneseq Accession No. V84525 (Dec. 10, 1998).
Stratagene 1991 product catalog, Prime-It™ Random Labeling Kit, catalog No. 300387, p. 66.

* cited by examiner

*Primary Examiner*—Sean McGarry
*Assistant Examiner*—Janet L. Epps
(74) *Attorney, Agent, or Firm*—Seed Intectual Property Law Group PLLC

(57) ABSTRACT

Compositions and methods for the therapy and diagnosis of cancer, such as breast cancer, are disclosed. Compositions may comprise one or more breast tumor proteins, immunogenic portion thereof, or polynucleotides that encode such portions. Alternatively, a therapeutic composition may comprise an antigen presenting cell that expresses a breast tumor protein, or a T cell that is specific for cells expressing such a protein. Such compositions may be used, for example, for the prevention and treatment of diseases such as breast cancer. Diagnostic methods based on detecting a breast tumor protein, or mRNA encoding such a protein, in a sample are also provided.

14 Claims, 1 Drawing Sheet

SYN18C6 NORTHERN BLOT

Figure 1:
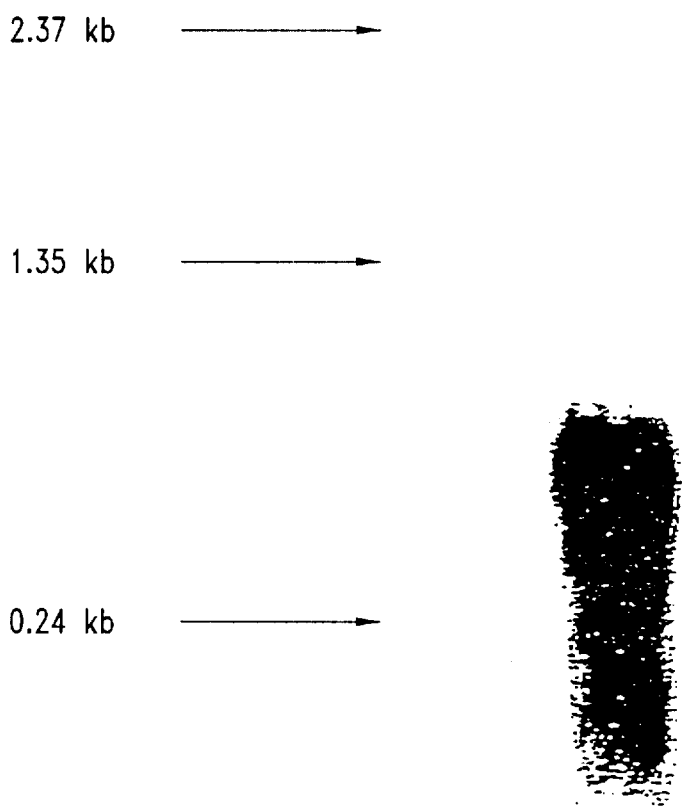

SEQUENCE LISTING

<160> NUMBER OF SEQ ID NOS: 474

<210> SEQ ID NO 1
<211> LENGTH: 281
<212> TYPE: DNA
<213> ORGANISM: Homo sapien

<400> SEQUENCE: 1

```
caatgacagt caatctctat cgacagcctg cttcatattt agctattgtt cgtattgcct    60
tctgtcctag aacagtcat atctcaagtt caaatgccac aacctgagaa gcggtgggct     120
aagataggtc ctactgcaaa ccaccctcc atatttccgt acgcaattac aattcagttt     180
ctgtgacatc tctttacacc actggaggaa aaatgagata ttctctgatt tattctacta   240
taacactcta catagagcta tggtgagtgc taaccacatc g                         281

<210> SEQ ID NO 2
<211> LENGTH: 300
<212> TYPE: DNA
<213> ORGANISM: Homo sapien

<400> SEQUENCE: 2
gaggtcctgg gctaacctaa tggtttatta ttggtggaga gaaagatctg gaaatacttg    60
aggttattac atactagatt agcttctaat gtgaaccatt tttcttttaa cagtgataaa   120
ttattatttc cgaagttaac tgttcccttg gtcgtgatac acactcgatt aacaaacata   180
ctgttgtatt ttttccagtt tgtttggct atgccaccac agtcatcccc aggtctata     240 catactatgt ctcaactgta ttatttgcca ttttttggcat tagaatgctt cgggaaggct  300

<210> SEQ ID NO 3
<211> LENGTH: 302
<212> TYPE: DNA
<213> ORGANISM: Homo sapien

<400> SEQUENCE: 3
ggccgaggta attggttaag tctaaagaga ttattattcc ttgatgtttg ctttgtattg    60
gctacaaatg tgcagaggta atacatatgt gatgtcgatg tctctgtctt ttttttttgtc 120 tttaaaaaat aattggcagc aactgtattt gaataaaatg atttcttagt atgattgtac   180
agtaatgaat gaaagtggaa catgtttctt tttgaaaggg agagaattga ccatttattg   240
ttgtgatgtt taagttataa cttatcgagc acttttagta gtgataactg tttttaaact   300
tg                                                                    302

<210> SEQ ID NO 4
<211> LENGTH: 293
<212> TYPE: DNA
<213> ORGANISM: Homo sapien

<400> SEQUENCE: 4
tgtaccaatc ctttggcaca agaatatgta agaactatag ttgtttttat tggttttgt    60 tcttgagatt gtttttcattc tgttttttgac tgtatctctt taggaggctg aggatggcat 120
tattgcttat gatgactgtg gggtgaaact gactattgct tttcaagcca aggatgtgga  180
aggatctact tctcctcaaa tacgagataa ggcaagataa ttctgctcat cgagagagg   240 gttaagagtt gtcatcttaa tcataaatcc tgcaggatgg gttcttcaaa ttt            293

<210> SEQ ID NO 5
<211> LENGTH: 275
<212> TYPE: DNA
<213> ORGANISM: Homo sapien

<400> SEQUENCE: 5
cgaggtttgg aatcagactt ctgtgtccag taaaaaactc ctgcactgaa gtcattgtga    60
cttgagtagt tacagactga ttccagtgaa cttgatctaa tttcttttga tctaatgaat   120
```

```
gtgtctgctt accttgtctc cttttaattg ataagctcca agtagttgct aattttttga      180
caactttaaa tgagtttcat tcacttcttt tacttaatgt tttaagtata gtaccaataa      240
tttcattaac ctgttctcaa gtggtttagc tacca                                 275
```

<210> SEQ ID NO 6
<211> LENGTH: 301
<212> TYPE: DNA
<213> ORGANISM: Homo sapien

<400> SEQUENCE: 6

```
gaggtctggt ttcctgggta tgcctggact gttgcccagt gtaagatctg tgcaagccat       60
attggatgga agtttacggc caccaaaaaa gacatgtcac ctcaaaaatt ttggggctta      120
acgcgatctg ctctgttgcc cacgatccca gacactgaag atgaaataag tccagacaaa      180
gtaatacttt gcttgtaaac agatgtgata gagataaagt tatctaacaa attggttata      240
ttctaagatc tgctttggaa attattgcct ctgatacata cctaagtaaa cataacatta      300
a                                                                      301
```

<210> SEQ ID NO 7
<211> LENGTH: 301
<212> TYPE: DNA
<213> ORGANISM: Homo sapien

<400> SEQUENCE: 7

```
gtccagtttg tacacagtga ttccttatgc acgccgaaag ggtttccgta aaaatgacat       60
tatatacaaa tctgtacacc catccaccag agcgattctc cagctcccag agggagttat      120
caacttaaag caggataccct gaggtttcat gtctttagtt gccttatcat aatcccaaat      180
atacatttca gggtttgttt ttgtttttaa agacactttc ctggaatatg tgcactatgg      240
ttaaaattaa aaacaaaagt aataaaataa atgatcgct ggaaggactg acctccccac       300
c                                                                      301
```

<210> SEQ ID NO 8
<211> LENGTH: 301
<212> TYPE: DNA
<213> ORGANISM: Homo sapien

<400> SEQUENCE: 8

```
ctgtcctcat ctctgcaaag ttcagcttcc ttccccaggt ctctgtgcac tctgtcttgg       60
atgctctggg gagctcatgg gtggaggagt ctccaccaga gggaggctca ggggactggt      120
tgggccaggt atgaatattt gagggataaa aattgtgtaa gagccaaaga attggtagta      180
gggggagaac agagaggagc tgggctatgg gaaatgattt gaataatgga gctgggaata      240
tggctggata tctggtacta aaaagggtc tttaagaacc tacttcctaa tctcttcccc       300
a                                                                      301
```

<210> SEQ ID NO 9
<211> LENGTH: 301
<212> TYPE: DNA
<213> ORGANISM: Homo sapien

<400> SEQUENCE: 9

```
gaggtctgcc taagtagagg acaaagactt cctcctttca aaggagaact gagcccagga       60
ttggtaagtt taaggcactt aaccttgacc agctctgtag gtctggagca ttctggtccc      120
tggccgcttt caccaccagg cccttctcac ttatccacct cacatactgc cccagcattc      180
```

```
ctttggcatt gcgagctgtg acttgacaca ttttaatgac aagattgaag tagctacctt    240
gcaggataga ttttctgggg tatagggac  aaaccaacag tgccatcagg tgtcttaaca    300
c                                                                   301
```

<210> SEQ ID NO 10
<211> LENGTH: 301
<212> TYPE: DNA
<213> ORGANISM: Homo sapien

<400> SEQUENCE: 10

```
ggcaggtcca acagttcttc cagttctggt cgagctttga atcgtccctt gaagtcttct    60
tcagtgtgct ccttcactga cagtctgact ccttcaggaa gactgctttg gattatttcc   120
aagaaaattt ctgcaaacgt agcactcaaa ccgctgatct gaaccactcg ctcatgggtg   180
gtaagcactg agtccaggag catttgctg  ccttggtcct gcaactgcaa cacttctatg   240
gttttggttg gcattgcata actttcctcg actttaatgg agagagattg cagaggttgt   300
g                                                                  301
```

<210> SEQ ID NO 11
<211> LENGTH: 301
<212> TYPE: DNA
<213> ORGANISM: Homo sapien

<400> SEQUENCE: 11

```
aggtctgtga ctttcaccca ggacccagga cgcagccctc cgtgggcact gccggcgcct    60
tgtctgcaca ctggaggtcc tccattacag aggcccagcg cacatcgctg cccccacaaa   120
cgttcagggg tacagccatg gcagctcctt cctctgccgt gagaaaagtg cttggagtac   180
ggtttgccac acacgtgact ggacagtgtc caattcaaat ctttcaggc agagtccgag   240 cagcgcttgg tgacagcctg tcctctcctg ctctccaaag gccctgctcc ctgtcctctc   300
t                                                                  301
```

<210> SEQ ID NO 12
<211> LENGTH: 301
<212> TYPE: DNA
<213> ORGANISM: Homo sapien

<400> SEQUENCE: 12

```
gaggtctggg attacaggca cgtgccacca cacctagcta attttgagc  atggggctca    60 aaggaactgc tctctgggc  atgtcagatt tcggatttgg ggctgcacac tgatactctc   120
taagtggtgg aggaacttca tcccactgaa attccttggg catttggggt tttgtttttc   180 ttttttcct  tcttcatcct cctccttttt taaaagtcaa cgagagcctt cgctgactcc   240
accgaagaag tgcaccactg ggagccaccc cagtgccagg cgcccgtcca gggacacaca   300
c                                                                  301
```

<210> SEQ ID NO 13
<211> LENGTH: 256
<212> TYPE: DNA
<213> ORGANISM: Homo sapien

<400> SEQUENCE: 13

```
ttttttggca taaaaacac  aatgatttaa tttctaaagc acttatatta ttatggcatg    60
gtttgggaaa caggttatta tattccacat aggtaattat gcagtgcttc tcatggaaaa   120
```

```
aatgcttagg tattggcctt ttctctggaa accatatttt tccttttta ataatcaact    180 aaaatgtata tgttaaaaag cctcatcttt tgattttcaa tatacaaaat gctttcttta   240
aaagaacaag attcaa                                                    256
```

```
<210> SEQ ID NO 14
<211> LENGTH: 301
<212> TYPE: DNA
<213> ORGANISM: Homo sapien

<400> SEQUENCE: 14
ggtccttgat agaggaagag gaatatccaa ggcaaagcca ccaccacgtc caacctcctc    60
atcctctacc tttcctgtcc ccagaggtat gagatagacc ccctggcctg gttcctgcac   120
tgtgctaggc ccacagtgga cacttccacc ttaatggaga ataggcccca tggagtggag   180
gtccctcctc catggcctgc aacccaatga ctatgggggt gacacaagtg acctctgccc   240
tgtgatggct caacaccatc acacgcaact gtccagacaa gccccctcaa cgggctgctg   300
t                                                                    301
```

```
<210> SEQ ID NO 15
<211> LENGTH: 259
<212> TYPE: DNA
<213> ORGANISM: Homo sapien

<400> SEQUENCE: 15
gtcttgaaag tatttattgt ttaataattc tttctcccct cagccccatc cggccactct    60
ctctttctgc ttttctgatc atcctaaagg ctgaatacat cctcctcctg tgtggaggac   120
acgaagcaat actaaaatca atacactcga tcaggtcttc atcagatacc acgtcactgt   180
gggtagagtg ctaattttca acaaatgtgg tgttcttagg gccccacaag gtagtccttt   240
ctcaaggtcg ctgggccac                                                 259
```

```
<210> SEQ ID NO 16
<211> LENGTH: 301
<212> TYPE: DNA
<213> ORGANISM: Homo sapien

<400> SEQUENCE: 16
cgaggttgtt cacattttca aataaataat actccccgta agtaataact gcaaccaatc    60
agtgttattc agtgctatgc ctccttgtaa tgggtagtta ttaattattt tcagagcttt   120
ctggaaatac tgtcctaact ggctatgttt aggatctttg ttatctctga agacaaagaa   180
agaactagga ctcttaattt tggggtgctt cttgactctt agttgggaaa ctgaaaatat   240
ttccaacctt ttacccacgt caatggcata ttctgggaat caccaccacc accaccacta   300
c                                                                    301
```

```
<210> SEQ ID NO 17
<211> LENGTH: 301
<212> TYPE: DNA
<213> ORGANISM: Homo sapien

<400> SEQUENCE: 17
gcccgggcag gtctggggcc tagggtggct ctttgcaaag ctgagggggca agctaaggaa    60 gccaggcagg tcaggggccc tttcggcctt ctcaagcctc cacctgagtt ctcgtcaatg   120
ccagtctccc tggtatgatt ggggacatta tcagagaaac atctaatagc gcacatctgg   180
gcacccacac tctgcttcag ttgcatccat cctcccaccc caaattcaac tcctgaccca   240
```

```
atacaaaaga cttttttaac caggatttct tcttgcagga aagctgactt ggaaacacgg    300
g                                                                   301
```

<210> SEQ ID NO 18
<211> LENGTH: 301
<212> TYPE: DNA
<213> ORGANISM: Homo sapien

<400> SEQUENCE: 18

```
attacaggca cgtgccacca cacctagcta attttgagc atggggctca aaggaactgc     60
tctctgggc atgtcagatt cggatttgg ggctgcacac tgatactctc taagtggtgg    120
aggaacttca tcccactgaa attcctttgg catttggggt tttgttttc ttttttttcct  180
tcttcatcct cctcctttt taaaagtcaa cgagagcctt cgctgactcc accgaagaag   240
tgcaccactg gggaccaccc agtgccaggc gcccgtccag ggacacacac agtcttcact   300
g                                                                   301
```

<210> SEQ ID NO 19
<211> LENGTH: 301
<212> TYPE: DNA
<213> ORGANISM: Homo sapien

<400> SEQUENCE: 19

```
agaatctctg cactgtcatc aggtacaaca aaagatcaaa cccctgtccc gatgttaact    60
ttttaactta aagaatgcc agaaaaccca gatcaacact ttccagctac gagccgtcca   120
caaaggccac ccaaaggcca gtcagactcg tgcagatctt attttttaat agtagtaacc   180
acaatacaca gctctttaaa gctgttcata ttcttccccc attaaacacc tgccccgggc   240
ggccaagggc gaattctgca gatatccatc acactggcgg ccgctcgagc atgcatctag   300
a                                                                   301
```

<210> SEQ ID NO 20
<211> LENGTH: 290
<212> TYPE: DNA
<213> ORGANISM: Homo sapien

<400> SEQUENCE: 20

```
aggttttttt tttttttttt ttttttttt ttttcccctt tcaattcatt taatttcaac    60
aatctgtcaa aaacagcca ataaacaaat actgaattac attctgctgg gttttttaaa   120
ggctctaaac tataaaaaca tcttgtgtct cccacccctga ccaccctgct acttttccat  180
ataccacagg ccacccataa acacaaagcc aggggggtgaa gctgacatgg tctatttgga  240
gccagtaaac aggagggcga taagtcctga taagcactta tggacaatat               290
```

<210> SEQ ID NO 21
<211> LENGTH: 301
<212> TYPE: DNA
<213> ORGANISM: Homo sapien

<400> SEQUENCE: 21

```
agaaaggtaa ctgccagcca ggcttgcatt gtttagccag aaattgctgc ttggttctag    60
actctttaaa aaaaaaaaat acccaggggtt tgtcatcatt tcagaggca gagtgccaaa   120
tatcacccaa agctcttgtg tctttttttt accccttat tttatttta tttattaatt    180
ttttgtgcaa acatcaaatg tcactggtgt tcacagaagg ctttttgac tagccttaaa   240
```

```
ttcctgagtc aaaagattaa tcagattttc aggcagtgtt taatcaggtg ctttgtcctg    300
t                                                                    301

<210> SEQ ID NO 22
<211> LENGTH: 301
<212> TYPE: DNA
<213> ORGANISM: Homo sapien

<400> SEQUENCE: 22
gacgccatgc accctccggt aaccagcagc cgcctgtcca tcccccaaga ccggaaaggc     60
agcagcagcc cccgggagcc cagggctgtc ctcggtgcat ctggctgcag agggaaattg    120
atgaccttac acagcaacta gcggccatgc agtccttcac tgacaagttc caggaccttt    180
gaagttggag ccagcgtccg gagctgcagc caagcgagtt tcctccttat cctccttagc    240
cagggctttt tctcttccgc tgcatttgcc cccttcccaa cgcaattcaa agcagttgtg    300
a                                                                    301

<210> SEQ ID NO 23
<211> LENGTH: 381
<212> TYPE: DNA
<213> ORGANISM: Homo sapien

<400> SEQUENCE: 23
cgaggtccag acagtggacc aagagatacg ctacataaat tggggtttca caattcttac     60
attatttgtc tgtcacagaa gagagctgct tatgattttg aaggggtcag ggagggtggg    120
agttggtaaa gagtagggta tttctataac agatattatt cagtcttatt tcctaagatt    180
ttgttgtaac ttaaggtatc ttgctacagt agacagaatt ggtaatagca acttttaaaa    240
ttgtcattag ttctgcaata ttagctgaaa tgtagtacag aaaagaatgt acatttagac    300
atttgggttc agttgcttgt agtctgtaaa tttaaaacag cttaatttgg tacaggttac    360
acatatggac ctcccgggcg g                                              381

<210> SEQ ID NO 24
<211> LENGTH: 214
<212> TYPE: DNA
<213> ORGANISM: Homo sapien

<400> SEQUENCE: 24
aatgatgtaa aaattaatca acagggctgc cacttgcgaa tcccctccaa ggatgctgtg     60
caaagggtct cattggtcct gatgaataat cttgtgactg tacatattcc tgggtgcatg    120
tccacaaata ctgaggtata gcctgcatgc cactaaaaat aacaaaggtt tcaggggtgg    180
aaacattgtc caccacactg tcatgaccat cttt                                214

<210> SEQ ID NO 25
<211> LENGTH: 302
<212> TYPE: DNA
<213> ORGANISM: Homo sapien

<400> SEQUENCE: 25
gggggcactg agaactccct ctggaattct tgggggtgt tggggagaga ctgtgggcct      60
ggagataaaa cttgtctcct ctaccaccac cctgtaccct agcctgcacc tgtcctcatc    120
tctgcaaagt tcagcttcct tccccaggtc tctgtgcact ctgtcttgga tgctctgggg    180
agctcatggg tggaggagtc tccaccagag ggaggctcag ggactggtt gggccaggga    240 tgaatatttg aggataaaaa attgtgtaag aagccaaaga aattggtagt agggggagaa    300
```

```
ac                                                                       302

<210> SEQ ID NO 26
<211> LENGTH: 301
<212> TYPE: DNA
<213> ORGANISM: Homo sapien

<400> SEQUENCE: 26
ttggagaacg cgctgacata ctgctcggcc acagtcagtg aagctgctgc atctccatta        60
tgttgtgtca gagctgcagc caggattcga atagcttcag ctttagcctt ggccttcgcc       120
agaactgcac tggcctctcc tgctgcctga tttatctgtg cagccttttc tgcttcggag       180
gccaggatct gggcctgttt cttcccttct gccacattga tggccgactc tcgggtcccc       240
tcagactcta gaactgtggc ccgtttccgc cgctctgcct ccacctgcat ctgcatagac       300
t                                                                       301

<210> SEQ ID NO 27
<211> LENGTH: 301
<212> TYPE: DNA
<213> ORGANISM: Homo sapien

<400> SEQUENCE: 27
aaatcagtca tcacatctgt gaaaagagtg ctagttataa caaatgagat cacaaatttg        60
accattttat tagacaccct ctattagtgt taacagacaa agatgaaggt taagttgaaa       120
tcaaattgaa atcatcttcc ctctgtacag attgcaatat ctgataatac cctcaacttt       180
cttggtgcaa attaattgcc tggtactcac agtccagtgt taacaggcaa taatggtgtg       240
attccagagg agaggactag gtggcaggaa aataaatgag attagcagta tttgacttgg       300
a                                                                       301

<210> SEQ ID NO 28
<211> LENGTH: 286
<212> TYPE: DNA
<213> ORGANISM: Homo sapien

<400> SEQUENCE: 28 ttttttttg cacaggatgc acttattcta ttcattctcc cccacccttc ccatatttac         60
atccttagag gaagagaggg gtaaggtgat aaagtaactg aaggaccgca agacgggtat       120
gtcccttgtt caccaaatgg tcaaagggtc aaagatcgga ggaggtcagg gggtaacgca       180
ggaacaggtg agggcgtttc gccctctctc cctctcccct tttcaacctc ttaatcactg       240
gctaactcgc gacctcatgg gttaattcgt aagcttacac gcgttg                      286

<210> SEQ ID NO 29
<211> LENGTH: 301
<212> TYPE: DNA
<213> ORGANISM: Homo sapien

<400> SEQUENCE: 29
gtcatgttct tgctcttcct tctttacaca tttgagttgt gccttctgtt cttaaagaga        60
ttttcctttg ttcaaaggat ttattcctac catttcacaa atccgaaaat aattgaggaa       120
acaggttaca tcattccaat tttgccttgg gtttgaagag tctctcatgg tggcacagtc       180
ctccagggta gctatgttgt tgggctcccc tacatcccag aagctcagag actttgtcaa       240
aggtgtgccg tccaccccatt gccactgacc ctcgacaacc tggtctgaca gtccaataaa      300
```

| | |
|---|---|
| a | 301 |

<210> SEQ ID NO 30
<211> LENGTH: 332
<212> TYPE: DNA
<213> ORGANISM: Homo sapien

<400> SEQUENCE: 30

| | |
|---|---:|
| gagcagaatt gatgcctatg gctccaagtc aaatactgct aatctcattt attttcctgc | 60 |
| cacctagtcc tctcctctgg aatcacacca ttattgcctg ttaacactgg actgtgagta | 120 |
| ccaggcaatt aatttgcacc aagaaagttg agggtattat cagatattgc aatctgtaca | 180 |
| gagggaagat gatttcaatt tgatttcaac ttaaccttca tctttgtctg ttaacactaa | 240 |
| tagagggtgt ctaataaaat ggtcaaattt gtgatctcat ttgttataac tagcactctt | 300 |
| ttcacagatg tgatgactga tttccagcag ac | 332 |

<210> SEQ ID NO 31
<211> LENGTH: 141
<212> TYPE: DNA
<213> ORGANISM: Homo sapien

<400> SEQUENCE: 31

| | |
|---|---:|
| aaaggctatc aagtactttg aaggacagga aggaatgaac acacccaggt ggacgtttgg | 60 |
| tttcatttgc agggttcag ggagggttgc aggggttcag ggagggctct tgtcccacaa | 120 |
| ccggggggaag ggagagggca c | 141 |

<210> SEQ ID NO 32
<211> LENGTH: 201
<212> TYPE: DNA
<213> ORGANISM: Homo sapien

<400> SEQUENCE: 32

| | |
|---|---:|
| gagctgatct cacagcacat acagaatgat gctactatgt agaccctcac tcccttggga | 60 |
| aatctgtcat ctaccttaaa gagagaaaaa agatggaaca taggcccacc tagtttcatc | 120 |
| catccaccta cataaccaac atagatgtga ggtccactgc actgatagcc agactgcctg | 180 |
| gggtaaacct tttcagggag g | 201 |

<210> SEQ ID NO 33
<211> LENGTH: 181
<212> TYPE: DNA
<213> ORGANISM: Homo sapien

<400> SEQUENCE: 33

| | |
|---|---:|
| tttcaaaaca ctcatatgtt gcaaaaaaca catagaaaaa taaagtttgg tgggggtgct | 60 |
| gactaaactt caagtcacag acttttatgt gacagattgg agcagggttt gttatgcatg | 120 |
| tagagaaccc aaactaattt attaaacagg atagaaacag gctgtctggg tgaaatggtt | 180 |
| c | 181 |

<210> SEQ ID NO 34
<211> LENGTH: 151
<212> TYPE: DNA
<213> ORGANISM: Homo sapien

<400> SEQUENCE: 34

| | |
|---|---:|
| atgtcctgca cagtatagct tggacctctg ggcctgaacc agggtgagca tcaaggcccc | 60 |
| catttctcct caccacgggg tcgcttgtca gctccaagaa ccagtctggc cccactgaga | 120 |

```
acttttcagt cgagggcctg atgaatcttg g                                    151
```

<210> SEQ ID NO 35
<211> LENGTH: 291
<212> TYPE: DNA
<213> ORGANISM: Homo sapien

<400> SEQUENCE: 35

```
tctttagggc aaaatcatgt ttctgtgtac ctagcaatgt gttcccattt tattaagaaa     60
agctttaaca cgtgtaatct gcagtcctta acagtggcgt aattgtacgt acctgttgtg    120
tttcagtttg tttttcacct ataatgaatt gtaaaaacaa acatacttgt ggggtctgat    180
agcaaacata gaaatgatgt atattgtttt ttgttatcta tttattttca tcaatacagt    240
attttgatgt attgcaaaaa tagataataa tttatataac aggttttctg t             291
```

<210> SEQ ID NO 36
<211> LENGTH: 201
<212> TYPE: DNA
<213> ORGANISM: Homo sapien

<400> SEQUENCE: 36

```
ctgatacaat tataataacg gttccctgaa ccttttagag tgcaattaag aacaaaaact     60
aaattttgtt tacatgaata tggaataaat acaataatca aaatatgact ctccctaaaa    120
gtgaaacaca caagccaatc cggaactgct gtgcgaaaga taaatcgag aaaggcaagg    180
tttcggtagg aggacgcgat g                                              201
```

<210> SEQ ID NO 37
<211> LENGTH: 121
<212> TYPE: DNA
<213> ORGANISM: Homo sapien

<400> SEQUENCE: 37

```
catcacactg gcggccgctc gagcatgcat ctagagggcc caattcgccc tataatgagt     60
cgtattacaa ttcactggcc gtcgttttac aacgtcgtga ctgggaaaac cctggcgtta    120
c                                                                    121
```

<210> SEQ ID NO 38
<211> LENGTH: 200
<212> TYPE: DNA
<213> ORGANISM: Homo sapien

<400> SEQUENCE: 38

```
aaacatgtat tactctatat ccccaagtcc tagagcatga cctgcatgtt ggagatgttg     60
tacagcaatg tatttatcca gacatacata tatgatattt agagacacag tgattctttt    120
gataacacca cacatagaac attataatta cacacaaatt tatggtaaaa gaattaatat    180
gctgtctggt gctgctgtta                                                200
```

<210> SEQ ID NO 39
<211> LENGTH: 760
<212> TYPE: DNA
<213> ORGANISM: Homo sapien

<400> SEQUENCE: 39

```
gcgtggtcgt cggccgaggt cctgggctag acctaatggt ttattattgg tggagagaaa     60
gatctggaaa tacttgaggt tattacatac tagattagct tctaatgtga accatttttc    120
```

```
ttttaacagt gatcaaatta ttatttcgaa gttaatcgtt cccttggtgg ctgcatacac    180
atcgcattaa caaacatact gttgtatttt ttcccagttt tgtttggcta tgccaccaca    240
gtcatcccca ggtctatac atactatgtt tcaactgtat tatttgccat ttttggcatt    300
agaatgcttc gggaaggctt aaagatgagc cctgatgagg gtcaagagga actggaagaa    360
gttcaagctg aattaaagaa gaaagatgaa gaagtaagcc atggcactgt tgatctggac    420
caaaaaggca ctcaactagg aataaacact ctacagaggt ttctcagtgg ccccatctgt    480
gtgatatgcg gggctacaca aaaatagctt cttttgcttt gttctgttct tatacctgtc    540
tgtgatctga cttggggttg gtgtgaatgt agtagagaaa ggaagctgac agatgaatac    600
tgaacacagg taatcagttt ccttaattag gttgattata agctcctgaa aagcaggaac    660
tgtattttat aattttacct gtttctcccg tggtgtctag gatagtaagt gagcagagca    720
gtaaatactg tttggtttgt tcagacctgc ccgggcggcc                         760

<210> SEQ ID NO 40
<211> LENGTH: 452
<212> TYPE: DNA
<213> ORGANISM: Homo sapien

<400> SEQUENCE: 40
aatcactaaa gatattgact agagaatgct gtgtgctatt tcaattacat ttgttttct    60 tttattaaca ggaattttga ttcttcaagg aagtggctca atttcaattt caggtgacca    120
ggtttatcgt gacttttcct tcttgtttac ttttcgctag gaaggggagt tgtaggggca    180
gattcaggta ttggaatagg aaaattacgt ctaaaccatg gaaatcttgg aaatggaatt    240
ggtggaagtg ggcgaaatgg gatatgggta aggaacacaa aaaaccctga agctaattca    300
tcgctgtcac tgatacttct tttttctcgt tcctggtctt gagagactgg gaaaccaaca    360
gccactgcca gatggctgt gatcaggagg agaacttcct tcatctcaaa cgtttcagtc    420
agttctttct ctcacctcgg ccgcgaccac gc                                 452

<210> SEQ ID NO 41
<211> LENGTH: 676
<212> TYPE: DNA
<213> ORGANISM: Homo sapien

<400> SEQUENCE: 41
aatctttgaa tgccaagtct cttctgtact ttcttttatt aacatcatag tctttgcatc    60
aagatacata gcaatgatag caggtttctt tttaaagctt agtattaata ttaaatattt    120
ttccccattt aaattttaca ttacttgcca agaaaaaaaa aaaattaaaa ctcaagttac    180
ttgaagcctg gacacacttc catgattagc cgggctaggt aaaagttggt ggctttattc    240
ttcctgctct ataagcagat ccaggcccta gaaagatggg accagggtat ataattgttt    300
ttgaaaagtg tgctacaaaa atggatggcc tgttataagc caggatacaa agttaaggat    360
gggggtaagg gagggacatt tcttccagag agaaaagaca gaatttctga agagtcccag    420
tccataattt tcccaaaatg gttggaggag agggtaaaat ctcaacatga gtttcaaagt    480
actgtctctg tgaggggccg gtagatgcct tgctgaggag ggatggctaa tttggaccat    540
gccccatccc cagctaggag aatggaaatg gaaacttaa ttgcccagtg ggtgtgaaag    600
tgggctgaag cttggttggt actgaattct ctaagaggtt tcttctagaa acagacaact    660
cagacctgcc cgggcg                                                   676
```

<210> SEQ ID NO 42
<211> LENGTH: 468
<212> TYPE: DNA
<213> ORGANISM: Homo sapien

<400> SEQUENCE: 42

| agcgtggtcg cggccgaggt ttggccggga gcctgatcac ctgccctgct gagtcccagg | 60 |
| ctgagcctca gtctccctcc cttggggcct atgcagaggc ccacaacaca cagatttgag | 120 |
| ctcagccctg gtgggcagag aggtagggat ggggctgtgg ggatagtgag gcatcgcaat | 180 |
| gtaagactcg ggattagtac acacttgttg attaatggaa atgtttacag atccccaagc | 240 |
| ctggcaaggg aatttcttca actccctgcc cccagccct ccttatcaaa ggacaccatt | 300 |
| ttggcaagct ctatgaccaa ggagccaaac atcctacaag acacagtgac catactaatt | 360 |
| aaaacccct gcaaagccca gcttgaaacc ttcacttagg aacgtaatcg tgtcccctat | 420 |
| cctacttccc cttcctaatt ccacagacct gcccgggcgg ccgctcga | 468 |

<210> SEQ ID NO 43
<211> LENGTH: 408
<212> TYPE: DNA
<213> ORGANISM: Homo sapien

<400> SEQUENCE: 43

| atcatatcaa aacactatct tcccatctgt ttctcaatgc ctgctacttc ttgtagatat | 60 |
| ttcatttcag gagagcagca gttaaacccg tggattttgt agttaggaac ctgggttcaa | 120 |
| acctctttcc actaattggc tatgtctctg gacagttttt tttttttttt tttttttaa | 180 |
| accctttctg aactttcact ttctatggct acctcaaaga attgttgtga ggcttgagat | 240 |
| aatgcatttg taagggtct gccagatagg aagatgctag ttatggattt acaaggttgt | 300 |
| taaggctgta agagtctaaa acctacagtg aatcacaatg catttacccc cactgacttg | 360 |
| gacataagtg aaaactagcc cgaagtctct ttttcaaatt acttacag | 408 |

<210> SEQ ID NO 44
<211> LENGTH: 160
<212> TYPE: DNA
<213> ORGANISM: Homo sapien

<400> SEQUENCE: 44

| tggtcgcggc cgaggtcttg tgtgccctgt ggtccagggg accaagaaca acaagatcca | 60 |
| ctctctgtgc tacaatgatt gcaccttctc acgcaacact ccaaccagga ctttcaacta | 120 |
| caacttctcc gctttggcaa acaccgtcac tcttgctgga | 160 |

<210> SEQ ID NO 45
<211> LENGTH: 231
<212> TYPE: DNA
<213> ORGANISM: Homo sapien

<400> SEQUENCE: 45

| cgagcggccg cccgggcagg tctggggagg tgattccatc cagagtcata tctgttgtca | 60 |
| ccccaataag tcgatcagca aggctgacag gctgtgagga accccggcc ttgtagcctg | 120 |
| tcacctctgg ggggatgatg actgcctggc agacgtaggc tgtgatagat ttgggagaaa | 180 |
| acctgactca ccctcaggaa tccggaggtc ggtgacattg tcggtgcaca c | 231 |

<210> SEQ ID NO 46
<211> LENGTH: 371
<212> TYPE: DNA

<213> ORGANISM: Homo sapien

<400> SEQUENCE: 46

| cccgggcagg tctgtgtaac atgccaaggc tttgcacttt ctgcagagca gttttttatt | 60 |
| ttccttatca ggtacaggtt ttggtttttc ttgactatct ctgatgaatt tttcatgagt | 120 |
| ctgtatatgc agaatctttt ccctaaatac tgcttcgtcc catgtctgaa ggcgtaaaat | 180 |
| aaagtcattc atcattttt ctttgtacat gtttatttgt tcttttcaa ttacaccaag | 240 |
| cattactagt cagaaggaag cacttgctac ctcttgctct tcctctgcct ctggtttgga | 300 |
| tcattttgat gacattgccc acattactca tgaaggatga caagattgca ctgtgcaatg | 360 |
| tcaattgcct t | 371 |

<210> SEQ ID NO 47
<211> LENGTH: 261
<212> TYPE: DNA
<213> ORGANISM: Homo sapien

<400> SEQUENCE: 47

| gccctgtttt tatacacttc acatttgcag aaatataatg atgccctcat tatcagtgag | 60 |
| catgcacgaa tgaaagatgc tctggattac ttgaaagact tcttcagcaa tgtccgagca | 120 |
| gcaggattcg atgagattga gcaagatctt actcagagat ttgaagaaaa gctgcaggaa | 180 |
| ctagaaagtg tttccaggga tcccagcaat gagaatccta aacttgaaga cctctgcttc | 240 |
| atcttacaag aagagtacca c | 261 |

<210> SEQ ID NO 48
<211> LENGTH: 701
<212> TYPE: DNA
<213> ORGANISM: Homo sapien

<400> SEQUENCE: 48

| cgagcggccc ccgggcaggt ccaattagta caagtctcat gatataatca ctgcctgcat | 60 |
| acatatgcac agatccagtt agtgagtttg tcaagcttaa tctaattggt taagtctcaa | 120 |
| agagattatt attcttgatg tttgctttgt attggctaac aaatgtgcag aggtaataca | 180 |
| tatgtgatgt ccgatgtctc tgtctttttt tttgtcttta aaaataatt ggcagcaact | 240 |
| gtatttgaat aaaatgattt cttagtatga ttgtaccgta atgaatgaaa gtggaacatg | 300 |
| tttcttttg aaagggagag aattgaccat ttattattgt gatgtttaag ttataactta | 360 |
| ttgagcactt ttagtagtga taactgtttt taaacttgcc taatacctt cttgggtatt | 420 |
| gtttgtaatg tgacttattt aaccccctt tttgtttgtt taagttgctg ctttaggtta | 480 |
| acagcgtgtt ttagaagatt taaattttt tcctgtctgc acaattagtt attcagagca | 540 |
| agagggcctg attttataga agcccttga aagaggtcc agatgagagc agagatacag | 600 |
| tgagaaatta tgtgatctgt gtgttgtggg aagagaattt tcaatatgta actacggagc | 660 |
| tgtagtgcca ttagaaactg tgaatttcca aataaatttg a | 701 |

<210> SEQ ID NO 49
<211> LENGTH: 270
<212> TYPE: DNA
<213> ORGANISM: Homo sapien

<400> SEQUENCE: 49

| agcggccgcc cgggcaggtc tgatattagt agctttgcaa ccctgataga gtaaataaat | 60 |
| tttatgggcg ggtgccaaat actgctgtga atctatttgt atagtatcca tgaatgaatt | 120 |

```
tatggaaata gatatttgtg cagctcaatt tatgcagaga ttaaatgaca tcataatact      180
ggatgaaaac ttgcatagaa ttctgattaa atagtgggtc tgtttcacat gtgcagtttg      240
aagtatttaa attaaccact cctttcacag                                      270

<210> SEQ ID NO 50
<211> LENGTH: 271
<212> TYPE: DNA
<213> ORGANISM: Homo sapien

<400> SEQUENCE: 50
atgcatttat ccatatgaac ttgattattc tgaattactg actataaaaa ggctattgtg       60
aaagatatca cactttgaaa cagcaaatga attttcaatt ttacatttaa ttataagacc      120
acaataaaaa gttgaacatg cgcatatcta tgcatttcac agaagattag taaaactgat      180
ggcaacttca gaattatttc atgaagggta caaacagtct ttaccacaat tttcccatgg      240
tcttatcctt caaaataaaa ttccacacac t                                     271

<210> SEQ ID NO 51
<211> LENGTH: 241
<212> TYPE: DNA
<213> ORGANISM: Homo sapien

<400> SEQUENCE: 51
tggtcgcggc cgaggtgtga ggagatgaac tttgtgttaa tgggggggcac tttaaatcga       60 aatggcttat ccccaccgcc atgtaagtta ccatgcctgt ctcctccctc ctacacattt      120
ccagctcctg ctgcagttat tcctacagaa gctgccattt accagccctc tgtgattttg      180
aatccacgag cactgcaggc cctccacagc gttactaccc agcaggcact cagctcttca      240
t                                                                      241

<210> SEQ ID NO 52
<211> LENGTH: 271
<212> TYPE: DNA
<213> ORGANISM: Homo sapien

<400> SEQUENCE: 52
tccaagactt aaaacttagg aaacacctat gatgccactt taactggaag taatggagac       60
atctgattcc aaattcacat tttaaatgcc tatttgcaat cagcaaagag ccaggtatgc      120
tgcatgctgc ttgctgtaag ttacgatttg gcttcactag ctcaaatttt ttcactccac      180
caaaagataa ggcacaggcc cgtttgtcca atcaagtttg ctgaaaatac tgcagcctga      240
gtgtagacaa acttcccctg aatttgctag a                                     271

<210> SEQ ID NO 53
<211> LENGTH: 493
<212> TYPE: DNA
<213> ORGANISM: Homo sapien

<400> SEQUENCE: 53
ttagcgtggt cgcggtccga ggtctggcct gactagctca ctctgaagag tgtctttcac       60
atggattaac caaaaaatgc attactgcct ttggcacact gtcttgaata ttctttctga      120
caatgagaaa atatgatttta atggagtcgt tcaataacct cacaatctcg ctgttccgag      180
cagatagttt tcgtgccaac aggaactggc acatctagca ggttcacggc atgacctttt      240
tgtggactgg ctggcataat tggaatgggt tttgattttt cttctgctaa taactcttca      300
```

| | |
|---|---|
| agcttttgaa gttttcaagc attcctctcc agttgcctgt ggttggttct tgaacaccat | 360 |
| ctccaacccc accacctcca gatgcaacct tgtctcgtga tacagacctg cccgggcggc | 420 |
| cctcaagggc gaattctgca gatatccatc acactggcgg ccgctcgagc atgcatctag | 480 |
| agggcccaat tcg | 493 |

<210> SEQ ID NO 54
<211> LENGTH: 321
<212> TYPE: DNA
<213> ORGANISM: Homo sapien

<400> SEQUENCE: 54

| | |
|---|---|
| cgtggtcgcg gccgaggtct gtttgcttgt tggtgtgagt ttttcttctg gagactttgt | 60 |
| actgaatgtc aataaactct gtgattttgt taggaagtaa aactgggatc tatttagcca | 120 |
| ctggtaagct tctgaggtga aggattcagg gacatctcgt ggaacaaaca ctccccactg | 180 |
| gactttctct ctggagatac ccttttgaat atacaatggc cttggctcac taggtttaaa | 240 |
| tacaaacaag tctgaaaccc actgaagact gagagattgc agcaatattc tctgaattag | 300 |
| gatcgggttc cataactcta a | 321 |

<210> SEQ ID NO 55
<211> LENGTH: 281
<212> TYPE: DNA
<213> ORGANISM: Homo sapien

<400> SEQUENCE: 55

| | |
|---|---|
| ttgcaaatga aactgtggat gtataataag aaaacacaag ggtttattct taacactaaa | 60 |
| attaacatgc cacacgaaga ctgcattaca gctctctgtt tctgtaatgc agaaaaatct | 120 |
| gaacagccca ccttggttac agctagcaaa gatggttact tcaaagtatg gatattaaca | 180 |
| gatgactctg acatatacaa aaaagctgtt ggctggacct gtgactttgt tggtagttat | 240 |
| cacaagtatc aagcaactaa ctgttgtttc tccgaagatg g | 281 |

<210> SEQ ID NO 56
<211> LENGTH: 612
<212> TYPE: DNA
<213> ORGANISM: Homo sapien

<400> SEQUENCE: 56

| | |
|---|---|
| gcgtggtcgc ggccgaggtc ctgtccgggg gcactgagaa ctccctctgg aattcttggg | 60 |
| gggtgttggg gagagactgt gggcctggag ataaaacttg tctcctctac caccaccctg | 120 |
| taccctagcc tgcacctgtc ctcatctctg caaagttcag cttccttccc caggtctctg | 180 |
| tgccactctg tcttggatgc tctggggagc tcatgggtgg aggagtctcc accagaggga | 240 |
| ggctcagggg actggttggg ccagggatga atatttgagg gataaaaatt gtgtaagagc | 300 |
| caaagaattg gtagtagggg gagaacagag aggagctggg ctatgggaaa tgatttgaat | 360 |
| aatggagctg ggaatatggc tggatatctg gtactaaaaa agggtctta agaacctact | 420 |
| tcctaatctc ttccccaatc caaaccatag ctgtctgtcc agtgctctct tcctgcctcc | 480 |
| agctctgccc caggctcctc ctagactctg tccctgggct agggcagggg aggagggaga | 540 |
| gcagggttgg gggagaggct gaggagagtg tgacatgtgg ggagaggacc agacctgccc | 600 |
| gggcggccgt cg | 612 |

<210> SEQ ID NO 57
<211> LENGTH: 363

```
<212> TYPE: DNA
<213> ORGANISM: Homo sapien

<400> SEQUENCE: 57
gtcgcggccg aggtcctgag cgtcacccta gttctgcccc tttttagctg tgtagacttg      60
gacaagacat ttgacttccc tttctccttg tctataaaat gtggacagtg gacgtctgtc     120
acccaagaga gttgtgggag acaagatcac agctatgagc acctcgcacg tgtccagga     180 tgcacagcac aatccatgat gcgttttctc cccttacgca ctttgaaacc catgctagaa     240
aagtgaatac atctgactgt gctccactcc aacctccagc gtggatgtcc ctgtctgggc     300 ccttttctg tttttattc tatgttcagc accactggca ccaaatacat tttaattcac       360
cga                                                                   363

<210> SEQ ID NO 58
<211> LENGTH: 750
<212> TYPE: DNA
<213> ORGANISM: Homo sapien

<400> SEQUENCE: 58
cgtggtcgcg gccgaggtct aattccacct gactggcaga acctgcgccc ctcgcctaac     60
ctgcgccctt ctcccaactc gcgtgcctca cagaacccag gtgctgcaca gccccgagat    120
gtggcccttc ttcaggaaag agcaaataag ttggtccaag tacttgatgc ttaaggaata    180
cacaaaggtg cccatcaagc gctcagaaat gctgagagat catccgtg aatacactga      240 tgtttatcca gaaatcattg aacgtgcatg ctttgtccta gagaagaaat ttgggattca    300
actgaaagaa attgacaaag aagaacacct gtatattctc atcagtaccc ccgagtccct    360
ggctggcata ctgggaacga ccaaagacac acccaagctc ggtctcttct tggtgattct    420
gggtgtcatc ttcatgaatg caaccgtgc cagtgaggct gtcttttggg aggcactacg     480
caagatggga ctgcgtcctg gggtgagaca tccctccct tggagatcta aggaaacttc     540
tcacctatga gtttgtaaag cagaaatacc tggactacag acgagtgccc aacagcaacc    600
ccccggagta tgagttcctc tggggcctcc gtccctacca tgagactagc aagatgaaaa    660
tgctgagatt cattgcagag gttcagaaaa gagaccctcg tgactggact gcacagttca    720
tggaggctgc agatgaggac ctgcccgggc                                      750

<210> SEQ ID NO 59
<211> LENGTH: 505
<212> TYPE: DNA
<213> ORGANISM: Homo sapien

<400> SEQUENCE: 59
tggccgcccg ggcaggtcca gtctacaagc agagcactct catggggagc accagatgag     60
ttccagccgc agttcttta taagctttaa gtgcctcatg aagacgcgag gatctcttcc    120
aagtgcaacc tggtcacatc agggcacatt cagcagcaga gtctgtttc cagtatagtc    180 cttggtatgg ctaaattcca ctgtcccttt ctcagcagtc aataatccat gataaattct   240
gtacaacact gtagtcaata acagcagcac cagacagcat attaattctt ttaccataaa    300
tttgtgtgta attataatgt tctatgtgtg gtgttatcaa agaatcact gtgtctctaa     360 atatcatata tgtatgtctg gataaataca ttgctgtaca acatctccaa catgcaggtc    420
atgctctaag acttggggat atagagtaat acatgtttcg tggacctcgg ccgcgaccac   480
gctaagggcg aattctgcag atatc                                           505
```

<210> SEQ ID NO 60
<211> LENGTH: 520
<212> TYPE: DNA
<213> ORGANISM: Homo sapien

<400> SEQUENCE: 60

| | | | | | |
|---|---|---|---|---|---|
| cgtggtcgcg | gccgaggtcc | tcaggacaag | gaaacaggta | tcagcatgat | ggtagcagaa | 60 |
| accttatcac | caaggtgcag | gagctgactt | cttccaaaga | gttgtggttc | cgggcagcgg | 120 |
| tcattgcctg | cccttgctgg | agggctgatt | ttagtgttgc | ttattatgtt | ggccctgagg | 180 |
| atgcttcgaa | gtgaaaataa | gaggctgcag | gatcagcggc | aacagatgct | ctcccgtttg | 240 |
| cactacagct | ttcacggaca | ccattccaaa | aaggggcagg | ttgcaaagtt | agacttggaa | 300 |
| tgcatggtgc | cggtcagtgg | gcacgagaac | tgctgtctga | cctgtgataa | aatgagacaa | 360 |
| gcagacctca | gcaacgataa | gatcctctcg | cttgttcact | ggggcatgta | cagtgggcac | 420 |
| gggaagctgg | aattcgtatg | acggagtctt | atctgaacta | cacttactga | acagcttgaa | 480 |
| ggacctgccc | gggcggccgc | tcgaaagggg | cgaattctgc | | | 520 |

<210> SEQ ID NO 61
<211> LENGTH: 447
<212> TYPE: DNA
<213> ORGANISM: Homo sapien

<400> SEQUENCE: 61

| | | | | | |
|---|---|---|---|---|---|
| agagaggtgt | ttttattctt | tggggacaaa | gccgggttct | gtgggtgtag | gattctccag | 60 |
| gttctccagg | ctgtagggcc | cagaggctta | atcagaattt | tcagacaaaa | ctggaacctt | 120 |
| tcttttttcc | cgttggttta | tttgtagtcc | ttgggcaaac | caatgtcttt | gttcgaaaga | 180 |
| gggaaaataa | tccaaacgtt | tttctttttaa | cttttttttt | aggttcaggg | gcacatgtgt | 240 |
| aggcttgcta | tataggtaaa | ttgcatgtca | ccagggtttg | ttgtacagat | tatttcatca | 300 |
| tccagataaa | aagcatagta | ccagataggt | agttttttga | tcctcaccct | ccttccatgc | 360 |
| tccgacctca | ggtaggcccc | agtgtctgac | ctgcccggcg | gcccgctcga | aagggccaat | 420 |
| tctgcagata | tccatcacac | tggccgg | | | | 447 |

<210> SEQ ID NO 62
<211> LENGTH: 83
<212> TYPE: PRT
<213> ORGANISM: Homo sapien

<400> SEQUENCE: 62

Lys Lys Val Leu Leu Leu Ile Thr Ala Ile Leu Ala Val Ala Val Gly
 1               5                  10                  15

Phe Pro Val Ser Gln Asp Gln Glu Arg Glu Lys Arg Ser Ile Ser Asp
            20                  25                  30

Ser Asp Glu Leu Ala Ser Gly Phe Val Phe Pro Tyr Pro Tyr Pro
        35                  40                  45

Phe Arg Pro Leu Pro Ile Pro Phe Pro Arg Phe Pro Trp Phe Arg
    50                  55                  60

Arg Asn Phe Pro Ile Pro Ile Pro Ser Ala Pro Thr Thr Pro Leu Pro
65                  70                  75                  80

Ser Glu Lys

<210> SEQ ID NO 63
<211> LENGTH: 683
<212> TYPE: DNA

<213> ORGANISM: Homo sapien

<400> SEQUENCE: 63

| | | | | | |
|---|---|---|---|---|---|
| acaaagattg | gtagctttta | tatttttta | aaatgctat | actaagagaa | aaacaaaag | 60 |
| accacaacaa | tattccaaat | tataggttga | gagaatgtga | ctatgaagaa | agtattctaa | 120 |
| ccaactaaaa | aaatattga | aaccactttt | gattgaagca | aaatgaataa | tgctagattt | 180 |
| aaaaacagtg | tgaaatcaca | ctttggtctg | taaacatatt | tagctttgct | tttcattcag | 240 |
| atgtatacat | aaacttattt | aaaatgtcat | ttaagtgaac | cattccaagg | cataataaaa | 300 |
| aaagwggtag | caaatgaaaa | ttaaagcatt | tattttggta | gttcttcaat | aatgatrcga | 360 |
| gaaactgaat | tccatccagt | agaagcatct | cctttgggt | aatctgaaca | agtrccaacc | 420 |
| cagatagcaa | catccactaa | tccagcacca | attccttcac | aaagtccttc | cacagaagaa | 480 |
| gtgcgatgaa | tattaattgt | tgaattcatt | tcagggcttc | cttggtccaa | ataaattata | 540 |
| gcttcaatgg | gaagaggtcc | tgaacattca | gctccattga | atgtgaaata | ccaacgctga | 600 |
| cagcatgcat | ttctgcattt | tagccgaagt | gagccactga | acaaaactct | tagagcacta | 660 |
| tttgaacgca | tctttgtaaa | tgt | | | | 683 |

<210> SEQ ID NO 64
<211> LENGTH: 749
<212> TYPE: DNA
<213> ORGANISM: Homo sapien
<220> FEATURE:
<221> NAME/KEY: misc_feature
<222> LOCATION: (1)...(749)
<223> OTHER INFORMATION: n = A,T,C or G

<400> SEQUENCE: 64

| | | | | | |
|---|---|---|---|---|---|
| ctgttcattt | gtccgccagc | tcctggactg | gatgtgtgaa | aggcatcaca | tttccatttt | 60 |
| cctccgtgta | aatgttttat | gtgttcgcct | actgatccca | ttcgttgctt | ctattgtaaa | 120 |
| tatttgtcat | ttgtatttat | tatctctgtg | ttttccccct | aaggcataaa | atggtttact | 180 |
| gtgttcattt | gaacccattt | actgatctct | gttgtatatt | tttcatgcca | ctgctttgtt | 240 |
| ttctcctcag | aagtcgggta | gatagcattt | ctatcccatc | cctcacgtta | ttggaagcat | 300 |
| gcaacagtat | ttattgctca | gggtcttctg | cttaaaactg | aggaaggtcc | acattcctgc | 360 |
| aagcattgat | tgagacattt | gcacaatcta | aaatgtaagc | aaagtaagtc | attaaaaata | 420 |
| caccctctac | ttgggctta | tactgcatac | aaatttactc | atgagccttc | ctttgaggaa | 480 |
| ggatgtggat | ctccaaataa | agatttagtg | tttatttga | gctctgcatc | ttancaagat | 540 |
| gatctgaaca | cctctccttt | gtatcaataa | atagccctgt | tattctgaag | tgagaggacc | 600 |
| aagtatagta | aaatgctgac | atctaaaact | aaataatag | aaaacaccag | gccagaacta | 660 |
| tagtcatact | cacacaaagg | gagaaattta | aactcgaacc | aagcaaaagg | cttcacggaa | 720 |
| atagcatgga | aaaacaatgc | ttccagtgg | | | | 749 |

<210> SEQ ID NO 65
<211> LENGTH: 612
<212> TYPE: DNA
<213> ORGANISM: Homo sapien

<400> SEQUENCE: 65

| | | | | | |
|---|---|---|---|---|---|
| acagcagcag | tagatggctg | caacaacctt | cctcctaccc | cagcccagaa | aatatttctg | 60 |
| ccccacccca | ggatccggga | ccaaaataaa | gagcaagcag | gccccttca | ctgaggtgct | 120 |
| gggtagggct | cagtgccaca | ttactgtgct | ttgagaaaga | ggaagggat | ttgtttggca | 180 |

```
ctttaaaaat agaggagtaa gcaggactgg agaggccaga gaagatacca aaattggcag      240
ggagagacca tttggcgcca gtccctagg  agatgggagg agggagatag gtatgagggt      300
aggcgctaag aagagtagga ggggtccact ccaagtggca gggtgctgaa atgggctagg      360
accaacagga cactgactct aggtttatga cctgtccata cccgttccac agcagctggg      420
tgggagaaat caccattttg tgacttctaa taaaataatg ggtctaggca acagttttca      480
atggatgcta aaacgattag gtgaaaagtt gatggagaat tttaattcag gggaattagg      540
ctgataccat ctgaaaccat ttggcatcat taaaaatgtg acaacctggt ggctgccagg      600
gaggaagggg ag                                                          612

<210> SEQ ID NO 66
<211> LENGTH: 703
<212> TYPE: DNA
<213> ORGANISM: Homo sapien

<400> SEQUENCE: 66
tagcgtggtc gcggccgagg tacattgatg ggctggagag cagggttggc agcctgttct       60
gcacagaacc aagaattaca gaaaaagtc  caggagctgg agaggcacaa catctccttg      120
gtagctcagc tccgccagct gcagacgcta attgctcaaa cttccaacaa agctgcccag      180
accagcactt gtgttttgat tcttcttttt tccctggctc tcatcatcct gcccagcttc      240
agtccattcc agagtcgacc agaagctggg tctgaggatt accagcctca cggagtgact      300
tccagaaata tcctgaccca caaggacgta acagaaaatc tggagaccca agtggtagag      360
tccagactga gggagccacc tggagccaag gatgcaaatg gctcaacaag gacactgctt      420
gagaagatgg gagggaagcc aagacccagt gggcgcatcc ggtccgtgct gcatgcagat      480
gagatgtgag ctggaacaga ccttcctggc ccacttcctg atcacaagga atcctgggct      540
tccttatggc tttgcttccc actgggattc ctacttaggt gtctgccctc aggggtccaa      600
atcacttcag gacaccccaa gagatgtcct ttagtctctg cctgaggcct agtctgcatt      660
tgtttgcata tatgagaggg tacctgcccg ggcggccgct cga                        703

<210> SEQ ID NO 67
<211> LENGTH: 1022
<212> TYPE: DNA
<213> ORGANISM: Homo sapien

<400> SEQUENCE: 67
cttgagaaag caggattgtt ttaagttcca agatttaaca aacttactgt tcagcatcat       60
attcaagcct aaaaggaaga taggattttc aagatatatt tccaacttct ttaacatggc      120
accatggatg aactgtttct cagcactgtg ctgcttcact tggaattaag gatgaattgg      180
gaggagacag tatgacatag gtgggtaggt tgggtggtga gggaaccag  ttctaatagt      240 cctcaactcc actccagctg ttcctgttcc acacggtcca ctgagctggc ccagtccctt      300
tcactcagtg tgtcaccaaa ggcagcttca aggctcaatg caagagacc  acctataacc      360 tcttcacctt ctgctgcctc tttctgctgc cactgactgc catggccatc tgctatagcc      420
gcattgtcct cagtgtgtcc aggccccaga caaggaaggg gagccatggt gagactccaa      480
ttcccaggcc ttaatcctta accctagacc tgttgcctct agcatcattt atttatctac      540
ctacctaata gctatctacc agtcattaaa ccatggtgag attctaacca tgtctagcac      600
ctgatgctag agataatttt gttgaatccc ttcaattata aacagctgag ttagctggac      660
```

-continued

```
aaggactagg gaggcaatca gtattattta ttcttgaaca ccatcaagtc tagacttggt        720
ggcttcatat ttctatcata atccctgggg gtaagaaatc atatagcccc aggttgggaa        780
ggggaaaacg gtttgcaaca ttctcctcct tgtaggaggc gagctctgtc tcactagcta        840
tgcccctcca tcaattcacc ctatactcag atcagaagct gagtgtctga attacagtat        900
attttctaaa ttcctagccc ctgctggtga atttgccctc cccgctcct ttgacaattg         960 tccccgtgtt cgtctccggg ccctgagact ggccctgctt atcttgctga ccttcatcct       1020
ct                                                                      1022
```

<210> SEQ ID NO 68
<211> LENGTH: 449
<212> TYPE: DNA
<213> ORGANISM: Homo sapien

<400> SEQUENCE: 68

```
ccagatccat tttcagtggt ctggatttct ttttattttc ttttcaactt gaaagaaact         60
ggacattagg ccactatgtg ttgttactgc cactagtgtt caagtgcctc ttgttttccc        120
agagatttcc tgggtctgcc agaggcccag acaggctcac tcaagctctt taactgaaaa       180
gcaacaagcc actccaggac aaggttcaaa atggttacaa cagcctctac ctgtcgcccc       240
agggagaaag gggtagtgat acaagtctca tagccagaga tggttttcca ctccttctag      300
atattcccaa aaagaggctg agacaggagg ttattttcaa ttttattttg gaattaaata      360
cttttttccc tttattactg ttgtagtccc tcacttggat atacctctgt tttcacgata      420
gaaataaggg aggtctagag cttctattc                                         449
```

<210> SEQ ID NO 69
<211> LENGTH: 387
<212> TYPE: DNA
<213> ORGANISM: Homo sapien
<220> FEATURE:
<221> NAME/KEY: misc_feature
<222> LOCATION: (1)...(387)
<223> OTHER INFORMATION: n = A,T,C or G

<400> SEQUENCE: 69

```
gcccttagcg tgggtcgcgg cncgangtct ggagcntatg tgatncctat ggtncncagg         60
cnnatactgc tantctcatt tattctcctg cnacctantc ctctnctctg gaatcacacc       120
attattgcct gttaacactg gactgtgagt accangcaat taatttgcac caanaaagtt       180
gagggtatta tcanatattg caatctgtac agagggaaga tgatttcaat ttgatttcaa       240
cttaaccttc atctttgtct gttaacacta atagagggtc tctaataaaa tggcaaattt       300
gngatctcat tnggtataac tacactcttt ttcacagatg tgatgactga atttccanca       360
acctgcccgg gcggncgntc naagggc                                           387
```

<210> SEQ ID NO 70
<211> LENGTH: 836
<212> TYPE: DNA
<213> ORGANISM: Homo sapien

<400> SEQUENCE: 70

```
tattccattt acaaaataaa ttcagccctg cactttcttt agatgccttg atttccagaa         60
tggagcttag tgctactgaa taccctggcc acagagccac ctcaggatat tcttttctcc       120
accctagttt atttatttat agatatcgt ttacaaagtc tgtagtaaat cctgatgctg        180
accatctgaa atgtactttt tttctgaatg ctgtttcaat ctaaaatagc agcttttgag       240
```

-continued

```
aaaacaatga tgtaaattcc ttatgataaa aggatgattc tatatattct ttaatgatat      300
taaatatgcc gaagccaagc acacagtctt tctaaagtgt gtgtatgttt gtgtgaatgt      360
gaatgatact gatcttatat ctgttaaaag ttgtttaaa aagctgtggc atcccattgt       420
tcatatttgc caagtcttct gtaaagatgt ctaggacgaa atattttatg tgctaatgca      480
tgtatttgta aaccagattt gtttaccact caaaattaac ttgttttctt catccaaaaa     540
agtttatttc ttccacgtac ttaaattttc tgtgtgggta taatatagct ttctaatttt      600
tttctttcac aaaggcaggt tcaaaattct gttgaaagaa aaatgctttc tgaaactgag     660
gtataacacc agagcttgct gtttaaagga ttatatgatg tacatcagtt ctataaatgt     720
gctcagcagt ttaacatgtg aatcctgttt taaagtgctc agatttcaac tgtgtaagcc     780
attgatataa cgctgtaatt aaaaatgttt atatgaaaaa aaaaaaaaaa aaaaaa         836
```

<210> SEQ ID NO 71
<211> LENGTH: 618
<212> TYPE: DNA
<213> ORGANISM: Homo sapien

<400> SEQUENCE: 71

```
gttgcagtga gctcaagtgt tgggtgtatc agctcaaaac accatgtgat gccaatcatc       60
tccacaggag caatttgttt acctttttt tctgatgctt tactaacttc atcttttaga      120
tttaaatcat tagtagatcc tagaggagcc agtttcagaa aatatagatt ctagttcagc      180
accacccgta gttgtgcatt gaaataatta tcattatgat tatgtatcag agcttctggt      240
tttctcattc tttattcatt tattcaacaa ccacgtgaca aacactggaa ttacaggatg     300
aagatgagat aatccgctcc ttggcagtgt tatactatta tataacctga aaaacaaac      360 aggtaatttt cacacaaagt aatagatatc atgacacatt taaaataggg cactactgga     420
acacacagat aggacatcca ggttttgggt caatattgta gacttttgg tggatgagat      480 atgcaggttg atrccagaag acaacaaaa acatatgtca gatagaaggg aggagcaaat      540
gccaagagct ggagctgagg aagatcactg tgaaattcta tgtagtctag ttggctggat     600
gctagagcaa agaggtgg                                                    618
```

<210> SEQ ID NO 72
<211> LENGTH: 806
<212> TYPE: DNA
<213> ORGANISM: Homo sapien

<400> SEQUENCE: 72

```
tctacgatgg ccatttgctc attgtctttc ctctgtgtgt agtgagtgac cctggcagtg       60
tttgcctgct cagagtggcc cctcagaaca acagggctgg ccttggaaaa accccaaaac     120
aggactgtgt tgacaactct ggtcaggtgt gatttgacat gagggccgga ggcggttgct      180
gacggcagga ctggagaggc tgcgtgcccg gcactggcag cgaggctcgt gtgtccccca      240
ggcagatctg ggcactttcc caacccaggt ttatgccgtc tccagggaag cctcggtgcc     300
agagtggtgg gcagatctga ccatccccac agaccagaaa caaggaattt ctgggattac     360
ccagtccccc ttcaacccag ttgatgtaac cacctcattt tttacaaata cagaatctat     420
tctactcagg ctatgggcct cgtcctcact cagttattgc gagtgttgct gtccgcatgc      480
tccgggcccc acgtggctcc tgtgctctag atcatggtga ctccccgcc ctgtggttgg       540 aatcgatgcc acggattgca ggccaaattt cagatcgtgt ttccaaacac ccttgctgtg     600
```

```
cccttttaatg ggattgaaag cacttttacc acatggagaa atatatttttt aatttgtgat      660 gcttttctac aagtccact atttctgagt ttaatgtgtt tccaacactt aaggagactc        720
taatgaaagc tgatgaattt tcttttctgt ccaaacaagt aaaataaaaa taaaagtcta      780
tttagatgtt gaaaaaaaaa aaaaaa                                            806
```

<210> SEQ ID NO 73
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 73

```
actctggtaa gcttgttgtt gtccaagtga agctccctca gatgaggcgt gttggccana       60
gagccattgt caacagcaga gatgctgttg aaactcaatc ccaacttagc caaattattc     120
agtcctttca ggctagctgc atcaactctg ctgattttgt tgccatcaag atgtaattcc     180
gtaagggaag gaggaagacc ttgaggaatg ctggygatat tggyatcagc aatgcggatg     240
tasgaagagc ttcttcmttc cctggaaagc cccattttca atyccttgag ctcttcakcg     300
g                                                                      301
```

<210> SEQ ID NO 74
<211> LENGTH: 401
<212> TYPE: DNA
<213> ORGANISM: Homo sapien

<400> SEQUENCE: 74

```
agtttacatg atccctgtaa cagccatggt ctcaaactca gatgcttcct ccatctgcca       60
agtgtgttct ggatacagag cacatcgtgg cttctgggggt cacactcagc ttaggctgtg   120
ggtccacaga gcactcatct ggctgggcta tggtggtggt ggctctactc aagaagcaaa    180
gcagttacca gcacattcaa acagtgtatt gaacatcttt taaatatcaa agtgagaaac    240
aagaaggcaa cataataatg ttatcagaaa gatgttagga agtaaggaca gctgtgtaaa    300
gcttgaggct gaaaagtagc ttgccagctt catttctttg gtttcttggg tagtgggccg    360
ccggaacagc aagatgtgag gttctggttc atggatcata t                          401
```

<210> SEQ ID NO 75
<211> LENGTH: 612
<212> TYPE: DNA
<213> ORGANISM: Homo sapien

<400> SEQUENCE: 75

```
ttattttttca attttttattt tggtttttctt acaaaggttg acatttttcca taacaggtgt     60 aagagtgttg aaaaaaaaat tcaaattttt ggggagcgag ggaaggagtt aatgaaactg    120
tattgcacaa tgctctgatc aatccttctt ttttctctttt gcccacaatt taagcaagta    180
gatgtgcaga agaaatggaa ggattcagct ttcagttaaa aagaagaag aagaaatggc      240 aaagagaaag tttttttcaaa tttctttctt tttttaattta gattgagttc atttattttga   300 aacagactgg gccaatgtcc acaaagaatt cctggtcagc accaccgatg tccaaaggtg    360
caatatcaag gaagggcagg cgtgatggct tatttgttttt gtattcaatg attgtctttc    420
cccattcatt tgtctttttta gagcagccat ctacaagaac agtgtaagtg aacctgctgt   480
tgccctcagc aacaagttca acatcattag agccctgtag aatgacagcc ttttttcaggt    540
```

```
tgccagtctc ctcatccatg tatgcaatgc tgttcttgca gtggtaggtg atgttctgag    600
aggcatagtt gg                                                        612
```

<210> SEQ ID NO 76
<211> LENGTH: 844
<212> TYPE: DNA
<213> ORGANISM: Homo sapien

<400> SEQUENCE: 76

```
ggctttcgag cggccgcccg ggcaggtctg atggttctcg taaaaacccc gctagaaact     60
gcagagacct gaaattctgc catcctgaac tcaagagtgg agaatactgg gttgaccct a   120 accaaggatg caaattggat gctatcaagg tattctgtaa tatggaaact ggggaaacat   180
gcataagtgc caatcctttg aatgttccac ggaaacactg gtggacagat tctagtgctg   240
agaagaaaca cgtttggttt ggagagtcca tggatggtg ttttcagttt agctacggca    300
atcctgaact tcctgaagat gtccttgatg tgcagcykgc attccttcga cttctctcca   360
gccgagcttc ccagaacatc acatatcact gcaaaaatag cattgcatac atggatcagg   420
ccagtggaaa tgtaaagaag gccctgaagc tgatgggtc aaatgaaggt gaattcaagg    480
ctgaaggaaa tagcaaattc acctacacag ttctggagga tggttgcacg aaacacactg   540
gggaatggag caaaacagtc tttgaatatc gaacacgcaa tgctgttcct tgacattgca   600
ccaccaatgt ccagaggtgc aatgtcaagg aacggcaggc gagatggctt atttgttttg   660
tattcaatga ttgtcttgcc ccattcattt gtcttttgg agcagccatc gactaggaca    720
gagtaggtga acctgctgtt gccctcagca acaagttcca catcgttgga accctgcaga   780
agcacagcct tgttcaarct gcccgtctcc tcatccagat acctcggccg cgaccacgct   840
aatc                                                                 844
```

<210> SEQ ID NO 77
<211> LENGTH: 314
<212> TYPE: DNA
<213> ORGANISM: Homo sapien

<400> SEQUENCE: 77

```
ccagtcctcc acttggcctg atgagagtgg ggagtggcaa gggacgtttc tcctgcaata     60
gacacttaga tttctctctt gtgggaagaa accacctgtc catccactga ctcttctaca   120
ttgatgtgga aattgctgct gctaccacca cctcctgaag aggcttccct gatgccaatg   180
ccagccatcc tggcatcctg gccctcgagc aggctgcggt aagtagcgat ctcctgctcc   240
agccgtgtct ttatgtcaag cagcatcttg tactcctggt tctgagcctc catctcgcat   300
cggagctcac tcag                                                     314
```

<210> SEQ ID NO 78
<211> LENGTH: 548
<212> TYPE: DNA
<213> ORGANISM: Homo sapien

<400> SEQUENCE: 78

```
accaagagcc aagtgttaca caggatattt taaaaataaa atgttttttgg aatcctcacc    60 tcccatgcta tcttctaaga taactacaaa tattcttcaa agatttaact gagttctgcc   120
aaggacctcc caggactcta tccagaatga ttattgtaaa gctttacaaa tcccaccttg   180
gccctagcga taattaggaa atcacaggca aacctcctct ctcggagacc aatgaccagg   240
```

| | |
|---|---|
| ccaatcagtc tgcacattgg ttttgttaga tactttgtgg agaaaaacaa aggctcgtga | 300 |
| tagtgcagct ctgtgcctac agagagcctc ccttttggtt ctgaaattgc tgatgtgaca | 360 |
| gagacaaagc tgctatgggt ctaaaacctt caataaagta actaatgaca ctcaaggtcc | 420 |
| tgggactctg agacagacgg tggtaaaacc cacagctgcg attcacattt ccaatttatt | 480 |
| ttgagctctt tctgaagctg ttgcttccta cctgagaatt cccatttaga gagctgcaca | 540 |
| gcacagtc | 548 |

<210> SEQ ID NO 79
<211> LENGTH: 646
<212> TYPE: DNA
<213> ORGANISM: Homo sapien

<400> SEQUENCE: 79

| | |
|---|---|
| accccgtcac tatgtgaata aaggcagcta gaaaatggac tcaattctgc aagccttcat | 60 |
| ggcaacagcc catattaaga cttctagaac aagttaaaaa aaatcttcca tttccatcca | 120 |
| tgcatgggaa aagggcttta gtatagttta ggatggatgt gtgtataata ataaaatgat | 180 |
| aagatatgca tagtggggga ataaagcctc agagtccttc cagtatgggg aatccattgt | 240 |
| atcttagaac cgagggattt gtttagattg ttgatctact aattttttc ttcacttata | 300 |
| tttgaattt caatgatagg acttattgga aattggggat aattctgttg tggtattaaa | 360 |
| taatattcat ttttaaaaa ctcatcttgg tattgagtta gtgcattgac ttccaatgaa | 420 |
| ttgacataag cccatatttc attttaacca gaaacaaaaa ctagaaaatg ttactcccta | 480 |
| aataggcaac aatgtatttt ataagcactg cagagattta gtaaaaaaca tgtatagtta | 540 |
| ctttagaaac aacttctgac acttgagggt tacccaatgg tctccttccc attctttata | 600 |
| tgaggtaaat gcaaaccagg gagccaccga ataaacagcc ctgagt | 646 |

<210> SEQ ID NO 80
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 80

| | |
|---|---|
| gtctgaatga gcttcnctgc gagatgganc ancataaccc agaantccaa aancntanng | 60 |
| aacgnnaaaa cccgntngaa caagnaaacn gcaactnacg gccgcctgnt gnagggcgag | 120 |
| gacgcccacc tctcctcctc ccagttctcc tctggatcgc agncatccan agatgtgacc | 180 |
| tcttccagcc gccaaatccg caccaaggtc atggatgtgc acgatggcaa ggtgggtgtc | 240 |
| cacccacgaa caggtccttc gcaccaagaa ctgagg | 276 |

<210> SEQ ID NO 81
<211> LENGTH: 647
<212> TYPE: DNA
<213> ORGANISM: Homo sapien

<400> SEQUENCE: 81

| | |
|---|---|
| gtcctgcctt tcatcttttc tttaaaaaaa ataaatgttt acaaacatt tccctcagat | 60 |
| tttaaaattc atggaagtaa taaacagtaa taaatatgg atactatgaa aactgacaca | 120 |
| cagaaaaaca taaccataaa atattgttcc aggatacaga tattaattaa gagtgacttc | 180 |
| gttagcaaca cgtagacatt catacatatc cggtggaaga ctggtttctg agatgcgatt | 240 |

| | |
|---|---|
| gccatccaaa cgcaaatgct tgatcttgga gtaggrtaat ggccccagga tcttgcagaa | 300 |
| gctctttatg tcaaacttct caagttgatt gacctccagg taatagtttt caaggttttc | 360 |
| attgacagtt ggtatgtttt taagcttgtt ataggacaga tccagctcaa ccagggatga | 420 |
| cacattgaaa gaatttccag gtattccact atcagccagt tcgttgtgag ataaacgcag | 480 |
| atactgcaat gcattaaaac gcttgaaata ctcatcaggg atgttgctga tcttattgtt | 540 |
| gtctaagtag agagttagaa gagagacagg gagaccagaa ggcagtctgg ctatctgatt | 600 |
| gaagctcaag tcaaggtatt cgagtgattt aagacccttta aaagcag | 647 |

<210> SEQ ID NO 82
<211> LENGTH: 878
<212> TYPE: DNA
<213> ORGANISM: Homo sapien

<400> SEQUENCE: 82

| | |
|---|---|
| ccttctttcc ccactcaatt cttcctgccc tgttattaat taagatatct tcagcttgta | 60 |
| gtcagacaca atcagaatya cagaaaaatc ctgcctaagg caaagaaata taagacaaga | 120 |
| ctatgatatc aatgaatgtg ggttaagtaa tagatttcca gctaaattgg tctaaaaaag | 180 |
| aatattaagt gtggacagac ctatttcaaa ggagcttaat tgatctcact tgttttagtt | 240 |
| ctgatccagg gagatcaccc ctctaattat ttctgaactt ggttaataaa agtttataag | 300 |
| atttttatga agcagccact gtatgatatt ttaagcaaat atgttatttta aaatattgat | 360 |
| ccttcccttg gaccaccttc atgttagttg ggtattataa ataagagata caaccatgaa | 420 |
| tatattatgt ttatacaaaa tcaatctgaa cacaattcat aaagatttct cttttatacc | 480 |
| ttcctcactg gcccccctcca cctgcccata gtcaccaaat tctgttttaa atcaatgacc | 540 |
| taagatcaac aatgaagtat tttataaatg tatttatgct gctagactgt gggtcaaatg | 600 |
| tttccatttt caaattattt agaattctta tgagtttaaa atttgtaaat ttctaaatcc | 660 |
| aatcatgtaa aatgaaactg ttgctccatt ggagtagtct cccacctaaa tatcaagatg | 720 |
| gctatatgct aaaaagagaa aatatggtca agtctaaaat ggctaattgt cctatgatgc | 780 |
| tattatcata gactaatgac atttatcttc aaaacaccaa attgtcttta gaaaaattaa | 840 |
| tgtgattaca ggtagagaac ctcggccgcg accacgct | 878 |

<210> SEQ ID NO 83
<211> LENGTH: 645
<212> TYPE: DNA
<213> ORGANISM: Homo sapien

<400> SEQUENCE: 83

| | |
|---|---|
| acaaacattt tacaaaaaag aacattacca atatcagtgg cagtaagggc aagctgaaga | 60 |
| ataaatagac tgagtttccg ggcaatgtct gtcctcaaag acatccaaac tgcgttcagg | 120 |
| cagctgaaac aggcttcttt cccagtgaca agcatatgtg gtcagtaata caacgatgg | 180 |
| taaatgaggc tactacatag gcccagttaa caaactcctc ttctcctcgg gtaggccatg | 240 |
| atacaagtgg aactcatcaa ataatttaaa cccaaggcga taacaacgct atttcccatc | 300 |
| taaactcatt taagccttca caatgtcgca atggattcag ttacttgcaa acgatcccgg | 360 |
| gttgtcatac agatacttgt ttttacacat aacgctgtgc catcccttcc ttcactgccc | 420 |
| cagtcaggtt tcctgttgtt ggaccgaaag gggatacatt ttagaaatgc ttccctcaag | 480 |
| acagaagtga gaaagaaagg agaccctgag gccaggatct attaaacctg gtgtgtgcgc | 540 |

```
aaaagggagg gggaaggcag gaatttgaaa ggataaacgt ctcctttgcg ccgaggaatc        600
aggaagcgtg actcacttgg gtctgggacg ataccgaaat ccggt                       645
```

<210> SEQ ID NO 84
<211> LENGTH: 301
<212> TYPE: DNA
<213> ORGANISM: Homo sapien
<220> FEATURE:
<221> NAME/KEY: misc_feature
<222> LOCATION: (1)...(301)
<223> OTHER INFORMATION: n = A,T,C or G

<400> SEQUENCE: 84

```
tctgatgtca atcacaactt gaaggatgcc aatgatgtac caatccaatg tgaaatctct        60
cctcttatct cctatgctgg agaaggatta gaaggttatg tggcagataa agaattccat       120
gcacctctaa tcatcgatga gaatggagtt catgggctgg tgaaaaatgg tatttgaacc       180
agataccaag ttttgtttgc cacgatagga atagctttta tttttgatag accaactgtg       240
aacctacaag acgtcttgga caactgaagn ttaaatatcc acangggttt attttgcttg       300
g                                                                      301
```

<210> SEQ ID NO 85
<211> LENGTH: 296
<212> TYPE: DNA
<213> ORGANISM: Homo sapien
<220> FEATURE:
<221> NAME/KEY: misc_feature
<222> LOCATION: (1)...(296)
<223> OTHER INFORMATION: n = A,T,C or G

<400> SEQUENCE: 85

```
agcgtgggtc gcggcncgan gtagagaacc gactgaaacg tttgagatga agaaagttct        60
cctcctgatc acagccatct tggcagtggc tgttggtttc ccagtctctc aagaccagga       120
acgagaaaaa agaagtatca gtgacagcga tgaattagct tcagggtttt ttgtgttccc       180
ttacccatat ccatttcgcc cacttccacc aattccattt ccaagatttc catggtttan       240
acgtaatttt cctattccaa tacctgaatc tgccctaca actccccttc ctagcg           296
```

<210> SEQ ID NO 86
<211> LENGTH: 806
<212> TYPE: DNA
<213> ORGANISM: Homo sapien

<400> SEQUENCE: 86

```
tctacgatgg ccatttgctc attgtctttc ctctgtgtgt agtgagtgac cctggcagtg        60
tttgcctgct cagagtggcc cctcagaaca acagggctgg ccttggaaaa accccaaaac       120
aggactgtgg tgacaactct ggtcaggtgt gatttgacat gagggccgga ggcggttgct       180
gacggcagga ctggagaggc tgcgtgcccg gcactggcag cgaggctcgt gtgtccccca       240
ggcagatctg ggcactttcc caacccaggt ttatgccgtc tccagggaag cctcggtgcc       300
agagtggtgg gcagatctga ccatccccac agaccagaaa caaggaattt ctgggattac       360
ccagtccccc ttcaacccag ttgatgtaac cacctcattt tttacaaata cagaatctat       420
tctactcagg ctatgggcct cgtcctcact cagttattgc gagtgttgct gtccgcatgc       480
tccgggcccc acgtgctcc tgtgctctag atcatggtga ctccccgcc ctgtggttgg         540 aatcgatgcc acggattgca ggccaaattt cagatcgtgt ttccaaacac ccttgctgtg       600 cccttttaatg ggattgaaag cacttttacc acatggagaa atatatttt aatttgtgat      660
```

| | |
|---|---|
| gcttttctac aaggtccact atttctgagt ttaatgtgtt tccaacactt aaggagactc | 720 |
| taatgaaagc tgatgaattt tcttttctgt ccaaacaagt aaaataaaaa taaaagtcta | 780 |
| tttagatgtt gaaaaaaaaa aaaaaa | 806 |

<210> SEQ ID NO 87
<211> LENGTH: 620
<212> TYPE: DNA
<213> ORGANISM: Homo sapien

<400> SEQUENCE: 87

| | |
|---|---|
| tttttgcatc agatctgaaa tgtctgagag taatagtttc tgttgaattt ttttttgttc | 60 |
| attttctgc acagtccatt ctgttttat tactatctag cttgaaata tatagtttga | 120 |
| aattatgaca tccttcctct ttgttatttt cctcatgatt gctttggcta ttcaaagttt | 180 |
| attttagttt catgtaaatt tttgaattgt attttccatt attgtgaaaa tagtaccact | 240 |
| gcaattttaa taggaagttt attgaatcta tagattactt tggataatat ggcacttcaa | 300 |
| taatattcat gttttcaatt catagacaaa atattttaaa atttatttgt atcttttcta | 360 |
| atttttcctt ttttttattgt aaagatttac ctccttggtt aatattttcc tcagaaattt | 420 |
| attatttaag gtatagtcaa taaaatttc ttcctctatt ttgtcagata gtttaagtgt | 480 |
| atgaaaccat agatatactt gtatgttaat tttatatttt gctaatttac tgagtgtatt | 540 |
| tattagttta gagaggtttt aatgtactgt ttatggtttt ttaaatataa gattacttat | 600 |
| tttttaaaaa aaaaaaaaaa | 620 |

<210> SEQ ID NO 88
<211> LENGTH: 308
<212> TYPE: DNA
<213> ORGANISM: Homo sapien
<220> FEATURE:
<221> NAME/KEY: misc_feature
<222> LOCATION: (1)...(308)
<223> OTHER INFORMATION: n = A,T,C or G

<400> SEQUENCE: 88

| | |
|---|---|
| tagctgtgnt cagcaggccg aggttttttt tttttttgag atggagtctc gccctgtcac | 60 |
| ccaggctgga gtgcagtggc ctgatctcag ctcactgcaa gctccacctc ctggattcac | 120 |
| gctattctcc tgcctcagcc tcccaagtag ctgggactac aggcgcccgc caccacgccc | 180 |
| agctaattnt ttgnattttt agtacnagat gcggtttcat cgtgttagcc agcatggnct | 240 |
| cgatctcctg acctcgtgaa ctgcccgcct cggcctccca agacctgcc cgggcnggcc | 300 |
| gctcgaaa | 308 |

<210> SEQ ID NO 89
<211> LENGTH: 492
<212> TYPE: DNA
<213> ORGANISM: Homo sapien
<220> FEATURE:
<221> NAME/KEY: misc_feature
<222> LOCATION: (1)...(492)
<223> OTHER INFORMATION: n = A,T,C or G

<400> SEQUENCE: 89

| | |
|---|---|
| agcggccgcc cgggcaggtc tgttaagtaa catacatatc accttaataa aaatcaagat | 60 |
| gaaatgtttt agaaactatt ttatcaaaag tggctctgat acaaagactt gtacatgatt | 120 |
| gttcacagca gcactattaa tgccaaaaag tagacaaaac ctaaatgtcc attaactgat | 180 |

```
aagcaaaatg tggtatatcc atacaatgga atattatgta gcccacaaca tggcatggag    240
tactacaaca tggatgagcc tcaaaaacgt tatgctaaat gaaaaaagtc agatatagga    300
aaccacatgt catatgatcc catttatatg aaatagccag aaaaggcaag tcatagaaac    360
aagatagatc ggaaaatggg ttggaggact acaaatggca ccagggatct tgaagttga    420 tggaaatggt ctaaaatcag actgtggntg tggttgaaca agtctgtaaa tttaccaaaa    480
tgcgttaata ca                                                        492
```

<210> SEQ ID NO 90
<211> LENGTH: 390
<212> TYPE: DNA
<213> ORGANISM: Homo sapien
<220> FEATURE:
<221> NAME/KEY: misc_feature
<222> LOCATION: (1)...(390)
<223> OTHER INFORMATION: n = A,T,C or G

<400> SEQUENCE: 90

```
tcgagcggcc gcccgggcag gtacaagctt tttttttttt tttttttttt ttttctaaca     60
gttctctgtt ttattgcaat acagcaaagt ctggttaata ttaagngata tcaacataaa    120
gtattggtga ggagtctttt gtgacatttt ttaccatccc accttaaata tttctgtgca    180
aaanaatcca catcattgtt tggtancana ggatctctta aaaagttccc taanacactg    240
agggcataaa accaaacaaa ataaaataag gagtgatagg ctaaagcagt atcttcccct    300
ccatccacat ttgncaagca ttatattcta accaaaaaat gatcacacca ggccatgcaa    360
aactgtccaa tattaccgag aaaaaaccct                                     390
```

<210> SEQ ID NO 91
<211> LENGTH: 192
<212> TYPE: DNA
<213> ORGANISM: Homo sapien

<400> SEQUENCE: 91

```
agcgtggtcg cggccgaggt ctgtcaatta atgctagtcc tcaggattta aaaaataatc     60
ttaactcaaa gtccaatgca aaaacattaa gttggtaatt actcttgatc ttgaattact    120
tccgttacga aagtccttca cattttcaa actaagctac tatatttaag gcctgcccgg    180
gcggccgctc ga                                                        192
```

<210> SEQ ID NO 92
<211> LENGTH: 570
<212> TYPE: DNA
<213> ORGANISM: Homo sapien
<220> FEATURE:
<221> NAME/KEY: misc_feature
<222> LOCATION: (1)...(570)
<223> OTHER INFORMATION: n = A,T,C or G

<400> SEQUENCE: 92

```
agcgtggtcg cggccgaggt ctgacaacta acaaagaagc aaaaactggc atcttggaca     60
tcctagtatt acacttgcaa gcaattagaa cacaaggagg gccaaggaaa aagtttagct    120
ttgaatcact tccaaatcta ctgatttga ggttccgcag tagttctaac aaaacttttc    180
agacaatgtt aactttcgat taagaaagaa aaaaccccca acatcttca ggaattccat    240 gccaggttca gtctcttcca gtgagcccgc ttgctaaaag tccacgtgca ccattaatta    300
gctgggctga cagcaccatg taaaaagaag cctattcacc accaaccaca cagactagac    360
atgtaaagta ggatcaagta atggatgaca accatggtcg tggaatatgg tcaatgagag    420
```

```
tcagaaaagt acaggcacca gtacaagcag cagataacag aattgacggg ccaaaggata        480
aaaataggct tatttaaata ggatgctaca gaacacatnc acttctaatt ggaagctgct        540
ttacactggg tggcattgna ccatatgcat                                         570
```

<210> SEQ ID NO 93
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 93

```
tcgagcggcc gcccgggcag gtccaggttt ttatttagtt gtgtaatctt ggacaagtta         60
cctaactttt ttgagtctga atatatttaa tctgcaaaat gagaatcatg ataatacgtc        120
ataggcttaa ttaggaggat taaatgaaat aatttatagg tggtgccatg gttacataca       180
agtattagta gttaattctt ttcctttgtt tacttttata gtataggttg gatgaaggtt       240
ccagtatagg caaaaatact acttgggggt aaagtagagt gtgatacttt atttgaaatg       300
ttccctgaat ctgatcttta ctttttgnta ctgctgcact acccaaatcc aaattttcat       360
cccaacattc ttggatttgt gggacagcng tagcagcttt tccaatataa tctatactac       420
atcttttctt actttggtgc tttttg                                            446
```

<210> SEQ ID NO 94
<211> LENGTH: 409
<212> TYPE: DNA
<213> ORGANISM: Homo sapien

<400> SEQUENCE: 94

```
cgagcggccg cccgggcagg tccatcagct cttctgctta gaatacgagg cagacagtgg         60
agaggtcaca tcagttatcg tctatcaggg tgatgaccca agaaaggtga gtgagaaggt        120
gtcggcacac acgcctctgg atccacccat gcgagaagcc ctcaagttgc gtatccagga        180
ggagattgca aagcgccaga gccaacactg accatgttga aggcgttctc tccaggctgg       240
attcactgca ctcggaagaa ttctgcccag ggaatttagt gtgggggtac caggaccagt       300
ttgtcttgat cttgagaccc ccagagctgc tgcatccata gggtgttgca ggactacacc       360
tggcctgcct tgcagtcatt ctttcttata tgttgaccca tttgcccaa                  409
```

<210> SEQ ID NO 95
<211> LENGTH: 490
<212> TYPE: DNA
<213> ORGANISM: Homo sapien
<220> FEATURE:
<221> NAME/KEY: misc_feature
<222> LOCATION: (1)...(490)
<223> OTHER INFORMATION: n = A,T,C or G

<400> SEQUENCE: 95

```
tcgagcggcc gcccgggcag gtcctacttg tttgcagctt ccacacactg cacctaccta         60
ctacctctct tccatgctta actgggttta gaaaggtgag ctatgcgtag aagaactact        120
tgggatattc aagtgctgta tttgaacgat aagcctatag ataacagtct gaagctgcaa       180
gggagacttt gttagtacac tactataaac aggtaaaacta cctgtttgta cttgatatag      240
tgcatatgaa atgactgatt taatacaaaa ctacagaaca tgcaaaattt tttctgagat       300
```

| gttaagtatt acttcagtgg agaacaaaac ttacttaacc tttcgctaat gcatgtagta | 360 |
| ccagaaagca aacatggttt tagcttcctt tactcaaaat atgaacatta agtggttgtg | 420 |
| aattttgtct gccaagtggt tcagaaaata cattataaat aacctaagtt aaaaaaaaga | 480 |
| aactgngaac | 490 |

<210> SEQ ID NO 96
<211> LENGTH: 223
<212> TYPE: DNA
<213> ORGANISM: Homo sapien

<400> SEQUENCE: 96

| agcgtggtcg cggccgaggt ctggaagccc accctaggac ttgaatggca ccttgtcctt | 60 |
| tctctgccag taatgcaatc caacacaata tgctacaggg aaaacagaat ttccacggtg | 120 |
| ccgccctctg gtacaaggga acagcacgc aaagcaaaag gccacagagg gctccctgag | 180 |
| aatccagtac aactaagcga ggacctgccc gggcggccgc tcg | 223 |

<210> SEQ ID NO 97
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 97

| tcgagcggcc gcccgggcag gtctgtgcag gagacactga agtgggtagt gtccataatc | 60 |
| tttttagcct gttgctgaaa ttccagttgt actcctttcaa accaaaatgc ttacaggatc | 120 |
| atgggaaagc ctcggttgca gaaatcaaga caggcaagtg ggaagataac tcggctttga | 180 |
| ggttaaacag atctgggttc aaagcatagt ttcactctct gtcttgtgaa gtgtcctggg | 240 |
| tgaagtcatt tcctctcttg aatttcagag aggatgaaaa tataaaaagt ataataacta | 300 |
| tcttcataat ctttgtgagg attaaagaag acgaagtgtg tgaaaagcta agcacagagc | 360 |
| aggcattcta caataagtag ttattatttt tggaaccatc ccgncctag ccccagccca | 420 |
| attaccttct cttagnctct tcatatcgaa ngccgtaatc ttgaccttct cttgcnactg | 480 |
| gattggtgct ggttgatgcc caaacttccc gagatgctgt ctgggaa | 527 |

<210> SEQ ID NO 98
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 98

| tcgagcggcc gcccgggcag gtctggctcc catggcccctt ggggtggcct gactctgtca | 60 |
| ctattcctaa aaccttctag gacatctgct ccaggaagaa ctttcaacac caaaattcat | 120 |
| ctcaattta cagatgggaa aagtgattct gagaccagac cagggtcagg ccaaggtcat | 180 |
| ccagcatcag tggctgggct gagactgggc ccagggaacc ctgtctgctc ctcttttcc | 240 |
| cagagctgtg agttctctag ccaaggctgc actcttgagg gagagccagg aagcatagct | 300 |
| gaggccatga caacctcact cttcacctga aaatttaacc cgtggcagag gatccaggca | 360 |
| catataggct tcggagccaa acaggacctc ggccgcgacc acgctaagcc gaattccagc | 420 |

```
acactggcgg ccgttactag tggatcccga gcttnggtac caagcttggc gtaatcatgg    480
gcatagctgg ttcctggggt gaaaatggta tccg                                514
```

<210> SEQ ID NO 99
<211> LENGTH: 530
<212> TYPE: DNA
<213> ORGANISM: Homo sapien
<220> FEATURE:
<221> NAME/KEY: misc_feature
<222> LOCATION: (1)...(530)
<223> OTHER INFORMATION: n = A,T,C or G

<400> SEQUENCE: 99

```
tcgagcggcc gcccgggcag gtctgaagaa acaggtataa atttggcagc cagtaatttt     60
gacagggaag ttacagcttg catgacttta aatatgtaaa tttgaaaata ctgaatttcg    120
agtaatcatt gtgctttgtg ttgatctgaa aaatataaca ctggctgtcg aagaagcatg    180
ttcaaaaata tttaattcac ttcaaaatgt catacaaatt atggtggttt ctatgcaccc    240
ctaaagcttc aagtcattta gctcaggtac atactaaagt aatatattaa ttcttccagt    300
acagtggtgt ttcataccat tgacatttgc atacccctaga ataatttaag aaagacatgt    360
gtaatattca caatgttcag aaaagcaagc aaaaggtcaa ggaacctgct ttggttcttc    420
tggagatggn ctcatatcag cttcataaac attcattcta caaaatagta agctaaccat    480
ttgaacccca atttccagat taagcatatt ttctcataaa tnatgaagcc               530
```

<210> SEQ ID NO 100
<211> LENGTH: 529
<212> TYPE: DNA
<213> ORGANISM: Homo sapien

<400> SEQUENCE: 100

```
agcgtggtcg cggccgaggt ccaggcacgg tggcttatgt gtgtaatccc agcacttggg     60
gaggctgagg gaggtggatc acttgagtcc aggagtttga gaccagtctg ggcaacatgg    120
cgaaacttca tcactaccaa agaagaaaaa aattagccag gtgtggtggt gtatgcctgt    180
agtcccagat actctggtgg ctgaggtgag aggatagctt gagcccagga aattgaggct    240
gcagtgaact atgattgcac tactgtgctc cagcttgggc aacagagtga gatcttgtct    300
ccaaaagtcc ttgaaggatt ttaggaagtt gttaaaagtc ttgaaacgat gtttgggggc    360
atgttagggt tcttgaatgt ttaattcctc taataactgc ttattcaaga gaagcatttc    420
tgactgggtg cggggcagtg gcttcatgcc ccataatccc agtactttgg gaggctgaag    480
caggaacatt gcttgagccc aggacttcaa gaacagcctg ggtaacata                529
```

<210> SEQ ID NO 101
<211> LENGTH: 277
<212> TYPE: DNA
<213> ORGANISM: Homo sapien

<400> SEQUENCE: 101

```
tcgagcggcc gcccgggcag gtcgcaggaa gaggatggaa actgaggagt ccaggaagaa     60
gagggaacga gatcttgagc tggaaatggg agatgattat attttggatc ttcagaagta    120 ctgggatttta atgaatttgt ctgaaaaaca tgataagata ccagaaatct gggaaggcca    180
taatatagct gattatattg atccagccat catgaagaaa ttggaagaat tagaaaaaga    240
agaagagctg agaacagacc tcggccgcga ccacgct                              277
```

<210> SEQ ID NO 102
<211> LENGTH: 490
<212> TYPE: DNA
<213> ORGANISM: Homo sapien

<400> SEQUENCE: 102

| | | | | | |
|---|---|---|---|---|---|
| gcgtggtcgc | ggccgaggtc | tgacggcttt | gctgtcccag | agccgcctaa | acgcaagaaa | 60 |
| agtcgatggg | acagttagag | gggatgtgct | aaagcgtgaa | atcagttgtc | cttaattttt | 120 |
| agaaagattt | tggtaactag | gtgtctcagg | gctgggttgg | ggtccaaagt | gtaaggaccc | 180 |
| cctgcccttta | gtggagagct | ggagcttgga | gacattaccc | cttcatcaga | aggaattttc | 240 |
| ggatgttttc | ttgggaagct | gttttggtcc | ttggaagcag | tgagagctgg | gaagcttctt | 300 |
| ttggctctag | gtgagttgtc | atgtgggtaa | gttgaggtta | tcttgggata | aagggtcttc | 360 |
| tagggcacaa | aactcactct | aggtttatat | tgtatgtagc | ttatatttt | tactaaggtg | 420 |
| tcaccttata | agcatctata | aattgacttc | ttttctttag | ttgtatgacc | tgccccgggc | 480 |
| ggccgctcga | | | | | | 490 |

<210> SEQ ID NO 103
<211> LENGTH: 490
<212> TYPE: DNA
<213> ORGANISM: Homo sapien

<400> SEQUENCE: 103

| | | | | | |
|---|---|---|---|---|---|
| gagcggccgc | ccgggcaggt | ccaaaccagc | ttgctcataa | gtcattaacc | aaatccatta | 60 |
| taggtaattt | gttcagttca | atgtttacaa | ttcttatgga | aaaaattagc | aacacacaca | 120 |
| tttaaaacgt | gtgcatttac | ctttgcgtga | gtgcttaaaa | tacatatttc | tatttcaaga | 180 |
| tgacatttaa | aaattattct | aatatatcag | cagcaaaaat | ataatttgca | attacaaaaa | 240 |
| actaaactag | aatccttaag | ttattctcat | gtttacagtt | gtgattcttt | aataaatact | 300 |
| attatgcagc | tctattgttt | aagctttctg | gatttggttt | aaacacatgc | atatatattg | 360 |
| tcaattgtgg | gaagctttac | aagttatatt | ccatgcactt | tttggacaga | gttctaacag | 420 |
| agccagccag | tccacaaaac | aggcaagaca | aaagttgaat | taactggggc | aaaataggac | 480 |
| tcttatgcaa | | | | | | 490 |

<210> SEQ ID NO 104
<211> LENGTH: 489
<212> TYPE: DNA
<213> ORGANISM: Homo sapien

<400> SEQUENCE: 104

| | | | | | |
|---|---|---|---|---|---|
| cgtggtcgcg | gccgaggtcc | aggctggtct | cgaactcctg | accttgtgat | ctgcccgcct | 60 |
| cggcctccca | aagtgttggg | attacaggca | tgagccactg | cgcccgaccg | agttgaacat | 120 |
| ttaatgtcag | actaggccag | agtttctcaa | tctttttatt | ctcacttccc | aaaggagccg | 180 |
| ttggagattt | tcccctcaat | ctctctcctt | catgaaattt | cataccacaa | atatagtatg | 240 |
| ttttatttat | gtactgtgac | cctttgaagg | atcacaaacc | aatataatag | tttttctttt | 300 |
| taacccgtca | aggaccaagt | ttttgcccct | gttggaaatg | cataaactgg | actgatgaat | 360 |
| tggtatagat | ggcttttatc | atgaggatca | gaaaaacttg | aaattccttg | gctacgacac | 420 |
| tccatatttta | tcaccgtata | gggaggacct | tggtatgggg | aagtagaaac | acttctacac | 480 |
| tttacagca | | | | | | 489 |

<210> SEQ ID NO 105
<211> LENGTH: 479
<212> TYPE: DNA
<213> ORGANISM: Homo sapien
<220> FEATURE:
<221> NAME/KEY: misc_feature
<222> LOCATION: (1)...(479)
<223> OTHER INFORMATION: n = A,T,C or G

<400> SEQUENCE: 105

```
gcgtggtcgc ggccgaggtc tgactggctt cagccccaga agttgagctg gcctttagac      60
aaataattg cacctccctc tgctgcttat tcccttccgt ttttcatttg agtgtgaaca      120
gttagataaa atctgtggct gnctcttcca ccttgctcta gtttccattg ctgtgagcag     180
gccctcctat gccccgcatt tagctacaat gctgtggact cacttgattc ttttttctccg    240
agctttgtct agaaatatgt gaaggtgagg ttaagtgctt ctctgtgtag atccacttag     300
ccctgtctgc tgtctcgatg ggcgttgctt cgtctctcct ctcttccatc ctttccattt    360
gcttctcacc accttctggc ttctttctt aatgcaataa aggcagtttc taacaaagaa     420
agaatgtggg ctttggagtt agacagacct ggntttaaat tctgcttctg gctctccaa     479
```

<210> SEQ ID NO 106
<211> LENGTH: 511
<212> TYPE: DNA
<213> ORGANISM: Homo sapien

<400> SEQUENCE: 106

```
tcgcggccga ggtccaaaac gtggattcca atgacctgcc ttgagcccgc ggttgccagg      60
agttggacct gcagtagtat gggaagctca cggcctaaat accgactgcc ctctgacccc    120
accgtccagc gattctagaa catttctagt aggaaagaca tagcaaggga ttttcatgat    180
tgggaaatac tgggagacaa gctgaagatt tgttaaggc tatgcttctg tcatctttta    240
ggtatttaag gctactcctt tagctagcta ctttgagctg tttaaagtga ctatctccct    300
acacagagtt acacaatgag catctctgaa agagaatatt accctggatt tccaaagatg    360
tactctaaca ggatgaccag gcaaaaggtg acccggggga ggagtctgtt ataacactcg    420
gacccacatg ttctcaaggc acttcagaac tttgggaaat cattttgtac cggatcctca    480
gaaagcattt atggaaatac acatccttta g                                    511
```

<210> SEQ ID NO 107
<211> LENGTH: 451
<212> TYPE: DNA
<213> ORGANISM: Homo sapien

<400> SEQUENCE: 107

```
ggccgcccgg gcaggtccag aatatcaaat caaaaggtca caaatgttca cttcctcctc      60
caccctctta catattggat cttcaattgc aataggagt gtaagatggg cattttagag      120
acgtagttgc atcagcagaa gcaaaccat cttatacaaa tgggttttgg ggataggaaa      180
aggctgctaa aaattcacaa gtcaccattc cccagaagca atgaatagcc gtagaagacc    240
aaggaagatc aacaagtttc caagtgctaa agccagaga tttggccctt ccaaaatacc     300
accaggacgc ctgacccgt gggctctccg catgtcacca ctgactgcca ggatgctgct     360
gcacctccct tccttgagac acaacagaga gacagtgaag tcacccaaga ctgggatcat    420
cagaggctcc tcatgcttgc tacagagaag c                                   451
```

<210> SEQ ID NO 108

<211> LENGTH: 461
<212> TYPE: DNA
<213> ORGANISM: Homo sapien

<400> SEQUENCE: 108

| ccgcccgggc | aggtcctgaa | acattcaga | ctaatcaaaa | tggtactact | gtaacttctt | 60 |
| ataatacata | atataaaagt | ttttgaaaga | tatagacaca | attaacccct | aaacaacaca | 120 |
| ctatctgatt | ctcaaaagca | atggctattt | aacaagatgt | aaaaggacaa | taacatatca | 180 |
| aagaactttc | acacacctaa | agatagcatt | tagcagcaag | ttagtcagac | aaaacaaaca | 240 |
| caaatatttt | cacatttcct | atgtttgttt | ttaactttac | ttcataaagc | cactgataat | 300 |
| tgaggtttct | ttcaagtata | agatttctaa | aattaaaaac | tgttttttgac | atattttttat | 360 |
| aaagaaataa | aaagcaaaac | gcaatccaac | tatttatatg | agtccctctt | ctccaacagc | 420 |
| tttagatggt | tttctgagta | cttttttaca | cagaatattt | t | | 461 |

<210> SEQ ID NO 109
<211> LENGTH: 441
<212> TYPE: DNA
<213> ORGANISM: Homo sapien

<400> SEQUENCE: 109

| ggccgcccgg | gcaggtctga | ttataagaga | aagaaatcca | gtgacacgag | ggcaggcagg | 60 |
| ccccgctctg | ctctgatcga | gaaaagcttc | ctgatgtcag | ggagatggaa | ctgccaccat | 120 |
| cagaaccatg | gcactttggg | tgaaggtgtg | tcagcgacca | aggggggcagg | aaatgggcag | 180 |
| tgactaaggg | ggcaggaaac | aggcaggcac | atggcaaggt | tctcccagcc | catcagccca | 240 |
| gtgatggcct | cgattttgaa | gctgcactac | tgtctgaaaa | gcacaattac | tggtgactct | 300 |
| taacaaactt | cagcatactg | gggaaggaga | ctgtcaagta | actgaattgg | aaagatgaaa | 360 |
| aagaaccatc | tctaaaagtt | gatgcttgtc | agaagaataa | cctcctttgt | gcaagtcttg | 420 |
| caacatcttc | attcaaccac | a | | | | 441 |

<210> SEQ ID NO 110
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 110

| ggtcgcggcc | gaggtctggg | gaagggggtga | gaatccctgg | gccttgccca | gtcctgagct | 60 |
| ctgggtgtct | gcagggaagc | acagtggtga | gttagtgtta | aagaaagcat | ccagagaggt | 120 |
| aagagggggct | tgggtagcac | cctttgcctc | tgtcacttcc | gcaaaaactt | cttgttgagg | 180 |
| aggaagatga | gaaggttgac | attgactttg | gccttgttga | agagtttcat | gacagccaca | 240 |
| ccctcatact | ggagctgcan | gagatcctga | tagtgaagct | tgaaatcgct | ccatgtccac | 300 |
| acccaggaac | ttggcattta | cttcaaactt | tcctgcctca | tctcccggcg | tgatgtcaaa | 360 |
| natgacgttt | cttgaagtga | gaggcgggaa | agatcttcaa | tttccaccaa | agacacccctt | 420 |
| tttccaggaa | gcttgagcaa | caagtgtaat | g | | | 451 |

<210> SEQ ID NO 111
<211> LENGTH: 407
<212> TYPE: DNA
<213> ORGANISM: Homo sapien
<220> FEATURE:
<221> NAME/KEY: misc_feature
<222> LOCATION: (1)...(407)
<223> OTHER INFORMATION: n = A,T,C or G

<400> SEQUENCE: 111

| | | | | | |
|---|---|---|---|---|---|
| ggccgacgtt | cgacctgact | tctttngagc | agntgncact | acccgtcttg | aggaatgccg | 60 |
| actgcagaca | gtggcccang | gcaaagagtg | tgcgtcatcg | atganattgg | naagatggag | 120 |
| ctcttcagtc | agnttttcat | tcaagctgnt | cgtcagacgc | tgtctacccc | aggactata | 180 |
| atcctnggca | caatcccagt | tcctanagga | aagccactgn | ctcttgtaga | agaaatcana | 240 |
| cacanaaagg | atgtgaacng | tgtttaatgt | caccaaggga | aaacatgaaa | ccaccttctg | 300 |
| ccagatatcg | ggacgttgcg | tgcagatcaa | gcacgnaagt | gaagacgcgt | gcattccttg | 360 |
| ccttccgtga | acgantgccc | agntcaagaa | gancctgatg | gaaccct | | 407 |

<210> SEQ ID NO 112
<211> LENGTH: 401
<212> TYPE: DNA
<213> ORGANISM: Homo sapien
<220> FEATURE:
<221> NAME/KEY: misc_feature
<222> LOCATION: (1)...(401)
<223> OTHER INFORMATION: n = A,T,C or G

<400> SEQUENCE: 112

| | | | | | |
|---|---|---|---|---|---|
| tcgcggccga | ggtcggccga | ggtctgacat | ctgttgtctg | tgataaccac | ttctgtattg | 60 |
| cgtcttaacc | acttctgtat | tgtgtggttt | taactgccta | aggcggcaat | gggcagtggg | 120 |
| cccctttccc | ttaggatggg | tatcaattca | acaatattta | taaggcattt | actgtgtgct | 180 |
| aagcatttgg | aagacccagg | ctacaaaata | agacatagtt | cctgccctcc | aggccagcag | 240 |
| agggaggcac | aaatacccag | gaatctctga | tgggtgtgaa | gtgcggtcgt | gggccacaga | 300 |
| aaatgaccgt | catggagacc | tgctaaaggt | cggaccctg | agcccaaagg | ggtattcaga | 360 |
| agnggagatg | attttggccc | cactcataga | tgggtggcaa | a | | 401 |

<210> SEQ ID NO 113
<211> LENGTH: 451
<212> TYPE: DNA
<213> ORGANISM: Homo sapien

<400> SEQUENCE: 113

| | | | | | |
|---|---|---|---|---|---|
| gtcgcggccg | aggtccatat | taaaaagtcc | atcataaaca | aagactcctc | ctcatggtat | 60 |
| gaatatgctc | catatgccca | taatggtgca | taacggactt | agaaattcca | atgagtctta | 120 |
| gggttgaaat | ttccaatgac | ctgagcaagg | cagctcccta | tagcttctgg | ataacatttt | 180 |
| acacccagag | ttcaggctta | aacagaccta | tcaacacaat | tattttcgga | ttgtctgtct | 240 |
| agaaaacggc | aatgctcaaa | ggaatataaa | taagggtggg | gggacatatg | cttccagcct | 300 |
| ggcctttctc | catgtggtaa | aaaacaatgg | aatggctgtg | ttaatttttt | tttaatcttt | 360 |
| tctgaccttt | actatgtttg | gtaatggaaa | taagtcaggg | aaaacaaaat | gaacaggtct | 420 |
| catcacttaa | ttaatactgg | gttttcttct | t | | | 451 |

<210> SEQ ID NO 114
<211> LENGTH: 441
<212> TYPE: DNA
<213> ORGANISM: Homo sapien

<400> SEQUENCE: 114

```
ggccgcccgg gcaggtccat cctgtcagag atgggagaag tcacagacgg aatgatggat      60
acaaagatgg ttcactttct tacacactat gctgacaaga ttgaatctgt tcattttttca   120 gaccagttct ctggtccaaa aattatgcaa gaggaaggtc agcctttaaa gctacctgac   180
actaagagga cactgttgtt tacatttaat gtgcctggct caggtaacac ttacccaaag   240
gatatggagg cactgctacc cctgatgaac atggtgattt attctattga taaagccaaa   300
aagttccgac tcaacagaga aggcaaacaa aaagcagata agaaccgtgc ccgagtagaa   360
gagaacttct tgaaacttga cacatgtgca aagacaggaa gcagcacagt ctcggcggga   420
ggaagaaaaa aagaacagag a                                              441

<210> SEQ ID NO 115
<211> LENGTH: 431
<212> TYPE: DNA
<213> ORGANISM: Homo sapien
<220> FEATURE:
<221> NAME/KEY: misc_feature
<222> LOCATION: (1)...(431)
<223> OTHER INFORMATION: n = A,T,C or G

<400> SEQUENCE: 115
gccgcccggg caggtccatt ggcggtgaca aaaggaaaag aagcaaagag actcagtcca      60
taatgctgat tagttagaag aaagggctag gattgagaaa gtaccaggaa cttttaatta   120
tttaaaagag aatgctgact gttaatgttt taaatcttac tgttcaaatg tactaatatg   180
aatttttacc ctttgtgcat gaatattcta acaactaga agacctccac aatttagcag   240
ttatgaaagt taaacttttt attataaaaa ttctaaacct tactgctcct ttaccaggaa   300
catgacacac tatttancat cagttgcata cctcgccaat agtataattc aactgtcttg   360
cccgaacaat catctccatc tggaagacgt aagcctttag aaacacattt ttctattaat   420
ttctctagaa c                                                         431

<210> SEQ ID NO 116
<211> LENGTH: 421
<212> TYPE: DNA
<213> ORGANISM: Homo sapien

<400> SEQUENCE: 116
gtcgcggccg aggtccagaa atgaagaaga agtttgcaga tgtatttgca agaagacga       60 aggcagagtg tgtcaaatc tttgacggca cagatgcctg tgtgactccg gttctgactt    120
ttgaggaggt tgttcatcat gatcacaaca aggaaccggg gctcgtttat caccagtgag   180
gagcaggacg tgagcccccg ccctgcacct ctgctgttaa acaccccagc catcccttct   240
ttcaaaaggg atcctttcat aggagaacac actgaggaga tacttgaaga atttggattc   300
agcccgcgaa gagatttatc aagcttaact cagataaaat cattgaaagt aataaggtaa   360
aagctaagtc tctaacttcc aggcccacgg ctcaagtgaa tttcgaatac tgcatttaca   420
g                                                                    421

<210> SEQ ID NO 117
<211> LENGTH: 489
<212> TYPE: DNA
<213> ORGANISM: Homo sapien

<400> SEQUENCE: 117
agcgtggtcg cggccgaggt aaggctgcga ggttgtggtg tctgggaaac tccgaggaca      60
gagggctaaa tccatgaagt ttgtggatgg cctgatgatc cacagcggag accctgttaa   120
```

```
ctactacgtt gacactgctg tgcgccacgt gttgctcaga cagggtgtgc tgggcatcaa    180
ggtgaagatc atgctgccct gggacccaac tggtaagatt ggccctaaga agcccctgcc    240
tgaccacgtg agcattgtgg aacccaaaga tgagatactg cccaccaccc ccatctcaga    300
acagaagggt gggaagccag agccgcctgc catgccccag ccagtcccca cagcataaca    360
gggtctcctt ggcagacctg cccgggcggc cgctcgaaag cccgaattcc agcacactgg    420
cggccgttac tagtggatcc cagctcggta ccaagcttgg cgtaatcatg gtcatagctg    480
gtttcctgt                                                           489

<210> SEQ ID NO 118
<211> LENGTH: 489
<212> TYPE: DNA
<213> ORGANISM: Homo sapien

<400> SEQUENCE: 118
tcgagcggcc gcccgggcag gtattgaata cagcaaaatt ctatatacaa agtgacctgg     60
acctgctgct tcaaaacatg atcctttctt actaatatct tgatagtcgg tccatagagc    120
attagaaagc aattgactct taaataaaca gaaaagtgcc taatgcacat taaatgaatg    180
gcctaactac tggaaccttta gtagttctat aaggtgatta acataggtag gatccagttc    240
ctatgacagg ctgctgaaga acagatatga gcatcaagag gccattttgt gcactgccac    300
cgtgatgcca tcgtgtttct ggatcataat gttcccatta tctgattcta gacacaccac    360
aggaatatca gtggggtcag aggttagctt agctgcttgc tgggctagaa cagatatcac    420
tccagcatgc tcatctgaca gggtcccgcg gcaacccaga ttaagtcctt gtgaatctgt    480
gcacaggga                                                           489

<210> SEQ ID NO 119
<211> LENGTH: 181
<212> TYPE: DNA
<213> ORGANISM: Homo sapien

<400> SEQUENCE: 119
taggttccag agactttlgg cccaggagga atatttactt ttagctctgg acatcattac     60
aaaaaggaat atttcccaaa cctcttcaga ccgagaatac atgggtaaaa ttattaaata    120
gttgtataat aaaaataatt ttttccttaa aaaaaaaaa aacctcggcc gcgaccacgc    180
t                                                                   181

<210> SEQ ID NO 120
<211> LENGTH: 489
<212> TYPE: DNA
<213> ORGANISM: Homo sapien
<220> FEATURE:
<221> NAME/KEY: misc_feature
<222> LOCATION: (1)...(489)
<223> OTHER INFORMATION: n = A,T,C or G

<400> SEQUENCE: 120
gcgtggtcgc ggccgaggtc catttaaaac aaagaaaaat actaaagcca ctagtaaaca     60
tctgatgtgc aaaatacaac atcctctagt tggctttatg ccattattac ataagctcca    120
aatagctcat cttaaattaa aaagaaaaag tggctgtccc atctctgctg cataaatcag    180
attttttttt aaaggtttag agtactttaa ggaagggaag ttcaaaactg ccagtgaaat    240
tcacagagaa tacaaattta gcaatttaat ttcccaaagc tctttgaaga agcaagagag    300
```

-continued

| | |
|---|---|
| tctctcttct taatgcagtg ttctcccaag aggaactgta attttgcttg gtacttatgc | 360 |
| tgggagatat gcaaaatgtg tttttcaatg tttgctagaa tataatggtt cctcttcagt | 420 |
| gnctggttca tcctggaact catgggttaa gaaggacttc ttggagccga actgcccggg | 480 |
| cgggccntt | 489 |

<210> SEQ ID NO 121
<211> LENGTH: 531
<212> TYPE: DNA
<213> ORGANISM: Homo sapien

<400> SEQUENCE: 121

| | |
|---|---|
| cgagcggccg cccgggcagg tggccagcgc tggtcccgca gacgccgaga tggaggaaat | 60 |
| atttgatgat gcgtcacctg gaaagcaaaa ggaaatccaa gaaccagatc ctacctatga | 120 |
| agaaaaaatg caaactgacc gggcaaatag attcgagtat ttattaaagc agacagaact | 180 |
| ttttgcacat tcattcaac ctgctgctca gaagactcca acttcacctt tgaagatgaa | 240 |
| accagggcgc ccacgaataa aaaaagatga gaagcagaac ttactatccg ttggcgatta | 300 |
| ccgacaccgt agaacagagc aagaggagga tgaagagcta ttaacagaaa gctccaaagc | 360 |
| aaccaatgtt tgcactcgat ttgaagactc tccatcgtat gtaaaatggg gtaaactgag | 420 |
| agattatcag gtcccgagga ttaaactggc tcatttcttt gtatgagaat ggcatcaatg | 480 |
| gtatccttgc agatgaaatg ggcctaggaa agactcttca acaatttctc t | 531 |

<210> SEQ ID NO 122
<211> LENGTH: 174
<212> TYPE: DNA
<213> ORGANISM: Homo sapien

<400> SEQUENCE: 122

| | |
|---|---|
| tcgagcggcc gcccgggcag gtctgccaac agcagaggcg gggcctccgg catcttcaaa | 60 |
| gcacctctga gcaggctcca gccctctggc tgcgggaggg gtctgggggtc tcctctgagc | 120 |
| tcggcagcaa agcagatgtt atttctctcc cgcgacctcg gccgcgacca cgct | 174 |

<210> SEQ ID NO 123
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 123

| | |
|---|---|
| agcgtggtcg cggccgaggt cctcaaccaa gagggttgat ggcctccagt caagaaactg | 60 |
| tggctcatgc cagcagagct ctctcctcgt ccagcaggcg ccatgcaagg gcaggctaaa | 120 |
| agacctccag tgcatcaaca tccatctagc anagagaaaa ggggcactga agcagctatg | 180 |
| tctgccaggg gctaggggct cccttgcaga cagcaatgct acaataaagg acacagaaat | 240 |
| gggggaggtg ggggaagccc tattttttata acaaagtcaa acagatctgt gccgttcatt | 300 |
| cccccagaca cacaagtaga aaaaaaccaa tgcttgtggt ttctgccaag atggaatatt | 360 |
| cctccttcct aanttccaca catggccgtt tgcaatgctc acagcattg cactgggctg | 420 |
| cttgtctctg tggtctgggc accagtagct tgggccccat atacacttct cagttcccac | 480 |
| anggcttatg gccnangggc angctccaat tttcaagcac cacgaaggaa g | 531 |

<210> SEQ ID NO 124
<211> LENGTH: 416
<212> TYPE: DNA
<213> ORGANISM: Homo sapien

<400> SEQUENCE: 124

```
tcgagcggcc gcccgggcag gtccatctat actttctaga gcagtaaatc tcataaattc      60
acttaccaag cccaggaata atgactttta aagccttgaa tatcaactaa gacaaattat     120
gccaattctg atttctcaca tatacttaga ttacacaaag ataaagcttt agatgtgatc     180
attgtttaat gtagacttat ctttaaagtt tttaattaaa aactacagaa gggagtaaac     240
agcaagccaa atgatttaac caaatgattt aagagtaaaa ctcactcaga aagcattata     300
cgtaactaaa tatacatgag catgattata tacatacatg aaactgcaat tttatggcat     360
tctaagtaac tcatttaagt acatttttgg catttaaaca aagatcaaat caagct        416
```

<210> SEQ ID NO 125
<211> LENGTH: 199
<212> TYPE: DNA
<213> ORGANISM: Homo sapien
<220> FEATURE:
<221> NAME/KEY: misc_feature
<222> LOCATION: (1)...(199)
<223> OTHER INFORMATION: n = A,T,C or G

<400> SEQUENCE: 125

```
agcgtggtcg cggccgaggt gcttttttttt tttttttttt tttttttttt gctattctaa      60
aggggaaggc ccctttttat taaacttgta cattttactt tccttctttc anaatgctaa     120
taaaaaactt ttgtttatac ttaaaaaaac cataaatcan acaaacaaaa gaaacgattc     180
caacatcact tctgngatg                                                   199
```

<210> SEQ ID NO 126
<211> LENGTH: 490
<212> TYPE: DNA
<213> ORGANISM: Homo sapien

<400> SEQUENCE: 126

```
cgtggtcgcg gccgaggtcc agttgctcta agtggattgg atatggttgg agtggcacag      60
actggatctg ggaaaacatt gtcttatttg cttcctgcca ttgtccacat caatcatcag     120
ccattcctag agagaggcga tgggcctatt tgtttggtgc tggcaccaac tcgggaactg     180
gcccaacagg tgcagcaagt agctgctgaa tattgtagag catgtcgctt gaagtctact     240
tgtatctacg gtggtgctcc taagggacca caaatacgtg atttggagag aggtgtggaa     300
atctgtattg caacacctgg aagactgatt gacttttag agtgtggaaa aaccaatctg     360
agaagaacaa cctaccttgt ccttgatgaa gcagatagaa tgcttgatat gggctttgaa     420
ccccaaataa ggaagattgt ggatcaaata agacctgata ggcaaactct aatgtggagt     480
gcgacttggc                                                            490
```

<210> SEQ ID NO 127
<211> LENGTH: 490
<212> TYPE: DNA
<213> ORGANISM: Homo sapien

<400> SEQUENCE: 127

```
cgtggtcgcg gccgaggtcg gccgaggtct ggagatctga gaacgggcag actgcctcct      60
caagtgggtc cctgacccct gaccccgag cagcctaact gggaggcacc cccagcagg      120
```

| | |
|---|---|
| ggcacactga cacctcacac ggcagggtat tccaacagac ctgaagctga gggtcctgtc | 180 |
| tgttagaagg aaaactaaca agcagaaagg acagccacat caaaaaccca tctgtacatc | 240 |
| accatcatca aagaccaaaa gtaaataaaa ccacaaagat gggaaaaaaa cagaacagaa | 300 |
| aaactggaaa ctctaaaaag cagagcacct ctcctcttcc aaaggaacgc agttcctcac | 360 |
| cagcaatgga acaaagctgg atggagaatg actttgacga gctgagaaaa gaacgcttca | 420 |
| gacgatcaaa ttactctgag ctacgggagg acattcaaac caaaggcaaa gaagttgaaa | 480 |
| actttgaaaa | 490 |

<210> SEQ ID NO 128
<211> LENGTH: 469
<212> TYPE: DNA
<213> ORGANISM: Homo sapien
<220> FEATURE:
<221> NAME/KEY: misc_feature
<222> LOCATION: (1)...(469)
<223> OTHER INFORMATION: n = A,T,C or G

<400> SEQUENCE: 128

| | |
|---|---|
| cgtggtcgcg gccgaggtgc tttttttttt tttttttttt tttttttttt tgctgattta | 60 |
| ttttttctnt ttattgttac atacaatgta taaacacata aaacanaaaa cagtagggat | 120 |
| cctctaggat ctctagggan acagtaaagt anaagaggt ctcanaaaca tttttttaaa | 180 |
| gtacaagaca ttcagngctc ggcccaaagg cgtaaaaggt ttanagccag canatagctg | 240 |
| nactaaaggc tccgtctntn tccccanagc caggacaacc ccaggagct ntccattagc | 300 |
| agccagtcca cgcaggcagg atgctgcgga aaaagctcta tgctganaac attcccttg | 360 |
| atggaaagaa gggcaacaca aaagggtaa ctaanagctc cttcctctcg tgagggcgac | 420 |
| aactgaggaa cagaaaagga gtgtcccatg tcacttttga ccccctccc | 469 |

<210> SEQ ID NO 129
<211> LENGTH: 419
<212> TYPE: DNA
<213> ORGANISM: Homo sapien

<400> SEQUENCE: 129

| | |
|---|---|
| gcgtggtcgc ggccgaggtc tgattttcat ttaaatattt cagagctata gcatttgcct | 60 |
| ccatgctcaa atccacacca ttggggctta agccgctcat gccaacatta gcaaatgaca | 120 |
| tgcagtttaa tccagagatc actgcttctg ggctgatgca tgccaacaca ctggcgtgat | 180 |
| ccacgttatg tgcattttc ttcactttag tgggagaatc aattttact ccaaggcttc | 240 |
| ttagttgctt aagagttgca ttaaggacac aatctttgtc caccagtctt gaatgatgtg | 300 |
| tttttttctt tgtatggtaa acgttttggg ttctggtgca ttcatgactg ataattactg | 360 |
| ctttggtaga cggctgctca agtttccttg gaggaactat ttaataggtg ggttacttg | 419 |

<210> SEQ ID NO 130
<211> LENGTH: 354
<212> TYPE: DNA
<213> ORGANISM: Homo sapien

<400> SEQUENCE: 130

| | |
|---|---|
| agcgtggtcg cggccgaggt ccatctgagg agataaccac atcactaaca aagtgggagt | 60 |
| gaccccgcag agcacgctgt ggaattccat agttggtctc atccctggtc agtttccaca | 120 |
| tgatgatggt cttatctcga gaggcggaga ggatcatgtc cggaactgc ggggtagtag | 180 |
| cgatctgggt tacccagccg ttgtggccct tgagggtgcc acgaagggtc atctgctcag | 240 |

```
tcatggcggc ggcgagagcg tgtgtcgctg cagcgacgag gatggcactg gatggcttag    300
agaaactagc accacaacct ctcctgccgc acctgcccgg gcggcccgct cgaa          354
```

<210> SEQ ID NO 131
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 131

```
cgagcggccg cccgggcagg tctggcagca gcttcctctg gaataattga cagctttgtg     60
ctgcctgact aaaatttgaa atgacaaccg ctgaatgtaa aatgatgtac ctacaatgag    120
agagatttag gaatactatc tgtcaatcca tagatgtaga aacaaaacaa actacagaat    180 gaaacaaac ttattttaaa ccaaagaaac aaatgtatcc aaaatatagt ccatgatata    240
tttgattact agtataacca cagttgaaaa cttaaaaaaa aaaattgaca tttttttgtaa   300 tgggtactaa tggatttata aaaggtttct gtttccaaag atgttattgg ggtccacata   360
ttccttgaag acttcagcat cccaaagccc gacatcagag atactttcct ttagccattg    420
nttcccgtaa cttgcccact ccatggtgat gtgacaggct tcccttcatt agca          474
```

<210> SEQ ID NO 132
<211> LENGTH: 474
<212> TYPE: DNA
<213> ORGANISM: Homo sapien
<220> FEATURE:
<221> NAME/KEY: misc_feature
<222> LOCATION: (1)...(474)
<223> OTHER INFORMATION: n = A,T,C or G

<400> SEQUENCE: 132

```
ggccgaggtg gggaattcat gtggaggtca gagtggaagc aggtgtgaga gggtccagca     60
gaaggaaaca tggctgccaa agtgtttgag tccattggca agtttggcct ggccttagct    120
gttgcaggag gcgtggtgaa ctctgcctta tataatgtgg atgctgggca cagagctgtc    180
atctttgacc gattccgtgg agtgcaggac attgtggtag gggaagggac tcattttctc    240
atcccgtggg tacagaaacc aattatcttt gactgccgtt ctcgaccacg taatgtgcca    300
gtcatcactg gtagcaaaga tttacagaat gtcaacatca cactgcgcat cctcttccgg    360
cctgtcgcca gccagcttcc tcgcatcttc accagcatcg ganaggacta tgatgaaccg    420
tgtgctgcca tccatcacaa ctgagatcct caagtcagtg gtggctcgct ttga          474
```

<210> SEQ ID NO 133
<211> LENGTH: 387
<212> TYPE: DNA
<213> ORGANISM: Homo sapien

<400> SEQUENCE: 133

```
tgctcgagcg gccgccagtg tgatggatat ctgcagaatt cggcttagcg tggtcgcggc     60
cgaggtctgc gggccccta gcctgccctg cttccaagcg acggccatcc cagtagggga   120 cttttcccaca ctgtgccttt acgatcagcg tgacagagta aagctggag tgcctcacca    180 cacggcccgg aaacagcggg aagtaactgg aaagagcttt aggacagctt agatgccgag    240
tgggcgaatg ccagaccaat gataccccaga gctacctgcc gccaacttgt tgagatgtgt    300
```

```
gtttgactgt gagagagtgt gtgtttgtgt gtgtgttttg ccatgaactg tggccccagt      360
gtatagtgtt tcagtggggg agaactg                                          387

<210> SEQ ID NO 134
<211> LENGTH: 401
<212> TYPE: DNA
<213> ORGANISM: Homo sapien

<400> SEQUENCE: 134
ggccgcccgg gcaggtctga tgaagaacac gggtgtgatc cttgccaatg acgccaatgc       60
tgagcggctc aagagtgttg tgggcaactt gcatcggctg ggagtcacca acaccattat      120
cagccactat gatgggcgcc agttccccaa ggtggtgggg ggcttttgacc gagtactgct     180 ggatgctccc tgcagtggca ctggggtcat ctccaaggat ccagccgtga agactaacaa      240
ggatgagaag gacatcctgc gcttgtgctc acctccagaa ggaagttgct cctgagtgct      300
attgactctt gtcaatgcga ccttcaagac aggaggctac ctggtttact gcacctgttc      360
tatcacagtg agacctctgc catggcagaa caggggaagc t                          401

<210> SEQ ID NO 135
<211> LENGTH: 451
<212> TYPE: DNA
<213> ORGANISM: Homo sapien

<400> SEQUENCE: 135
ggtcgcggcc gaggtctgtt cctgagaaca gcctgcattg gaatctacag agaggacaac       60
taatgtgagt gaggaagtga ctgtatgtgg actgtggaga agtaagtca cgtgggccct      120 tgaggacctg gactgggtta ggaacagttg tactttcaga ggtgaggtgt cgagaaggga      180
aagtgaatgt ggtctggagt gtgtccttgg ccttggctcc acagggtgtg ctttcctctg      240
gggccgtcag ggagctcatc ccttgtgttc tgccagggtg gggtaccggg gtttgacact      300
gaggagggta acctgctggc tggagcggca aacagtggc cttgatttgt cttttggaag       360 atttttaaaaa ccaaaaagca taaacattct ggtccttcac aatgctttct ctgaagaaat     420
acttaacgga aggacttctc cattcaccat t                                     451

<210> SEQ ID NO 136
<211> LENGTH: 411
<212> TYPE: DNA
<213> ORGANISM: Homo sapien

<400> SEQUENCE: 136
ggccgcccgg gcaggtctga atcacgtaga atttgaagat caagatgatg aagccagagt       60
tcagtatgag ggttttcgac ctgggatgta tgtccgcgtt gagattgaaa atgttccctg      120
tgaatttgtg cagaactttg acccccttta ccccattatc ctgggtggct gggcaacag      180 tgagggaaat gttggacatg tgcaggtggg tcccttttgct gcgtatttgg tgcctgaggc     240
tctgtggatt tcccctccat caatcatctt accctctcat cccccctcaga tgcgtctgaa     300 gaaacatctc tggtataaga aaatcctcaa gtcccaagat ccaatcatat tttctgtagg      360
gtggaggaag tttcagacca tcctgctcta ttatatccga agaccacaat g               411

<210> SEQ ID NO 137
<211> LENGTH: 211
<212> TYPE: DNA
<213> ORGANISM: Homo sapien
<220> FEATURE:
<221> NAME/KEY: misc_feature
```

```
<222> LOCATION: (1)...(211)
<223> OTHER INFORMATION: n = A,T,C or G

<400> SEQUENCE: 137
cggccgcccg ggcaggtcgg ttggtgcggc ctccattgtt cgtgttttaa ggcgccatga    60
ggggtgacag aggccgtggt cgtggtgggc gctttggttc cagaggaggc ccaggaggag   120
ggttcaggcc ctttgcacca catatcccat ttgacttcta tttgtgtgaa atggcctttc   180
cccggntcaa gccagcacct cgatgaaact t                                  211

<210> SEQ ID NO 138
<211> LENGTH: 471
<212> TYPE: DNA
<213> ORGANISM: Homo sapien

<400> SEQUENCE: 138
gccgcccggg caggtctggg ctggcgactg gcatccaggc cgtaactgca aatctatgct    60 aggcgggtc tcccttctgt gtgttcaagt gttctcgact tggattctta actattttaa   120
aaaatgcact gagtttgggt taaaaaccaa ccaccaaaat ggatttcaac acagctctaa   180
agccaagggc gtggccggct ctcccaacac agcgactcct ggaggccagg tgcccatggg   240
cctacatccc ctctcagcac tgaacagtga gttgattttt cttttttacaa taaaaaaagc   300 tgagtaatat tgcataggag taccaagaaa ctgcctcatt ggaaacaaaa actatttaca   360
ttaaataaaa agcctggccg caggctgcgt ctgccacatt tacagcacgg tgcgatgcac   420
acggtgacca aaccacggag gcaagcttct ggcactcaca ccacgacccg c            471

<210> SEQ ID NO 139
<211> LENGTH: 481
<212> TYPE: DNA
<213> ORGANISM: Homo sapien
<220> FEATURE:
<221> NAME/KEY: misc_feature
<222> LOCATION: (1)...(481)
<223> OTHER INFORMATION: n = A,T,C or G

<400> SEQUENCE: 139
gtcgcggccg aggtctgttc tttagctcag atttaaacct gctgtctctt ctttatttgc    60
agaatgaatt cccagttcct gagcagttca agacccatg gaacgggcag aagttggtca   120
ccacagtgac agaaattgct ggataagcga agtgccactg ggttctttgc cctcccttca   180
caccatggga taaatctgta tcaagacggt tcttttctag atttcctcta cctttttgct   240
cttaaaactg cttctctgct ctgagaagca cagctacctg ccttcactga aatatacctc   300
aggctgaaat ttggggtggg atagcaggtc agttgatctt ctgcaggaag gtgcagcttt   360
tccatatcag ctcaaccacg ccgncagtcc attcttaagg aactgccgac taggactgat   420
gatgcatttt agcttttgag cttttgggggg gtattctacc aaccaacagt ccatttggaa   480
a                                                                  481

<210> SEQ ID NO 140
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 140
```

```
gtcgcggccg aggtttccca tttaagaaaa atagatcttg agattctgat tcttttccaa      60
acagtcccct gctttcatgt acagcttttt ctttaccttg cccaaaattc tggccttgaa     120
gcagttttcc tctatggctt tgcctttctg attttctcag aggctcgagt ctttaatata     180
accccaaatg aaagaaccaa ggggaggggt gggatggcac ttttttttgt tggtcttgtt     240
ttgttttgtt ttttggttgg ttgggttccg ttatttttta agattagcca ttctctgctg     300
ctatttccct acataatgtc aattttaac  cataatttg  acatgattga gatgtacttg     360 aggcttttt  gntttaattg agaaaagact ttgcaatttt tttttagga  tgagcctctc     420 c                                                                     421

<210> SEQ ID NO 141
<211> LENGTH: 242
<212> TYPE: DNA
<213> ORGANISM: Homo sapien
<220> FEATURE:
<221> NAME/KEY: misc_feature
<222> LOCATION: (1)...(242)
<223> OTHER INFORMATION: n = A,T,C or G

<400> SEQUENCE: 141
cgantngccc gcccgggcan gtctgtctaa ntttntcang gaccacgaac agaaactcgt      60
gcttcaccga anaacaatat cttaaacatc gaanaattta atattatga  aaaaaaacat    120 tgcaaaatat aaataaaata nnaaaaggaa aggaaacttt gaaccttatg taccgagcaa     180
atccaggtct agcaaacagt gctagtccta nattacttga tntacaacaa cacatgaata    240
ca                                                                     242

<210> SEQ ID NO 142
<211> LENGTH: 551
<212> TYPE: DNA
<213> ORGANISM: Homo sapien
<220> FEATURE:
<221> NAME/KEY: misc_feature
<222> LOCATION: (1)...(551)
<223> OTHER INFORMATION: n = A,T,C or G

<400> SEQUENCE: 142
agcgtggtcg cggcncgang tccacagggc anatattctt ttagtgtctg gaattaaaat      60
gtttgaggtt tangtttgcc attgtctttc caaaaggcca ataattcan  atgtaaccac    120 accaagtgca aacctgtgct ttctatttca cgtactgttg tccatacagt tctaaataca     180
tgtgcagggg attgtagcta atgcattaca cagtcgttca gtcttctctg cagacacact    240
aagtgatcat accaacgtgt tatacactca actagaanat aataagcttt aatctgaggg    300
caagtacagt cctgacaaaa gggcaagttt gcataataga tcttcgatca attctctctc    360
caaggggccc gcaactaggc tattattcat aaaacacaac tgaanagggg attggtttta    420
ctggtaaatc atgtgntgct aaatcatttt ctgaacagtg gggtctaaat cantcattga    480
tttagtggca gccacctgcc cggcggccgn tcgaagccca attctgcaga tatccatcac    540
actggcggcc g                                                           551

<210> SEQ ID NO 143
<211> LENGTH: 515
<212> TYPE: DNA
<213> ORGANISM: Homo sapien
<220> FEATURE:
<221> NAME/KEY: misc_feature
<222> LOCATION: (1)...(515)
<223> OTHER INFORMATION: n = A,T,C or G
```

<400> SEQUENCE: 143

| | | |
|---|---|---|
| cgagnggccc gcccgggcag gtatcttcac aaactcaaca aaggcactac atgagacttc | 60 |
| acattcccct agtccaatag ctgacaaatt tttgcaacgt tctgcaatgc gaattaactc | 120 |
| ttcatcaagt ggccgtaatc catttgcaca cactactagt tcaaccagtc tagggcatgt | 180 |
| cattcccaca cggccaagca catctttgct tactgatctc ccaaagtaca gatgggtggc | 240 |
| aggtatttca tagcgaaaga aggggtcaaa ttcttcttca tataanaaaa aatacatcac | 300 |
| taagttcact ttgggtgaat gtctgatgaa agcatcccag ctactcttct gaatagtatg | 360 |
| gaagtgtgtc tgtccaggat tctcactgac tacatcaatg cgcaaatgtt ctaatcgaac | 420 |
| atgtttttca gaagacaatg caagtaacaa ctcatcactc aataagtggt aagttcaggg | 480 |
| ctagttctct taagccgnga cactgatcag cacac | 515 |

<210> SEQ ID NO 144
<211> LENGTH: 247
<212> TYPE: DNA
<213> ORGANISM: Homo sapien
<220> FEATURE:
<221> NAME/KEY: misc_feature
<222> LOCATION: (1)...(247)
<223> OTHER INFORMATION: n = A,T,C or G

<400> SEQUENCE: 144

| | | |
|---|---|---|
| tgcattctct ntggatgcan acctgcccgt tggtagggac tntgctcaca cggaacatgg | 60 |
| acggttacac ctgtgccgtg ggtgacgtcc accagcttct ggatcatctc ggcgngggtg | 120 |
| ttgtggaagg gcagactatc cacctccatg cncacgatgc ccganacgcc actccggact | 180 |
| ntgtgctgca ccaanatgcc cagcattnta tcttcaagca nagcacttat cagggtcctt | 240 |
| ggcacac | 247 |

<210> SEQ ID NO 145
<211> LENGTH: 309
<212> TYPE: DNA
<213> ORGANISM: Homo sapien
<220> FEATURE:
<221> NAME/KEY: misc_feature
<222> LOCATION: (1)...(309)
<223> OTHER INFORMATION: n = A,T,C or G

<400> SEQUENCE: 145

| | | |
|---|---|---|
| cgtgggtcgc ggcccgangt ctgctgtaac aaaacaccat agtctgggca gctcatagac | 60 |
| aatggaattt tatttctcac gcttctggag gctggattcc aagatcaagg ttccaggaga | 120 |
| ctcagtgtct ggcaaggtct cggtttctgc ctcanagatg gtgccatctg gctgtgtcct | 180 |
| cacaagtagg aaggtgcaag aagctcccct caggctctgt ctgtaagaca ctgatcccat | 240 |
| tcatganggg gaaacgtaat gacctaatca gcccccagag accccacttc taacaccatc | 300 |
| accttgggg | 309 |

<210> SEQ ID NO 146
<211> LENGTH: 486
<212> TYPE: DNA
<213> ORGANISM: Homo sapien
<220> FEATURE:
<221> NAME/KEY: misc_feature
<222> LOCATION: (1)...(486)
<223> OTHER INFORMATION: n = A,T,C or G

<400> SEQUENCE: 146

| | |
|---|---|
| agcgtgggtc gcggcncgac gtcctgtcca tatttcacag cccgagaact aatacaagat | 60 |
| gctgacatca tattttgtcc ctacaactat cttctanatg cacaaataag ggaaagtatg | 120 |
| gatttaaatc tgaaagaaca ggttgtcatt ttanatgaag ctcataacat cgaggactgt | 180 |
| gctcgggaat cagcaagtta cagtgtaaca gaagttcagc ttcggtttgc tcgggatgaa | 240 |
| ctanatagta tggtcaacaa taatataagg aaganagatc atgaacccct acgagctgtg | 300 |
| tgctgtagcc tcattaattg gntagaagca aacgctgaat atcttgnana angagantat | 360 |
| gaatcagctt gtaaaatatg gagtggaaat gaaatgctct taactttaca caaaatgggt | 420 |
| atcaccactg ctacttttcc cattttgcng gtaagatatn ttttctacct gngaaacgta | 480 |
| tttaag | 486 |

<210> SEQ ID NO 147
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 147

| | |
|---|---|
| gccgcccggg cangttcgac attacntnga gttccatgat gtacaattct ttcacgaaaa | 60 |
| acaatgaatg caagaatttg aggatctcct tactcctccc ttttacagat ggtctctcaa | 120 |
| tcccttcttc ttcctcttca tcttcatctt cttctgaacg cgctgccggg taccacggct | 180 |
| ttctttgtct ttatcgtgag atgaaggtga tgcttctgtt tcttctacca taactgaaga | 240 |
| aatttcgctg caagtctctt gactggctgt ttctccgact tcgcctttnt gtcaaacgng | 300 |
| agtcttttta cctcatgccc ctcagcttca cagcatcttc atctggatgt tnatttctca | 360 |
| aagggctcac tgaggaaact tctgattcan atgtcgaana gcactgtgaa gttttctctt | 420 |
| cattttgctg | 430 |

<210> SEQ ID NO 148
<211> LENGTH: 483
<212> TYPE: DNA
<213> ORGANISM: Homo sapien
<220> FEATURE:
<221> NAME/KEY: misc_feature
<222> LOCATION: (1)...(483)
<223> OTHER INFORMATION: n = A,T,C or G

<400> SEQUENCE: 148

| | |
|---|---|
| cccgggcagg tctgtgttgn tttncaaccg gtgtcctccc cagcgtccag aananggaaa | 60 |
| tgtggagcgg gtgatgatga cccctcgctg tcctgtcacc tcctgcacag cttcgtatgt | 120 |
| gggtctggtc tgggaccacc cgtacaggtt gtgcacgttg tagtgctcca cgggggagct | 180 |
| gtccggcagg atctgctgac tctccatgca cagagtcttg ctgctcaggc ccttgtccct | 240 |
| agattccaaa tatggcatat agggtggggt tatttagcat tcattgctg cagcccctga | 300 |
| cagatccatc cacaaaattt gatggctcat tcatatcaat ccacaatcca tcaaacttca | 360 |
| agctcttctc tggntctcga nggtttgcat agaactcttc tatctctttc ttccaccacg | 420 |
| canacctcgg ncgcgaccac gctaagccga attctgcana tatccatcac actggcggcc | 480 |
| gct | 483 |

<210> SEQ ID NO 149
<211> LENGTH: 439

<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 149

| | | | | | |
|---|---|---|---|---|---|
| ctttcacgaa | nacaatgaat | gcaagaattt | gaggatctcc | ttactcctcc | cttttacaga | 60 |
| tggtctctca | atcccttctt | cttcctcttc | atcttcatct | tcttctgaac | gcgctgccgg | 120 |
| gtaccacggc | tttctttgtc | tttatcgtga | gatgaaggtg | atgcttctgt | ttcttctacc | 180 |
| ataactgaag | aaatttcgct | gcaagtctct | tgactggctg | tttctccgac | ttcgcctttt | 240 |
| tgcaaacgtg | agtcttttta | cctcatgccc | ctcagcttcc | acagcatctt | catctggatg | 300 |
| ttcatttctc | aaagggctca | ctgaggaaac | ttctgactca | catgtcgaag | aagcactgng | 360 |
| agtttctctt | catttgctgc | aaanttgctc | tttgctggct | gngctctcag | accacccatt | 420 |
| tggctgcatg | ggggctgac | | | | | 439 |

<210> SEQ ID NO 150
<211> LENGTH: 578
<212> TYPE: DNA
<213> ORGANISM: Homo sapien
<220> FEATURE:
<221> NAME/KEY: misc_feature
<222> LOCATION: (1)...(578)
<223> OTHER INFORMATION: n = A,T,C or G

<400> SEQUENCE: 150

| | | | | | |
|---|---|---|---|---|---|
| ggcncgcccg | ggcangtcca | ctccactttt | gagctctgag | ggaataccct | caggagggac | 60 |
| agggtcaggg | agtcctggca | gctccgcagc | agagattcac | attcattcag | agacttgttg | 120 |
| tccagtgcaa | tgccattgat | cgcaacgatc | ctgtctccca | cagcaaggga | cccttcttta | 180 |
| gcggcagggc | ttccaggcag | cacagcggca | gcatacactc | cattctccag | actgatgcca | 240 |
| ctgtctttct | gtccactgan | gttgatgtgc | agcggcgtga | ccaccttccc | acccagggac | 300 |
| ttcctccgcc | gcacgaccat | gttgatgggc | cccctnccca | ttgaggagcg | ccttgatggc | 360 |
| ctgcttcttg | nccttggtga | tgaagtccac | atcggtgatt | ctcacagcca | gtcattgacc | 420 |
| cttaagcggn | catcagcaat | gcttcctttg | gccactttag | ngacaaatat | gccacagtcc | 480 |
| ccgggaaaca | agggtcattc | acaccttctg | gcatatcaaa | cacctcggcc | gggancacta | 540 |
| agccgaattc | tgcagatatc | catcacactg | gngggccg | | | 578 |

<210> SEQ ID NO 151
<211> LENGTH: 503
<212> TYPE: DNA
<213> ORGANISM: Homo sapien
<220> FEATURE:
<221> NAME/KEY: misc_feature
<222> LOCATION: (1)...(503)
<223> OTHER INFORMATION: n = A,T,C or G

<400> SEQUENCE: 151

| | | | | | |
|---|---|---|---|---|---|
| cgagcggccc | gcccgggcag | gtctgggaga | tcagcgactg | ctgccacgtg | cccagaaatg | 60 |
| gctcgtcctt | tcactacagc | ggaatgcaat | gagggtgggt | gagaagatga | tgggtcggtt | 120 |
| atttcattcc | ttttcttttt | acaacttcac | tttcagagac | ttcagcgttc | catgtctgct | 180 |
| gtgctgtgga | acccagagtg | ctcttgcctg | gatggctgag | aatcccttgg | accctggaag | 240 |
| cacctactcc | atgatggccc | ggtatagtgc | aggctcaata | taatcttccc | ggtatcttga | 300 |

```
gttgataact cgttgccgtt tctttcttg cttaacctct ttctctgtga aaatctcatt    360
gaagcgcatg tctgaagcta ctgacagtct anatttgact ctcttgggaa gctcttcatc    420
cagtgtgtat acatcatctc tcttaaccac aagttggagc catncttaaa cttcacctgg    480
tacatttgga tagggtggga ggc                                            503
```

<210> SEQ ID NO 152
<211> LENGTH: 553
<212> TYPE: DNA
<213> ORGANISM: Homo sapien
<220> FEATURE:
<221> NAME/KEY: misc_feature
<222> LOCATION: (1)...(553)
<223> OTHER INFORMATION: n = A,T,C or G

<400> SEQUENCE: 152

```
agcgtggtcg cggcccgagg tccactgagc tccgccttcc ccgggctccc tgaggaagca    60
gagtcctgac ttccaggaag gacaggacac agaggcaaga actcagcctg tgaggctctg   120
ggtggctcct gaggccagag gacgccttcc gcgatccatg gctcagcatc gtccttctgg   180
cttcccagcc ccgggccgaa cgttcgggtt aataagcaga gcagttattc ggctcctggc   240
aggagctccc ccgttagttt ccacgttgtg agcacattca tacttaagac tgnttctctt   300
tgtgttttaa gcgtctgtct ctgtagtaaa ctgaaatgtt aacagaaatg cagacctgcc   360
cgggcggccg ctcgaaagcc gaattctgca gatatccatc acactggcgg ccgctcgagc   420
atgcatctag anggcccaat tcgccctata gtgagtcgna ttacaattca ctgggccgcg   480
ntttacaacg tcgtgactgg gaaaaccctg cggtacccac ttaatcgcct tgcagnacat   540
ccccctttcg cca                                                      553
```

<210> SEQ ID NO 153
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 153

```
tcgagcggct cgcccgggca ggtccaccta gcatggctcc tctaaacacg caactcagcg    60
aggggacccc cttcacctct ggcaagagag ctgggtagat cagaaacttg gtgacacctg   120
gctagcacag agcaggctca cttgtcttgg tcccactacc cagattcctg cagacattgc   180
aaaccaaatg aaggttgntg aatgacccct gtccccagcc acttgttttg gtatcatctg   240
ctctgcagtg gaatgcctgt gtgtttgagt tcactctgca tctgtatatt tgagtataga   300
aaccgantca agtgatctgt gcatncagac acactggggc acctgancac agaacaaatc   360
accttaacga tctgaatga aactgnganc antgcccgcc tgggtgggtc tgganaaact    420
gccgncttct tgttggacct tggccgcacc acct                                454
```

<210> SEQ ID NO 154
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 154

```
agcgtggtcg cggcccgang gcggcctcct gantganggg aagggacgtg ggggcggcca    60
cggcaggatt aacctccatt tcagctaatc atgggagaga ttaaagtctc tcctgattat   120
aactggttta naggtacagt tccccttaaa aagattattg tggatgatga tgacagtaag   180
atatggtcgc tctatgacgc gggcccccga agtatcaggt gtcctctcat attcctgccc   240
cctgtcagtg gaactgcaga tgtctttttc cggcagattt tggctctgac tggatggggt   300
taccgggtta tcgctttgca gtatccagtt tattgggacc atctcgagtt cttgtgatgg   360
attcacaaaa cttttanacc atttacaatt ggataaagtt catcttttg gcgcttcttt    420 gggangcttt ttggcccana aatttgctga atacactcac aaatctccta gaagccattc   480
cctaatcctc tgcaattcct tcagngcaca ctctatcttc aaccaacttg gactggaaac   540
agctttggct gatgcctgca tttatgctca aaaatagtt cttggaaatt ttcatc        596
```

<210> SEQ ID NO 155
<211> LENGTH: 343
<212> TYPE: DNA
<213> ORGANISM: Homo sapien
<220> FEATURE:
<221> NAME/KEY: misc_feature
<222> LOCATION: (1)...(343)
<223> OTHER INFORMATION: n = A,T,C or G

<400> SEQUENCE: 155

```
ctcganttgg cncgcccggg cangtctgcc tggtttttga ccgngcgagc tatttagnct    60
ctggctctgt ttccggagct caaggnaaaa atcttgaana actcgagcag cttctgtgga   120
tagccttggg tacacatact gccgagcata gccaatgtac tttctcaata gctggtgggg   180
aatgggatct attgtttctc caggaaccac ctttagtctt tctgataatg gcttctcaga   240
aactacttca gtacggaag tatttgaatc ttgactatnc atacgagcta ctgtggcact    300
gctaatgggn tctctgctnt ccagctctta ttgcaatcac atg                     343
```

<210> SEQ ID NO 156
<211> LENGTH: 556
<212> TYPE: DNA
<213> ORGANISM: Homo sapien
<220> FEATURE:
<221> NAME/KEY: misc_feature
<222> LOCATION: (1)...(556)
<223> OTHER INFORMATION: n = A,T,C or G

<400> SEQUENCE: 156

```
tcgagcggcc cgcccgggca ggtctggcac cacncagatc gattaactgg ctcatctgat    60
ctcgtggccc ccaccctgga actgacttag cacaaaagga cacctcaatt ccttatgatt   120
tcatctccga cccaaccaat caacacccctt gactcactgg ccttcccct cccaccaaat   180 tatccttaaa aactctgatc cccgaatgct cagggagatc gatttgagta ctaataagac   240
tccagtctcc tgcacaagca gctctgtgta ctcttcctct attgcaattc ctgtcttgat   300
aaatcggctc tgtgtaggcg gcggaagaag tgaacctgtt gggcggttac cacctctgtc   360
gtgtgtgaca gttgntttga atctctaatt gctcagtaca gatccacatg caggttaagt   420
aagaagcttt tgaagaaat ggaaagtctt aagtgatggc ttccaagaaa tcaaacctac    480
attaattagg gaacaacgga ctttacgtat cacaaatgaa gagactgacn aagtaaatca   540
acttggcctt ttctta                                                   556
```

<210> SEQ ID NO 157

<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 157

| | | | | | |
|---|---|---|---|---|---|
| ggtccacaaa | aatatatnaa | ataagctgga | tatataaaan | caaacactta | acatngncan | 60 |
| cattccttca | gttattcaaa | ctcactgata | nctaacnggg | agnagttggn | attctggaag | 120 |
| acttcctaag | ctaaaagtat | atttacatat | ttacaacaca | ngtaaatata | acngaagaac | 180 |
| tacttcaaat | aangnngaaa | ttccagaatt | ctanagattt | atagctatag | ntnacaanta | 240 |
| tcaccaattg | gtttgcaatc | aanngnccag | cactacttat | gannaangtt | taactannaa | 300 |
| accaaaaggg | gagaaaacct | ggnagggaaa | nat | | | 333 |

<210> SEQ ID NO 158
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 158

| | | | | | |
|---|---|---|---|---|---|
| tcgagcggcc | gcccgggcag | gtctggtaca | tttgtgcgag | gtccggcact | ctgttctcat | 60 |
| ccagtaagtg | gtcgagccct | ttctgcagaa | ttgctgttaa | atgttctcct | aatagctgtt | 120 |
| tctccacaca | agcaatcagt | ggtttctgtg | tgctgtggtc | caagtaagtg | attactctgt | 180 |
| ctccctcttc | ttctaagcgt | ttacttacat | ggttaagata | ttctggaacc | tctctttcct | 240 |
| gcattaacct | ttggccttcg | gcagcatata | agcaattagt | ctcttccaaa | aatttcagtt | 300 |
| caaatgaatc | tttatacacc | tgcaggtcag | acagcatgcc | caggnaggct | ccgcaacagg | 360 |
| ctccggtcca | cggcctcgcc | gctcctctcg | cgctcgatca | gcagtaggat | tccatcaatg | 420 |
| gttttactct | gaaccatttt | atcactaata | atatgggttc | taaacagttc | taatcccata | 480 |
| tcccagatgg | agggcagcgt | ggagttctgc | agcacatagg | tgcggtccaa | gaacaggaag | 540 |
| atgcttctga | tcatgaatca | tttgnctggc | aatggtcctg | ccagcacgtg | gtaatctttc | 600 |
| ttttaaaaat | aaacccttat | ctaaacgtc | | | | 629 |

<210> SEQ ID NO 159
<211> LENGTH: 629
<212> TYPE: DNA
<213> ORGANISM: Homo sapien
<220> FEATURE:
<221> NAME/KEY: misc_feature
<222> LOCATION: (1)...(629)
<223> OTHER INFORMATION: n = A,T,C or G

<400> SEQUENCE: 159

| | | | | | |
|---|---|---|---|---|---|
| tcgagcggcc | gcccgggcag | gttctagagg | ganaatctgg | ctgatttggg | aataaaatat | 60 |
| aatcgaatat | tcaacaccat | gaagataaat | cttattttgg | aaatctactg | accttaatac | 120 |
| cccaagcttg | ccctgaatac | tttgattgga | attggaatat | atcaaaaaag | gttagtattt | 180 |
| ttgttgtagt | taggatacta | aaaggatatt | agttacccaa | gagatccaat | ttgttttttct | 240 |
| gatgaatagt | gttcagtaaa | atgaagcagt | cttaagagtg | actaataatt | tcaaagtgat | 300 |
| ttttcgtcta | ttcttaatat | tttttaatta | tttatttttta | agagttttat | accttgagca | 360 |

```
gatacaatga tccgctttag tgagaggaca atttctgatt gattgttttc tcttcaggcc        420
atctcacctc ttcattctct tgttacattt gaagcagttg atataatggg tttatacttt        480
aaaagataga catggtgcca tgaagtttgg ggaagttggg tgaattatcc cattctagtt        540
acagangagc tttccttaaa tgcccttttac ttctangttt ggtcaagaag tcattttctg       600
agtaaaagtt attttcatat atgttggggg                                         629
```

<210> SEQ ID NO 160
<211> LENGTH: 519
<212> TYPE: DNA
<213> ORGANISM: Homo sapien
<220> FEATURE:
<221> NAME/KEY: misc_feature
<222> LOCATION: (1)...(519)
<223> OTHER INFORMATION: n = A,T,C or G

<400> SEQUENCE: 160

```
tcgagcggcg cgcccgggca ggtctgctgg gattaatgcc aagttnttca gccataaggt         60
agcgaaatct agcagaatcc agattacatc cacttccaat cacgcggtgt ttgggtaatc        120
cacttagttt ccagataaca tacgtaagaa tgtccactgg gttggaaacc acaattatga        180
tgcaatcagg actgtacttg acgatctgag gaataatgaa tttgaagaca ttaacatttc        240
tctgcaccag attgagccga ctctccccett cttgctgacg gactcctgca gttaccacta       300
caatcttana attgggcggg tcacagaata atctttatct gccacaattt taggtgctga       360
agaaataagc tcccatgctg cagatccatc atttctncett taagcttatc ttccaaaaca      420
tccacaagan caangttcat cagccagaga ctttcccaga atgctgatag nacacgccat       480
accaacttgt ccaacancca ctacagcgat cttattggt                               519
```

<210> SEQ ID NO 161
<211> LENGTH: 446
<212> TYPE: DNA
<213> ORGANISM: Homo sapien
<220> FEATURE:
<221> NAME/KEY: misc_feature
<222> LOCATION: (1)...(446)
<223> OTHER INFORMATION: n = A,T,C or G

<400> SEQUENCE: 161

```
cgagnggccc gcccgggcag gtccagtaag cntttnacga tgatgggaaa ggttatgcaa         60
ggtcccagcg gtacaacgag ctgtttctac atcatttgta ttctgcatgg tacgtacaat       120
agcagacacc atctgaggag aacgcatgat agcgtgtctg gaagcttcct ttttagaaag      180
ctgatggacc ataactgcag ccttattaac caccacctgg tcctcgtcat ttagcagttt       240
tgtcagttca gggattgcac gtgtggcang ttctgcatca tcttgatagt taatcaagtt       300
tacaactggc atgtttcagc atctgcgatg ggctcagcaa acgctggaca ttantgggat       360
gagcagcatc aaactgtgta natgggatct gcatgccctc atctaatgtc tcagggaaca      420
tagcagctcg taccctctga gctcga                                             446
```

<210> SEQ ID NO 162
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 162

```
agcgtngtcg cggcccgang tcctgggaag cctttnttgc tgagcctcac agcctctgtc      60
aggcggctgc ggatccagcg gtccaccagg ctctcatggc ctccgggctg ggaggngggt     120
gagggcacaa aaccctccc aaggccacga anggcaaact tggtggcatt ccanagcttg      180
ttgcanaagt ggcggnaacc cagtatccgg ttcacatcca ggntgatgtc acgaccctgg     240
gacatgtang cacataatcc aaaccggaga gcatcggtgc cacattcacg aatccccgct     300
gggaagtcag ctttctgccc ttctttggcc ttctccacct cgctgggatc cagg           354
```

<210> SEQ ID NO 163
<211> LENGTH: 258
<212> TYPE: DNA
<213> ORGANISM: Homo sapien
<220> FEATURE:
<221> NAME/KEY: misc_feature
<222> LOCATION: (1)...(258)
<223> OTHER INFORMATION: n = A,T,C or G

<400> SEQUENCE: 163

```
tttttcncca agtcctcttg ccgngggatc tngactgcaa tttaagacac ttctaattag      60
ttatacccag gccctgcaaa attgctgggt ttatataata tattcttgct gcacgaagat     120
ttattattct gttggatgat tctattttaa ttntatttat tctggccaaa aaagaacctt     180
ctccgctcgt caagagangc caatntgtct tgaaggacaa gagaaagatg ctaacacaca     240
ctttcttctt cttgagga                                                    258
```

<210> SEQ ID NO 164
<211> LENGTH: 282
<212> TYPE: DNA
<213> ORGANISM: Homo sapien
<220> FEATURE:
<221> NAME/KEY: misc_feature
<222> LOCATION: (1)...(282)
<223> OTHER INFORMATION: n = A,T,C or G

<400> SEQUENCE: 164

```
ggaacatatt acttttaaat tacttgggtc aatgaaacat ttaataaaaa catttgcttc      60
tctatataat acgtatgtat aaaataagcc ttttcanaaa ctctggttct cataatcctc     120
tataaatcan atgatctgac ttctaagagg aacaaattac agnaaggggt atacattnat     180
gaatactggt agtactagag ganngacgct aaaccactct actaccactt gcggaactct     240
cacagggtaa atgacaaagc caatgactga ctctaaaaac aa                         282
```

<210> SEQ ID NO 165
<211> LENGTH: 462
<212> TYPE: DNA
<213> ORGANISM: Homo sapien
<220> FEATURE:
<221> NAME/KEY: misc_feature
<222> LOCATION: (1)...(462)
<223> OTHER INFORMATION: n = A,T,C or G

<400> SEQUENCE: 165

```
gcccgggcan gtcctgtaat cccagctact cangangctg agtcatgana atcgcctgaa      60
tccgggaggt agaggccgca gcgagcaaag attaagccac tgcactccag tctgggtgac     120
agagtgagaa tctgtctgtt gctcctctgg cattggtctg aaatgggttt gtagaacatg     180
ccacagaagg accagcanca gcaacaaatg gatttgtgga angcgtagct ccaaatggag     240
cangcacact tgatgaagca cgctgtgtct gtgcagangc aaccactggc actgttccaa     300
```

```
aaacattgct gctagcatta cttgtggaag tatacgcatt actggaggtg gctgcanaac    360
tgaaaacgct gtctagttct gccanagctg catacttgnc tgaanatgca cttgactgac    420
tgggaactga accacanaac caacaggacc tttacctgtg ga                      462
```

<210> SEQ ID NO 166
<211> LENGTH: 365
<212> TYPE: DNA
<213> ORGANISM: Homo sapien
<220> FEATURE:
<221> NAME/KEY: misc_feature
<222> LOCATION: (1)...(365)
<223> OTHER INFORMATION: n = A,T,C or G

<400> SEQUENCE: 166

```
cgtgggtcgc ggcncgangt ctgaaaccaa tccagaacta acatcagca cacaaaaaat     60 accaggatag atggaatcaa aagactctga agccaaaagg aggctaggga gagcaactga   120
acttagcaag ctgaggactt cagtgtccat catccgatcc tgccctgtaa caacaggtct   180
atatgataga gatattccat ctgagctgga ggccattatc cttagcaaac taacacagaa   240
cagaaaacca aatacatgtt ctcatttaga agtaggagct aaatgatgag aactcaagga   300
cacaaagaaa ggaacaacag acactggggc ctacttgagg gtggagggtg ggaggaggga   360
gaaga                                                               365
```

<210> SEQ ID NO 167
<211> LENGTH: 364
<212> TYPE: DNA
<213> ORGANISM: Homo sapien
<220> FEATURE:
<221> NAME/KEY: misc_feature
<222> LOCATION: (1)...(364)
<223> OTHER INFORMATION: n = A,T,C or G

<400> SEQUENCE: 167

```
agcgtggtcg cggcgcgang tccagcccta gcttgcctgt gactccgcct tcactgggtg    60
ctctctctaa aagttgctga ctctttactg tatctcccaa ttcccactcc attggttcca   120 taagggggagg ggtgtctcac tcaacatggt gttcctggta ccaagaactg gctgacgaag   180
ctgggtgccg tggctcatgc ctgtaatccc agcacttttg ggaggccaag aagggcggat   240
cacctgaggt ctggagttca agatcagcct gaccaacatg atgaaaccaa gtctccacta   300
aaaatataaa acaattagcc aggcatggtg gtgggtgcct gnaatcccag ctactgggga   360 ngct                                                                364
```

<210> SEQ ID NO 168
<211> LENGTH: 447
<212> TYPE: DNA
<213> ORGANISM: Homo sapien
<220> FEATURE:
<221> NAME/KEY: misc_feature
<222> LOCATION: (1)...(447)
<223> OTHER INFORMATION: n = A,T,C or G

<400> SEQUENCE: 168

```
cccgggcagg tcaaaaccca aaacctttca ttttagccca aaccagctca tgattaggta    60
tacaaggata acagaaccag ttgtcaggac gagcatttga caagtaaaag caattcttgc   120
aaagctgcag ttcatccagc tcatggcatg tgtctttata tagcatcctc gcaatgtcag   180
cttgctcact gtctgctcca tagaaaatca cggtattgtg gagaagcaat tgggcatcag   240
```

```
ctttgaactc ttcataactt cggtatttcc cttcattcac tttctcttga atggtgggaa      300
cgtccacaga cctcggccgc gaccacgcta agcccgaatt ctgcagatat ccatcacact      360
ggcggccgtt cgagcatggc atctagaagg cccaattcgc ctatagngag tcgnattacc      420
aattcactgg ccgtcgnttt acaacgc                                         447
```

<210> SEQ ID NO 169
<211> LENGTH: 524
<212> TYPE: DNA
<213> ORGANISM: Homo sapien
<220> FEATURE:
<221> NAME/KEY: misc_feature
<222> LOCATION: (1)...(524)
<223> OTHER INFORMATION: n = A,T,C or G

<400> SEQUENCE: 169

```
cgantngcgc gcccgggcag gtctgagcag cctttctgnn tgctggacta ttgggattgg      60
gttcatccaa cagagactgt atggatgtta gaatggaaga cacatcatag gttggactcc     120
aacggttctg aagtatgtcc agacatatac taccatctgc atagactaag aacaaagaag     180
taggtacatt aaacgtaaca agaccactaa ggttttaaca ttatagacaa aacanaaata     240
gtcaaganta ctttgctttt gaagtttaaa gattcctatg ttgcttccca gttaactgcc     300
taaaaagata agncataacc accactagtg aaataatcan gatgatcaga gaatgtcana     360
tgtgatcagt ataaaactgg angatattna gtgtcatcct ttggaaaagg ctgccctatn     420
atccaggaaa tcanaaacat tnttgaacag ggncccctagc tatccacaga catgtgggaa     480
attcattccc caaatngtag gctggatccc ctatctgaaa taac                      524
```

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170

```
tcgancggcn cgcccgggca ggtgacaaac ctgttattga agatgttggt tctgatgagg      60
aanaanatca gaagggatgg tgacaagaan aanaanaaga agattaagga aaagtacatc     120
gatcaagaag agctcaacaa aacaaagccc atctggacca gaaatcccga cgatattact     180
aatgangagt acggagaatt ctataanagc ttgaccaatg actgggaaga tcacttggca     240
gtgaagcatt tttcagttga nggacagttg gaattcagag cccttctatn tgtcccacga     300
cgtgctcctt ttgatctgtt tganancaga aa                                   332
```

<210> SEQ ID NO 171
<211> LENGTH: 334
<212> TYPE: DNA
<213> ORGANISM: Homo sapien
<220> FEATURE:
<221> NAME/KEY: misc_feature
<222> LOCATION: (1)...(334)
<223> OTHER INFORMATION: n = A,T,C or G

<400> SEQUENCE: 171

```
cgagnggcnc gcccgggcag gtctgttgat agcgacttaa cagaaaagtc tagacaaaca      60
taagcataaa aaattacagt cttttctaccc ttgggaatgg ggagaaaaag gaatctctac     120
cccaagacca gaaataataa gtcctgtttc tggtcctgaa catccagaat tatggaggct     180
```
ttggcctgac accacattan aatttggtct ggaaatcaaa ctttaganac angagatcgt    240
aagccatttt atactatcga cctaaattcc agtctaacgg ttcctttaca aagttgcgga    300
aagccctctt atatgctagc tgtaggaaat atag                               334

<210> SEQ ID NO 172
<211> LENGTH: 439
<212> TYPE: DNA
<213> ORGANISM: Homo sapien
<220> FEATURE:
<221> NAME/KEY: misc_feature
<222> LOCATION: (1)...(439)
<223> OTHER INFORMATION: n = A,T,C or G

<400> SEQUENCE: 172
agcgtggtcg cggcccgang tctgcctata aaactagact tctgacgctg ggctccagct    60
tcattctcac aggtcatcat cctcatccgg gagagcagtt gtctgagcaa cctctaagtc   120
gtgctcatac tgtgctgcca aagctgggtc catgacaact tctggtgggg cgagagcagg   180
catggcaaca aattccaagt tagggtctcc aatgagcttc ctagcaagcc agaggaaggg   240
cttttcaaag ttgtagttac ttttggcaga aatgtcgtag tactgaagat tcttctttcg   300
gtggaagaca atggatttcg ccttcacttt ctgccttaat atccactttg gtgccacaca   360
acacaatggg gatgntttca cacacttngn accanatctc tatgccagnt aggccatttt   420
ggaagnactt cganggtac                                               439

<210> SEQ ID NO 173
<211> LENGTH: 599
<212> TYPE: DNA
<213> ORGANISM: Homo sapien
<220> FEATURE:
<221> NAME/KEY: misc_feature
<222> LOCATION: (1)...(599)
<223> OTHER INFORMATION: n = A,T,C or G

<400> SEQUENCE: 173
cgatnggccg cccgggcagg tcctgtaaaa naggaaattc agacatcgta cgactcgtaa    60
ttgaatgtgg agctgactgc aatattttgt caaagcacca gaatagtgcc ctgcactttg   120
cgaagcagtc taacaatgtg cttgtgtacg acttgctgaa gaaccattta gagacacttt   180
caagagtagc agaagagaca ataaaggatt actttgaagc tcgccttgct ctgctagaac   240 cagttttttcc aatcgcatgt catcgactct gtgagggtcc agattttttca acagatttca   300 attaccaacc cccacagaac ataccagaag gctctggcat cctgctgttt atcttccatg   360
caaacttttt gggtaaagaa gttattgctc ggctctgtgg accgtgtagt gtacaagctg   420
tagttctgaa tgataaattt cagcttcctg tttttctggg tctcgctctg ttgtccaggc   480
tggagtgcag tggcgcggat tacagctcac tggagtcttg acttcccagg cacaagcaat   540
cctcccacct cagcctccta actacctggg actaaaaatg caccgccacc acattccgg    599

<210> SEQ ID NO 174
<211> LENGTH: 458
<212> TYPE: DNA
<213> ORGANISM: Homo sapien
<220> FEATURE:
<221> NAME/KEY: misc_feature
<222> LOCATION: (1)...(458)
<223> OTHER INFORMATION: n = A,T,C or G

<400> SEQUENCE: 174

| | |
|---|---:|
| tcgatttggc cgcccgggca ggtccatgcn gnttntgccc attcccatgg ngcccgacaa | 60 |
| ncccatcccc gaggccgaca tccccatgtt catgttcatg cccaccatgc cctggctcat | 120 |
| ccctgcgctg ttccccagag gggccattcc catggtgccc gtcattacac cgggcatgtt | 180 |
| cataggcatg ggtccccca ggagagggtt agnttgaggc cggacaggaa gcatgtttga | 240 |
| tggagaactg aggttcacag nctccaaaac tttgagtcat cacattcata ggctgctgca | 300 |
| tattctgtct gctgaatcca ttgtatncag tgatggcctg ctggggnttt ggaaggctng | 360 |
| cataccaggt agtaagntcg tctaggctga tgtttacacc tggggtcaga ccaagtanga | 420 |
| gggcaaggtt ttgctgactg attttctgga cccatatc | 458 |

<210> SEQ ID NO 175
<211> LENGTH: 1206
<212> TYPE: DNA
<213> ORGANISM: Homo sapien

<400> SEQUENCE: 175

| | |
|---|---:|
| ggcacgagga agttttgtgt actgaaaaag aaactgtcag aagcaaaaga aataaaatca | 60 |
| cagttagaga accaaaaagt taaatgggaa caagagctct gcagtgtgag gtttctcaca | 120 |
| ctcatgaaaa tgaaaattat ctcttacatg aaaattgcat gttgaaaaag gaaattgcca | 180 |
| tgctaaaact ggaaatagcc acactgaaac accaatacca ggaaaaggaa ataaatact | 240 |
| ttgaggacat taagatttta aagaaaaga atgctgaact tcagatgacc ctaaaactga | 300 |
| agaggaatc attaactaaa agggcatctc aatatagtgg gcagcttaaa gttctgatag | 360 |
| ctgagaacac aatgctcact tctaaattga aggaaaaaca agacaaagaa atactagagg | 420 |
| cagaaattga atcacaccat cctagactgg cttctgctgt acaagaccat gatcaaattg | 480 |
| tgacatcaag aaaaagtcaa gaacctgctt tccacattgc aggagatgct tgtttgcaaa | 540 |
| gaaaaatgaa tgttgatgtg agtagtacga tatataacaa tgaggtgctc catcaaccac | 600 |
| tttctgaagc tcaaaggaaa tccaaaagcc taaaaattaa tctcaattat gccggagatg | 660 |
| ctctaagaga aaatacattg gtttcagaac atgcacaaag agaccaacgt gaaacacagt | 720 |
| gtcaaatgaa ggaagctgaa cacatgtatc aaaacgaaca agataatgtg aacaaacaca | 780 |
| ctgaacagca ggagtctcta gatcagaaat tatttcaact acaaagcaaa aatatgtggc | 840 |
| ttcaacagca attagttcat gcacataaga aagctgacaa caaaagcaag ataacaattg | 900 |
| atattcattt tcttgagagg aaaatgcaac atcatctcct aaaagagaaa atgaggaga | 960 |
| tatttaatta caataaccat ttaaaaaacc gtatatatca atatgaaaaa gagaaagcag | 1020 |
| aaacagaagt tatataatag tataacactg ccaaggagcg gattatctca tcttcatcct | 1080 |
| gtaattccag tgtttgtcac gtggttgttg aataaatgaa taagaatga gaaaccaga | 1140 |
| agctctgata cataatcata atgataatta tttcaatgca caactacggg tggtgctgct | 1200 |
| cgtgcc | 1206 |

<210> SEQ ID NO 176
<211> LENGTH: 317
<212> TYPE: PRT
<213> ORGANISM: Homo sapien

<400> SEQUENCE: 176

Met Gly Thr Arg Ala Leu Gln Cys Glu Val Ser His Thr His Glu Asn
1               5                   10                  15

Glu Asn Tyr Leu Leu His Glu Asn Cys Met Leu Lys Lys Glu Ile Ala
            20                  25                  30

```
Met Leu Lys Leu Glu Ile Ala Thr Leu Lys His Gln Tyr Gln Glu Lys
             35                  40                  45

Glu Asn Lys Tyr Phe Glu Asp Ile Lys Ile Leu Lys Glu Lys Asn Ala
 50                  55                  60

Glu Leu Gln Met Thr Leu Lys Leu Lys Glu Glu Ser Leu Thr Lys Arg
 65                  70                  75                  80

Ala Ser Gln Tyr Ser Gly Gln Leu Lys Val Leu Ile Ala Glu Asn Thr
                 85                  90                  95

Met Leu Thr Ser Lys Leu Lys Glu Lys Gln Asp Lys Glu Ile Leu Glu
            100                 105                 110

Ala Glu Ile Glu Ser His His Pro Arg Leu Ala Ser Ala Val Gln Asp
            115                 120                 125

His Asp Gln Ile Val Thr Ser Arg Lys Ser Gln Glu Pro Ala Phe His
130                 135                 140

Ile Ala Gly Asp Ala Cys Leu Gln Arg Lys Met Asn Val Asp Val Ser
145                 150                 155                 160

Ser Thr Ile Tyr Asn Asn Glu Val Leu His Gln Pro Leu Ser Glu Ala
                165                 170                 175

Gln Arg Lys Ser Lys Ser Leu Lys Ile Asn Leu Asn Tyr Ala Gly Asp
            180                 185                 190

Ala Leu Arg Glu Asn Thr Leu Val Ser Glu His Ala Gln Arg Asp Gln
            195                 200                 205

Arg Glu Thr Gln Cys Gln Met Lys Glu Ala Glu His Met Tyr Gln Asn
            210                 215                 220

Glu Gln Asp Asn Val Asn Lys His Thr Glu Gln Gln Glu Ser Leu Asp
225                 230                 235                 240

Gln Lys Leu Phe Gln Leu Gln Ser Lys Asn Met Trp Leu Gln Gln Gln
                245                 250                 255

Leu Val His Ala His Lys Lys Ala Asp Asn Lys Ser Lys Ile Thr Ile
            260                 265                 270

Asp Ile His Phe Leu Glu Arg Lys Met Gln His His Leu Leu Lys Glu
            275                 280                 285

Lys Asn Glu Glu Ile Phe Asn Tyr Asn Asn His Leu Lys Asn Arg Ile
            290                 295                 300

Tyr Gln Tyr Glu Lys Glu Lys Ala Glu Thr Glu Val Ile
305                 310                 315

<210> SEQ ID NO 177
<211> LENGTH: 20
<212> TYPE: DNA
<213> ORGANISM: Artificial Sequence
<220> FEATURE:
<223> OTHER INFORMATION: Made in the Lab

<400> SEQUENCE: 177
ccaatcatct ccacaggagc                                              20

<210> SEQ ID NO 178
<211> LENGTH: 1665
<212> TYPE: DNA
<213> ORGANISM: Homo sapien

<400> SEQUENCE: 178
gcaaactttc aagcagagcc tcccgagaag ccatctgcct tcgagcctgc cattgaaatg    60
caaaagtctg ttccaaataa agccttggaa ttgaagaatg aacaaacatt gagagcagat   120
```

-continued

| | |
|---|---|
| cagatgttcc cttcagaatc aaaacaaaag aaggttgaag aaaattcttg ggattctgag | 180 |
| agtctccgtg agactgtttc acagaaggat gtgtgtgtac ccaaggctac acatcaaaaa | 240 |
| gaaatggata aaataagtgg aaaattagaa gattcaacta gcctatcaaa atcttggat | 300 |
| acagttcatt cttgtgaaag agcaagggaa cttcaaaaag atcactgtga caacgtaca | 360 |
| ggaaaaatgg aacaaatgaa aaagaagttt tgtgtactga aaagaaact gtcagaagca | 420 |
| aaagaaataa aatcacagtt agagaaccaa aaagttaaat gggaacaaga gctctgcagt | 480 |
| gtgaggtttc tcacactcat gaaatgaaa attatctctt acatgaaaat tgcatgttga | 540 |
| aaaaggaaat tgccatgcta aaactggaaa tagccacact gaaacaccaa taccaggaaa | 600 |
| aggaaaataa atactttgag gacattaaga ttttaaaaga aaagaatgct gaacttcaga | 660 |
| tgaccctaaa actgaaagag gaatcattaa ctaaaagggc atctcaatat agtgggcagc | 720 |
| ttaaagttct gatagctgag aacacaatgc tcacttctaa attgaaggaa aaacaagaca | 780 |
| aagaaatact agaggcagaa attgaatcac accatcctag actggcttct gctgtacaag | 840 |
| accatgatca aattgtgaca tcaagaaaaa gtcaagaacc tgctttccac attgcaggag | 900 |
| atgcttgttt gcaagaaaaa atgaatgttg atgtgagtag tacgatatat aacaatgagg | 960 |
| tgctccatca accactttct gaagctcaaa ggaaatccaa aagcctaaaa attaatctca | 1020 |
| attatgccgg agatgctcta agagaaaata cattggtttc agaacatgca caaagagacc | 1080 |
| aacgtgaaac acagtgtcaa atgaaggaag ctgaacacat gtatcaaaac gaacaagata | 1140 |
| atgtgaacaa acacactgaa cagcaggagt ctctagatca gaaattattt caactacaaa | 1200 |
| gcaaaaatat gtggcttcaa cagcaattag ttcatgcaca taagaaagct gacaacaaaa | 1260 |
| gcaagataac aattgatatt cattttcttg agaggaaaat gcaacatcat ctcctaaaag | 1320 |
| agaaaaatga ggagatattt aattacaata accatttaaa aaaccgtata tatcaatatg | 1380 |
| aaaaagagaa agcagaaaca gaaaactcat gagagacaag cagtaagaaa cttcttttgg | 1440 |
| agaaacaaca gaccagatct ttactcacaa ctcatgctag gaggccagtc ctagcattac | 1500 |
| cttatgttga aaatcttacc aatagtctgt gtcaacagaa tacttatttt agaagaaaaa | 1560 |
| ttcatgattt cttcctgaag cctgggcgac agagcgagac tctgtctcaa aaaaaaaaa | 1620 |
| aaaaaagaa agaaagaaat gcctgtgctt acttcgcttc ccagg | 1665 |

<210> SEQ ID NO 179
<211> LENGTH: 179
<212> TYPE: PRT
<213> ORGANISM: Homo sapien

<400> SEQUENCE: 179

```
Ala Asn Phe Gln Ala Glu Pro Pro Glu Lys Pro Ser Ala Phe Glu Pro
 1               5                   10                  15

Ala Ile Glu Met Gln Lys Ser Val Pro Asn Lys Ala Leu Glu Leu Lys
             20                  25                  30

Asn Glu Gln Thr Leu Arg Ala Asp Gln Met Phe Pro Ser Glu Ser Lys
         35                  40                  45

Gln Lys Lys Val Glu Glu Asn Ser Trp Asp Ser Glu Ser Leu Arg Glu
     50                  55                  60

Thr Val Ser Gln Lys Asp Val Cys Val Pro Lys Ala Thr His Gln Lys
 65                  70                  75                  80

Glu Met Asp Lys Ile Ser Gly Lys Leu Glu Asp Ser Thr Ser Leu Ser
                 85                  90                  95

Lys Ile Leu Asp Thr Val His Ser Cys Glu Arg Ala Arg Glu Leu Gln
```

|   |   |   |   | 100 |   |   |   |   | 105 |   |   |   |   | 110 |   |   |
|---|---|---|---|-----|---|---|---|---|-----|---|---|---|---|-----|---|---|

Lys Asp His Cys Glu Gln Arg Thr Gly Lys Met Glu Gln Met Lys Lys
        115                  120                  125

Lys Phe Cys Val Leu Lys Lys Leu Ser Glu Ala Lys Glu Ile Lys
130                  135                 140

Ser Gln Leu Glu Asn Gln Lys Val Lys Trp Glu Gln Glu Leu Cys Ser
145                150               155               160

Val Arg Phe Leu Thr Leu Met Lys Met Lys Ile Ile Ser Tyr Met Lys
              165               170               175

Ile Ala Cys

<210> SEQ ID NO 180
<211> LENGTH: 1681
<212> TYPE: DNA
<213> ORGANISM: Homo sapien

<400> SEQUENCE: 180

| | | | | |
|---|---|---|---|---|
| gatacagtca ttcttgtgaa agagcaaggg aacttcaaaa agatcactgt gaacaacgta | 60 |
| caggaaaaat ggaacaaatg aaaagaagt tttgtgtact gaaaagaaa ctgtcagaag | 120 |
| caaaagaaat aaaatcacag ttagagaacc aaaaagttaa atgggaacaa gagctctgca | 180 |
| gtgtgagatt gactttaaac caagaagaag agaagagaag aaatgccgat atattaaatg | 240 |
| aaaaaattag ggaagaatta ggaagaatcg aagagcagca taggaaagag ttagaagtga | 300 |
| aacaacaact tgaacaggct ctcagaatac aagatataga attgaagagt gtagaaagta | 360 |
| atttgaatca ggtttctcac actcatgaaa atgaaaatta tctcttacat gaaaattgca | 420 |
| tgttgaaaaa ggaaattgcc atgctaaaac tggaaatagc cacactgaaa caccaatacc | 480 |
| aggaaaagga aataaatac tttgaggaca ttaagatttt aaaagaaaag aatgctgaac | 540 |
| ttcagatgac cctaaaactg aaagaggaat cattaactaa aagggcatct caatatagtg | 600 |
| ggcagcttaa agttctgata gctgagaaca caatgctcac ttctaaattg aaggaaaaac | 660 |
| aagacaaaga aatactagag gcagaaattg aatcacacca tcctagactg gcttctgctg | 720 |
| tacaagacca tgatcaaatt gtgacatcaa gaaaagtca agaacctgct ttccacattg | 780 |
| caggagatgc ttgtttgcaa agaaaaatga atgttgatgt gagtagtacg atatataaca | 840 |
| atgaggtgct ccatcaacca ctttctgaag ctcaaaggaa atccaaaagc ctaaaaatta | 900 |
| atctcaatta tgccggagat gctctaagag aaaatacatt ggtttcagaa catgcacaaa | 960 |
| gagaccaacg tgaaacacag tgtcaaatga aggaagctga acacatgtat caaaacgaac | 1020 |
| aagataatgt gaacaaacac actgaacagc aggagtctct agatcagaaa ttatttcaac | 1080 |
| tacaaagcaa aaatatgtgg cttcaacagc aattagttca tgcacataag aaagctgaca | 1140 |
| acaaaagcaa gataacaatt gatattcatt tccttgagag gaaatgcaa catcatctcc | 1200 |
| taaaagagaa aaatgaggag atatttaatt acaataacca tttaaaaaac cgtatatatc | 1260 |
| aatatgaaaa agagaaagca gaaacagaaa actcatgaga caagcagt aagaaacttc | 1320 |
| ttttggagaa acaacagacc agatctttac tcacaactca tgctaggagg ccagtcctag | 1380 |
| cattaccta tgttgaaaaa tcttaccaat agtctgtgtc aacagaatac ttattttaga | 1440 |
| agaaaaattc atgatttctt cctgaagcct acagacataa aataacagtg tgaagaatta | 1500 |
| cttgttcacg aattgcataa aagctgccca ggatttccat ctaccctgga tgatgccgga | 1560 |
| gacatcattc aatccaacca gaatctcgct ctgtcactca ggctggagtg cagtgggcgc | 1620 |
| aatctcggct cactgcaact ctgcctccca ggttcacgcc attctctggc acagcctccc | 1680 | g                                                                    1681

<210> SEQ ID NO 181
<211> LENGTH: 432
<212> TYPE: PRT
<213> ORGANISM: Homo sapien

<400> SEQUENCE: 181

Asp Thr Val His Ser Cys Glu Arg Ala Arg Glu Leu Gln Lys Asp His
 1               5                  10                  15

Cys Glu Gln Arg Thr Gly Lys Met Glu Gln Met Lys Lys Lys Phe Cys
                20                  25                  30

Val Leu Lys Lys Leu Ser Glu Ala Lys Glu Ile Lys Ser Gln Leu
            35                  40                  45

Glu Asn Gln Lys Val Lys Trp Glu Gln Glu Leu Cys Ser Val Arg Leu
    50                  55                  60

Thr Leu Asn Gln Glu Glu Lys Arg Arg Asn Ala Asp Ile Leu Asn
65                  70                  75                  80

Glu Lys Ile Arg Glu Glu Leu Gly Arg Ile Glu Gln His Arg Lys
                85                  90                  95

Glu Leu Glu Val Lys Gln Gln Leu Glu Gln Ala Leu Arg Ile Gln Asp
                100                 105                 110

Ile Glu Leu Lys Ser Val Glu Ser Asn Leu Asn Gln Val Ser His Thr
            115                 120                 125

His Glu Asn Glu Asn Tyr Leu Leu His Glu Asn Cys Met Leu Lys Lys
    130                 135                 140

Glu Ile Ala Met Leu Lys Leu Glu Ile Ala Thr Leu Lys His Gln Tyr
145                 150                 155                 160

Gln Glu Lys Glu Asn Lys Tyr Phe Glu Asp Ile Lys Ile Leu Lys Glu
                165                 170                 175

Lys Asn Ala Glu Leu Gln Met Thr Leu Lys Leu Lys Glu Glu Ser Leu
            180                 185                 190

Thr Lys Arg Ala Ser Gln Tyr Ser Gly Gln Leu Lys Val Leu Ile Ala
        195                 200                 205

Glu Asn Thr Met Leu Thr Ser Lys Leu Lys Glu Lys Gln Asp Lys Glu
    210                 215                 220

Ile Leu Glu Ala Glu Ile Glu Ser His His Pro Arg Leu Ala Ser Ala
225                 230                 235                 240

Val Gln Asp His Asp Gln Ile Val Thr Ser Arg Lys Ser Gln Glu Pro
                245                 250                 255

Ala Phe His Ile Ala Gly Asp Ala Cys Leu Gln Arg Lys Met Asn Val
            260                 265                 270

Asp Val Ser Ser Thr Ile Tyr Asn Asn Glu Val Leu His Gln Pro Leu
        275                 280                 285

Ser Glu Ala Gln Arg Lys Ser Lys Ser Leu Lys Ile Asn Leu Asn Tyr
    290                 295                 300

Ala Gly Asp Ala Leu Arg Glu Asn Thr Leu Val Ser Glu His Ala Gln
305                 310                 315                 320

Arg Asp Gln Arg Glu Thr Gln Cys Gln Met Lys Glu Ala Glu His Met
                325                 330                 335

Tyr Gln Asn Glu Gln Asp Asn Val Asn Lys His Thr Glu Gln Gln Glu
            340                 345                 350

Ser Leu Asp Gln Lys Leu Phe Gln Leu Gln Ser Lys Asn Met Trp Leu
        355                 360                 365

```
Gln Gln Gln Leu Val His Ala His Lys Lys Ala Asp Asn Lys Ser Lys
        370                 375                 380

Ile Thr Ile Asp Ile His Phe Leu Glu Arg Lys Met Gln His His Leu
385                 390                 395                 400

Leu Lys Glu Lys Asn Glu Glu Ile Phe Asn Tyr Asn Asn His Leu Lys
                405                 410                 415

Asn Arg Ile Tyr Gln Tyr Glu Lys Glu Lys Ala Glu Thr Glu Asn Ser
                420                 425                 430
```

<210> SEQ ID NO 182
<211> LENGTH: 511
<212> TYPE: DNA
<213> ORGANISM: Homo sapiens

<400> SEQUENCE: 182

```
gaagtttcat gaggtttagc ttttctgggc tggggagtgg agagaaagaa gttgcagggc    60
ttacaggaaa tcccagagcc tgaggttttc tcccagattt gagaactcta gattctgcat   120
cattatcttt gagtctatat tctcttgggc tgtaagaaga tgaggaatgt aataggtctg   180
ccccaagcct ttcatgcctt ctgtaccaag cttgtttcct tgtgcatcct tcccaggctc   240
tggctgcccc ttattggaga atgtgatttc caagacaatc aatccacaag tgtctaagac   300
tgaatacaaa gaacttcttc aagagttcat agacgacaat gccactacaa atgccataga   360
tgaattgaag gaatgttttc ttaaccaaac ggatgaaact ctgagcaatg ttgaggtgtt   420
tatgcaatta atatatgaca gcagtctttg tgatttattt taactttctg caagaccttt   480
ggctcacaga actgcagggt atggtgagaa a                                  511
```

<210> SEQ ID NO 183
<211> LENGTH: 260
<212> TYPE: DNA
<213> ORGANISM: Homo sapiens

<400> SEQUENCE: 183

```
cacctcgcgg ttcagctcct ctgtcttggt gaagaaccat tcctcggcat ccttgcggtt    60
cttctctgcc atcttctcat actggtcacg catctcgttc agaatgcggc tcaggtccac   120
gccaggtgca gcgtccatct ccacattgac atctccaccc acctggcctc tcagggcatt   180
catctcctcc tcgtggttct tcttcaggta ggccagctcc tccttcaggc tctcaatctg   240
catctccagg tcagctctgg                                               260
```

<210> SEQ ID NO 184
<211> LENGTH: 461
<212> TYPE: DNA
<213> ORGANISM: Homo sapiens

<400> SEQUENCE: 184

```
gtctgatggg agaccaaaga atttgcaagt ggatggtttg gtatcactgt aaataaaaag    60
agggcctttt ctagctgtat gactgttact tgaccttctt tgaaaagcat tcccaaaatg   120
ctctatttta gatagattaa cattaaccaa cataattttt tttagatcga gtcagcataa   180
atttctaagt cagcctctag tcgtggttca tctctttcac ctgcatttta tttggtgttt   240
gtctgaagaa aggaaagagg aaagcaaata cgaattgtac tatttgtacc aaatctttgg   300
gattcattgg caaataattt cagtgtggtg tattattaaa tagaaaaaaa aattttgtt   360
tcctaggttg aagtctaatt gataccgtt tgacttatga tgaccattta tgcactttca   420
```

-continued

| aatgaatttg ctttcaaaat aaatgaagag cagacctcgg c | 461 |

<210> SEQ ID NO 185
<211> LENGTH: 531
<212> TYPE: DNA
<213> ORGANISM: Homo sapiens

<400> SEQUENCE: 185

| tctgattta tttccttctc aaaaaaagtt atttacagaa ggtatatatc aacaatctga | 60 |
| caggcagtga acttgacatg attagctggc atgattttt cttttttttc ccccaaacat | 120 |
| tgttttgtg gccttgaatt ttaagacaaa tattctacac ggcatattgc acaggatgga | 180 |
| tggcaaaaaa aagtttaaaa acaaaaaccc ttaacgaaac tgccttaaaa aggcagacgt | 240 |
| cctagtgcct gtcatgttat attaaacata catacacaca atctttttgc ttattataat | 300 |
| acagacttaa atgtacaaag atgttttcca cttttttcaa tttttaaaca caacagctat | 360 |
| aaacctgaac acatatgcta tcatcatgcc ataagactaa aacaattata tttagcgaca | 420 |
| agtagaaagg attaaatagt caaatacaag aatgaaaaac gcagtacata gtgtcgcgaa | 480 |
| ctcaaatcgg catttagata gatccagtgg tttaaacggc acgttttttgc t | 531 |

<210> SEQ ID NO 186
<211> LENGTH: 441
<212> TYPE: DNA
<213> ORGANISM: Homo sapiens

<400> SEQUENCE: 186

| cattccttc ctcgcgttgg ggtttctctg tgtcagcgag cctcggtaca ctgatttccg | 60 |
| atcaaaagaa tcatcatctt taccttgact tttcaggaa ttactgaact ttcttctcag | 120 |
| aagatagggc acagccattg ccttggcctc acttgaaggg tctgcatttg ggtcctctgg | 180 |
| tctcttgcca agtttcccaa ccactcgagg gagaaatatc gggaggtttg acttcctccg | 240 |
| gggctttccc gagggcttca ccgtgagccc tgcggccctc agggctgcaa tcctggattc | 300 |
| aatgtctgaa acctcgctct ctgcctgctg gacttctgag gccgtcactg ccactctgtc | 360 |
| ctccagctct gacagctcct catctgtggt cctgttgtac tggacggggt ccccagggtc | 420 |
| ctggggcttt ttttcctgtc t | 441 |

<210> SEQ ID NO 187
<211> LENGTH: 371
<212> TYPE: DNA
<213> ORGANISM: Homo sapiens

<400> SEQUENCE: 187

| aaaagtgaat gagtaactat tatattgttg gcaataataa gttgcaaaat catcaggctg | 60 |
| caggctgctg atggtgagag tgaactctgt cccagatcca ctgccgctga accttgatgg | 120 |
| gaccccagat tctaaactag acgccttatg gatcaggagc tttggggctt tccctggttt | 180 |
| ctgttgatac caggccaacc aactactaac actctgactg gcccggcaag tgatggtgac | 240 |
| tctgtctcct acagttgcag acagggtgga aggagactgg gtcatctgga tgtcacattt | 300 |
| ggcacctggg agccagagca gcaggagccc caggagctga gcggggaccc tcatgtccat | 360 |
| gctgagtcct g | 371 |

<210> SEQ ID NO 188
<211> LENGTH: 226
<212> TYPE: DNA
<213> ORGANISM: Homo sapiens

<400> SEQUENCE: 188

| ggtatataaa ttgagatgcc cccccaggcc agcaaatgtt ccttttgtt caaagtctat | 60 |
| ttttattcct tgatattttt cttttttttt tttttgtgga tggggacttg tgaatttttc | 120 |
| taaaggtgct atttaacatg ggaggagagc gtgtgcggct ccagcccagc ccgctgctca | 180 |
| cttttccaccc tctctccacc tgcctctggc ttctcaggac ctgccc | 226 |

<210> SEQ ID NO 189
<211> LENGTH: 391
<212> TYPE: DNA
<213> ORGANISM: Homo sapiens
<220> FEATURE:
<221> NAME/KEY: misc_feature
<222> LOCATION: (1)...(391)
<223> OTHER INFORMATION: n=A,T,C or G

<400> SEQUENCE: 189

| tgggtgaagt ttattctgtt ttcacatcta ggttgttggg ganagtgata gacaaagttc | 60 |
| tggattctgg gcatcgtcgg cgcatgcttg taatcctact tgggaggttg anacaggaga | 120 |
| cctcggccgc naccacgcta agggcgaatt ctgcanatat ccatcacact ggcggccgct | 180 |
| cgagcatgca tctanagggc ccaattcncc ctatagtgag ncgtattaca attcactggc | 240 |
| cgtcgtttta caacgtcgtg actgggaaaa ccctggcgtt acccaactta atcgccttgc | 300 |
| agcacatccc cctttcncca gctggcttaa tancgaagag gcccgcaccg atcgcccttc | 360 |
| ccaacanttg cgcagcctga atggcgaatg g | 391 |

<210> SEQ ID NO 190
<211> LENGTH: 501
<212> TYPE: DNA
<213> ORGANISM: Homo sapiens

<400> SEQUENCE: 190

| catcttggcc tttttgagct gtttccgctt cttctcatcc cggtcactgt caccctcatt | 60 |
| actggaggag ctgcagagg cgttgctgtc aaactcctct gccacatctt cctcctcttc | 120 |
| acctgggttg aatgactcat cggtttcttc tcctgagtca tcgctgctgt cattggcatt | 180 |
| ctcctcccgg atcttgcctt cctccttcat cctctccaag taggcatcat gctggtcctc | 240 |
| atcagagtca gcatattcat cgtagcttgg gttcatgccc tctttcaatc ctcggttttt | 300 |
| gatgttgagc ttttttcgcgt tgacaaaatc aaacagtttc ccgtactcct ccctctcaat | 360 |
| gctgctgaag gtatactgag tgccctgctt ggtctcaatt tcaaagtcaa aggaacgagt | 420 |
| agtagtggta ccacgagcaa agttgacaaa ggagatctca tcgaagcgga tgtgcacagg | 480 |
| tggcttgtgg acgtagatga a | 501 |

<210> SEQ ID NO 191
<211> LENGTH: 241
<212> TYPE: DNA
<213> ORGANISM: Homo sapiens
<220> FEATURE:
<221> NAME/KEY: misc_feature
<222> LOCATION: (49)
<223> OTHER INFORMATION: n=A,T,C or G

<400> SEQUENCE: 191

| ggaaaaactg tgaaaatat atctgaattt attaagtaca gtataaaana gggttgtggc | 60 |
| aacagaaagt aaaaactaac atggattgct ataaatatgc tgaagcctag ttgttcaaat | 120 |

-continued

| | |
|---|---|
| gatacaattc tctcatgcta ctctaaagtt tataaagaaa aaggatttac actttacaca | 180 |
| ctgtacacaa aaggaatacc ttctgagagc cagggagtgg ggaaagggga aggagacttg | 240 |
| a | 241 |

<210> SEQ ID NO 192
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n=A,T,C or G

<400> SEQUENCE: 192

| | |
|---|---|
| tggtcntgga ttcacanata aantanatcg actaaaactg gcagaaattg tgaagcaggt | 60 |
| gatagaagan caaaccacgt cccacgaatc ccaataatga cagcttcaga ctttgctttt | 120 |
| ttaacaattt gaaaattat tctttaatgt ataaagtaat tttatgtaaa ttaataaatc | 180 |
| ataatttcat ttccacattg attaaagctg ctgtatagat ttagggngca ggacttaata | 240 |
| atagnggaaa tgaaattatg atttattaat c | 271 |

<210> SEQ ID NO 193
<211> LENGTH: 351
<212> TYPE: DNA
<213> ORGANISM: Homo sapiens

<400> SEQUENCE: 193

| | |
|---|---|
| gtcgaggcg ctgatcccta aaatggcgaa catgtgtttt catcatttca gccaaagtcc | 60 |
| aacttcctg tgcctttcct atcacctcga gaagtaatta tcagttggtt tggattttg | 120 |
| accaccgtt cagtcatttt gggttgccgt gctcccaaaa catttaaat gaaagtattg | 180 |
| cattcaaaa agacagcaga caaaatgaaa gaaatgaga cagaaagta agcatttcca | 240 |
| cctatctaa tttctttagt tttctatttg cctccagtgc agtccatttc ctaatgtata | 300 |
| cagcctact gtactattta aaatgctcaa tttcagcacc gatggacctg c | 351 |

<210> SEQ ID NO 194
<211> LENGTH: 311
<212> TYPE: DNA
<213> ORGANISM: Homo sapiens

<400> SEQUENCE: 194

| | |
|---|---|
| tgagacaca gaggcccact gcgaggggga cagtggcggt gggactgacc tgctgacagt | 60 |
| accctccct ctgctgggat gaggtccagg agccaactaa acaatggca gaggagacat | 120 |
| tctggtgtt cccaccaccc tagatgaaaa tccacagcac agacctctac cgtgtttctc | 180 |
| tccatccct aaaccacttc cttaaaatgt ttggatttgc aaagccaatt tggggcctgt | 240 |
| gagcctggg gttggatagg gccatggctg gtcccccacc atacctcccc tccacatcac | 300 |
| gacacagac c | 311 |

<210> SEQ ID NO 195
<211> LENGTH: 381
<212> TYPE: DNA
<213> ORGANISM: Homo sapiens

<400> SEQUENCE: 195

| | |
|---|---|
| tgtcagagtg gcactggtag aagttccagg aaccctgaac tgtaagggtt cttcatcagt | 60 |
| gccaacagga tgacatgaaa tgatgtactc agaagtgtcc tggaatgggg cccatgagat | 120 |

```
ggttgtctga gagagagctt cttgtcctgt cttttttcctt ccaatcaggg gctcgctctt      180
ctgattattc ttcagggcaa tgacataaat tgtatattcg gttcccggtt ccaggccagt      240
aatagtagcc tctgtgacac cagggcgggg ccgagggacc acttctctgg gaggagaccc      300
aggcttctca tacttgatga gtagccggt aatcctggca cgtggcggct gccatgatac       360
cagcagggaa ttgggtgtgg t                                                381
```

<210> SEQ ID NO 196
<211> LENGTH: 401
<212> TYPE: DNA
<213> ORGANISM: Homo sapiens

<400> SEQUENCE: 196

```
cacaaacaag aggagcacca gacctcctct tggcttcgag atggcttcgc cacaccaaga      60
gcccaaacct ggagacctga ttgagatttt ccgccttggc tatgagcact gggccctgta     120
tataggagat ggctacgtga tccatctggc tcctccaagt gagtaccccg gggctggctc     180
ctccagtgtc ttctcagtcc tgagcaacag tgcagaggtg aaacgggagc gcctggaaga     240
tgtggtggga ggctgttgct atcgggtcaa caacagcttg gaccatgagt accaaccacg     300
gcccgtggag gtgatcacca gttctgcgaa ggagatggtt ggtcagaaga tgaagtacag     360
tattgtgagc aggaactgtg agcactttgt cacccagacc t                         401
```

<210> SEQ ID NO 197
<211> LENGTH: 471
<212> TYPE: DNA
<213> ORGANISM: Homo sapiens

<400> SEQUENCE: 197

```
ctgtaatgat gtgagcaggg agccttcctc cctgggccac ctgcagagag ctttcccacc      60
aactttgtac cttgattgcc ttacaaagtt atttgtttac aaacagcgac catataaaag     120
cctcctgccc caaagcttgt gggcacatgg gcacatacag actcacatac agacacacac     180
atatatgtac agacatgtac tctcacacac acaggcacca gcatacacac gttttttctag    240 gtacagctcc caggaacagc taggtgggaa agtcccatca ctgagggagc taaccatgt      300 ccctgaacaa aaattgggca ctcatctatt ccttttctct tgtgtcccta ctcattgaaa     360
ccaaactctg gaaggaccc aatgtaccag tatttatacc tctagtgaag cacagagaga      420
ggaagagagc tgcttaaact cacacaacaa tgaactgcag acacagacct g              471
```

<210> SEQ ID NO 198
<211> LENGTH: 201
<212> TYPE: DNA
<213> ORGANISM: Homo sapiens

<400> SEQUENCE: 198

```
ggtccattga ggctctgtcg gccatgccca cagttcgaag ctttgccaac gaggagggcg      60
aagcccagaa gtttagggaa aagctgcaag aaataaagac actcaaccag aaggaggctg     120
tggcctatgc agtcaactcc tggaccacta gtatttcagg tatgctgctg aaagtgggaa     180
tcctctacat tggtgggcag a                                               201
```

<210> SEQ ID NO 199
<211> LENGTH: 551
<212> TYPE: DNA
<213> ORGANISM: Homo sapiens

```
<400> SEQUENCE: 199
tctggcacag atcttcaccc acacggcggt ccacgtgctg atcatcttcc gggtctcacc      60
gggcctggaa cacaccatct tccccatgag cccggtgccc agtctggtga cttccatctt     120 ggccctggc cttatgtccc agttatgacc cctgacttca actctggctc ttaccctgta      180
actccagtcc atctctgaca ttttaacac ccggccttgt gaccgtggac atagctcctg      240
acctcgattc ccatcttgag cccagtgtta gtccatgaga tcatgacctg actcctggtc     300
tccaaccttg tgatcctaat tctgggacct caatcctagc ctctgaactt gggaccctgg     360
agctcctgac cttagtcctg accgctaccc ttgattctga cctttgatcc tgtaacttag     420
gggtggcccc tgaccttatt actgtcattt agctccttga ccttgccact tcaatcctgg     480
ctttatgacc tcctactctc aattttaact ttaaccaaat gaccaaattt gtgacactaa     540
atgaccacaa t                                                          551

<210> SEQ ID NO 200
<211> LENGTH: 211
<212> TYPE: DNA
<213> ORGANISM: Homo sapiens
<220> FEATURE:
<221> NAME/KEY: misc_feature
<222> LOCATION: (1)...(211)
<223> OTHER INFORMATION: n=A,T,C or G

<400> SEQUENCE: 200
cagctcancg ggcgacatgc ccctacaagt tggcanaagn ggctgccact gctgggtttg      60
tgtaagagag gctgctgnca ccattacctg cagaaacctt ctcataggg  ctacgatcgg     120 tactgctagg gggcacatag cgcccatggg tgtggtaggt ggggnactcn ntnataggat     180
ggtaggtatc ccgggctgga aanatgnnca g                                    211

<210> SEQ ID NO 201
<211> LENGTH: 111
<212> TYPE: DNA
<213> ORGANISM: Homo sapiens

<400> SEQUENCE: 201
ccagtgaaag gaaacaaaac tggcagtttg tccatttgaa tatcagacct agtttcttct      60
taatttccac actatttctc ccatattcct taaacttctt ggcatccacc t              111

<210> SEQ ID NO 202
<211> LENGTH: 331
<212> TYPE: DNA
<213> ORGANISM: Homo sapiens

<400> SEQUENCE: 202 gaaaataca gaataccagg tggtcccaaa tgtttgaagt tctttgaaca gaaagagaga       60 gagagagag agagaggaaa attccctaac ccttggttta aagacaatat tcatttattg      120 tcaaatgat gcttttaagg gaggacagtg gaataaaata aactttttt ttctccctac       180 atacataga agggttatca aaccactcaa gtttcaaaat ctttccaggg tccaatatca      240 ttttttct ttcggttcaa tgaaaagcta aatgtaataa tactaattat agataaaatt       300 tattttact ttttaaaaat ttgtccagac c                                    331

<210> SEQ ID NO 203
<211> LENGTH: 491
<212> TYPE: DNA
<213> ORGANISM: Homo sapiens
```

<400> SEQUENCE: 203

```
agtcacccag tctacttagt acctggttgc tgcctctgac cttttcagct tgatacccctg      60 ggctttagtg taaccaataa atctgtagtg accttacctg tattccctgt gctatcctgt     120
gggaaggtag gaatgggcta agtatgatga atgtataggt tagggatctt ttggttttaa     180
atcacagaaa acctaattca aactggctta aaataaaaag gatttattgg ttcatgtaac     240
tagaaagtcc ataggtagtg ctggctccag gtgaagactt gacccagtag ttcagtatgt     300
ctctaaatac cggactgact tttttctcac tgttgcatct tctgtaggac catttaagtc     360
tgggccactt aatggctgcc agcattccta agattacact tttccccatt tatgtccaat     420
cagaaaaaga aggcatcttt gtaccagaaa tctcagcaaa gccctaata ttcacactga      480 ttaggacctg c                                                          491
```

<210> SEQ ID NO 204
<211> LENGTH: 361
<212> TYPE: DNA
<213> ORGANISM: Homo sapiens

<400> SEQUENCE: 204

```
tcccttcctc ccccatgtga taaatgggtc cagggctgat caaagaactc tgactgcaga      60
actgccgctc tcagtggaca gggcatctgt tatcctgaga cctgtggcag acacgtcttg     120
ttttcatttg attttttgtta agagtgcagt attgcagagt ctagaggaat ttttgtttcc     180
ttgattaaca tgatttttcct ggttgttaca tccagggcat ggcagtggcc tcagccttaa    240
acttttgttc ctactcccac cctcagcgaa ctgggcagca cggggagggt ttggctaccc     300
ctgcccatcc ctgagccagg taccaccatt gtaaggaaac actttcagaa attcagacct     360
c                                                                     361
```

<210> SEQ ID NO 205
<211> LENGTH: 471
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G
<221> NAME/KEY: misc_feature
<222> LOCATION: (3)
<223> OTHER INFORMATION: n=A,T,C or G

<400> SEQUENCE: 205

```
cnngtacagt tcttcctgga tggccgacac agatcctggg gaaaggcaat cctggcactg      60
ctctgaaacc agagctcctc ctccctcccc gggcagggtg gagctgagaa gggctgctct     120
agcgttggga ctccacctcc atacacctga tattttgata gggcaggtcc ctgctatggg     180
ccactgttct gggcagtata gtatgcttga cagcatcctt ggcatctatc caccagatcc     240
cagagcaccc gctactagct gtgacaacat cctccaaaca ttgcaaaatt tccctgggga    300
ggcaagattg cctcagatgg gagaatcacg ctctaggaa atctgctggt atgagaaccc     360
caactcccca ctccactgag cctccagatg gcgagcaggc tgcagctcca gcacagacac     420
gaagctccct ccagccactg acggtccatg gctggggtta cccaggacct c              471
```

<210> SEQ ID NO 206
<211> LENGTH: 261
<212> TYPE: DNA
<213> ORGANISM: Homo sapiens

<400> SEQUENCE: 206

| | |
|---|---|
| tagagtattt agagtcctga gataacaagg aatccaggca tcctttagac agtcttctgt | 60 |
| tgtcctttct tcccaatcag agatttgtgg atgtgtggaa tgacaccacc accagcaatt | 120 |
| gtagccttga tgagagaatc caattcttca tctccacgaa tagcaagttg caagtgacga | 180 |
| ggggtaatac gctttacctt taagtctttt gatgcatttc ctgccagttc aagtacctct | 240 |
| gcggtgaggt actccaggat g | 261 |

<210> SEQ ID NO 207
<211> LENGTH: 361
<212> TYPE: DNA
<213> ORGANISM: Homo sapiens

<400> SEQUENCE: 207

| | |
|---|---|
| gctctccggg agcttgaaga agaaactggc tacaaagggg acattgccga atgttctcca | 60 |
| gcggtctgta tggacccagg cttgtcaaac tgtactatac acatcgtgac agtcaccatt | 120 |
| aacggagatg atgccgaaaa cgcaaggccg aagccaaagc caggggatgg agagtttgtg | 180 |
| gaagtcattt ctttacccaa gaatgacctg ctgcagagac ttgatgctct ggtagctgaa | 240 |
| gaacatctca cagtggacgc cagggtctat tcctacgctc tagcactgaa acatgcaaat | 300 |
| gcaaagccat tgaagtgcc cttcttgaaa ttttaagccc aaatatgaca ctggacctgc | 360 |
| c | 361 |

<210> SEQ ID NO 208
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 208

| | |
|---|---|
| agaggagatn tttgccatgc ctgaatnctt tcctatncca ccctancact taacatatta | 60 |
| cttagtctgc tttgntaaaa gcaagtatta ccttnaactt gnctcttact cttttgccctt | 120 |
| tagctaacta ataaagnttg atntaggcat tattatataa ttctgagtca ttcatggtat | 180 |
| ctctcatgtt tgatgtattt tncaaactaa gatctatgat agtttttttt ccanagttcc | 240 |
| attaaatcat ttatttcctt tactttctca cctctgtnga aacatttaga aactggattt | 300 |
| gggaacccan ttttggaaaa ccagattcat agtcatgaaa atggaaactt ncatattctg | 360 |
| ttttttgaaaa gatgtggacc t | 381 |

<210> SEQ ID NO 209
<211> LENGTH: 231
<212> TYPE: DNA
<213> ORGANISM: Homo sapiens
<220> FEATURE:
<221> NAME/KEY: misc_feature
<222> LOCATION: (83)
<223> OTHER INFORMATION: n=A,T,C or G

<400> SEQUENCE: 209

| | |
|---|---|
| gtggagagca agtgatttat taaagcaaga cgttgaaacc tttacattct gcagtgaaga | 60 |
| tcagggtgtc attgaaagac agnggaaacc aggatgaaag tttttacatg tcacacacta | 120 |
| catttcttca atattttcac caggacttcc gcaatgaggc ttcgtttctg aagggacatc | 180 |

```
tgatccgtgc atctcttcac tcctaacttg gctgcaacag cttccacctg c            231
```

```
<210> SEQ ID NO 210
<211> LENGTH: 371
<212> TYPE: DNA
<213> ORGANISM: Homo sapiens

<400> SEQUENCE: 210
tccatcctgg ttttgcagag atcaggttgt tgacagttcc tggttgaccc acagctaccc    60
atgtcagtta tctccactaa catatccaag aatctttgta ggacaatttc tccacctgca   120
aggttttta ggtagaactc ttcttttaag gcaattagcc cattgccaaa aggttttact   180
gtcttaaagc tgtctttctg agatctaatt ccaaggactt ctccacagct aagtgagatg   240
cctcacacca ttaggtgatg ctttggacag aacagagtat tttcatcttg tgtttaaagc   300
aattccttgg cttcggctcc tcaccacttt ctatgccagt ctcccattta tgtccctagt   360
aatgcctatg c                                                        371

<210> SEQ ID NO 211
<211> LENGTH: 471
<212> TYPE: DNA
<213> ORGANISM: Homo sapiens

<400> SEQUENCE: 211
tttattttaa aagaaaaaaa ttaaaataga gccaacaaat gcaattaaga aaaaaaagt     60
attgagacac aagggacct acatgttctg gtctaagaag catgcaagta ttacaaagca   120
ttccagatac agtatgacag aggaacagtg aacaagcatt ggaacgatgc tctttctttc   180
agaaacggga agtctaacag ttatgttttc acaatggtag tgattaaacc atctttattt   240
ttaaggaatt ttataggaag aattttagca ccatcattaa aggaaaaata ataataccttt  300
tttagccctg cctatctcca gtcttggaat aataacagaa gcatagcacc tttcagtatc   360
taaaatataa acaagaatag taagtccatc ccagcttcta gagatgaggt agctcatgct   420
aagaaatgtt gggtcatttt tcctatgaaa gttcaaaggc caaatggtca c            471

<210> SEQ ID NO 212
<211> LENGTH: 401
<212> TYPE: DNA
<213> ORGANISM: Homo sapiens

<400> SEQUENCE: 212
tggcctgtct ccttcacata gtccatatca ccacaaatca cacaacaaaa gggagaggat    60
atattttggg ttcaaaaaaa gtaaaaagat aatgtagctg catttctttg gttattttgg   120
gccccaaata tttcctcatc ttttgttgt tgtcatggat ggtggtgaca tggacttgtt    180
tatagaggac aggtcagctc tctggctcgg tgatctacat tctgaagttg tctgaaaatg   240
tcttcatgat taaattcagc ctaaacgttt tgccgggaac actgcagaga caatgctgtg   300
agtttccaac ctcagcccat ctgcgggcag agaaggtcta gtttgtccat caccattatg   360
atatcaggac tggttacttg gttaaggagg ggtctacctc g                       401

<210> SEQ ID NO 213
<211> LENGTH: 461
<212> TYPE: DNA
<213> ORGANISM: Homo sapiens
<220> FEATURE:
<221> NAME/KEY: misc_feature
<222> LOCATION: (1)...(461)
<223> OTHER INFORMATION: n=A,T,C or G
```

<400> SEQUENCE: 213

```
tgtgaagcat acataaataa atgaagtaag ccatactgat ttaatttatt ggatgttatt      60
ttccctaaga cctgaaaatg aacatagtat gctagttatt tttcagtgtt agccttttac     120
tttcctcaca caatttggaa tcatataata taggtacttt gtccctgatt aaataatgtg     180
acggatagaa tgcatcaagt gtttattatg aaaagagtgg aaaagtatat agcttttanc     240
aaaaggtgtt tgcccattct aagaaatgag cgaatatata gaaatagtgn gggcatttct     300
tcctgttagg tggagtgtat gtgttgacat ttctccccat ctcttcccac tctgttttnnt    360
ccccattatt tgaataaagt gactgctgaa nangactttg aatccttatc cacttaattt     420
aatgtttaaa gaaaaaccta taatggaaag tgagactcct t                         461
```

<210> SEQ ID NO 214
<211> LENGTH: 181
<212> TYPE: DNA
<213> ORGANISM: Homo sapiens

<400> SEQUENCE: 214

```
cctgagcttc tactcctttc ccttaagatt cctccaaagc accagctcca taaaatcctt      60
cagctcccca gacccacacc aagaaccca  catgttaatt ggatcagcca aatctacaag     120
cagataagtc ctaaggagaa tgccgaagcg ttttcttct  tcctcaagcc tagcatgaga    180
c                                                                    181
```

<210> SEQ ID NO 215
<211> LENGTH: 581
<212> TYPE: DNA
<213> ORGANISM: Homo sapiens

<400> SEQUENCE: 215

```
ctgctttaag aatggttttc caccttttcc ccctaatctc taccaatcag acacatttta      60
ttatttaaat ctgcacctct ctctatttta tttgccaggg gcacgatgtg acatatctgc     120
agtcccagca cagtgggaca aaaagaattt agaccccaaa agtgtcctcg gcatggatct     180
tgaacagaac cagtatctgt catggaactg aacattcatc gatggtctcc atgtattcat     240
ttattcactt gttcattcaa gtatttattg aatacctgcc tcaagctaga gagaaaagag     300
agtgcgcttt ggaaatttat tccagttttc agcctacagc agattatcag ctcggtgact     360
tttctttctg ccaccattta ggtgatggtg tttgattcag agatggctga atttctattc     420
ttagcttatt gtgactgttt cagatctagt ttgggaacag attagaggcc attgtcctct     480
gtcctgatca ggtggcctgg ctgtttcttt ggatccctct gtcccagagc cacccagaac     540
cctgactctt gagaatcaag aaaacaccca gaaggacct c                          581
```

<210> SEQ ID NO 216
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 216

```
ccgatgtcct gcttctgtgg accaggggct cctctgnngg tggcctcaac cacggctgag      60
atccctagaa gtccaggagc tgtggggaag agaagcactt agggccagcc agccgggcac     120
```

-continued

| | |
|---|---|
| ccccacttgc gccccgaccc acgctcacgc accagacctg cccnggcggt cgctcnaaag | 180 |
| ggcgaattct gcagatatcc atcacactgg cggacgctcg agcatgcatc tagagggccc | 240 |
| aattcaccct atantgagtc gtattacaat tcactggccg t | 281 |

<210> SEQ ID NO 217
<211> LENGTH: 356
<212> TYPE: DNA
<213> ORGANISM: Homo sapiens
<220> FEATURE:
<221> NAME/KEY: misc_feature
<222> LOCATION: (1)...(356)
<223> OTHER INFORMATION: n=A,T,C or G

<400> SEQUENCE: 217

| | |
|---|---|
| tagcaggtt tcaacaattg tcttgtagtt tgnagtaaaa agacataaga aagagaaggt | 60 |
| tggtttgca gcaatccgta gttggtttct caccataccc tgcagttctg tgagccaaag | 120 |
| tcttgcaga aagttaaaat aaatcacaaa gactgctgtc atatattaat tgcataaaca | 180 |
| ctcaacatt gctcagagtt tcatccgttt ggttaagaaa acattccttc aattcatcta | 240 |
| ggcatttgt agtggcattg tcgtctatga actcttgaag aagttctttg tattcagtct | 300 |
| agacacttg tggattgatt gncttggaaa tcacattctc caataaggga cctcgg | 356 |

<210> SEQ ID NO 218
<211> LENGTH: 321
<212> TYPE: DNA
<213> ORGANISM: Homo sapiens

<400> SEQUENCE: 218

| | |
|---|---|
| tgtccatcg ggagaaaggt gtttgtcagt tgtttcataa accagattga ggaggacaaa | 60 |
| tgctctgcc aatttctgga tttctttatt ttcagcaaac actttcttta aagcttgact | 120 |
| tgtgggcac tcatccaagt gatgaataat catcaagggt tgttgcttg tcttggattt | 180 |
| tatagagct tcttcatatg tctgagtcca gatgagttgg tcaccccaac ctctggagag | 240 |
| gtctgggc agtttgggtc gagagtcctt tgtgtccttt ttggctccag gtttgactgt | 300 |
| gtatctctg gacctgcctg g | 321 |

<210> SEQ ID NO 219
<211> LENGTH: 271
<212> TYPE: DNA
<213> ORGANISM: Homo sapiens
<220> FEATURE:
<221> NAME/KEY: misc_feature
<222> LOCATION: (41)
<223> OTHER INFORMATION: n=A,T,C or G

<400> SEQUENCE: 219

| | |
|---|---|
| ccggttaggt ccacgcgggg gcagtggagg cacaggctca nggtggccgg gctacctggc | 60 |
| accctatggc ttacaaagta gagttggccc agtttccttc cacctgaggg gagcactctg | 120 |
| actcctaaca gtcttccttg ccctgccatc atctggggtg gctggctgtc aagaaaggcc | 180 |
| gggcatgctt tctaaacaca gccacaggag gcttgtaggg catcttccag gtggggaaac | 240 |
| agtcttagat aagtaaggtg acttgtctaa g | 271 |

<210> SEQ ID NO 220
<211> LENGTH: 351
<212> TYPE: DNA
<213> ORGANISM: Homo sapiens
<220> FEATURE:
<221> NAME/KEY: misc_feature

```
<222> LOCATION: (1)...(351)
<223> OTHER INFORMATION: n=A,T,C or G

<400> SEQUENCE: 220 tcctacgac gaggaccagc ttttcttctt cnactttcc canaacactc gggtgcctcg      60 ctgcccgaa tttgctgact gggctcagga acagggagat gctcctgcca ttttatttga    120 aaagagttc tgcgagtgga tgatccagca aatagggcca aaacttgatg ggaaaatccc    180 gtgtccaga gggtttccta tcgctgaagt gttcacgctg aagcccctgg agtttggcaa    240 cccaacact ttggtctgtt ttgtcagtaa tctcttccca cccatgctga cagtgaactg    300 tagcatcat tccgtccctg tggaaggatt tgggcctact tttgtctcag a             351

<210> SEQ ID NO 221
<211> LENGTH: 371
<212> TYPE: DNA
<213> ORGANISM: Homo sapiens

<400> SEQUENCE: 221
gtctgcagaa gcgtgtctga ggtgtccggt ggaggtggca gccgagctct gggactaatc     60
accgtgctgg ggacggcacc gcgtcaggat gcaggcagat ccctgcagaa gtgtctaaaa   120
ttcacactcc tcttctggag ggacgtcgat ggtattagga tagaagcacc aggggacccc   180
acgaacggtg tcgtcgaaac agcagccctt atttgcacac tgggagggcg tgacaccagg   240
aaaaccacaa ttctgtcttt cacgggggc cactgtacac gtctctgtct gggcctcggc    300
cagggtgccg agggccagca tggacaccag gaccagggcg cagatcacct tgttctccat    360
ggtggacctc g                                                          371

<210> SEQ ID NO 222
<211> LENGTH: 471
<212> TYPE: DNA
<213> ORGANISM: Homo sapiens

<400> SEQUENCE: 222
gtccatgttc catcattaat gttccaacat caccagggac acaaagctgc aaaaatgaga     60
agggaaataa ggttagagaa aggatccggg caatcttaag gactgaggaa gacatgttcc   120
ccaacccttg aactcacaaa ccctgaagct caaggattgc atccttcctc caaatctcac   180
tcaacataat aagtgcagaa caacatgcca aagcactgta tgaagcacta gggacaaaga   240
caaggtcaaa atccttgtaa ccaaatttaa tggtattgta atgcagtgtt aacacaggac   300
agtaacagaa cacccaagaa ccaaacagaa gagggtaggg ataagcataa atgaagtaac   360
atgaaataaa cttccaaatg gaaaacttgt ccataccccc agggcaagtc aactacagtc   420
tcccaaagga cataaattcc acttagggca cactagacag aaaacaatat t             471

<210> SEQ ID NO 223
<211> LENGTH: 411
<212> TYPE: DNA
<213> ORGANISM: Homo sapiens

<400> SEQUENCE: 223
agttgctcta caatgacaca caaatcccgt taaataaatt ataaacaagg gtcaattcaa     60
atttgaagta atgttttagt aaggagagat tagaagacaa caggcatagc aaatgacata   120
agctaccgat taactaatcg gaacatgtaa aacagttaca aaaataaacg aactctcctc   180
ttgtcctaca atgaaagccc tcatgtgcag tagagatgca gtttcatcaa agaacaaaca   240
```

```
tccttgcaaa tgggtgtgac gcggttccag atgtggattt ggcaaaacct catttaagta      300
aaaggttagc agagcaaagt gcggtgcttt agctgctgct tgtgccgctg tggcgtcggg      360
gaggctcctg cctgagcttc cttccccagc tttgctgcct gagaggaacc a              411
```

<210> SEQ ID NO 224
<211> LENGTH: 321
<212> TYPE: DNA
<213> ORGANISM: Homo sapiens
<220> FEATURE:
<221> NAME/KEY: misc_feature
<222> LOCATION: (31)
<223> OTHER INFORMATION: n=A,T,C or G

<400> SEQUENCE: 224

```
gtctgaagt ttgataacaa agaaatatat ntaagacaaa aatagacaag agttaacaat        60 aaaacacaa ctatctgttg acataacata tggaaacttt ttgtcagaaa gctacatctt       120 ttaatctga ttgtccaaat cattaaaata tggatgattc agtgccattt tgccagaaat       180 cgtttggct ggatcataga ttaacattt cgagagcaaa tccaagccat tttcatccaa       240 tttttgaca tgggatgcta ggcttcctgg tttccatttg ggaaatgtat tcttatagtc      300 tgtaaagat tccacttctg g                                                 321
```

<210> SEQ ID NO 225
<211> LENGTH: 251
<212> TYPE: DNA
<213> ORGANISM: Homo sapiens
<220> FEATURE:
<221> NAME/KEY: misc_feature
<222> LOCATION: (34)
<223> OTHER INFORMATION: n=A,T,C or G

<400> SEQUENCE: 225

```
atgtctgggg aaagagttca ttggcaaaag tgtnctccca agaatggttt acaccaagca       60
gagaggacat gtcactgaat ggggaaaggg aaccccgta tccacagtca ctgtaagcat      120
ccagtaggca ggaagatggc tttgggcagt ggctggatga agcagattt gagatacccca     180 gctccggaac gaggtcatct tctacaggtt cttccttcac tgagacaatg aattcagggt     240
gatcattctc t                                                           251
```

<210> SEQ ID NO 226
<211> LENGTH: 331
<212> TYPE: DNA
<213> ORGANISM: Homo sapiens
<220> FEATURE:
<221> NAME/KEY: unsure
<222> LOCATION: (1)...(331)
<223> OTHER INFORMATION: n=A,T,C or G

<400> SEQUENCE: 226

```
ttaggtccc aggcccccg ccaagnggtt accnnnntna ccactcctga cccaaaaatc         60 ggcatggca ttaaaacgtt gcaaattcct ttactgttat ccccccacc accaggacca       120 gtagggtgc agtctttact ccctaacccg tttcccgaaa aagtgctac ctcctttcca      180 acagatgag agagggcagg acttcaggct ggatccacca ctgggctctc cctcccccag     240 ctggagcac gggaggggag gtgacggctg gtgactgatg gatgggtagt gggctgagaa     300 aggggacta ggaagggcta ttccaggctc a                                      331
```

<210> SEQ ID NO 227
<211> LENGTH: 391

```
<212> TYPE: DNA
<213> ORGANISM: Homo sapiens

<400> SEQUENCE: 227
aggtctgccc ttgaagtata ggaaggaatc atagttggag gacttctgca ttatttgttg      60
gctgaagcta gaagtgcaac ccctcctga tttctgcagc aagatgaact gccttatccc     120
cagcccgcag gaatgttcat atctgagcaa tcaatgggca ctgtgttcaa ccacgccatt    180
ttcaagattg gctccttaaa ccacccacaa ggcaccagct ctgggagaag ctgcagggag    240
aagagaacaa agccctcgct gtgatcagga tgggtgtctc atacctttc tctgggtca    300 ttccaggtat gagacagagt tgaacctgcg catgagcgtg gaggccgaca tcaacggcct    360
gcgcagggtg ctggatgagc tgaccctgga c                                   391

<210> SEQ ID NO 228
<211> LENGTH: 391
<212> TYPE: DNA
<213> ORGANISM: Homo sapiens
<220> FEATURE:
<221> NAME/KEY: misc_feature
<222> LOCATION: (35)
<223> OTHER INFORMATION: n=A,T,C or G

<400> SEQUENCE: 228
gttgtccata gccacctcct gggatagaag ctttntagtt catagttcga ttagtgtgtc     60
cttaggacat aggtccagcc ctacagatta gctgggtgaa gaaggcaagt gtctcgacag    120
ggcttagtct ccaccctcag gcatggaacc attcagggtg aagcctggga tgtgggcaca    180
ggagactcag gctgatataa aataacaaa atcagtaata aaaaaattat aaaacctgtt    240
gcttgtctga atagatttga gcaacagtct tgcttttgtt aaaatcctgg agccgttaag    300
tcctgaatat tcttctggac atcattgctg gctggagaaa ggagcccag gcccggctcg    360 gctgacatct gtcaggtttg gaagtctcat c                                   391

<210> SEQ ID NO 229
<211> LENGTH: 341
<212> TYPE: DNA
<213> ORGANISM: Homo sapiens
<220> FEATURE:
<221> NAME/KEY: misc_feature
<222> LOCATION: (202)
<223> OTHER INFORMATION: n=A,T,C or G

<400> SEQUENCE: 229 tccatggct tctcacccag acagtctttc tgggcaactt ggggaagccc ctgttctgct       60 aagtctcac cccatggaag aggtggggga aggggccttt ggttttcag gaagacgggt      120 ggagagcac gagtcactac aaagcagtaa aagtgaatgg tgtctccagg ggctgggtcc    180 gaacaccgc ggagagcccc anccataaag gtgtgttccg cctctggcct gcaggaatct    240 tttgaatct ctttgattgg tggctccaag agcaatggga agtcaacagc caggaggctg    300 actgggttc cctgggaccc cgaggtccca gaggctgctg g                         341

<210> SEQ ID NO 230
<211> LENGTH: 511
<212> TYPE: DNA
<213> ORGANISM: Homo sapiens

<400> SEQUENCE: 230
gtccaagcca aggaaaccat tcccttacag gagacctccc tgtacacaca ggaccgcctg      60
```

-continued

| | |
|---|---|
| gggctaaagg aaatggacaa tgcaggacag ctagtgtttc tggctacaga aggggaccat | 120 |
| cttcagttgt ctgaagaatg gttttatgcc cacatcatac cattccttgg atgaaacccg | 180 |
| tatagttcac aatagagctc agggagcccc taactcttcc aaaccacatg ggagacagtt | 240 |
| tccttcatgc ccaagcctga gctcagatcc agcttgcaac taatccttct atcatctaac | 300 |
| atgccctact tggaaagatc taagatctga atcttatcct ttgccatctt ctgttaccat | 360 |
| atggtgttga atgcaagttt aattaccatg agattgttt tacaaacttt tgatgtggtc | 420 |
| aagttcagtt ttagaaaagg gagtctgttc cagatcagtg ccagaactgt gcccaggccc | 480 |
| aaaggagaca actaactaaa gtagtgagat a | 511 |

<210> SEQ ID NO 231
<211> LENGTH: 311
<212> TYPE: DNA
<213> ORGANISM: Homo sapiens

<400> SEQUENCE: 231

| | |
|---|---|
| gtccaagta agctgtgggc aggcaagccc ttcggtcacc tgttggctac acagacccct | 60 |
| ccctcgtgt cagctcaggc agctcgaggc ccccgaccaa cacttgcagg ggtccctgct | 120 |
| gttagcgcc ccaccgccgt ggagttcgta ccgcttcctt agaacttcta cagaagccaa | 180 |
| ctccctgga gcccgttgg cagctctagc tttgcagtcg tgtaattggc ccaagtcatt | 240 |
| tttttctcg cctcactttc caccaagtgt ctagagtcat gtgagcctcg tgtcatctcc | 300 |
| gggtggacc t | 311 |

<210> SEQ ID NO 232
<211> LENGTH: 351
<212> TYPE: DNA
<213> ORGANISM: Homo sapiens

<400> SEQUENCE: 232

| | |
|---|---|
| cgtttagct aataatccct tccttgatga tacactccaa cttcttgttt ttctttattt | 60 |
| taaaaagcg gttctgtaac tctcaatcca gagatgttaa aaatgtttct aggcacggta | 120 |
| tagtaaatc aagtaaattt catgtcctct taaggacaa acttccagag atttgaatat | 180 |
| aatttttat atgtgttatt gattgtcgtg taacaaatgg cccccacaaa ttagtagctt | 240 |
| aaatagcat ttatgatgtc actgttttct ttgccttttc attaatgttc tgtacagacc | 300 |
| atgtaaaca acttttgtat atgcatatag gatagctttt ttgagggtat a | 351 |

<210> SEQ ID NO 233
<211> LENGTH: 511
<212> TYPE: DNA
<213> ORGANISM: Homo sapiens

<400> SEQUENCE: 233

| | |
|---|---|
| aggtctggat gtaaggatgg atgctctcta tacatgctgg gttggggatg ctgggactgc | 60 |
| acagccaccc ccagtatgcc gctccaggac tctgggacta gggcgccaaa gtgtgcaaat | 120 |
| gaaaatacag gatacccagg gaactttgaa tttcagattg tgaaagaaa acaaatcttg | 180 |
| agactccaca atcaccaagc taaggaaaa agtcaagctg ggaactgctt agggcaaagc | 240 |
| tgcctcccat tctattcaca gtcatccccc tgaggctcac ctgcatagct gattgcttcc | 300 |
| tttcccctat cgcttctgta aaatgcaga ctcactgagc cagactaaat tgtgtgttca | 360 |
| gtggaaggct gatcaagaac tcaaaagaat gcaaccttt gtctcttatc tactacaacc | 420 |
| aggaagcccc cacttaaggg ttgtcccacc ttactggact gaaccaaggt acatcttaca | 480 |

```
cctactgatt gatgtctcat gtcccccctaa g                                  511
```

<210> SEQ ID NO 234
<211> LENGTH: 221
<212> TYPE: DNA
<213> ORGANISM: Homo sapiens

<400> SEQUENCE: 234

```
caggtccagc gaagggggctt cataggctac accaagcatg tccacataac cgaggaagct   60
ctctccatca gcatagcctc cgatgaccat ggtgttccac aaagggttca tcttcgagcg   120
ccggctgtac atggccctgg tcagccatga atgaatagct ctaggactat agctgtgtcc   180
atctcccaga agctcctcat caatcaccat ctggccgaga c                        221
```

<210> SEQ ID NO 235
<211> LENGTH: 381
<212> TYPE: DNA
<213> ORGANISM: Homo sapiens
<220> FEATURE:
<221> NAME/KEY: misc_feature
<222> LOCATION: (33)
<223> OTHER INFORMATION: n=A,T,C or G

<400> SEQUENCE: 235

```
ggtccaagaa agggacatct atgtgaaagt ganactgaga cagtgctggt cacaggtcat   60
gctgcagaat aatacattcc caggcactgt cacgtggggg acccaagagg ccccaggagt   120
gacctataac ctctccagaa agaccactct gtgtggcatc acagtccaca cagtttaagg   180
aaatatttag acttaacaat cagacaccag ctcttactca cacttacact cacagcccac   240
acacaagtgt gcaaacatac acacacatat atatttcctg atacattcat ggaatatcag   300
agccctgccc tgaagtcgtt agtgtctctg ctcccccaaac cgctgctccc acattggcta   360
agctccctca agagacctca g                                              381
```

<210> SEQ ID NO 236
<211> LENGTH: 441
<212> TYPE: DNA
<213> ORGANISM: Homo sapiens

<400> SEQUENCE: 236

```
aggtcctgtt gcccctttct tttgcccaac ttcgccattt gggaattgga atatttaccc   60
aacacctgta ctgcattgaa tattggaagc aaataacttg gctttgatct tataggctca   120
cagatggagg aacgtacctt gaagttcaga tgagatttcg acttttgag ttgatgctga    180
aacagcttga gattttttggg gactactgag agatgataat tgtattgtgc aatatgagaa   240
ggacatgaga tttggtgggc ataggtgtga atgacattg tttggatgtg tttaccctcc    300
aaatctcttg ttgaatgtga tcttaaacgt tggtggtggg cctagtggaa ggtgttgaat   360
catgggggtg gactcttcat aatttgctta gctccatccc cttggtgatg agcaagtcct   420
tgctctgttg tgtcacatga g                                              441
```

<210> SEQ ID NO 237
<211> LENGTH: 281
<212> TYPE: DNA
<213> ORGANISM: Homo sapiens
<220> FEATURE:
<221> NAME/KEY: misc_feature
<222> LOCATION: (1)...(281)
<223> OTHER INFORMATION: n=A,T,C or G

<400> SEQUENCE: 237

```
tcctaaaaaa ttagctgacc ttgttaaaaa tgttggcgtg agcagtatat tattacctat    60
cttttttat tgtgtgtgtg ngtgtgtgtn ttaaactaat tggctgaaat atctgcctgt    120
ttccctcttt acatttttct tgtttctttc cttatttatc tttgtccatc ttgagatcta    180
ctgtaaagtg aatnttttaa tgaaaacann nccaagttnt actctcactg ggnttgggac    240
atcagatgta attgagaggc aacaggtaa gtcttcatgt c                        281
```

<210> SEQ ID NO 238
<211> LENGTH: 141
<212> TYPE: DNA
<213> ORGANISM: Homo sapiens
<220> FEATURE:
<221> NAME/KEY: misc_feature
<222> LOCATION: (1)...(141)
<223> OTHER INFORMATION: n=A,T,C or G

<400> SEQUENCE: 238

```
gtctgcctcc tcctactgtt tccctctatn aaaaagcctc cttggcgcag gttccctgag    60
ctgtgggatt ctgcactggt gcttnggatt ccctgatatg ttccttcaaa tccactgaga    120
attaaataaa catcgctaaa g                                              141
```

<210> SEQ ID NO 239
<211> LENGTH: 501
<212> TYPE: DNA
<213> ORGANISM: Homo sapiens
<220> FEATURE:
<221> NAME/KEY: misc_feature
<222> LOCATION: (1)...(501)
<223> OTHER INFORMATION: n=A,T,C or G

<400> SEQUENCE: 239

```
aacaatctaa acaaatccct cggttctann atacaatgga ttccccatat tggaaggact    60
ctgangcttt attccccac tatgcntatc ttatcatttt attattatac acacatccat    120
cctaaactat actaaagccc ttttcccatg catggatgga aatggaagat ttttttttaa    180
cttgttctag aagtcttaat atgggctgtt gccatgaagg cttgcagaat tgagtccatt    240
ttctagctgc ctttattcac atagtgatgg ggtactaaaa gtactgggtt gactcagaga    300
gtcgctgtca ttctgtcatt gctgctactc taacactgag caacactctc ccagtggcag    360
atccctgta tcattccaag aggagcattc atcccctttgc tctaatgatc aggaatgatg    420
cttattagaa acaaactgc ttgacccagg aacaagtggc ttagcttaag naaacttggc    480
tttgctcana tccctgatcc t                                              501
```

<210> SEQ ID NO 240
<211> LENGTH: 451
<212> TYPE: DNA
<213> ORGANISM: Homo sapiens

<400> SEQUENCE: 240

```
tgtcctgaaa ggccattact aatagaaaca cagcctttcc aatcctctgg aacatattct    60
gtctgggttt ttaatgtctg tggaaaaaaa ctaaacaagt ctctgtctca gttaagagaa    120
atctattggt ctgaaggttt ctgaacctct ttctggttct cagcagaagt aactgaagta    180
gatcaggaag gggctgcctc aggaaaaattc ctagatccta ggaattcagt gagaccctgg    240
gaaggaccag catgctaatc agtgtcagtg aatccacagt ctttacttcc tgcctcataa    300
agggccaggt ctccccagta ccaagtcctt tcctcatgaa gttgtgttgc ctcaggctgt    360
```

```
ttagggacca ttgcctgtct tggtcacatg agtctgtctc cttactttag tccctgggca      420
atccttgctt aatgcttttg ttgactcaac g                                     451

<210> SEQ ID NO 241
<211> LENGTH: 411
<212> TYPE: DNA
<213> ORGANISM: Homo sapiens
<220> FEATURE:
<221> NAME/KEY: misc_feature
<222> LOCATION: (1)...(411)
<223> OTHER INFORMATION: n=A,T,C or G

<400> SEQUENCE: 241
aatctccagt gtgatggtat cggggttaga gcttcaatct ccagtgtgat ggtactgcag       60
cnagagcttc aatctccagt gngatggtat tagggttaga tcttcaatct ccagtgtgat      120
ggtatcaggg ttagagcttc agcctccagt gtgatggtat cagggttaga gcttcagcct      180
ccagtgtgat ggtatcgggg ttagatcttc aatccccagt ggtggtggtt agagcttcaa     240
tctccagtgt gatggtattg gggttagagc ttcaatctcc agtctgatgg tgtttcggga      300
tggggctttt aagatgtaat tagggtttaa gatcataagg gacctggtct gatggggatt      360
agtncgcttn tatgaagaga cacangaggg cttgctctat ctctgactct c                411

<210> SEQ ID NO 242
<211> LENGTH: 351
<212> TYPE: DNA
<213> ORGANISM: Homo sapiens

<400> SEQUENCE: 242 tccccttca caacagtaga gacctacaca gtgaactttg gggacttctg agatcagcgt        60 ctaccaaga ccccagccca actcaagcta cagcagcagc acttcccaag cctgctgacc       120 cagtcacat cacccatcag cacatggaag gcccctggta tggacactga aaggaagggc       180 ggtcctgcc cctttgaggg ggtgcaaaca tgactgggac ctaagagcca gaggctgtgt      240 gaggctcct gctccacctg ccagtctcgt aagaaatggg gttgctgcag tgttggagta      300 gggcagagg gagggagcca aggtcactcc aataaaacaa gctcatggca c                351

<210> SEQ ID NO 243
<211> LENGTH: 241
<212> TYPE: DNA
<213> ORGANISM: Homo sapiens

<400> SEQUENCE: 243
gtctgtgctt tatcaggaaa agcacaagaa tatgttttc tacctaaaac cctcttctac        60
tttaaaaatg gtttgctgaa tttttctatg ttttttaaat gttttttatgc tttttttttaa   120 acacgtaaag gatggaacct aatcctctcc cgagacgcct cctttgtgtt aatgcctatt      180
cttacaacag agaaacaagt acattaatat aaaaacgagt tgattattgg ggtataaaat      240
a                                                                      241

<210> SEQ ID NO 244
<211> LENGTH: 301
<212> TYPE: DNA
<213> ORGANISM: Homo sapiens

<400> SEQUENCE: 244
ggtccagagc aatagcgtct gtggtgaagc gcctgcactc ctcgggagac atgcctggct        60
```

```
tatatgctgc atccacataa ccatagataa aggtgctgcc ggagccacca atggcaaaag      120
gctgtcgagt cagcattcct cccagggttc catatacctg acctccttca cgttggtccc      180
agccagctac catgagatgt gcagacaagt cctctcgata tttatagctg atatttctca      240
ccacatttgc agcagccaaa acaagtggag gttcctccag ttctatccca tggagctcca      300
g                                                                     301

<210> SEQ ID NO 245
<211> LENGTH: 391
<212> TYPE: DNA
<213> ORGANISM: Homo sapiens

<400> SEQUENCE: 245
ctgacactgc tgatgtgggc cggggggcgc cgaggcacaa ctggtggccg gaccattgag       60
gcacctggag ggtaggcagc ttgtggtgca gacaccacag agagagaaaa gttggatgga      120
gtggtgggaa taatcagggt ggcacactgt gcctagaagc ttccagggcc accaagagaa      180
tgggaaggga aactacaaca ttcacaacag aaataggagt caattcactt agacccagaa      240
ctccagaaag ggggagtgta ggaatctaca atttcaaagc cagctcgtgt ctacctagag      300
ccccaaactg cataagcacc aggattgtac accttagtcc ctcaagatag tttcaagtga      360
gcgtgcaatt cactcttaca gaggagggcc t                                    391

<210> SEQ ID NO 246
<211> LENGTH: 291
<212> TYPE: DNA
<213> ORGANISM: Homo sapiens
<220> FEATURE:
<221> NAME/KEY: misc_feature
<222> LOCATION: (1)...(291)
<223> OTHER INFORMATION: n=A,T,C or G

<400> SEQUENCE: 246
tcctccacag gggaagcagg aagttngacc agcttcaggc tggaacgtgc ccagggcaca       60
gagctggcaa ggtgcaaagn cntctgcaga atattcacca ggttgacaca gacctccaca      120
ttcagacata ttccaagctt ctggggtctt cagggcccca gaatttcctg gtcttgggca      180
tggtncacaa gtcatttgtc cttcctcatt ttggaaggtt ccatttggac ataaaatgca      240
agcgttctcg tgctncatna taataggtcc cagcctgcac tgacacattt g               291

<210> SEQ ID NO 247
<211> LENGTH: 471
<212> TYPE: DNA
<213> ORGANISM: Homo sapiens
<220> FEATURE:
<221> NAME/KEY: misc_feature
<222> LOCATION: (1)...(471)
<223> OTHER INFORMATION: n=A,T,C or G

<400> SEQUENCE: 247
cactgagtga atgagtatat aatttatgaa aacagaaaag tgctttggaa aaaaaaaag        60 acaacaggag tacatacagn gaaccaaaaa gagtgtacca ggaggagcan accctgaaca      120
gttanaacta tggaaatcgc tatgctttgt gttgtcacag gagttaaaat aggaataccc      180
tgcatacaat aaatatttat tggataaata actaagcctg ataccctttt caatgcgtta      240
tacanactnt atcatcacac cactaatcta agttctcana agttaaacat tacaagactt      300
cagaacaaca taggcgtntt tggctccatt taacanaana aggaccatag tgatcattta      360
atctctatga gtctgtctta tcttctggaa aaggggccta acaccatttc cttttgcaaa      420
```

-continued

| | |
|---|---|
| aaggtagctg ccttgcttcc agttctacca tcctntagca acccatcttt n | 471 |

<210> SEQ ID NO 248
<211> LENGTH: 551
<212> TYPE: DNA
<213> ORGANISM: Homo sapiens

<400> SEQUENCE: 248

| | |
|---|---|
| ccatgggatc aggaatgggg tcaggtcagt tgacctgagc atacccatta aacatgttca | 60 |
| aatgtcccca tcccacccac tcacatgaca tggctcccga gccctgagat ctgtatccca | 120 |
| agaacctcag ttgagaaata tttatggcag cttcactgtt gctcaagagc ctgggtattg | 180 |
| tagcagcctg ggggcaggtt gtccctaatg ttctccaagt tcttcacatc agccagaatc | 240 |
| ccatctatgc ttgtctccag caaatggagg tggcccctct gctgacgtgc cctctcttcc | 300 |
| agctctgaca tcatgggccg cagttggctg ttgatctggg tcttggctcg ggaaagcttc | 360 |
| tgctccagta agaccagccc ctcttcatct acactgagag gctggtccat cagatgcagg | 420 |
| aggccgtcta atgtgttgag tgtgtcttgg attgtaaccc cagcgttctt ggctctggta | 480 |
| tcaaccttct gggcttctgt aatcaccatc tgtactgcat ccatattcgt gtcgaactcc | 540 |
| agctccttcc t | 551 |

<210> SEQ ID NO 249
<211> LENGTH: 181
<212> TYPE: DNA
<213> ORGANISM: Homo sapiens
<220> FEATURE:
<221> NAME/KEY: misc_feature
<222> LOCATION: (1)...(181)
<223> OTHER INFORMATION: n=A,T,C or G

<400> SEQUENCE: 249

| | |
|---|---|
| atntccagag ggaccgtaag actggtacaa gtttacacca taagaggcga cgtggtcagc | 60 |
| cacaatgtct tcacctccac aggggctcat cacggnggtc agggcaaggg cccccagcat | 120 |
| cagagctttg tttaggatca tcctcttccc aaggcagcct tagcagttgc tgacctgccc | 180 |
| g | 181 |

<210> SEQ ID NO 250
<211> LENGTH: 551
<212> TYPE: DNA
<213> ORGANISM: Homo sapiens

<400> SEQUENCE: 250

| | |
|---|---|
| tctgtagcta ggatgagctg gctctcaagc aaaagtttgt cttcctgggt ccatttgtgg | 60 |
| ttatcacttg ttattgaatg tacatcacaa attaaagtct gcattgttgg acgtaagaga | 120 |
| atgtgccgac tttggtaacc aggagatttc atgttactgg actgcctgta gtcacgtatt | 180 |
| tctgctatga cacatccgca atgaaaaata ttaacctgag atttttctag gagatcaacc | 240 |
| aaaataggag gtaattcttc tgcatccaaa tattcaagca actctccttc ttcatagggc | 300 |
| agtcgaatgg tctcggaatc tgatccgttt tttcccctga gcatcagaga atatccctca | 360 |
| tttcctgggt atagattgac cactaaacat gacaaagtct cttgcataac aagcttctct | 420 |
| aacaagttca catttcttct taatttctta acttcaggtt ctttttcaca ttcttcaata | 480 |
| tacaagtcat aaagttttg aaatacagat tttcttccac ttgataggta tttcctttta | 540 |
| ggaggtctct g | 551 |

<210> SEQ ID NO 251
<211> LENGTH: 441
<212> TYPE: DNA
<213> ORGANISM: Homo sapiens

<400> SEQUENCE: 251

| | | | | | |
|---|---|---|---|---|---|
| tgtctgctct | cccatcctgg | ttactatgag | tcgctcttgg | cagaaaggac | cacagatgga | 60 |
| gagcttggca | ctcgctccaa | ctttgccgaa | agaggacaa | ccaccaaagt | agtaggtaaa | 120 |
| aacacaattt | tagcagcagt | gaaataaaaa | gaggaagtga | ggatggggcc | aggccgcaac | 180 |
| tataattaaa | ctgtctgttt | aggagaagct | gaatccagaa | gaaacacaag | ctgtaaagtg | 240 |
| agagaggaca | gggagcaggg | cctttggaga | gcaggagagg | acaggctgtc | accaagcgct | 300 |
| gctcggactc | tgccctgaaa | gatttgaatt | ggacactgtc | cagtcacgtg | tgtggcaaac | 360 |
| cgtactccaa | gcactttct | cacggcagag | gaaggagctg | ccatggctgt | accctgaac | 420 |
| gtttgtgggg | ccagcgatgt | g | | | | 441 |

<210> SEQ ID NO 252
<211> LENGTH: 406
<212> TYPE: DNA
<213> ORGANISM: Homo sapiens

<400> SEQUENCE: 252

| | | | | | |
|---|---|---|---|---|---|
| ttttttttg | aacaagtaaa | aatttctta | tttgctgaca | ataagataac | ctacagggaa | 60 |
| aacctgatga | aatctattaa | aaagttacta | aaactaataa | aagaatttag | gaaggttata | 120 |
| gaatgtaaga | ccaagacaca | aaatcaatt | acatttctat | ataatagcaa | tgaacagata | 180 |
| ctgaaatttt | aaaactaaa | tcattttaca | aagtatcac | aatatgaaac | actccgggat | 240 |
| aaattggata | aagatgtgc | aagactgtac | aaaagctaca | aacatttat | gaaggaaatt | 300 |
| ggaagataga | aacaagatag | aaaatgaaaa | tattgtcaag | agtttcagat | agaaaatgaa | 360 |
| aaacaagcta | agacaagtat | tggagaagta | tagaagatag | aaaaat | | 406 |

<210> SEQ ID NO 253
<211> LENGTH: 544
<212> TYPE: DNA
<213> ORGANISM: Homo sapiens
<220> FEATURE:
<221> NAME/KEY: misc_feature
<222> LOCATION: (224)
<223> OTHER INFORMATION: n=A,T,C or G

<400> SEQUENCE: 253

| | | | | | |
|---|---|---|---|---|---|
| gaaggagttc | agtagcaaag | tcacacctgt | ccaattccct | gagctttgct | cactcagcta | 60 |
| atgggatggc | aaaggtggtg | gtgctttcat | cttcaggcag | aagcctctgc | ccatccccct | 120 |
| caagggctgc | aggcccagtt | tcatgctgc | ccttgggtgg | gcatctgtta | acagaggaga | 180 |
| acgtctgggt | ggcggcagca | gctttgctct | gagtgcctac | aaanctaatg | cttggtgcta | 240 |
| gaaacatcat | cattattaaa | cttcagaaaa | gcagcagcca | tgttcagtca | ggctcatgct | 300 |
| gcctcactgc | ttaagtgcct | gcaggagccg | cctgccaagc | tccccttcct | acacctggca | 360 |
| cactgggtc | tgcacaaggc | tttgtcaacc | aaagacagct | tccccctttt | gattgcctgt | 420 |
| agactttgga | gccaagaaac | actctgtgtg | actctacaca | cacttcaggt | ggtttgtgct | 480 |
| tcaaagtcat | tgatgcaact | tgaaaggaaa | cagtttaatg | gtggaaatga | actaccattt | 540 |
| ataa | | | | | | 544 |

<210> SEQ ID NO 254
<211> LENGTH: 339
<212> TYPE: DNA
<213> ORGANISM: Homo sapiens

<400> SEQUENCE: 254

| | | | | | |
|---|---|---|---|---|---|
| tggcattcag | ggcagtgtct | tctgcatctc | ctaggaacct | cgggagcggc | agctccggcg | 60 |
| cctggtagcg | agaggcgggt | tccggagatc | ccggcctcac | ttcgtcccac | tgtggttagg | 120 |
| ggtgagtcct | gcaaatgtta | agtgatttgc | tcaaggtgcc | catttcgcag | gaattggagc | 180 |
| ccaggccagt | tctctgagcc | tatcattagg | gctaaaggag | tgcgtgatca | gaatggtgtc | 240 |
| tggacggttc | tacttgtcct | gcctgctgct | ggggtccctg | gctctatgt | gcatcctctt | 300 |
| cactatctac | tggatgcagt | actggcgtgg | tggctttgc | | | 339 |

<210> SEQ ID NO 255
<211> LENGTH: 405
<212> TYPE: DNA
<213> ORGANISM: Homo sapiens
<220> FEATURE:
<221> NAME/KEY: misc_feature
<222> LOCATION: (1)...(405)
<223> OTHER INFORMATION: n=A,T,C or G

<400> SEQUENCE: 255

| | | | | | |
|---|---|---|---|---|---|
| gaggttttt | nttttttttt | tttttttttt | caattaaana | tttgatttat | tcaagtatgt | 60 |
| gaaacattn | tacaatggaa | acttttntta | aatgctgcat | gtnctgtgct | atggaccacn | 120 |
| cacatacagc | catgctgttt | caaaaaactt | gaaatgccat | tgatagttta | aaaactntac | 180 |
| ncccgatgga | aaatcgagga | aaacaattta | atgtttcatn | tgaatccana | ggngcatcaa | 240 |
| attaaatgac | agctccactt | ggcaaataat | agctgttact | tgatggtatc | caaaaaaaaa | 300 |
| tggttgggga | tggataaatt | caaaaatgct | tccccaaagg | ngggnggttt | ttaaaaagtt | 360 |
| tcaggncaca | acccttgcan | aaaacactga | tgcccaacac | antga | | 405 |

<210> SEQ ID NO 256
<211> LENGTH: 209
<212> TYPE: DNA
<213> ORGANISM: Homo sapiens
<220> FEATURE:
<221> NAME/KEY: misc_feature
<222> LOCATION: (6)
<223> OTHER INFORMATION: n=A,T,C or G

<400> SEQUENCE: 256

| | | | | | |
|---|---|---|---|---|---|
| gggcangtct | ggtcctctcc | ccacatgtca | cactctcctc | agcctctccc | ccaaccctgc | 60 |
| tctccctcct | cccctgccct | agcccaggga | cagagtctag | gaggagcctg | ggcagagct | 120 |
| ggaggcagga | agagagcact | ggacagacag | ctatggtttg | gattggggaa | gaggttagga | 180 |
| agtaggttct | taaagaccct | tttttagta | | | | 209 |

<210> SEQ ID NO 257
<211> LENGTH: 343
<212> TYPE: DNA
<213> ORGANISM: Homo sapiens
<220> FEATURE:
<221> NAME/KEY: misc_feature
<222> LOCATION: (1)...(343)
<223> OTHER INFORMATION: n=A,T,C or G

<400> SEQUENCE: 257

| | | | | | |
|---|---|---|---|---|---|
| tctggacacc | ataatccctt | ttaagtggct | ggatggtcac | acctctccca | ttgacaagct | 60 |

-continued

| | |
|---|---|
| gggttaagtc aataggttga ctaggatcaa cacgacccaa atcaataaga tactgcagtc | 120 |
| tattgagact caaaggctta tactggcgtc tgaaactatg tccttcgtta aacccgtatt | 180 |
| ttgggattcg gatgtaaaat ggagtctggc ctccctcaaa gcccaagcgg ggccgggttc | 240 |
| ctctttgcct ttctccttta tggcctctgc cacattttct acctcttctc cgacctcttg | 300 |
| gtcttntctc nggtttcttg gagccgggat tcggctttaa gtn | 343 |

<210> SEQ ID NO 258
<211> LENGTH: 519
<212> TYPE: DNA
<213> ORGANISM: Homo sapiens

<400> SEQUENCE: 258

| | |
|---|---|
| gcggcttctg acttctagaa gactaaggct ggtctgtgtt tgcttgtttg cccacctttg | 60 |
| gctgataccc agagaacctg ggcacttgct gcctgatgcc caccctgcc agtcattcct | 120 |
| ccattcaccc agcgggaggt gggatgtgag acagcccaca ttggaaaatc cagaaaaccg | 180 |
| ggaacaggga tttgcccttc acaattctac tccccagatc ctctcccctg gacacaggag | 240 |
| acccacaggg caggacccta agatctgggg aaaggaggtc ctgagaacct tgaggtaccc | 300 |
| ttagatcctt ttctacccac tttcctatgg aggattccaa gtcaccactt ctctcaccgg | 360 |
| cttctaccag ggtccaggac taaggcgttt ctcccatagc ctcaacattt tgggaatctt | 420 |
| cccttaatca cccttgctcc tcctgggtgc ctggaagatg gactggcaga gacctctttg | 480 |
| ttgcgttttg tgctttgatg ccaggaatgc cgcctagtt | 519 |

<210> SEQ ID NO 259
<211> LENGTH: 371
<212> TYPE: DNA
<213> ORGANISM: Homo sapiens

<400> SEQUENCE: 259

| | |
|---|---|
| attgtcaact atatacacag tagtgaggaa taaaatgcac acaaaacaat ggatagaata | 60 |
| tgaaaatgtc ttctaaatat gaccagtcta gcatagaacc ttcttctctt ccttctcagg | 120 |
| tcttccagct ccatgtcatc taacccactt aacaaacgtg gacgtatcgc ttccagaggc | 180 |
| cgtcttaaca actccatttc caaaagtcat ctccagaaga catgtatttt ctatgatttc | 240 |
| ttttaaacaa atgagaattt acaagatgtg taactttcta actctatttt atcatacgtc | 300 |
| ggcaacctct ttccatctag aagggctaga tgtgacaaat gttttctatt aaaaggttgg | 360 |
| ggtggagttg a | 371 |

<210> SEQ ID NO 260
<211> LENGTH: 430
<212> TYPE: DNA
<213> ORGANISM: Homo sapiens
<220> FEATURE:
<221> NAME/KEY: misc_feature
<222> LOCATION: (1)...(430)
<223> OTHER INFORMATION: n=A,T,C or G

<400> SEQUENCE: 260

| | |
|---|---|
| ttggattttt tgacttgcga tttcagtttt tttacttttt tttttttttt ttttganaaa | 60 |
| tactatattt attgtcaaag agtggtacat aggtgagtgt tcatcttccc tctcatgccg | 120 |
| gtatactctg cttcgctgtt tcagtaaaag ttttccgtag ttctgaacgt cccttgacca | 180 |
| caccataana caagcgcaag tcactcanaa ttgccactgg aaaactggct caactatcat | 240 |
| ttgaggaaag actganaaag cctatcccaa agtaatggac atgcaccaac atcgcggtac | 300 |

```
ctacatgttc cgttttctct gccaatctac ctgtgtttcc aagataaatt accacccagg        360
gagtcacttc ctgctatgtg aacaaaaacc cggtttcttt ctggaggtgc ttgactactc        420 tctcgngagc                                                               430
```

<210> SEQ ID NO 261
<211> LENGTH: 365
<212> TYPE: DNA
<213> ORGANISM: Homo sapiens
<220> FEATURE:
<221> NAME/KEY: misc_feature
<222> LOCATION: (178)
<223> OTHER INFORMATION: n=A,T,C or G

<400> SEQUENCE: 261

```
tcctgacgat agccatggct gtaccactta actatgattc tattccaact gttcagaatc         60
atatcacaaa atgacttgta cacagtagtt tacaacgact cccaagagag gaaaaaaaaa        120 aaaaagacg cctcaaaatt cactcaactt ttgagacagc aatggcaata ggcagcanag         180
aagctatgct gcaactgagg gcacatatca ttgaagatgt cacaggagtt taagagacag        240
gctggaaaaa atctcatact aagcaaacag tagtatctca taccaagcaa aaccaagtag        300
tatctgctca gcctgccgct aacagatctc acaatcacca actgtgcttt aggactgtca        360
ccaaa                                                                    365
```

<210> SEQ ID NO 262
<211> LENGTH: 500
<212> TYPE: DNA
<213> ORGANISM: Homo sapiens

<400> SEQUENCE: 262

```
cctagatgtc atttgggacc cttcacaacc attttgaagc cctgtttgag tccctgggat         60
atgtgagctg tttctatgca taatggatat tcggggttaa caacagtccc ctgcttggct        120
tctattctga atccttttct ttcaccatgg ggtgcctgaa gggtggctga tgcatatggt        180
acaatggcac ccagtgtaaa gcagctacaa ttaggagtgg atgtgttctg tagcatccta        240
tttaaataag cctattttat cctttggccc gtcaactctg ttatctgctg cttgtactgg        300
tgcctgtact tttctgactc tcattgacca tattccacga ccatggttgt catccattac        360
ttgatcctac tttacatgtc tagtctgtgt ggttggtggt gaataggctt ctttttacat        420
ggtgctgcca gcccagctaa ttaatggtgc acgtggactt ttagcaagcg ggctcactgg        480
aagagactga acctggcatg                                                    500
```

<210> SEQ ID NO 263
<211> LENGTH: 413
<212> TYPE: DNA
<213> ORGANISM: Homo sapiens

<400> SEQUENCE: 263

```
ctcagagagg ttgaaagatt tgcctacgaa agggacagtg atgaagctaa gctctagatc         60
caggatgtct gacttcaaat tgaaactccc aaagtaatga gtttggaagg gtggggtgtg        120
gcctttccag gatgggggtc ttttctgctc ccagcggata gtgaaacccc tgtctgcacc        180
tggttgggcg tgttgctttc ccaaaggttt ttttttttagg tccgtcgctg tcttgtggat        240
taggcattat tatctttact ttgtctccaa ataacctgga gaatgagag agtagtgacc         300 agctcagggc cacagtgcga tgaggaccat cttctcacct ctctaaatgc aggaagaaac        360
```

```
gcagagtaac gtggaagtgg tccacaccta ccgccagcac attgtgaatg aca           413
```

<210> SEQ ID NO 264
<211> LENGTH: 524
<212> TYPE: DNA
<213> ORGANISM: Homo sapiens

<400> SEQUENCE: 264

```
tccaatgggg ccctgagagc tgtgacagga actcacactc tggcactggc agcaaaacac    60
cattccaccc cactcatcgt ctgtgcacct atgttcaaac tttctccaca gttccccaat   120
gaagaagact catttcataa gtttgtggct cctgaagaag tcctgccatt cacagaaggg   180
gacattctgg agaaggtcag cgtgcattgc cctgtgtttg actacgttcc cccagagctc   240
attaccctct ttatctccaa cattggtggg aatgcaccct cctacatcta ccgcctgatg   300
agtgaactct accatcctga tgatcatgtt ttatgaccga ccacacgtgt cctaagcaga   360
ttgcttaggc agatacagaa tgaagaggag acttgagtgt tgctgctgaa gcacatcctt   420
gcaatgtggg agtgcacagg agtccaccta aaaaaaaaaa tccttgatac tgttgcctgc   480
ctttttagtc accccgtaac aagggcacac atccaggact gtgt                    524
```

<210> SEQ ID NO 265
<211> LENGTH: 344
<212> TYPE: DNA
<213> ORGANISM: Homo sapiens

<400> SEQUENCE: 265

```
tcctttcttc tacttcagga gatgattcaa agttacttgt ggacatttct ttaagttctg    60
aagacaaatg agacaggatt tggcctgcgg gttcttcaga cttctctacc acctccatta   120
actcttcatc ttggcttgac gtaggcaatg cactattttg ctcttttgtt tctggagatg   180
acccagcacc acttctttct cttggcgggg ttctaagtgt gtctttgaat accagtgaag   240
actcaggcct atcctgtact ggaaagggac taaatttgtc tttctgtcta ggaggtgatg   300
cagtagcatc ctcctgaggg ggtaaggcca ttttctcttt ttga                    344
```

<210> SEQ ID NO 266
<211> LENGTH: 210
<212> TYPE: DNA
<213> ORGANISM: Homo sapiens
<220> FEATURE:
<221> NAME/KEY: misc_feature
<222> LOCATION: (78)
<223> OTHER INFORMATION: n=A,T,C or G

<400> SEQUENCE: 266

```
ccacaatgtc cataacttga gcaggctttg gcatcccacc accccttca gaccaataca     60
cactatgttg gaggaacnac tttaaaatgt aaaatgagaa atgggcactg aacactccat   120
cctcactccc aacagcccac ccacacacct cttcaactgc tatccaaaca tggaggagct   180
cttgtggaag agaggctcaa caccaaataa                                    210
```

<210> SEQ ID NO 267
<211> LENGTH: 238
<212> TYPE: DNA
<213> ORGANISM: Homo sapiens
<220> FEATURE:
<221> NAME/KEY: misc_feature
<222> LOCATION: (1)...(238)
<223> OTHER INFORMATION: n = A,T,C or G

<400> SEQUENCE: 267

```
tcggncctcc cacccccttctna ctgaaattct ntgaaattct cccctttggg atgaggatgg    60
caaccccagg catgtaccct cccaacctgg gacccgacct aatacccctaa catcctgctg    120 acagtggctg ttctcgctgg gcaggcgtcc caaagcacat cgagccagat tcaggcagag    180
tggaactggc ccctcagcca tcagtggagg tggcctggga ggctctaccc tgaacggg      238
```

<210> SEQ ID NO 268
<211> LENGTH: 461
<212> TYPE: DNA
<213> ORGANISM: Homo sapiens
<220> FEATURE:
<221> NAME/KEY: misc_feature
<222> LOCATION: (459)
<223> OTHER INFORMATION: n=A,T,C or G

<400> SEQUENCE: 268

```
tcctcaagga catgccccttt gatagaaact cagttcctgt ctccagttcc ctcctggacc    60
tgatccccca aatgcagggc ctgggactat atccagttcc ttattttcag aggcccatgc    120
acaagatgca cagcaaataa gtgctgaata aagacccagc tactgctagc ttaccctgct    180
ccaaacattc accaagtcct cagcaaagag ggccatccat tcacctcttc taaaaacaca    240
ctgagctccc cagtctatac cccaagatat gcttggctcc caactatccc tcctctctca    300
tctccaagcc agtttcccct ttctaagtat actgatatta ccaaagacac tgacaatctt    360
cttttcctac ctctccccag tgactaggtt tgcagcagga gctctataag tcctagtata    420
cagcagaagc tccataaatg tgtgctgacc taacattang c                        461
```

<210> SEQ ID NO 269
<211> LENGTH: 434
<212> TYPE: DNA
<213> ORGANISM: Homo sapiens

<400> SEQUENCE: 269

```
ctgtgttggt gagcaccgat tcccactcaa tatggcgtgg cttacagtct tcattaggtt    60
cccgctccca accagaatga ggaatgatca cttcatctgt caaggcatgc agtgcatggt    120
ccacaatctc cattttgatt gagtcatggg atgaaagatt ccacagggtt ccggtaataa    180
cttcagtaag gtccatatca cgagcctttc gaagcaatcg cacaagggca ggcacaccat    240 cacagtttt tatggcaatc ttgttatcct ggtcacgtcc aaaagagata ttcttgagag    300
ctccacaggc tccaaggtgc acttcctttt tgggatggtc taacaatccc accagtactg    360
ggatgccctt gagcttccgc acgtcagtct tcaccttgtc attgcggtag cataagtgtt    420
gcaggtatgc aaga                                                      434
```

<210> SEQ ID NO 270
<211> LENGTH: 156
<212> TYPE: DNA
<213> ORGANISM: Homo sapiens

<400> SEQUENCE: 270

```
ctgcaccagc gattaccagt ggcattcaaa tactgtgtga ctaaggattt tgtatgctcc    60
ccagtagaac cagaatcaga caggtatgag ctagtcaaca gcaagtctttt gttggattcg    120 agtaggctca ggatctgctg aaggtcggag gagtta                              156
```

<210> SEQ ID NO 271
<211> LENGTH: 533
<212> TYPE: DNA

<213> ORGANISM: Homo sapiens
<220> FEATURE:
<221> NAME/KEY: misc_feature
<222> LOCATION: (1)...(533)
<223> OTHER INFORMATION: n=A,T,C or G

<400> SEQUENCE: 271

| | | | | | |
|---|---|---|---|---|---|
| ccactgtcac | ggtctgtctg | acacttactg | ccaaacgcat | ggcaaggaaa | aactgcttag | 60 |
| tgaagaactt | agaagctgtg | gagaccttgg | ggtccacgtn | caccatctgc | tctgataaaa | 120 |
| ctggaactct | gactcanaac | cggatgacag | tgcccacat | gtggtttgac | aatcaaatcc | 180 |
| atgaagctga | tacgacagag | aatcagagtg | gtgtctcttt | tgacaagact | tcagctacct | 240 |
| ggcttgctct | gtccagaatt | gcaggtcttt | gtaacagggc | agtgtttcag | gctaaccagg | 300 |
| aaaacctacc | tattcttaag | cgggcagttg | caggagatgc | ctctgagtca | gcactcttaa | 360 |
| agtgcataga | gctgtgctgt | ggntncgtga | aggagatgag | agaaagatac | nccaaaatcg | 420 |
| tcgagatacc | cttcaactcc | accaacaagt | accagttgtc | tattcataag | aaccccaaca | 480 |
| catcggagcc | ccaacacctg | ttggtgatga | agggcgcccc | agaaaggatc | cta | 533 |

<210> SEQ ID NO 272
<211> LENGTH: 630
<212> TYPE: DNA
<213> ORGANISM: Homo sapiens

<400> SEQUENCE: 272

| | | | | | |
|---|---|---|---|---|---|
| tggtattttt | cttttcttt | tggatgtttt | atactttttt | ttcttttttc | ttctctattc | 60 |
| ttttcttcgc | cttcccgtac | ttctgtcttc | cagttttcca | cttcaaactt | ctatcttctc | 120 |
| caaattgttt | catcctacca | ctcccaatta | atctttccat | tttcgtctgc | gtttagtaaa | 180 |
| tgcgttaact | aggctttaaa | tgacgcaatt | ctccctgcgt | catggatttc | aaggtctttt | 240 |
| aatcaccttc | ggtttaatct | cttttttaaaa | gatcgcttc | aaattatttt | aatcacctac | 300 |
| aactttttaaa | ctaaacttta | agctgtttaa | gtcaccttca | ttttaatcta | aaagcattgc | 360 |
| ccttctattg | gtattaattc | ggggctctgt | agtcctttct | ctcaattttc | ttttaaatac | 420 |
| atttttact | ccatgaagaa | gcttcatctc | aacctccgtc | atgttttaga | aaccttttat | 480 |
| cttttccttc | ctcatgctac | tcttctaagt | cttcatattt | tctcttaaaa | tcttaagcta | 540 |
| ttaaaattac | gttaaaaact | taacgctaag | caatatctta | gtaacctatt | gactatattt | 600 |
| tttaagtagt | tgtattaatc | tctatctttc | | | | 630 |

<210> SEQ ID NO 273
<211> LENGTH: 400
<212> TYPE: DNA
<213> ORGANISM: Homo sapiens

<400> SEQUENCE: 273

| | | | | | |
|---|---|---|---|---|---|
| tctggtttgc | cctccagttc | attctgaatc | tagacttgct | cagcctaatc | aagttcctgt | 60 |
| acaaccagaa | gcgacacagg | ttcctttggt | atcatccaca | agtgaggggt | acacagcatc | 120 |
| tcaacccttg | taccagcctt | ctcatgctac | agagcaacga | ccacagaagg | aaccaattga | 180 |
| tcagattcag | gcaacaatct | ctttaaatac | agaccagact | acagcatcat | catcccttcc | 240 |
| tgctgcgtct | cagcctcaag | tatttcaggc | tgggacaagc | aaacctttac | atagcagtgg | 300 |
| aatcaatgta | aatgcagctc | cattccaatc | catgcaaacg | gtgttcaata | tgaatgcccc | 360 |
| agttcctcct | gttaatgaac | cagaaacttt | aaaacagcaa | | | 400 |

<210> SEQ ID NO 274
<211> LENGTH: 351
<212> TYPE: DNA
<213> ORGANISM: Homo sapiens
<220> FEATURE:
<221> NAME/KEY: misc_feature
<222> LOCATION: (2)
<223> OTHER INFORMATION: n=A,T,C or G

<400> SEQUENCE: 274

| | | | | | |
|---|---|---|---|---|---|
| tntgagtatg | tcccagagaa | ggtgaagaaa | gcggaaaaga | aattagaaga | gaatccatat | 60 |
| gaccttgatg | cttggagcat | tctcattcga | gaggcacaga | atcaacctat | agacaaagca | 120 |
| cggaagactt | atgaacgcct | tgttgcccag | ttccccagtt | ctggcagatt | ctggaaactg | 180 |
| tacattgaag | cagaggttac | tattttattt | tattttttct | tatatcagta | ttgcagcatt | 240 |
| cactgtagtg | atagaaaaca | agttaggaac | atagccaatt | aggacaagga | ggatttaaat | 300 |
| gtgtcttacc | tttattttgt | aaaataggta | taaaggagta | attaaaatga | a | 351 |

<210> SEQ ID NO 275
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n=A,T,C or G

<400> SEQUENCE: 275

| | | | | | |
|---|---|---|---|---|---|
| gcgnggtcgc | nnncgaggtc | tgagaagccc | ataccactat | ttgttgagaa | atgtgtggaa | 60 |
| tttattgaag | atacagggtt | atgtaccgaa | ggactctacc | gtgtcagcgg | gaataaaact | 120 |
| gaccaagaca | atattcaaaa | gcagtttgat | caagatcata | atatcaatct | agtgtcaatg | 180 |
| gaagtaacag | taaatgctgt | agctggagcc | cttaaagctt | tctttgcaga | tctgccagat | 240 |
| cctttaattc | catattctct | tcatccagaa | ctattggaag | cagcaaaaat | cccggataaa | 300 |
| acagaacgtc | ttcatgcctt | gaaagaaatt | gttaagaaat | tcatcctgt | aaactatgat | 360 |
| gtattcagat | acgtgataac | a | | | | 381 |

<210> SEQ ID NO 276
<211> LENGTH: 390
<212> TYPE: DNA
<213> ORGANISM: Homo sapiens
<220> FEATURE:
<221> NAME/KEY: misc_feature
<222> LOCATION: (5)
<223> OTHER INFORMATION: n=A,T,C or G

<400> SEQUENCE: 276

| | | | | | |
|---|---|---|---|---|---|
| gctcngactc | cggcgggacc | tgctcggagg | aatggcgccg | ccggggttcaa | gcactgtctt | 60 |
| cctgttggcc | ctgacaatca | tagccagcac | ctgggctctg | acgccactc | actacctcac | 120 |
| caagcatgac | gtggagagac | taaaagcctc | gctggatcgc | cctttcacaa | atttggaatc | 180 |
| tgccttctac | tccatcgtgg | gactcagcag | ccttggtgct | caggtgccag | atgcaaagaa | 240 |
| agcatgtacc | tacatcagat | ctaaccttga | tcccagcaat | gtggattccc | tcttctacgc | 300 |
| tgcccaggcc | agccaggccc | tctcaggatg | tgagatctct | atttcaaatg | agaccaaaga | 360 |
| tctgcttctg | gcagacctcg | gccgcgacca | | | | 390 |

<210> SEQ ID NO 277
<211> LENGTH: 378
<212> TYPE: DNA

<213> ORGANISM: Homo sapiens

<400> SEQUENCE: 277

| | | | | | |
|---|---|---|---|---|---|
| tgggaacttc | tggggtagga | cgttgtctgc | tatctccagt | tccacagacc | caaccagtta | 60 |
| cgatggtttt | ggaccattta | tgccgggatt | cgacatcatt | ccctataatg | atctgcccgc | 120 |
| actggagcgt | gctcttcagg | atccaaatgt | ggctgcgttc | atggtagaac | caattcaggg | 180 |
| tgaagcaggc | gttgttgttc | cggatccagg | ttacctaatg | ggagtgcgag | agctctgcac | 240 |
| caggcaccag | gttctctttta | ttgctgatga | aatacagaca | ggattggcca | gaactggtag | 300 |
| atggctggct | gttgattatg | aaaatgtcag | acctgatata | gtcctccttg | aaaggccct | 360 |
| ttctgggggc | ttataccc | | | | | 378 |

<210> SEQ ID NO 278
<211> LENGTH: 366
<212> TYPE: DNA
<213> ORGANISM: Homo sapiens

<400> SEQUENCE: 278

| | | | | | |
|---|---|---|---|---|---|
| ggagggcaca | ttccttttca | cctcagagtc | ggtcgggaa | ggccacccag | ataagatttg | 60 |
| tgaccaaacc | agtgatgctg | tccttgatgc | ccaccttcag | caggatcctg | atgccaaagt | 120 |
| agcttgtgaa | actgttgcta | aaactggaat | gatccttctt | gctggggaaa | ttacatccag | 180 |
| agctgctgtt | gactaccaga | aagtggttcg | tgaagctgtt | aaacacattg | gatatgatga | 240 |
| ttcttccaaa | ggttttgact | acaagacttg | taacgtgctg | gtagccttgg | agcaacagtc | 300 |
| accagatatt | gctcaaggtg | ttcatcttga | cagaaatgaa | gaagacattg | gtgctggaga | 360 |
| ccaggg | | | | | | 366 |

<210> SEQ ID NO 279
<211> LENGTH: 435
<212> TYPE: DNA
<213> ORGANISM: Homo sapiens

<400> SEQUENCE: 279

| | | | | | |
|---|---|---|---|---|---|
| cctaagaact | gagacttgtg | acacaaggcc | aacgacctaa | gattagccca | gggttgtagc | 60 |
| tggaagacct | acaacccaag | gatggaaggc | ccctgtcaca | agcctacct | agatggatag | 120 |
| aggacccaag | cgaaaaagat | atctcaagac | taacggccgg | aatctggagg | cccatgaccc | 180 |
| agaacccagg | aaggatagaa | gcttgaagac | ctggggaaat | cccaagatga | gaaccctaaa | 240 |
| ccctacctct | tttctattgt | ttacacttct | tactcttaga | tatttccagt | tctcctgttt | 300 |
| atctttaagc | ctgattcttt | tgagatgtac | tttttgatgt | tgccggttac | ctttagattg | 360 |
| acaagtatta | tgcctggcca | gtcttgagcc | agctttaaat | cacagctttt | acctatttgt | 420 |
| taggctatag | tgttt | | | | | 435 |

<210> SEQ ID NO 280
<211> LENGTH: 435
<212> TYPE: DNA
<213> ORGANISM: Homo sapiens

<400> SEQUENCE: 280

| | | | | | |
|---|---|---|---|---|---|
| tctggatgag | ctgctaactg | agcacaggat | gacctgggac | ccagcccagc | caccccgaga | 60 |
| cctgactgag | gccttcctgg | caaagaagga | gaaggccaag | gggagccctg | agagcagctt | 120 |
| caatgatgag | aacctgcgca | tagtggtggg | taacctgttc | cttgccggga | tggtgaccac | 180 |
| ctcgaccacg | ctggcctggg | gcctcctgct | catgatccta | cacctggatg | tgcagcgtga | 240 |

```
gcccagacct gtccgggcgg ccgctcgaaa ttccagcaca ctggcggccg ttactagtgg      300
atccgagctc ggtaccaagc ttggcgtaat catggtcata gctgtttcct gtgtgaaatt      360
gttatccgct cacaattcca cacaacatac gagccggaag cataaagtgt aaagcctggg      420
gtgcctaatg agtga                                                       435
```

<210> SEQ ID NO 281
<211> LENGTH: 440
<212> TYPE: DNA
<213> ORGANISM: Homo sapiens

<400> SEQUENCE: 281

```
catctgatct ataaatgcgg tggcatcgac aaaagaacca ttgaaaaatt tgagaaggag       60
gctgctgaga tgggaaaggg ctccttcaag tatgcctggg tcttggataa actgaaagct      120
gagcgtgaac gtggtatcac cattgatatc tccttgtgga aatttgagac cagcaagtac      180
tatgtgacta tcattgatgc cccaggacac agagacttta tcaaaaacat gattacaggg      240
acatctcagg ctgactgtgc tgtcctgatt gttgctgctg gtgttggtga atttgaagct      300
ggtatctcca gaatgggca gacccgagag catgcccttc tggcttacac actgggtgtg      360
aaacaactaa ttgtcggtgt taacaaaatg gattccactg agccccctac agccagaaga      420
gatatgagga aattgttaag                                                  440
```

<210> SEQ ID NO 282
<211> LENGTH: 502
<212> TYPE: DNA
<213> ORGANISM: Homo sapiens

<400> SEQUENCE: 282

```
tctgtggcgc aggagccccc tcccccggca gctctgacgt ctccaccgca gggactggtg       60
cttctcggag ctcccactcc tcagactccg gtggaagtga cgtggacctg gatcccactg      120
atggcaagct cttccccagc gatggttttc gtgactgcaa gaaggggat cccaagcacg       180 ggaagcggaa acgaggccgg ccccgaaagc tgagcaaaga gtactgggac tgtctcgagg      240
gcaagaagag caagcacgcg cccagaggca cccacctgtg ggagttcatc cgggacatcc      300
tcatccaccc ggagctcaac gagggcctca tgaagtggga gaatcggcat gaaggcgtct      360
tcaagttcct gcgctccgag gctgtggccc aactatgggg ccaaaagaaa agaacagca      420 acatgaccta cgagaagctg agccgggcca tgaggtacta ctacaaacgg gagatcctgg      480
aacgggtgga tggccggcga ct                                               502
```

<210> SEQ ID NO 283
<211> LENGTH: 433
<212> TYPE: DNA
<213> ORGANISM: Homo sapiens
<220> FEATURE:
<221> NAME/KEY: misc_feature
<222> LOCATION: (1)...(433)
<223> OTHER INFORMATION: n=A,T,C or G

<400> SEQUENCE: 283

```
ccatattaga ttactggaac atctaagcat cagtgtgtga ccatgcgaac aaaagacttc       60
ggggagtgtc tattttttaaa aaggtttatg tgtgtcgagg cagttgtaaa agatttactg     120
cagaatcaan cccacttttta ggcttangac caggttctaa ctatctaaaa atattgactg     180
ataacaaaaa gtgttctaaa tgtggctatt ctgatccata nttgnttttt aaagaaaaaa      240
```

```
antgtntata cagaaagagt ntaaaagttc tgtgaattna atgcaaatta gncnccantc    300
ttgacttccc aaanacttga ttnataccct tnactcctnt cnnttcctgn ncttcnttaa    360
nntcaatnat tnggnagtnn anggccntcn gnanaacacc nttncncgnt ccncgcaatc    420
canccgcctt nan                                                       433

<210> SEQ ID NO 284
<211> LENGTH: 479
<212> TYPE: DNA
<213> ORGANISM: Homo sapiens

<400> SEQUENCE: 284
tctggaagga tcagggatct gagcaaagcc aagtttactt aagctaagcc acttgttcct     60
gggtcaagca gtttgttttc taataagcat cattcctgat cattagagca aagggatgaa    120
tgctcctctt ggaatgatac aggggatctg ccactgggag agtgttgctc agtgttagag    180
tagcagcaat gacagaatga cagcgactct ctgagtcaac ccagtacttt tagtaccccg    240
tcactatgtg aataaaggca gctagaaaat ggactcaatt ctgcaagcct tcatggcaac    300
agcccatatt aagacttcta gaacaagtta aaaaaaaatc ttccatttcc atccatgcat    360
gggaaaaggg ctttagtata gtttaggatg gatgtgtgta taataataaa atgataagat    420
atgcatagtg ggggaataaa gcctcagagt ccttccagta tggggaatcc attgtatct     479

<210> SEQ ID NO 285
<211> LENGTH: 435
<212> TYPE: DNA
<213> ORGANISM: Homo sapiens
<220> FEATURE:
<221> NAME/KEY: misc_feature
<222> LOCATION: (1)...(435)
<223> OTHER INFORMATION: n=A,T,C or G

<400> SEQUENCE: 285
tttttttttt tttttttttt tcaatanaaa tgccataatt tattccattg tataaaaaag     60
tcatccttat gtaacaaaat gtnttcttan aanaanaaat atattatttc aggtcataaa    120
taatcagcaa acatacaact gttggcaact aaaaaaaaac ccaacactgg tattttccat    180
cagngctgaa aacaaacctg cttaaanata tatttacagg gatagtncag tnctcaaaaa    240
caaaaattga ggtattttgg ttcttctagg agtagacaat gacattttgg ganggcaga     300 cccctnnccc aaaaaataaa ataagggnat nttcttcant atngaananm ggggcgccc     360 cggggaaaan naaaccttgg gnnggggggtt tggcccaagc ccttgaaaaa aaantttntt    420
tcccaaaaaa aacng                                                     435

<210> SEQ ID NO 286
<211> LENGTH: 301
<212> TYPE: DNA
<213> ORGANISM: Homo sapiens

<400> SEQUENCE: 286
cctggtttct ggtggcctct atgaatccca tgtagggtgc agaccgtact ccatccctcc     60
ctgtgagcac cacgtcaacg gctcccggcc cccatgcacg ggggagggag ataccccaa     120 gtgtagcaag atctgtgagc ctggctacag cccgacctac aaacaggaca agcactacgg    180
atacaattcc tacagcgtct ccaatagcga aaggacatc atggccgaga tctacaaaaa     240
cggccccgtg gagggagctt tctctgtgta ttcggacttc ctgctctaca agtcaggagt    300
g                                                                    301
```

<210> SEQ ID NO 287
<211> LENGTH: 432
<212> TYPE: DNA
<213> ORGANISM: Homo sapiens

<400> SEQUENCE: 287

| tccagcttgt tgccagcatg agaaccgcca ttgatgacat tgaacgccgg gactggcagg | 60 |
| atgacttcag agttgccagc caagtcagcg atgtggcggt acaggggac cccttctca | 120 |
| acggcaccag ctttgcagac ggcaaggac accccagaa tggcgttcgc accaaactta | 180 |
| gatttatttt ctgttccatc catctcgatc atcagtttgt caatcttctc ttgttctgtg | 240 |
| acgttcagtt tcttgctaac cagggcaggc gcaatagttt tattgatgtg ctcaacagcc | 300 |
| tttgagacac ccttccccat atagcgagtc ttatcattgt cccggagctc tagggcctca | 360 |
| tagataccag ttgaagcacc actgggcaca gcagctctga agagaccttt tgaggtgaag | 420 |
| agatcaacct ca | 432 |

<210> SEQ ID NO 288
<211> LENGTH: 326
<212> TYPE: DNA
<213> ORGANISM: Homo sapiens
<220> FEATURE:
<221> NAME/KEY: misc_feature
<222> LOCATION: (254)
<223> OTHER INFORMATION: n=A,T,C or G

<400> SEQUENCE: 288

| tctggctcaa gtcaaagtcc tggtcctctt ctccgcctcc ttcttcatca tagtaataaa | 60 |
| cgttgtcccg ggtgtcatcc tctggggca gtaagggctc tttgaccacc gctctcctcc | 120 |
| gaagaaacag caagagcagc agaatcagaa ttagcaaagc aagaattcct ccaagaatcc | 180 |
| ccagaatggc aggaatttgc aatcctgctt cgacaggctg tgccttccta cagacgccgg | 240 |
| cggccccttc acantcacac acgctgacct ctaaggtggt cacttggtct ttattctggt | 300 |
| tatccatgag cttgagattg attttg | 326 |

<210> SEQ ID NO 289
<211> LENGTH: 451
<212> TYPE: DNA
<213> ORGANISM: Homo sapiens

<400> SEQUENCE: 289

| gtcccggtgt ggctgtgccg ttggtcctgt gcggtcactt agccaagatg cctgaggaaa | 60 |
| cccagaccca agaccaaccg atggaggagg aggaggttga gacgttcgcc tttcaggcag | 120 |
| aaattgccca gttgatgtca ttgatcatca atactttcta ctcgaacaaa gagatctttc | 180 |
| tgagagagct catttcaaat tcatcagatg cattggacaa aatccggtat gaaagcttga | 240 |
| cagatcccag taaattagac tctgggaaag agctgcatat taaccttata ccgaacaaac | 300 |
| aagatcgaac tctcactatt gtggatactg gaattggaat gaccaaggct gacttgatca | 360 |
| ataaccttgg tactatcgcc aagtctggga ccaaagcgtt catggaagct ttgcaggctg | 420 |
| gtgcagatat ctctatgatt ggacctcggc c | 451 |

<210> SEQ ID NO 290
<211> LENGTH: 494
<212> TYPE: DNA
<213> ORGANISM: Homo sapiens
<220> FEATURE:

<221> NAME/KEY: misc_feature
<222> LOCATION: (421)
<223> OTHER INFORMATION: n=A,T,C or G

<400> SEQUENCE: 290

| | | | | | |
|---|---|---|---|---|---|
| tttttttttt | tcaaaacagt | atattttatt | ttacaatagc | aaccaactcc | ccagtttgtt | 60 |
| tcaattgtga | catctagatg | gcttaagatt | actttctggt | ggtcacccat | gctgaacaat | 120 |
| attttcaat | cttccaaaca | gcaaagactc | aaaagagatt | ctgcatttca | catcagttca | 180 |
| caagttcaag | agtcttccat | ttatcttagc | ttttggaata | aattatcttt | gaggtagaag | 240 |
| gacaatgacg | aagccactta | attccttgtg | tctgcataaa | agcagattta | ttcatcacaa | 300 |
| cttcatttat | gtgaataaag | cagatgatga | taaaatgttc | tcttattctt | gtttaatcag | 360 |
| tagtggtagt | gatgccagaa | acttgtaaat | gcacttcaaa | ccaattgtgg | ctcaagtgta | 420 |
| ngtggttccc | caaggctggt | accaatgaga | ctggggtttg | ggaattagtt | ggtcatcatc | 480 |
| cctcctgctg | ccca | | | | | 494 |

<210> SEQ ID NO 291
<211> LENGTH: 535
<212> TYPE: DNA
<213> ORGANISM: Homo sapiens

<400> SEQUENCE: 291

| | | | | | |
|---|---|---|---|---|---|
| tcgcgtgctt | aacatgaaaa | caaactttgt | gctgtttggt | tcattgtatg | cattgatgga | 60 |
| gtcttgtctc | tcatcatggg | gtgtctgacc | atccaacctg | cagtactcat | aatttctcca | 120 |
| catgcaataa | tcttccaaaa | tgtccaatac | ccttgtcatt | tgactgaaga | ttagtactcg | 180 |
| tgaaccttgt | tcttttaact | tagggagcag | cttgtctaaa | accaccatt | tgccactgtt | 240 |
| ggttactaga | tgcatatctg | ttgtataagg | tggaccaggt | tctgctccat | caaagagata | 300 |
| tggatgatta | caacatttc | tcaactgcat | taggatgttc | aataacctca | ttttgtccat | 360 |
| cttgcctgct | gagttgagta | tatctatatc | cttcattaat | atccgagtat | accattccct | 420 |
| ttgcattttg | ctgaggccca | catagatttt | tacttccttc | tttggaggca | aactcttttc | 480 |
| aacatcagcc | ttaattcgac | gaaggaggaa | tggacgcaaa | accatatgaa | gcctc | 535 |

<210> SEQ ID NO 292
<211> LENGTH: 376
<212> TYPE: DNA
<213> ORGANISM: Homo sapiens
<220> FEATURE:
<221> NAME/KEY: misc_feature
<222> LOCATION: (1)...(376)
<223> OTHER INFORMATION: n=A,T,C or G

<400> SEQUENCE: 292

| | | | | | |
|---|---|---|---|---|---|
| tacnagcccg | tgctgatcga | gatcctggtg | gaggtgatgg | atccttcctt | cgtgtgcttg | 60 |
| aaaattggag | cctgcccctc | ggcccataag | cccttgttgg | gaactgagaa | gtgtatatgg | 120 |
| ggcccaagct | actggtgcca | gaacacagag | acagcagccc | agtgcaatgc | tgtcgagcat | 180 |
| tgcaaacgcc | atgtgtggaa | ctaggaggag | gaatattcca | tcttggcaga | aaccacagca | 240 |
| ttggttttt | tctacttgtg | tgtctggggg | aatgaacgca | cagatctgtt | tgactttgtt | 300 |
| ataaaaatag | ggctccccca | cctcccccat | ttttgtgtcc | tttattgnag | cattgctgtc | 360 |
| tgcaagggag | cccta | | | | | 376 |

<210> SEQ ID NO 293
<211> LENGTH: 320

```
<212> TYPE: DNA
<213> ORGANISM: Homo sapiens

<400> SEQUENCE: 293
tcggctgctt cctggtctgg cggggatggg tttgctttgg aaatcctcta ggaggctcct    60
cctcgcatgg cctgcagtct ggcagcagcc ccgagttgtt tcctcgctga tcgatttctt   120
tcctccaggt agagttttct ttgcttatgt tgaattccat tgcctctttt ctcatcacag   180
aagtgatgtt ggaatcgttt cttttgtttg tctgatttat ggttttttta agtataaaca   240
aaagtttttt attagcattc tgaaagaagg aaagtaaaat gtacaagttt aataaaaagg   300
ggccttcccc tttagaatag                                                320

<210> SEQ ID NO 294
<211> LENGTH: 359
<212> TYPE: DNA
<213> ORGANISM: Homo sapiens

<400> SEQUENCE: 294
ctgtcataaa ctggtctgga gtttctgacg actccttgtt caccaaatgc accatttcct    60
gagacttgct ggcctctccg ttgagtccac ttggctttct gtcctccaca gctccattgc   120
cactgttgat cactagcttt ttcttctgcc cacaccttct tcgactgttg actgcaatgc   180
aaactgcaag aatcaaagcc aaggccaaga gggatgccaa gatgatcagc cattctggaa   240
tttggggtgt cctatagga ccagaggttg tgtttgctcc accttcttga ctcccatgtg    300
agtgtccatc tgattcagat ccatgagtgg tatgggaccc ccactggggg tggaatgtg   359

<210> SEQ ID NO 295
<211> LENGTH: 584
<212> TYPE: DNA
<213> ORGANISM: Homo sapiens
<220> FEATURE:
<221> NAME/KEY: misc_feature
<222> LOCATION: (558)
<223> OTHER INFORMATION: n=A,T,C or G

<400> SEQUENCE: 295
cctgagttgg gctgactgcc agagacagac ccctctgggt ctcggtgaac cagccaggca    60
tttacctcag tggttggcac ctggaacctg tccaggggcc tcacctgact gaggagccgc   120
cgggcagtga agtaattgtc caggtctatg ctcttgggt ggataccata gccatccaag    180
gtattcctca ggttgtggaa ctgggtctga gtataggcag aactgggccc caggatgatc   240
tcccggagtg ggggaagctg tgaggtcagg taagtatcca cgtccacccg tacccccaatc   300 aaactcagca gaatggtgaa ctgagagagt ccttccgtta agtatttctt cagagaaagc   360
attgctgaag gaccagaatg tttatgcttt ttggtttta aaatcttcca aaagacaaat    420
caaggccact gctctgccgc tccagccagc aggttaccct cctcagtgtc aaaccccgta   480 ccccacccctg gcagaacaca agggatgagc tccctgacgg ccccagagga agcacaccc   540 tgtggagcca aggccaanga cacactccag accacattca cttt                    584

<210> SEQ ID NO 296
<211> LENGTH: 287
<212> TYPE: DNA
<213> ORGANISM: Homo sapiens

<400> SEQUENCE: 296
ccttatcatt cattcttagc tcttaattgt tcattttgag ctgaaatgct gcattttaat    60
```

| | |
|---|---|
| tttaaccaaa acatgtctcc tatcctggtt tttgtagcct tcctccacat cctttctaaa | 120 |
| caagatttta aagacatgta ggtgtttgtt catctgtaac tctaaaagat ccttttaaa | 180 |
| ttcagtccta agaaagagga gtgcttgtcc cctaagagtg tttaatggca aggcagccct | 240 |
| gtctgaagga cacttcctgc ctaagggaga gtggtatttg cagacta | 287 |

<210> SEQ ID NO 297
<211> LENGTH: 457
<212> TYPE: DNA
<213> ORGANISM: Homo sapiens

<400> SEQUENCE: 297

| | |
|---|---|
| ccaattgaaa caaacagttc tgagaccgtt cttccaccac tgattaagag tggggtggca | 60 |
| ggtattaggg ataatattca tttagccttc tgagctttct gggcagactt ggtgaccttg | 120 |
| ccagctccag cagccttctt gtccactgct ttgatgacac ccaccgcaac tgtctgtctc | 180 |
| atatcacgaa cagcaaagcg acccaaaggt ggatagtctg agaagctctc aacacacatg | 240 |
| ggcttgccag gaaccatatc aacaatggca gcatcaccag acttcaagaa tttagggcca | 300 |
| tcttccagct ttttaccaga acggcgatca atctttttcct tcagctcagc aaacttgcat | 360 |
| gcaatgtgag ccgtgtggca atccaataca ggggcatagc cggcgcttat ttggcctgga | 420 |
| tggttcagga taatcacctg agcagtgaag ccagacc | 457 |

<210> SEQ ID NO 298
<211> LENGTH: 469
<212> TYPE: DNA
<213> ORGANISM: Homo sapiens

<400> SEQUENCE: 298

| | |
|---|---|
| tctttgactt tccttgtcta cctcctctgg agatctcaaa ttctccaggt tccatgctcc | 60 |
| cagagatctc aatgattcct gattctcctc ttccaggagt ctgaatgtct cttggttcac | 120 |
| ttccacagac tccagtggtt cttgaatttc cttttctaga ggattcattg cccctgatt | 180 |
| tatttcttct ggagtccaca gtggtgcttg agttctggga gatttcagtg tttccaggtt | 240 |
| ctcttgtccc gcagacttca gtgattctag gatctctgtt tctaaagatt ttactgcctc | 300 |
| tatgctctct tctttgagtg actttaagaa ctcttgattc tcattttcaa gaggtctagc | 360 |
| tatctcctgg tcaagagact tcagtggttc tagatccact ttttctgggg gtcttaatgt | 420 |
| catctgatcc tgttccccta gagacctccg tcgctgttga gtctctttt | 469 |

<210> SEQ ID NO 299
<211> LENGTH: 165
<212> TYPE: DNA
<213> ORGANISM: Homo sapiens
<220> FEATURE:
<221> NAME/KEY: misc_feature
<222> LOCATION: (1)...(165)
<223> OTHER INFORMATION: n=A,T,C or G

<400> SEQUENCE: 299

| | |
|---|---|
| tctgtggaga ggatgaggtt gagggaggtg gggtatntcg ctgctctgac cttaggtaga | 60 |
| gtcctccaca gaagcatcaa antggactgg cacatatgga ctcccttcac aggccacaat | 120 |
| gatgtgtctc tccttcgggc tggnccggta tgcacagttg gggta | 165 |

<210> SEQ ID NO 300
<211> LENGTH: 506
<212> TYPE: DNA
<213> ORGANISM: Homo sapiens

<400> SEQUENCE: 300

```
tctgaggaaa gtttgggctt attagtattt gctccagcga acctccaagt tttctccatt      60
gcggacaacg taactaccag ctccttggct cagtggttcg cctccactca gaagttccca     120
gtaggttctg tcattattgt tggcacatag gccctgaata caggtgatat agggccccca     180
tgagcgctcc tccattgtga aaccaaatat agtatcattc attttctggg ctttctccat     240
cacactgagg aagacagaac catttagcac agtgacattg gtgaaatatg tttcattgat     300
tctcacagag taattgacgg agatatatga ttgtgagtca ggaggtgtca cagttatagg     360
ctcatcagcg gagatgttga agttacctga agcagagacg caagaagagt ctttgttaat     420
atccaagaag gtctttccca tcagggcagg taagacctgg gctgcagcgt ttggattgct     480
gaatgctcct tgagaaattt ccgtga                                          506
```

<210> SEQ ID NO 301
<211> LENGTH: 304
<212> TYPE: DNA
<213> ORGANISM: Homo sapiens
<220> FEATURE:
<221> NAME/KEY: misc_feature
<222> LOCATION: (1)...(304)
<223> OTHER INFORMATION: n=A,T,C or G

<400> SEQUENCE: 301

```
tcctaaggca gagcccccat cacctcaggc ttctcagttc ccttagccgt cttactcaac      60
tgcccctttc ctctccctca gaatttgtgt ttgctgcctc tatcttgttt tttgtttttt     120
cttctggggg gggtctagaa cagtgcctgg cacatagtag gcgctcaata aatacttgtt     180
tgttgaatgt ctcctctctc tttccactct gggaaaccta ngnttctgcc attctgggtg     240
accctgtatt tntttctggt gcccattcca tttgnccagn taatacttcc tcttaaaaat     300
ctcc                                                                  304
```

<210> SEQ ID NO 302
<211> LENGTH: 492
<212> TYPE: DNA
<213> ORGANISM: Homo sapiens

<400> SEQUENCE: 302

```
ttttcagtaa gcaacttttc catgctctta atgtattcct ttttagtagg aatccggaag      60
tattagattg aatggaaaag cacttgccat ctctgtctag gggtcacaaa ttgaaatggc     120
tcctgtatca catacggagg tcttgtgtat ctgtggcaac agggagtttc cttattcact     180
ctttatttgc tgctgtttaa gttgccaacc tcccctccca ataaaaattc acttacacct     240
cctgcctttg tagttctggt attcacttta ctatgtgata gaagtagcat gttgctgcca     300
gaatacaagc attgcttttg gcaaattaaa gtgcatgtca tttcttaata cactagaaag     360
gggaaataaa ttaaagtaca caagtccaag tctaaaactt tagtactttt ccatgcagat     420
ttgtgcacat gtgagagggt gtccagtttg tctagtgatt gttatttaga gagttggacc     480
actattgtgt gt                                                         492
```

<210> SEQ ID NO 303
<211> LENGTH: 470
<212> TYPE: DNA
<213> ORGANISM: Homo sapiens

<400> SEQUENCE: 303

-continued

| | |
|---|---|
| tctggggcag caggtactcc ctacggcact agtctacagg gggaaggacg ctctgtgctg | 60 |
| gcagcggtgg ctcacatggc ctgtctgcac tgtaaccaca ggctgggatg tagccaggac | 120 |
| ttggtctcct tggaagacag gtctgatgtt tggccaatcc agtccttcag accctgcctg | 180 |
| aaacttgtat cttacgtgaa cttaaagaat aaaatgcatt tctaccccga tctcgccccc | 240 |
| aggactggca cgacaggccc acggcagatt agatcttttc ccagtactga tcggtgcgtg | 300 |
| gaattccagc caccacttct gattcgattc cacagtgatc ctgtcctctg agtattttaa | 360 |
| agaagccatt gtcaccccag tcagtgttcc aggagttggc aaccagccag tagggtgtgc | 420 |
| cattctccac tccccagccc aggatgcgga tggcatggac ctcggccgcg | 470 |

<210> SEQ ID NO 304
<211> LENGTH: 79
<212> TYPE: DNA
<213> ORGANISM: Homo sapiens

<400> SEQUENCE: 304

| | |
|---|---|
| tgtcccattg ttaactcagc ctcaaatctc aactgtcagg ccctacaaag aaaatggaga | 60 |
| gcctcttctg gtggatgcg | 79 |

<210> SEQ ID NO 305
<211> LENGTH: 476
<212> TYPE: DNA
<213> ORGANISM: Homo sapiens

<400> SEQUENCE: 305

| | |
|---|---|
| tcactgagcc accctacagc cagaagagat atgaggaaat tgttaaggaa gtcagcactt | 60 |
| acattaagaa aattggctac aaccccgaca cagtagcatt tgtgccaatt tctgttgga | 120 |
| atggtgacaa catgctggag ccaagtgcta acgtaagtgg ctttcaagac cattgttaaa | 180 |
| aagctctggg aatggcgatt tcatgcttac acaaattggc atgcttgtgt ttcagatgcc | 240 |
| ttggttcaag ggatggaaag tcacccgtaa ggatggcaat gccagtggaa ccacgctgct | 300 |
| tgaggctctg gactgcatcc taccaccaac tcgtccaact gacaagccct gcgcctgcc | 360 |
| tctccaggat gtctacaaaa ttggtggtaa gttggctgta aacaaagttg aatttgagtt | 420 |
| gatagagtac tgtctgcctt cataggtatt tagtatgctg taaatatttt taggta | 476 |

<210> SEQ ID NO 306
<211> LENGTH: 404
<212> TYPE: DNA
<213> ORGANISM: Homo sapiens

<400> SEQUENCE: 306

| | |
|---|---|
| tctgtctcgg agctcagggc gcagccagca cacacaggag cccacaggac agccacgtct | 60 |
| tcacagaaac tacagaagtc aggacccagg cgaggacctc aggaacaagt gcccctgca | 120 |
| gacagagaga cgcagtagca acagcttctg aacaactaca taataatgcg gggagaatcc | 180 |
| tgaagaccac tgcatcccac aagcactgac aaccacttca ggattttatt tcctccactc | 240 |
| taacccccag atccatttat gagaagtgag tgaggatggc aggggcatgg agggtgaagg | 300 |
| gacagcaagg atggtctgag ggcctggaaa caatagaaaa tcttcgtcct ttagcatatc | 360 |
| ctggactaga aaacaagagt tggagaagag ggggttgat acta | 404 |

<210> SEQ ID NO 307
<211> LENGTH: 260
<212> TYPE: DNA
<213> ORGANISM: Homo sapiens

```
<220> FEATURE:
<221> NAME/KEY: misc_feature
<222> LOCATION: (1)...(260)
<223> OTHER INFORMATION: n=A,T,C or G

<400> SEQUENCE: 307
tcctgcctan acatctgtga gggcctcaag ggctgctgcc tcgactttct ccctagctaa      60
gtccacccgt ccagggacac agccagggca ctgctctgtg ctgacttcca ctgcagccaa     120
gggtcaaaat gaagcatctg cggaggccag gactccttgg catcggacac agtcagggga    180
aaagccaccc tgactctgca ggacagaggg tctagggtca tttggcagga gaacactggt    240
gtgccaaggg aagcnancat                                                260

<210> SEQ ID NO 308
<211> LENGTH: 449
<212> TYPE: DNA
<213> ORGANISM: Homo sapiens

<400> SEQUENCE: 308
tctgtgctcc cgactcctcc atctcaggta ccaccgactg cactgggcgg ggccctctgg      60
ggggaaaggc tccacggggc aggatacat ctcgaggcca gtcatcctct ggaggcagcc     120
caatcaggtc aaagattttg cccaactggt cggcttcaga gtttccacag aagagaggct    180
ttcgacgaaa catctctgca aagatacagc caacactcca catgtccaca ggtgttgcat    240
atgtggactg cagaagaact tcgggagctc ggtaccagag tgtaacaacc ttgatcgttt    300
cggctggcaa gcctggtggg ggtgccttgt ccagatatgt ccttaggtcc tggtctacat    360
gctcaaacac cagggttacc ttgatctccc ggtcagttcg ggatgtggca cagacgtcca    420
tcagccggac aacattggga tgctcaaaa                                       449

<210> SEQ ID NO 309
<211> LENGTH: 411
<212> TYPE: DNA
<213> ORGANISM: Homo sapiens
<220> FEATURE:
<221> NAME/KEY: misc_feature
<222> LOCATION: (384)
<223> OTHER INFORMATION: n=A,T,C or G

<400> SEQUENCE: 309
ctgtggaaac ctggggtgcc gggtaaatgg agaactccag cttggatttc ttgccataat      60
caactgagag acgttccatg agcagggagg tgaacccaga accagttccc ccaccaaagc     120
tgtggaaaac caagaagccc tgaagaccgg tgcactggtc agccagcttg cgaattcgt     180 ccaacacaag gtcaatgatc tccttgccaa tggtgtagtg ccctcgggca tagttattgg    240
cagcatcttc cttgcctgtg atgagctgct cagggtggaa gagctggcgg taggtgccag    300
tgcgaacttc atcaatgact gtgggttcca agtctacaaa cacagcccgg ggcacgtgct    360
tgccagcgcc cgtctcactt gaanaagggt gtttgaagga agtcatctcc t             411

<210> SEQ ID NO 310
<211> LENGTH: 320
<212> TYPE: DNA
<213> ORGANISM: Homo sapiens
<220> FEATURE:
<221> NAME/KEY: misc_feature
<222> LOCATION: (250)
<223> OTHER INFORMATION: n=A,T,C or G

<400> SEQUENCE: 310
```

```
tcctcgtcca gcttgactcg attagtcctc ataaggtaag caaggcagat ggtggctgac    60
cgggaaatgc ctgcctggca gtggacaaac cccttcctc cagcattctt gatggagtct   120
atgaagtcaa tggcctcgtt gaaccaggag ctgatgtctg ccttgtggtt gtcctccaca   180
gggatgctct tgtactggta gtgaccctca aaatggttgg acaattggc tgagacgttg    240 atcaaggcan ttatgcccaa ggcatccagc atgtccttgc gggaagcgtg atacgcactg   300
cccaggtaca gaaagggcag                                               320
```

<210> SEQ ID NO 311
<211> LENGTH: 539
<212> TYPE: DNA
<213> ORGANISM: Homo sapiens

<400> SEQUENCE: 311

```
tctggcccat gaagctgaag ttgggagaga tgatgcttcg cctctgcttc acaaactcaa    60
aggcctcgtc cagcttgact cgattagtcc tcataaggta agcaaggcag atggtggctg   120
accgggaaat gcctgcctgg cagtggacaa acacccttcc tccagcattc ttgatggagt   180
ctatgaagtc aatggcctcg ttgaaccagg agctgatgtc tgccttgtgg ttgtcctcca   240
cagggatgct cttgtactgg tagtgaccct caaaatggtt gggacaattg gctgagacgt   300
tgatcaaggc agttatgccc aaggcatcca gcatgtcctt gcgggaagcg tgatacgcac   360
tgcccaggta cagaaagggc aggatttcca ccgggccacc ctgaaatcca gaaatatcca   420
acattcatca agcttgctca aagccaaggc cagtgcccat acccacaaaa actttctgct   480
ggaaaagtca atttcagata ccgagtgaac tcagttctgt tgctggagga taaataaat    539
```

<210> SEQ ID NO 312
<211> LENGTH: 475
<212> TYPE: DNA
<213> ORGANISM: Homo sapiens

<400> SEQUENCE: 312

```
tcaaggatct tcctaaagcc accatgtgag aggattcgga cgagagtctg agctgtatgg    60
cagaccatgt cctgctgttc tagggtcatg actgtgtgta ctctaaagtt gccactctca   120 cagggtcag tgatacccac tgaacctggc aggaacagtc ctgcagccag aatctgcaag    180
cagcgcctgt atgcaacgtt tagggccaaa ggctgtctgg tggggttgtt catcacagca   240
taatggccta gtaggtcaag gatccagggt gtgaggggct caaagccagg aaaacgaatc   300
ctcaagtcct tcagtagtct gatgagaact ttaactgtgg actgagaagc attttcctcg   360
aaccagcggg catgtcggat ggctgctaag gcactctgca atactttgat atccaaatgg   420
agttctggat ccagttttcg aagattgggt ggcactgttg taatgagaat cttca         475
```

<210> SEQ ID NO 313
<211> LENGTH: 456
<212> TYPE: DNA
<213> ORGANISM: Homo sapiens

<400> SEQUENCE: 313

```
tccacttaaa gggtgcctct gccaactggt ggaatcatcg ccacttccag caccacgcca    60
agcctaacat cttccacaag gatcccgatg tgaacatgct gcacgtgttt gttctgggcg   120
aatggcagcc catcgagtac ggcaagaaga agctgaaata cctgcccta aatcaccagc   180 acgaatactt cttcctgatt gggccgccgc tgctcatccc catgtatttc cagtaccaga   240
tcatcatgac catgatcgtc cataagaact gggtggacct ggcctgggcc gtcagctact   300
```

```
acatccggtt cttcatcacc tacatccctt tctacggcat cctgggagcc ctccttttcc      360
tcaacttcat caggttcctg gagagccact ggtttgtgtg ggtcacacag atgaatcaca      420
tcgtcatgga gattgaccag gaggacctcg gcccgc                               456

<210> SEQ ID NO 314
<211> LENGTH: 477
<212> TYPE: DNA
<213> ORGANISM: Homo sapiens

<400> SEQUENCE: 314
tgcgtgggct tctggaagcc tggatctgga atcattcacc agattattct ggaaaactat      60
gcgtaccctg gtgttcttct gattggcact gactcccaca cccccaatgg tggcggcctt     120
gggggcatct gcattggagt tgggggtgcc gatgctgtgg atgtcatggc tgggatcccc     180
tgggagctga agtgccccaa ggtgattggc gtgaagctga cgggctctct ctccggttgg     240
tcctcaccca agatgtgat cctgaaggtg gcaggcatcc tcacggtgaa aggtggcaca      300
ggtgcaatcg tggaatacca cggcctggt gtagactcca tctcctgcac tggcatggcg      360
acaatctgca acatgggtgc agaaattggg gccaccactt ccgtgttccc ttacaaccac     420
aggatgaaga agtatctgag caagaccggc cgggaagaca ttgccaatct agctgat       477

<210> SEQ ID NO 315
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 315
caggtactgg atgtcaggtc tgcgaaactt cttanatttt gacctcagtc cataaaccac      60
actatcacct cggccatcat atgtgtctac tgtggggaca actggagtga aaacttcggt     120
tgctgcaggt ccgtgggaaa atcagtgacc agttcatcag attcatcaga atggtgagac     180
tcatcagact ggtgagaatc atcagtgtca tctacatcat cagagtcgtt cgagtcaatg     240
g                                                                    241

<210> SEQ ID NO 316
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 316
nttntgtgat agtgtggttt atggactgag gncaaaatnt aagaagtttc gcagacctga      60
catccaancc tgcccgngcg gncgctcgaa aggncgaatt ctgcagatat ccatcacact     120
ggcggccgct cgagcatgca tctagagggc ccaattcgcc ctatantgag tnatattaca     180
attcactggc cgtcnnttta caacgtcgtg actgggaaaa ccctggcgtt acccaactta     240
a                                                                    241

<210> SEQ ID NO 317
<211> LENGTH: 241
<212> TYPE: DNA
```

```
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 317
aggtaccctg ctcancagcc tgggngcctg ggttgtctcc ttgtccatcc actggtccat      60
tctgctctgc atttttttgt tcctcttttg gaggttccac tttgggtttg ggctttgaaa     120
ttatagggct acaantacct cggccgaaac cacnctaagg gcgaattctg cagatatcca     180
tcacactggc ggncgctcga gcatgcatct agagggccca attcgcccta tagtgagtcg     240
t                                                                    241

<210> SEQ ID NO 318
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 318
cgngnacaan ntacattgat gganggtntg nggntctgan tntttantta cantggagca      60
ttaatatttt cttnaacgtn cctcaccttc ctgaantaaa nactctgggt tgtagcgctc     120
tgtgctnana accacntnaa ctttacatcc ctctttttgga ttaatccact gcgcggccac     180
ctctgccgcg accacgctaa gggcnaattc tgcagatatc catcacactg gcggccgctc     240
n                                                                    241

<210> SEQ ID NO 319
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 319
caggtactga tcggtgcgtg gaantccagc caccanttnt gattcgattc cacagtgatc      60
ctgtcctctg agtattttaa agaagccatt gtcaccccag tcagtgttcc aggagttggc     120
aaccagccag tagggtgtgc cattctccac tccccagccc aggatgcgga tggcatggcc     180
acccatcatc tctccggtga cgtgttggta cctcggccgc gaccacgcta agggcgaatt     240
c                                                                    241

<210> SEQ ID NO 320
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 320
ggcaggtacc aacagagctt agtaatntct aaaaagaaaa aatgatcttt ttccgacttc      60
taaacaagtg actatactag cataaatcat tctagtaaaa cagctaaggt atagacattc     120
taataatttg ggaaaaccta tgattacaag tgaaaactca gaaatgcaaa gatgttggtt     180
```

```
ttttgtttct cagtctgctt tagcttttaa ctctnnnaan cncatgcaca cttgnaactc    240
t                                                                   241
```

<210> SEQ ID NO 321
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 321

```
angtaccaac agagcttagt aattnntaaa aagaaaaaat gatcttttc cgacttctaa     60 acaagtgact atactagcat aaatcattct agtaaaacag ctaaggtata gacattctaa   120
taatttggga aaacctatga ttacaagtga aaactcagaa atgcaaagat gttggttttt   180
tgtttctcag tctgctttag cttttaactc tggaagcgca tgcacacntg aactctgctc   240
a                                                                   241
```

<210> SEQ ID NO 322
<211> LENGTH: 241
<212> TYPE: DNA
<213> ORGANISM: Homo sapiens

<400> SEQUENCE: 322

```
ggtaccaaca gagcttagta atttctaaaa agaaaaaatg atctttttcc gacttctaaa    60
caagtgacta tactagcata aatcattctt ctagtaaaac agctaaggta tagacattct   120
aataatttgg gaaaacctat gattacaagt aaaaactcag aaatgcaaag atgttggttt   180
tttgtttctc agtctgcttt agcttttaac tctggaagcg catgcacact gaactctgct   240
c                                                                   241
```

<210> SEQ ID NO 323
<211> LENGTH: 241
<212> TYPE: DNA
<213> ORGANISM: Homo sapiens

<400> SEQUENCE: 323

```
cgaggtactg tcgtatcctc agccttgttc tatttcttta ttttagcttt acagagatta    60
ggtctcaagt tatgagaatc tccatggctt tcagggcta aacttttctg ccattctttt    120
gctcttaccg ggctcagaag gacatgtcag gtgggatacg tgtttctctt tcagagctga   180
agaaagggtc tgagctgcgg aatcagtaga gaaagccttg gtctcagtga ctccttggct   240
t                                                                   241
```

<210> SEQ ID NO 324
<211> LENGTH: 241
<212> TYPE: DNA
<213> ORGANISM: Homo sapiens

<400> SEQUENCE: 324

```
aggtactgtc gtatcctcag ccttgttcta tttctttatt ttagctttac agagattagg    60
tctcaagtta tgagaatctc catggctttc agggctaaa cttttctgcc attcttttgc   120
tcttaccggg ctcagaagga catgtcaggt gggatacgtg tttctcttc agagctgaag   180 aaagggtctg agctgcggaa tcagtagaga aagccttggt ctcagtgact ccttggcttt   240
```

| | |
|---|---|
| c | 241 |

<210> SEQ ID NO 325
<211> LENGTH: 241
<212> TYPE: DNA
<213> ORGANISM: Homo sapiens

<400> SEQUENCE: 325

| | | | | | |
|---|---|---|---|---|---|
| ggcaggtaca | tttgttttgc | ccagccatca | ctcttttttg | tgaggagcct | aaatacattc | 60 |
| ttcctggggt | ccagagtccc | cattcaaggc | agtcaagtta | agacactaac | ttggccctttt | 120 |
| cctgatggaa | atatttcctc | catagcagaa | gttgtgttct | gacaagactg | agagagttac | 180 |
| atgttgggaa | aaaaaagaa | gcattaactt | agtagaactg | aaccaggagc | attaagttct | 240 |
| g | | | | | | 241 |

<210> SEQ ID NO 326
<211> LENGTH: 241
<212> TYPE: DNA
<213> ORGANISM: Homo sapiens

<400> SEQUENCE: 326

| | | | | | |
|---|---|---|---|---|---|
| gcaggtacat | ttgttttgcc | cagccatcac | tcttttttgt | gaggagccta | aatacattct | 60 |
| tcctggggtc | cagagtcccc | attcaaggca | gtcaagttaa | gacactaact | tggccctttc | 120 |
| ctgatggaaa | tatttcctcc | atagcagaag | ttgtgttctg | acaagactga | gagagttaca | 180 |
| tgttgggaaa | aaaagaagc | attaacttag | tagaactgat | ccaggagcat | aagttctga | 240 |
| a | | | | | | 241 |

<210> SEQ ID NO 327
<211> LENGTH: 241
<212> TYPE: DNA
<213> ORGANISM: Homo sapiens

<400> SEQUENCE: 327

| | | | | | |
|---|---|---|---|---|---|
| ggtaccagac | caagtgaatg | cgacagggaa | ttatttcctg | tgttgataat | tcatgaagta | 60 |
| gaacagtata | atcaaaatca | attgtatcat | cattagttt | ccactgcctc | acactagtga | 120 |
| gctgtgccaa | gtagtagtgt | gacacctgtg | ttgtcatttc | ccacatcacg | taagagcttc | 180 |
| caaggaaagc | caaatcccag | atgagtctca | gagagggatc | aatatgtcca | tgattatcag | 240 |
| g | | | | | | 241 |

<210> SEQ ID NO 328
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 328

| | | | | | |
|---|---|---|---|---|---|
| ggtacnagac | caaatgaang | ccacagggaa | ttatttcctg | tgttgataat | tcatgaagta | 60 |
| gaacantata | atcaaaatca | attgtatcat | cattagttt | ccactgcctc | acactagtga | 120 |
| gctgtgccaa | gtagtagtgt | gacacctgtg | ttgtcatttc | ccacatcacg | taagagcttc | 180 |
| caaggaaagc | caaatcccag | atgagtctca | gagagggatc | aatatgtcca | tnatcatcan | 240 |
| g | | | | | | 241 |

```
<210> SEQ ID NO 329
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 329
ttcaggtcga gttggctgca gatttgtggt gcnttctgag ccgtctgtcc tgcgccaaaa      60
ngcttcaaag tattattaaa acatatggga tccccatgaa gccctactac accaaagttt    120
accaggagat ttggatagga atggggctga tgggcttcat cgtttataaa atccgggctg    180
ctgataagaa gtaaggcttt gaaagcttca gcgcctgctn ctggtcanna ctaaccatan    240 n                                                                    241

<210> SEQ ID NO 330
<211> LENGTH: 241
<212> TYPE: DNA
<213> ORGANISM: Homo sapiens

<400> SEQUENCE: 330
ttttgtgcag atttgtggtg cgttctgagc cgtctgtcct gcgccaagat gcttcaaagt     60
attattaaaa acatatggat ccccatgaag ccctactaca ccaaagttta ccaggagatt    120
tggataggaa tggggctgat gggcttcatc gtttataaaa tccgggctgc tgataaagaa    180
gtaaggcttt gaaagcttca gcgcctgctc ctggtcatca ctaaccaga tttacttgga     240 g                                                                    241

<210> SEQ ID NO 331
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 331
nttttaggna ctttgggctc cagacttcac tggtcttagg nattgaaacc atcacctggn     60
ntgcattcct catgactgag gttaacttaa aacaaaaatg gtaggaaagc tttcctatnc    120
ttcnggtaag anacaaatnt nctttaaaaa aangtggaag gcatgacnta cgtgagaact    180
gcacaaactg gccactgaca aaaatgaccc ccatttgtgt gacttcattg agacacatta    240
c                                                                    241

<210> SEQ ID NO 332
<211> LENGTH: 241
<212> TYPE: DNA
<213> ORGANISM: Homo sapiens

<400> SEQUENCE: 332
tgtgaggaga gggaacatgc tgagaaactg atgaagctgc agaaccaacg aggtggccga     60
atcttccttc aggatatcaa gaaaccagac tgtgatgact gggagagcgg gctgaatgca    120
atggagtgtg cattacattt ggaaaaaaat gtgaatcagt cactactgga actgcacaaa    180
ctggccactg acaaaaatga cccccatttg tgtgacttca ttgagacaca ttacctgaat    240
g                                                                    241
```

<210> SEQ ID NO 333
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 333

| | | | | |
|---|---|---|---|---|
| caggtacaag cttttttttt tttttttttt tttttttttt ttgnaaatac tntttattgn | 60 |
| aaatattcta tcctaaattc catatagcca attaattntt acanaatntt ttgttaattt | 120 |
| ttgngngtat aaatttttaca aaaataaagg gtatgtttgt tgcacacaac ttacaaataa | 180 |
| taataaactn tttattgnaa atattntttta ttgnaaatat tctttatcct aaattccata | 240 |
| t | 241 |

<210> SEQ ID NO 334
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 334

| | |
|---|---|
| tacctgctgn agggntgaa gncntctctg ctgccccagg catctgcanc ccctgctgct | 60 |
| ggttctgccc ctgctgcagc agaggagaag aaagatgaga agaaggagga gtctgaagag | 120 |
| tcagatgatg acatgggatt tggccttttt gattaaannc ctgctcccct gcaaataaag | 180 |
| cctttttaca caaaaaaaaa aaaaaaaaa aaaaaaaaa aagcttgtac ctgcccnggc | 240 |
| g | 241 |

<210> SEQ ID NO 335
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 335

| | |
|---|---|
| ctatgtgctg ggatgactat ggagacccaa atgtctcana atgtatgtcc cagaaacctg | 60 |
| tggctgcttc aaccattgac agttttgctg ctgctggctt ctgcagacag tcaagctgca | 120 |
| gctcccccaa aggctgtgct gaaacttgag cccccgtgga tcaacgtgct ccaggaggac | 180 |
| tctgtgactc tgacatgcca gggggctcgc agccctgaga gcgactccat tcagtggttc | 240 |
| c | 241 |

<210> SEQ ID NO 336
<211> LENGTH: 241
<212> TYPE: DNA
<213> ORGANISM: Homo sapiens

<400> SEQUENCE: 336

| | |
|---|---|
| taccaaccta tgcagccaag caacctcagc agttcccatc aaggccacct ccaccacaac | 60 |
| cgaaagtatc atctcaggga aacttaattc ctgcccgtcc tgctcctgca cctcctttat | 120 |
| atagttccct cacttgattt ttttaacctt cttttttgcaa atgtcttcag ggaactgagc | 180 |

```
taatactttt ttttttcttg atgttttctt gaaaagcctt tctgttgcaa ctatgaatga      240
a                                                                     241

<210> SEQ ID NO 337
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 337
ggtactgtat gtagctgcac tacaacagat tcttaccgtc tccacanagg tcatanattg       60
taaatggtna atactgactt tttttttatt cccttgactc aagacagcta acttcatttt      120
cagaactgtt ttaaaccttt gtgtgctggt ttataaaata atgtgtgtaa tccttgttgc      180
tttcctgata ccagactgtt tcccgtggtt ggttagaata tattttgntt tgatgcttat      240
a                                                                     241

<210> SEQ ID NO 338
<211> LENGTH: 241
<212> TYPE: DNA
<213> ORGANISM: Homo sapiens

<400> SEQUENCE: 338
aggtacaggt gtgcgctgag ccgagtttac acggaaagga taaagcccat ttagtttctt       60
ctcaaatgga gttttccact ttcctttgaa gtagacagca ttcaccagga tcatcctggt      120
atccccatct acagaaacctt caggtaacaa gtttgggatt ttgcctttgg tttgagtctt     180
gacccaggaa ttaatctttt ttctagcttc ttctgcacat tctaggaagt ctactgcctg     240
g                                                                     241

<210> SEQ ID NO 339
<211> LENGTH: 241
<212> TYPE: DNA
<213> ORGANISM: Homo sapiens

<400> SEQUENCE: 339
taccgacggc tcctggaggg agagagtgaa gggacacggg aagaatcaaa gtcgagcatg       60
aaagtgtctg caactccaaa gatcaaggcc ataacccagg agaccatcaa cggaagatta      120
gttctttgtc aagtgaatga aatccaaaag cacgcatgag accaatgaaa gtttccgcct      180
gttgtaaaat ctattttccc ccaaggaaag tccttgcaca gacaccagtg agtgagttct      240
a                                                                     241

<210> SEQ ID NO 340
<211> LENGTH: 241
<212> TYPE: DNA
<213> ORGANISM: Homo sapiens

<400> SEQUENCE: 340
gtagccctca cacacacatg cccgtaacag gatttatcac aagacacgcc tgcatgtaga       60
ccagacacag ggcgtatgga agcacgtcc tcaagactgt agtattccag atgagctgca      120
gatgcttacc taccacggcc gtctccacca gaaaaccatc gccaactcct gcgatcagct      180
tgtgacttac aaaccttgtt taaaagctgc ttacatggac ttctgtcctt taaaagcttc      240
```

<210> SEQ ID NO 341
<211> LENGTH: 241
<212> TYPE: DNA
<213> ORGANISM: Homo sapiens

<400> SEQUENCE: 341

| gtaccgccta ctttcgtctc atgtctccga acttcttgct gatggccgtt ccaacgttgc | 60 |
| tgaaagctgc agttgccttt tgccctgcgt gactcagggt ttcatgtgtt ttcttgtagg | 120 |
| cagtggtagt ctgcatgtca tgccagcttt tgctgaagtt ctgttttaat tcattcatca | 180 |
| ggttcatgcc gagttttgtt ttatctcaac tagatgcctt tctttcgctg acaaaacttg | 240 |
| t | 241 |

<210> SEQ ID NO 342
<211> LENGTH: 241
<212> TYPE: DNA
<213> ORGANISM: Homo sapiens

<400> SEQUENCE: 342

| gtacattggt gctataaata taaatgctac ttatgaagca tgaaattaag cttcttttt | 60 |
| cttcaagttt tttctcttgt ctagcaatct gttaggcttc tgaaccaaga ccaaatgttt | 120 |
| acgttcctct gctgcatacc aacgttactc caaacaataa aaatctatca tttctgctct | 180 |
| gtgctgagga atggaaaatg aaacccccac cccctgaccc ctaggactat acagtggaaa | 240 |
| c | 241 |

<210> SEQ ID NO 343
<211> LENGTH: 241
<212> TYPE: DNA
<213> ORGANISM: Homo sapiens

<400> SEQUENCE: 343

| gtacatgtgg tagcagtaat tttttgaag caactgcact gacattcatt tgagttttct | 60 |
| ctcattatca gattctgttc caaacaagta ttctgtagat ccaaatggat taccagtgtg | 120 |
| ctacagactt cttattatag aacagcattc tattctacat caaaaatagt ttgtgtaagt | 180 |
| tagttttggt taccatctaa aatattttta aatgttcttt acataaaaat ttatgttgtg | 240 |
| t | 241 |

<210> SEQ ID NO 344
<211> LENGTH: 241
<212> TYPE: DNA
<213> ORGANISM: Homo sapiens

<400> SEQUENCE: 344

| ggtacaaaat tgttggaatt tagctaatag aaaaacatag taaatattta caaaaacgtt | 60 |
| gataacatta ctcaagtcac acacatataa caatgtagac aggtcttaac aaagtttaca | 120 |
| aattgaaatt atggagattt cccaaaatga atctaatagc tcattgctga gcatggttat | 180 |
| caatataaca tttaagatct tggatcaaat gttgtccccg agtcttctgc aatccagtcc | 240 |
| t | 241 |

<210> SEQ ID NO 345
<211> LENGTH: 241
<212> TYPE: DNA
<213> ORGANISM: Homo sapiens

<400> SEQUENCE: 345

```
ggtacgaagc tgagcgcacg ggggttgccc cagcgtggag cctggacctc aaacttcacg      60
gaaaatgctc tctctctttg acaggcttcc agctgtctcc taatttcctg gatgaactct     120
ccccggcgat ttaactgatc ctgaaaagtg gtgagaggac tgaggaagac aaccaggtca     180
gcgttagatc ggcctctgag ggtggtgccc ttgcctgagg agccacccTT taccaccttg     240
g                                                                     241
```

<210> SEQ ID NO 346
<211> LENGTH: 241
<212> TYPE: DNA
<213> ORGANISM: Homo sapiens

<400> SEQUENCE: 346

```
caggtaccac tgagcctgag atggggatga gggcagagag aggggagccc cctcttccac      60
tcagttgttc ctactcagac tgttgcactc taaacctagg gaggttgaag aatgagaccc     120
ttaggtttta acacgaatcc tgacaccacc atctataggg tcccaacttg gttattgtag     180
gcaaccttcc ctctctcctt ggtgaagaac atcccaagcc agaaagaagt taactacagt     240
g                                                                     241
```

<210> SEQ ID NO 347
<211> LENGTH: 241
<212> TYPE: DNA
<213> ORGANISM: Homo sapiens

<400> SEQUENCE: 347

```
aggtacatct aaaggcatga agcactcaat tgggcaatta acattagtgt ttgttctctg      60
atggtatctc tgagaatact ggttgtagga ctggccagta gtgccttcgg gactgggttc     120
accccccaggt ctgcggcagt tgtcacagcg ccagccccgc tggcctccaa agcatgtgca     180
ggagcaaatg gcaccgagat attccttctg ccactgttct cctacgtggt atgtcttccc     240
a                                                                     241
```

<210> SEQ ID NO 348
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 348

```
angtacttgg caagattnga tgctcttgng ctcantgaca tcattcataa cttgtnngtg      60
tgancagagg aggagnncat catcntgtcc tcattcgtca gnnnnctctc ctctctgaat     120
ctcaaacaag ttgataatgg agaaaaattt gaattctcag gattgaggct ggactggttc     180
cgcctacang catacactag cgtggctaag gcccctctgc accctgcatg anaaccctga     240
c                                                                     241
```

<210> SEQ ID NO 349
<211> LENGTH: 241
<212> TYPE: DNA
<213> ORGANISM: Homo sapiens

<400> SEQUENCE: 349

| | |
|---|---|
| gcaggtacca tttgtctgac ctctgtaaaa aatgtgatcc tacagaagtg gagctggata | 60 |
| atcagatagt tactgctacc cagagcaata tctgtgatga agacagtgct acagagacct | 120 |
| gctcacactta tgacagaaac aagtgctaca cagctgtggt cccactcgta tatggtggtg | 180 |
| agaccaaaat ggtggaaaca gccttaaccc cagatgcctg ctatcctgac taatttaagt | 240 |
| c | 241 |

<210> SEQ ID NO 350
<211> LENGTH: 241
<212> TYPE: DNA
<213> ORGANISM: Homo sapiens

<400> SEQUENCE: 350

| | |
|---|---|
| aggtactgtg gatatttaaa atatcacagt aacaagatca tgcttgttcc tacagtattg | 60 |
| cgggccagac acttaagtga aagcagaagt gtttgggtga cttttcctact taaaattttg | 120 |
| gtcatatcat ttcaaaacat tgcatcttg gttggctgca tatgctttcc tattgatccc | 180 |
| aaaccaaatc ttagaatcac ttcatttaaa atactgagcg gtattgaata cttcgaagca | 240 |
| g | 241 |

<210> SEQ ID NO 351
<211> LENGTH: 241
<212> TYPE: DNA
<213> ORGANISM: Homo sapiens

<400> SEQUENCE: 351

| | |
|---|---|
| tacagaaatc atttggagcc gttttgagac agaagtagag gctctgtcaa gtcaatactg | 60 |
| cattgcagct tggtccactg aagaagccac gcctgagata caaagatgc actacacttg | 120 |
| acccgcttta tgttcgcttc ctctcccctt ctctctcatc aactttatta ggttaaaaca | 180 |
| ccacatacag gctttctcca aatgactccc tatgtctggg gtttggttag aattttatgc | 240 |
| c | 241 |

<210> SEQ ID NO 352
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 352

| | |
|---|---|
| gtaccctgtn gagctgcacc aagattannt ggggccatca tgactgcanc cacnacgang | 60 |
| acgcaggcgt gnagtgcatc gtctgacccg gaaacccttt cacttctctg ctcccgaggt | 120 |
| gtcctcnggc tcatatgtgg gaaggcanan gatctctgan gagttncctg gggacaactg | 180 |
| ancagcctct ggagaggggc cattaataaa gctcaacatc attggcaaaa aaaaaaaaaa | 240 |
| a | 241 |

<210> SEQ ID NO 353
<211> LENGTH: 241
<212> TYPE: DNA
<213> ORGANISM: Homo sapiens

<400> SEQUENCE: 353

| | |
|---|---|
| aggtaccagt gcattaattt gggcaaggaa agtgtcataa tttgatactg tatctgtttt | 60 |
| ccttcaaagt atagagcttt tggggaagga agtattgaa ctgggggttg gtctggccta | 120 |

```
ctgggctgac attaactaca attatgggaa atgcaaaagt tgtttggata tggtagtgtg    180
tggttctctt ttggaatttt tttcaggtga tttaataata atttaaaact actataaaaa    240
c                                                                    241
```

<210> SEQ ID NO 354
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 354

```
ngcaggtccg ggcaggtacc aagattcatt ctcatcaaaa actagaaaca gaagggcaaa    60
ttccagtttc cttctgggat tgaatacttt caagtaaggt cttcgacaaa caatcagggg   120
gccaattaat ccactgtaga ggtccttaac ttgatccaca gttgaataat aagcccatgg   180
aatacaagca gaatcctctg ttccagctcc agatctttct gggattttcc atacgtaagt   240
g                                                                    241
```

<210> SEQ ID NO 355
<211> LENGTH: 241
<212> TYPE: DNA
<213> ORGANISM: Homo sapiens

<400> SEQUENCE: 355

```
ggtacccacc ctaaatttga actcttatca agaggctgat gaatctgacc atcaaatagg    60
ataggatgga ccttttttg agttcattgt ataaacaaat tttctgattt ggacttaatt    120
cccaaaggat taggtctact cctgctcatt cactctttca aagctctgtc cactctaact   180
tttctccagt gtcatagata gggaattgct cactgcgtgc ctagtctttc ttcacttacc   240
t                                                                    241
```

<210> SEQ ID NO 356
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 356

```
aggtactgta attgagcatc cggaatntgg agaagtaatt tagctacagg gtgaccaacg    60
caagaacata tgccagttcc tcgtagagat tggactggct aaggacgatc agctgaaggt   120
tcatgggttt taagtgcttg tggctcactg aagcttaagt gaggatttcc ttgcaatgag   180
tagaatttcc cttctctccc ttgtcacagg tttaaaaacc tcacagcttg tataatgtaa   240
c                                                                    241
```

<210> SEQ ID NO 357
<211> LENGTH: 241
<212> TYPE: DNA
<213> ORGANISM: Homo sapiens

<400> SEQUENCE: 357

```
ttttgtacca ccgatatgat caaggaaaat tctgcccatt tttatggctg aagttctaaa    60
```

```
aacctaattc aaagttcttc catgatccta cactgcctcc aagatggtcc aggctggcat      120
aaggcctgag cggcggtgag atccgcggct gccagcagct tgtcgctctt cagctggtat      180
gaagcccctc ggccacccga gtctccagga cctgcccggg cgccgctcga aagggcgaat      240
t                                                                      241

<210> SEQ ID NO 358
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 358
aggtacgggg agtgggggtg aagcntgttc tctacatagg caacacagcc gcctaantca       60
caaagtcagt ggtcggccgc ttcgaccaac atgtggtgag cattccacgg gcgcatgaag      120
tctgggtgct gtgctcgagt ctctgaatat tttgatagga agcgacaaga aaattcaaac      180
tgctctttgc tgactactgg aaagtgaaaa gatgctcaag tttaccattc aagaaacca      240 t                                                                      241

<210> SEQ ID NO 359
<211> LENGTH: 241
<212> TYPE: DNA
<213> ORGANISM: Homo sapiens

<400> SEQUENCE: 359
gaggtacaca aaaggaatac cttctgagag ccagggagtg aggaaagggg aaggagactt       60
gacgtcaagg gtgcttttga ggaacatgac gggccagcca gcctgcccca actttgaggc      120
cctgctgggc tcttgtgact ataaatatac tgtctatttc taatgcaatc cgtctttcct      180
gaaagatctt gttatctttt actattgaga catgctttca tttttgtggt cctgtttcca      240
a                                                                      241

<210> SEQ ID NO 360
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 360
ngtactctat actaattctg ccttttata cttaattcta aatttctccc ctctaattta       60
caacaaattt tgtgattttt ataagaatct atgcctcccc aattctcaga ttcttctctt      120
ttctccttta tttctttgct taaattcagt ataagctttc ttggtatttt aggcttcatg      180
cacattctta ttcctaaaca ccagcagttc ttcagagacc taaaatccag tataggaata      240
a                                                                      241

<210> SEQ ID NO 361
<211> LENGTH: 241
<212> TYPE: DNA
<213> ORGANISM: Homo sapiens

<400> SEQUENCE: 361
aggtactctc cgtgccccga cactgaacat tatccagcca gatctgccca gtgccagctc       60
```

```
ccactttgta cttttcttac tatcctgtct agaatcatgt cttatgattt taacagatat    120
agaaccactc ctagaaaatg ttctttcact ttctcgtttc ctttttaatc tatcatcctg    180
actactgaac ttaaaatctt tttcttccct tttttgtttc tcttttcttt tatcctgttc    240
a                                                                    241
```

<210> SEQ ID NO 362
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 362

```
aggtactttt atacctngct tangtcagtg acagatttac caatgacaac acaattttaa    60
aattccaaca catatattac tttgtcctat gaagggcaaa aagtcaatat attttaaatt   120
ttaaaaacag aatggatata atgaccttt tacacatcag tgatatttaa aagacttaaa   180
gagacaatac tatggttgag acactggctt cctattccag ccctaattaa agaaaaaata   240
g                                                                    241
```

<210> SEQ ID NO 363
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 363

```
ttangtacta aaaacaaaat cctaattctg ttttaaagag ctgggagatg ttaatcatat     60
gctcagtttt tccacgttat aatttcctaa atgcaaactt ttcaatcagg gcagttcaaa   120
ttcattacat cacagtaaat aacagtagcc aactttgatt ttatgcttat aggaaaaaaa   180
atcctgtaga tataaaaaca gcaaattttg acaaataaaa ctcaaaccat tcatccctaa   240
a                                                                    241
```

<210> SEQ ID NO 364
<211> LENGTH: 241
<212> TYPE: DNA
<213> ORGANISM: Homo sapiens

<400> SEQUENCE: 364

```
ggtacaagca gttagtcctg aaggcccctg ataagaatgt catcttctcc ccactgagca    60
tctccaccgc cttggccttc ctgtctctgg gggcccataa taccaccctg acagagattc   120
tcaaaggcct caagttcaac ctcacggaga cttctgaggc agaaattcac cagagcttcc   180
agcacctcct gcgcaccctc aatcagtcca gcgatgagct gcagctgagt atgggaaatg   240
c                                                                    241
```

<210> SEQ ID NO 365
<211> LENGTH: 241
<212> TYPE: DNA
<213> ORGANISM: Homo sapiens

<400> SEQUENCE: 365

```
cgaggtactg agattacagg catgagccac cacgcccggc caaaaacatt taaaaaatga      60
ctgtccctgc tcaaatactg cagtaggaaa tgtaatttga catatatcac ttccagaaaa     120
aaactttaaa tctttctata aaatgaattt gatacatcat cagcatgaag tgaagttaaa     180
atctcttaca aagtaaattc aggtatatca acaatgagat ccaaaagtat cggttcaaga     240
t                                                                     241
```

<210> SEQ ID NO 366
<211> LENGTH: 241
<212> TYPE: DNA
<213> ORGANISM: Homo sapiens

<400> SEQUENCE: 366

```
ggcaggtaca catcaaacac ttcattgcct aaatgcaggg acatgcttcc atctgaccac      60
ttgactatcc gagcattgct ttctttaatt tcatttcctt cttcatctcg gcgtatcctc     120
catcttatag tattttctac ctttaatttt aacctggttc taccttcttc atccagcatt     180
tcttcatctt caaattcatc ttcataatac tgggctctac acttgagaaa gttgggcagt     240
t                                                                     241
```

<210> SEQ ID NO 367
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 367

```
gcaggtacaa ataattcctg ttgtnacatt tagtggacgc gattatctgt atacctcaaa      60
ttttaattta agaaagtatc acttaaagag catctcattt tctatagatt gaggcttaat     120
tactgaaaag tgactcaacc aaaaagcaca taacctttta aaggagctac acctaccgca     180
gaaagtcaga tgccctgtaa ataactttgg tctttcaaaa tagtggcaat gcttaagata     240
c                                                                     241
```

<210> SEQ ID NO 368
<211> LENGTH: 241
<212> TYPE: DNA
<213> ORGANISM: Homo sapiens

<400> SEQUENCE: 368

```
tttgtacatt gttaatagtg accctcggag gaaatggatt tctcttctat taaaaactct      60
atggtatata agcattacat aataatgcta cttaaccacc ttttgtctca agaattatca     120
ccaaagtttt ctggaaataa gtccacataa gaattaaata tttaaaaggt gaaatgttcc     180
ttattttaac tttagcaaga tcttttcttt ttcattaaga aacactttaa taattttaaa     240
g                                                                     241
```

<210> SEQ ID NO 369
<211> LENGTH: 241
<212> TYPE: DNA
<213> ORGANISM: Homo sapiens

<400> SEQUENCE: 369

```
gcaggtactt tattcttatt tcttatccta tattctgtgt tacagaaaaa ctactaccat      60
aaacaaaaca ccaaccagcc acagcagttg tgtcaagcat gacaattggt ctagtcttca     120
```

```
cattttatta gtaagtctat caagtaagag atgaagggtc tagaaaacta gacacaaagc    180
aaccagggtc caaatcacca aggtagatct gtgcttagct aaagggaaac acccgaagat    240
t                                                                   241
```

<210> SEQ ID NO 370
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G
<400> SEQUENCE: 370

```
ngttcacagt gccctccgg cctcgccatg aggctcttcc tgtcgctccc ggtcctggtg     60
gtggttctgt cgatcgtctt ggaaggccca gccccagccc aggggacccc agacgtctcc   120
agtgccttgg ataagctgaa ggagtttgga acacactgg aggacaaggc tcgggaactc    180
atcagccgca tcaaacagag tgaactttct gccaagatgc gggagtggtt ttcagaagac   240
a                                                                   241
```

<210> SEQ ID NO 371
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G
<400> SEQUENCE: 371

```
ggcaggtcat cttgagcctt gcacatgata ctcagattcc tcaccttgc ttaggagtaa    60 aacaatatac tttacagggt gataataatc tccatagtta tttgaagtgg cttgaaaaag   120
gcaagattga cttttatgac attggataaa atctacaaat cagccctcga gttattcaat   180
gataactgac aaactaaatt atttccctag aaaggaagat gaaaggnagt ggagtgtggt   240
t                                                                   241
```

<210> SEQ ID NO 372
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G
<400> SEQUENCE: 372

```
aggtacagca aagcgaccct tggtgnnata gatcagacgg aaattctctc ccgtcttgnc    60
aatgctgatg acatccatga atccagcagg gtaggttata tcagttcgga ccttgccatc   120
gattttaatg aaccgctgca tgcaaatctt ctttacttca tctcctgtca gggcatactt   180
aagtctgttc ctcaggaaaa tgatgagggg gagacactct ctcaacttgt ggggaccggt   240
g                                                                   241
```

<210> SEQ ID NO 373
<211> LENGTH: 241
<212> TYPE: DNA
<213> ORGANISM: Homo sapiens -continued

```
<400> SEQUENCE: 373
tactgaaaca gaaaaaatgt attcccacaa aagctgttac acagcggttt cccgtcccca      60
gaagcagtag aaaatcttag cattccaatg gaaggcatgt atttgtaaaa tattctaaaa     120
tcagctctat agtttccttg tcctctttga taagggatca gacagagggt gtgtccccct     180
tcagcagcta cccttcttga caaactggtc tccaataata cctttcagaa acttacaaga     240
c                                                                     241

<210> SEQ ID NO 374
<211> LENGTH: 241
<212> TYPE: DNA
<213> ORGANISM: Homo sapiens

<400> SEQUENCE: 374
caggtactaa aacttacaat aaatatcaga gaagccgtta gttttttacag catcgtctgc     60 ttaaaagcta agttgaccag gtgcataatt tcccatcagt ctgtccttgt agtaggcagg    120 gcaattctg ttttcatgat cggaatactc aaatatatcc aaacatcttt ttaaaacttt     180
gatttatagc tcctagaaag ttatgttttt taatagtcac tctactctaa tcaggcctag    240
c                                                                     241

<210> SEQ ID NO 375
<211> LENGTH: 241
<212> TYPE: DNA
<213> ORGANISM: Homo sapiens

<400> SEQUENCE: 375
aggtacaaag gaccagtatc cctacctgaa gtctgtgtgt gagatggcag agaacggtgt     60
gaagaccatc acctccgtgg ccatgaccag tgctctgccc atcatccaga agctagagcc    120
gcaaattgca gttgccaata cctatgcctg taaggggcta gacaggattg aggagagact    180
gcctattctg aatcagccat caactcagat tgttgccaat gccaaaggcg ctgtgactgg    240
g                                                                     241

<210> SEQ ID NO 376
<211> LENGTH: 241
<212> TYPE: DNA
<213> ORGANISM: Homo sapiens

<400> SEQUENCE: 376
ggtacatttt actttccttc tttcagaatg ctaataaaaa actttgtttt atacttaaaa     60
aaaccataaa tcagacaaac aaaagaaacg attccaacat cacttctgtg atgagaaaag    120
aggcaatgga attcaacata agcaaagaaa actctacctg gaggaaagaa atcgatcagc    180
gaagaaacaa ctcggggctg ctgccagact gcaggccatg cgaggaggag cctcctagag    240
g                                                                     241

<210> SEQ ID NO 377
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 377
tcctttctgt ccaggtgatt cacagactag acctttctta tcctcctcct agagttttga     60
```

```
cttgggactc tagtgttaag atgatgagcc cgtgcatcag gtccttctgc actttggtgg      120
aagtctccca gggtaggttt cctatttgaa acagtggaat catgtttcca gtgataaagt      180
ttaatgacct catccttttt tttttttttc tcatctgcca tttgtgtgtc ttanatgggt      240
t                                                                     241
```

<210> SEQ ID NO 378
<211> LENGTH: 241
<212> TYPE: DNA
<213> ORGANISM: Homo sapiens

<400> SEQUENCE: 378

```
aggtcagcga tcaggtcctt tatgggcagc tgctgggcag ccccacaagc ccagggccag      60
ggcactatct ccgctgcgac tccactcagc ccctcttggc gggcctcacc cccagcccca     120
agtcctatga gaacctctgg ttccaggcca gccccttggg gaccctggta accccagccc     180
caagccagga ggacgactgt gtctttgggc cactgctcaa cttccccctc ctgcagggga     240
t                                                                     241
```

<210> SEQ ID NO 379
<211> LENGTH: 241
<212> TYPE: DNA
<213> ORGANISM: Homo sapiens

<400> SEQUENCE: 379

```
tacggagcaa tcgaagaggc atatccacac ttggggtggc tatagggctg gaaaatgctg      60
aagatgactg cttcactga ggtcaaggat tgtaatattg ccagctttgt aaagccatta      120
aagcagaagt ttcttcagtg atcttctctc taagaaacac catcacctcc atgtgcctta     180
cagaggcccc ctgcgttctg ctgcattgct tttgcgcaat cccttgatga tgaagatggt     240
c                                                                     241
```

<210> SEQ ID NO 380
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 380

```
acgtacacgc agaccgacat gggnnnttca ggcntnagat caaactcaaa acctgnaatg      60
atatccactc tcttttcctt aagctcaggg aaatattcca agtagaagtc canaaagtca     120
tcggctaana tgcttcngaa tttgaattca tgcacatagg ccttgaaaaa actgtcaaac     180
tgannctgat cacccaccaa gtgggccntn tatgacacaa agcagaaacc tttctcntan     240
g                                                                     241
```

<210> SEQ ID NO 381
<211> LENGTH: 241
<212> TYPE: DNA
<213> ORGANISM: Homo sapiens

<400> SEQUENCE: 381

```
aggtacaact taatggatta gcttttgggt ttaactgaat atatgaagaa attgggtctg      60
tctaaagaga gggtatttca tatggctttt agttcacttg tttgtatttc atcttgattt     120
```

```
ttttctttgg aaaataaagc attctatttg gttcagattt ctcagatttg aaaaaggctc      180
tatctcagat gtagtaaatt atttcctttc agtttgtgaa agcaggattt gactctgaaa      240
g                                                                     241
```

<210> SEQ ID NO 382
<211> LENGTH: 241
<212> TYPE: DNA
<213> ORGANISM: Homo sapiens

<400> SEQUENCE: 382

```
gtactgctat aatcaatacg tctgatagac aggtttatcc actatattga ccctacctct       60
aaaaggattg tcataattta tatgctttat gtttacacct atgatacagt tgccttggaa      120
cacaaaattt ttcattgtaa ttaaaaaaag aagagttgtg cagacagaag aaatcaaatc      180
taagaaaatc acaggagtag ataaatactc tagaattcat ataccttgg aagatgggtt      240 t                                                                     241
```

<210> SEQ ID NO 383
<211> LENGTH: 241
<212> TYPE: DNA
<213> ORGANISM: Homo sapiens

<400> SEQUENCE: 383

```
ggcaggtaca aagtcttctc tttgcttttt ataattttaa agcaaataac acatttaact       60
gtatttaagt ctgtgcaaat aatccttcag aagaaatatc caagattctg tttgcagagg      120
tcattttgtc tctcaaagat gattaaatga gtttgtcttc agataaagtg ctcctgtcca      180
gcagaactca aaaggccttc aagctgttca gtaagtgtag ttcagataag actccgtcat      240
a                                                                     241
```

<210> SEQ ID NO 384
<211> LENGTH: 241
<212> TYPE: DNA
<213> ORGANISM: Homo sapiens

<400> SEQUENCE: 384

```
ggtacacaaa atacacttgc aagcttgctt acagagacct gttaaacaaa gaacagacag       60
attctataaa atcagttata tcaacatata aaggagtgtg attttcagtt tgttttttta      120
agtaaatatg accaaactga ctaaataaga aggcaaaaca aaaaattatg cttccttgac      180
aaggcctttg gagtaaacaa aatgctttaa ggctcctggt gaatggggtt gcaaggatga      240
a                                                                     241
```

<210> SEQ ID NO 385
<211> LENGTH: 241
<212> TYPE: DNA
<213> ORGANISM: Homo sapiens

<400> SEQUENCE: 385

```
ggcaggtcta caatggctct gtcccttctg tggaatcgtt acaccaagag gtctcagtcc       60
tggtccctga ccccacagtg agctgtttag atgatccttc acatcttcct gatcaactgg      120
aagacactcc aatcctcagt gaagactctc tggagcccctt caactctctg gcaccaggta     180
ggtttggagg ctatgtccct ttaacttatc catgcagagt agccaaactt tacctgaaag      240
a                                                                     241
```

```
<210> SEQ ID NO 386
<211> LENGTH: 241
<212> TYPE: DNA
<213> ORGANISM: Homo sapiens

<400> SEQUENCE: 386
aggtaccttt tcctctcca aggaacagt ttctaaagtt ttctgggggg aaaaaaaact    60
tacatcaaat ttaaaccata tgttaaactg catattagtt gtgttacacc aaaaaattgc   120
ctcagctgat ctacacaagt ttcaaagtca ttaatgcttg atataaattt actcaacatt   180
aaattatctt aaattattaa ttaaaaaaaa aactttctaa gggaaaaata aacaaatgta   240
g                                                                  241

<210> SEQ ID NO 387
<211> LENGTH: 241
<212> TYPE: DNA
<213> ORGANISM: Homo sapiens

<400> SEQUENCE: 387
accccactgg ccgctgtgga gtatctccac tctcccctcg tgagggccgc tcccaccgac    60
cagtcgaact tcgtaaatg gagttaatgt gtttccactc ccctttccc ctttctggcc    120 ttttggtcca gaatttcctg gccttccggc atatcctggg agtcctcgac ttccaggaaa   180
gccaattgct ccccgatcac ctttaagacc cggaggacct attggacctg gaaatcctcg   240
t                                                                  241

<210> SEQ ID NO 388
<211> LENGTH: 241
<212> TYPE: DNA
<213> ORGANISM: Homo sapiens

<400> SEQUENCE: 388
tttgtactct tgtccacagc agagacattg agtataccat ggcatcaat gtcaaaagtg    60 acttcaatct gaggaacacc tcggggtgca ggaggtatgc ctgtgagttc aaacttgcca   120
agcaggttgt tatcctttgt catggcacgc tcgccttcat aaacctgaat aagtacacca   180
ggctggttgt cagaataggt agtgaaggtc tgtgtctgct tggtaggaat ggtggtatta   240
c                                                                  241

<210> SEQ ID NO 389
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 389
tacctntgtt agtgagcacc ttgtcttntg tgcttatntc ttnaagataa atacatggaa    60
ggatgtgaaa atcggaacac caactatgtg tctcactgca tctaagtgaa gcagccacag   120
ctgtgagagt tttcaaagca gaaagatgct gatgtgacct ctggaattca gacatactga   180
gctatgggtc agaagtgttt tacttaaaaa gcaaacaatc cccaggaaat actgaatagg   240
a                                                                  241

<210> SEQ ID NO 390
<211> LENGTH: 241
<212> TYPE: DNA
```

```
<213> ORGANISM: Homo sapiens

<400> SEQUENCE: 390
gcaggtacat ccacatgttc ctccaaatga cgtttggggt cctgcttgcc aacattcttt    60
attgccagct gttcaggtgt catcttatct tcttcttcta cagccttatt gtaattcttg   120
gctaattcca acatctcttt taccactgat tcattgcgtt tacaatgttc actgtagtcc   180
tgaagtgtca aaccttccat ccaactcttc ttatgcaaat ttagcaacat cttctgttcc   240
a                                                                   241

<210> SEQ ID NO 391
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 391
cnggcacaan cttntgtttt tnntnttttt ttttttttttn tctttatttn tttttantnt    60
taaanaaaaa nnntannnaa annngggttt aaatnctntn nncagancat taaaactgaa   120
ggggaaaaaa aaaccaaaaa cgagcttntt anttnacntg ggnttgggnn gntgctgatn   180
tnaagaagca anntttanan cnngcnnnat ganngagngn tcannttgaa atttnnaccc   240
t                                                                   241

<210> SEQ ID NO 392
<211> LENGTH: 241
<212> TYPE: DNA
<213> ORGANISM: Homo sapiens

<400> SEQUENCE: 392
gaggtactaa atggtatcct tagattaaaa ttttgtgctt gataacagct gttttttcta    60
cattagaaat aagatgccac acaaggaact acattccaga tttaaagaaa tgaaaggata   120
ccattagtgt gtataacaga ttattgttca tacttgtaaa gcatcttatg tcattgagaa   180
tataaagaac agtgccttag aagacagtga aggtaagct ctagcttaat gtctatgatt    240
t                                                                   241

<210> SEQ ID NO 393
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 393
ggcaggtaca taagcataat cagttatgga cagcttcttg tataaattgc tattcancaa    60
tacataaact gcctnaaaga tttatgctta caggtagaca ttcaatttac caataaaaca   120
gcatgttctg aaaatatggg cacatttaa aacatattaa gacagttctg ttaaccataa    180
tagtcccaca gtatgactga gtaataagaa tctacttcaa aagnaaaaaa aaattaatc   240
a                                                                   241

<210> SEQ ID NO 394
<211> LENGTH: 241
```

```
<212> TYPE: DNA
<213> ORGANISM: Homo sapiens

<400> SEQUENCE: 394
aggtacagca gcagtagatg gctgcaacaa ccttcctcct accccagccc agaaaatatt      60
tctgccccac cccaggatcc gggaccaaaa taaagagcaa gcaggccccc ttcactgagg     120
tgctgggtag ggctcagtgc cacattactg tgctttgaga aagaggaagg ggatttgttt     180
ggcactttaa aaatagagga gtaagcagga ctggagaggc cagagaagat accaaaattg     240
g                                                                    241

<210> SEQ ID NO 395
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 395
nggcnggnnc caanatatga aatntnanta tnatacatga tnaaaagctt tatntatttt      60
agtgagtaat taagtttaca ctgtgaataa ggattaattc ccagatgacc atctacagtt     120
actaccacat agagggtata cacggatgga tcgattacaa gaatataaaa cttattttcc     180
ttcctgtatc cacatttctt tgcaatgtga atttgcaggc cctctcaaga agtggagtct     240
a                                                                    241

<210> SEQ ID NO 396
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 396
gaggtacacc ttgaatgaca atgctnggag ccccccctgtg gtcatcgacg cctccactgc     60
cattgatgca ccatccaacc tgcgtttcct ggccaccaca cccaattcct tgctggtatc    120
atggcagccg ccacgtgcca ggattaccgg ctacatcatc aagtatgaga agcctgggtc    180
tcctcccaga gaagtggtcc ctcggccccg ccctggtgtc acagaggcta ctattactgg    240
c                                                                    241

<210> SEQ ID NO 397
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 397
ggcaggtacc agcaggggga tgtgtttctg gggaattgtg gctctggaag cttcacggtt      60
tcccagaatg tggaaaatat atctgtgcan gatagaaatc ctgcccagag gctgtttctg     120
tctcatttga gctctccttc atgtggcaga gctgactgtg gcggtttagg agcctacatt     180
ttagaaaagc ttacctcaaa gttctgcatt gagcctgagc actggaaagg agataaaata     240
```

```
a                                                                          241

<210> SEQ ID NO 398
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 398
gangtgacca ngacatcacc tnacacntgg aaagcganga nttgaatggt gcntacaang      60
ccntacccnt tgcccannac ctgaacgcgc cttntgattg ggacagccgt gggaaggaca     120
gttatgaaac nantcanctg gatgaccana gtgntgaaac cnacanncac angcnntcna     180
cattatataa ncggaaagct aatgatgaga gcaatgatca ttccgatgtn attgatagtc     240
a                                                                          241

<210> SEQ ID NO 399
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 399
cagagtgaga tgggagtggg agggccaatc tgatacagaa ggggtgaag ggtagggccc       60 ctgagcagcc cacccttac cctgacgaag gcaatcctcc tctggaatgt ctcttccctc      120
ttcagtctgg gttctgcctc agccacgaac tgggaaggag tgaggaacat cccaacggca    180
atgagagtat cccagtgact ccaaacagga angaatcagt gttcanaaag tcagggccct    240
t                                                                          241

<210> SEQ ID NO 400
<211> LENGTH: 241
<212> TYPE: DNA
<213> ORGANISM: Homo sapiens

<400> SEQUENCE: 400
ggtactcttg ctctttttagc tagagtgtat gtgaaaataa agaaatacat cattgtattc    60
acaaccatgt gtcttcattt ataactttt gtttaaaaaa ttttagttc aagtttagtt      120 cattgatatt atcctctgaa tgcagttaag gctgggcaga aattctactc atgtgacatc    180
tgccacaggt ctattttgaa gcttttcttc taatgggcaa tgtttgtcct taccaggatt   240
t                                                                          241

<210> SEQ ID NO 401
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 401
nncaggtact ttgtagagca gagagaggct ttggttcctc ctttcttcaa tcacgtggag     60
atgtgtcatc acctgggatt tcatctgggc cgccttttct gggtcaacag ccaacacatg   120
```

```
ctggtaatga cggatggtat gtaagcgatc tttgttctca gcacggacat aacgccgtaa      180
ggcctggaga atgcgatgag gccgtggcgg gtcagactgc aaggcagcca ggtagttctc      240
c                                                                      241

<210> SEQ ID NO 402
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 402
ggcaggtcca aaaaaaacct aaaaanngtt tcaggaatgt agagaaatat ccaacttaaa      60
tagcgaaaaa gtgcaccata attactgctg cactgcagtc atttctgcaa ttcccatgtt     120
tcttaaataa ctatcttgtc agataacaca caatataaag agcaattatg aaaaacagac     180
atttacatat acttctaaag tcttattggg aatatcctgt ttggccattg ggataaccaa     240
t                                                                      241

<210> SEQ ID NO 403
<211> LENGTH: 241
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 403
aggtgttaac tacccgctcc gagacgggat tgatgacgag tcctatgang ccattttcaa      60
gccggtcatg tccaaagtaa tggagatgtt ccagcctagt gcggtggtct tacagtgtgg     120
ctcagactcc ctatctgggg atcggttagg ttgcttcaat ctaactatca aaggacacgc     180
caagtgtgtg gaatttgtca agagctttaa cctgcctatg ctgatgctgg gaggcggtgg     240
t                                                                      241

<210> SEQ ID NO 404
<211> LENGTH: 241
<212> TYPE: DNA
<213> ORGANISM: Homo sapiens

<400> SEQUENCE: 404
caggtactgc aacccataaa atactgtttc ctcatatttc accttcctta atttggagtt      60
ttctgtcttc ttttcacggc attcaaagta ggaataaact ttgcttgtgt tgggtggata     120
ttgtttatag tgagtaacct tgtaggagtc ggtggccagg aggatgttga actcggcttc     180
tgccgcagga ttcatctcgg gccggaggac aaggggcccg cgcgccgcga gctccctgac     240
c                                                                      241

<210> SEQ ID NO 405
<211> LENGTH: 266
<212> TYPE: DNA
<213> ORGANISM: Homo sapiens

<400> SEQUENCE: 405
ttctgggctg gggagtggag agaaagaagt tgcagggctt acaggaaatc ccagagcctg      60
```

```
aggttttctc ccagatttga gaactctaga ttctgcatca ttatctttga gtctatattc      120
tcttgggctg taagaagatg aggaatgtaa taggtctgcc ccaagccttt catgccttct      180
gtaccaagct tgtttccttg tgcatccttc ccaggctctg ctgccccctt attggagaat      240
gtgatttcca agacaatcaa tccaca                                           266
```

<210> SEQ ID NO 406
<211> LENGTH: 231
<212> TYPE: DNA
<213> ORGANISM: Homo sapiens

<400> SEQUENCE: 406

```
ttggtgaaga accattcctc ggcatccttg cggttcttct ctgccatctt ctcatactgg      60
tcacgcatct cgttcagaat gcggctcagg tccacgccag gtgcagcgtc catctccaca     120
ttgacatctc cacccacctg gcctctcagg gcattcatct cctcctcgtg gttcttcttc     180
aggtaggcca gctcctcctt caggctctca atctgcatct ccaggtcagc t              231
```

<210> SEQ ID NO 407
<211> LENGTH: 266
<212> TYPE: DNA
<213> ORGANISM: Homo sapiens

<400> SEQUENCE: 407

```
cagcatcatt gtttataatc agaaactctg gtccttctgt ctggtggcac ttagagtctt      60
ttgtgccata atgcagcagt atggagggag gattttatgg agaaatgggg atagtcttca     120
tgaccacaaa taaataaagg aaaactaagc tgcattgtgg gttttgaaaa ggttattata     180
cttcttaaca attcttttttt tcagggactt ttctagctgt atgactgtta cttgaccttc     240
tttgaaaagc attcccaaaa tgctct                                           266
```

<210> SEQ ID NO 408
<211> LENGTH: 261
<212> TYPE: DNA
<213> ORGANISM: Homo sapiens

<400> SEQUENCE: 408

```
ctgtgtcagc gagcctcggt acactgattt ccgatcaaaa gaatcatcat ctttaccttg      60
acttttcagg gaattactga actttcttct cagaagatag ggcacagcca ttgccttggc     120
ctcacttgaa gggtctgcat ttgggtcctc tggtctcttg ccaagtttcc cagccactcg     180
agggagtaat atctggaggg caaagaagag acttatgtta ttgttgaacc tccagccaca     240
gggaggagca tgggcatggg t                                                261
```

<210> SEQ ID NO 409
<211> LENGTH: 266
<212> TYPE: DNA
<213> ORGANISM: Homo sapiens

<400> SEQUENCE: 409

```
gctgacagta atacactgcc acatcttcag cctgcaggct gctgatggtg agagtgaaat      60
ctgtcccaga cccgctgcca ctgaatcggt cagggatccc ggattcccgg gtagatgccc     120
agtaaatgag cagtttagga ggctgtcctg gtttctgctg gtaccaagct aagtagttct     180
tattgttgga gctgtctaaa acactctggc tggtcttgca gttgatggtg gccctctcgc     240
ccagagacac agccagggag tgtgga                                           266
```

<210> SEQ ID NO 410
<211> LENGTH: 181
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 410

```
caaaaggtnc tttttgntca aaancnattt ttattccttg atattttct ttttttttt       60
tttgnggatg gggacttgtg aatttttcta aaggggnnnn ttnannnngg aagaaaaccn    120
ngntccggtt ccagccaaac cngtngctna ctttccacct tntttccacc tccctcnggt    180
t                                                                    181
```

<210> SEQ ID NO 411
<211> LENGTH: 261
<212> TYPE: DNA
<213> ORGANISM: Homo sapiens

<400> SEQUENCE: 411

```
gccccctgcag tacttggccg atgtggacac ctctgatgag gaaagcatcc gggctcacgt    60
gatggcctcc caccattcca agcggagagg ccgggcgtct tctgagagtc agggtctagg   120
tgctggagtg cgcacggagg ccgatgtaga ggaggaggcc ctgaggagga agctggagga   180
gctggccagc aacgtcagtg accaggagac ctcgtccgag gaggaggaag ccaaggacga   240
aaaggcagag cccaacaggg a                                             261
```

<210> SEQ ID NO 412
<211> LENGTH: 171
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 412

```
nttttntctt tacaattcag tcttcaacaa cttgagagct ttcttcatgt tgncaagcaa    60
cagagctgta tctgcaggnt cgtaagcata nagacngttt gaatatcttc cagngatatc   120
ggctctaact gncagagatg ggtcaacaaa cataatcctg gggacatact g            171
```

<210> SEQ ID NO 413
<211> LENGTH: 266
<212> TYPE: DNA
<213> ORGANISM: Homo sapiens

<400> SEQUENCE: 413

```
ttaggaccaa agatagcatc aactgtattt gaaggaactg tagtttgcgc attttatgac    60
attttataa agtactgtaa ttctttcatt gagggctat gtgatggaga cagactaact    120
cattttgtta tttgcattaa aattattttg ggtctctgtt caaatgagtt tggagaatgc   180
ttgacttgtt ggtctgtgta aatgtgtata tatatatacc tgaatacagg aacatcggag   240
acctattcac tcccacacac tctgct                                        266
```

<210> SEQ ID NO 414
<211> LENGTH: 266
<212> TYPE: DNA
<213> ORGANISM: Homo sapiens
<220> FEATURE:

<221> NAME/KEY: misc_feature
<222> LOCATION: (1)...(241)
<223> OTHER INFORMATION: n = A,T,C or G

<400> SEQUENCE: 414

| | | | | | |
|---|---|---|---|---|---|
| tttgccataa | ttgagtgaaa | agtggcagat | ggcattaact | ctgctccgct | tcaagctggc      60 |
| tccatgacca | ctcaaggcct | ccccancctg | ttcgtcaagt | tgtcctcaag | tccaagcaat     120 |
| ggaatccatg | tgtttgcaaa | aaaagtgtgc | tanttttaag | gnctttcgta | taagaatnaa     180 |
| tganacaatt | ttcctaccaa | aggangaaca | aaaggataaa | tataatacaa | aatatatgta     240 |
| tatggttgtt | tgacaaatta | tataac     |            |            |                266 |

<210> SEQ ID NO 415
<211> LENGTH: 266
<212> TYPE: DNA
<213> ORGANISM: Homo sapiens
<220> FEATURE:
<221> NAME/KEY: misc_feature
<222> LOCATION: (1)...(241)
<223> OTHER INFORMATION: n = A,T,C or G

<400> SEQUENCE: 415

| | | | | | |
|---|---|---|---|---|---|
| cctccatcca | gtctattaat | tgttgccggg | aagctanagt | aagtagttcg | ccagttaata      60 |
| gtttgcgcaa | cgttgttgcc | attgctacag | gcatcgtggt | gtnacgctcg | tcgattggta     120 |
| tggcttcatt | cagctccggt | tcccaacgat | caaggcgagt | tacatgatcc | cccatgttgt     180 |
| gcaaaaaagc | ggttagctcc | ttcggtcctc | cgatcgttgt | canaagtaag | ttggccgcag     240 |
| tgttatcact | catggttatg | gcagca     |            |            |                266 |

<210> SEQ ID NO 416
<211> LENGTH: 878
<212> TYPE: DNA
<213> ORGANISM: Homo sapiens

<400> SEQUENCE: 416

| | | | | | |
|---|---|---|---|---|---|
| cctgacgata | gccatggctg | taccacttaa | ctatgattct | attccaactg | ttcagaatca      60 |
| tatcacaaaa | tgacttgtac | acagtagttt | acaacgactc | ccaagagagg | aaaaaaaaaa     120 |
| aaaaagacgc | ctcaaaattc | actcaacttt | tgagacagca | atggcaatag | gcagcagaga     180 |
| agctatgctg | caactgaggg | cacatatcat | tgaagatgtc | acaggagttt | aagagacagg     240 |
| ctggaaaaaa | tctcatacta | agcaaacagt | agtatctcat | accaagcaaa | accaagtagt     300 |
| atctgctcag | cctgccgcta | acagatctca | caatcaccaa | ctgtgcttta | ggactgtcac     360 |
| caaagtcaga | ttcggtgcta | accaggtggc | atctatgatc | aacgtcgccc | ctcttattta     420 |
| acaaagggct | ctgaaggagg | tgttctccaa | gcaacaagga | gactgcttca | gtacaagact     480 |
| ttgcaccttg | aattcaattg | catcaagtgt | ggatagcaaa | ataagtatct | taccattgaa     540 |
| atatgtgttc | agcctaagat | tttacccacc | agcagaacaa | aagtgagggt | gagagggatg     600 |
| ggccagtgag | gggatggggg | agaaaaaaaa | atcacaggat | taccaccaaa | gccttgtttt     660 |
| aaagggctc | ccttcactat | tcaggaaggg | aagtggaagg | agaaattaac | caattcctgc     720 |
| cacagcagcc | cttttggct | gcttccacaa | tagatacttt | atggagtggc | acagccaacc     780 |
| ctatctgtga | cctgccctgc | ggataaacac | agccaagcag | gtttaattag | atcaaagaca     840 |
| caaagggcta | ttccctcctt | tcataacaac | gcagacct   |            |                878 |

<210> SEQ ID NO 417
<211> LENGTH: 514

```
<212> TYPE: DNA
<213> ORGANISM: Homo sapiens

<400> SEQUENCE: 417
ttctgacttc tagaagacta aggctggtct gtgtttgctt gtttgcccac ctttggctga      60
tacccagaga acctgggcac ttgctgcctg atgcccaccc ctgccagtca ttcctccatt     120
cacccagcgg gaggtgggat gtgagacagc ccacattgga aaatccagaa aaccgggaac     180
agggatttgc ccttcacaat tctactcccc agatcctctc ccctggacac aggagaccca     240
cagggcagga ccctaagatc tggggaaagg aggtcctgag aaccttgagg tacccttaga     300 tcctttctcta cccactttcc tatggaggat tccaagtcac cacttctctc accggcttct     360
accagggtcc aggactaagg cgttttctcc atagcctcaa cattttggga atcttcccct     420 aatcacccctt gctcctcctg ggtgcctgga agatggactg gcagagacct ctttgttgcg    480
ttttgtgctt tgatgccagg aatgccgcct agtt                                 514

<210> SEQ ID NO 418
<211> LENGTH: 352
<212> TYPE: DNA
<213> ORGANISM: Homo sapiens

<400> SEQUENCE: 418
ctgcaccagc gattaccagt ggcattcaaa tactgtgtga ctaaggattt tgtatgctcc      60
ccagtagaac cagaatcaga caggtatgag ctagtcaaca gcaagtcttt gttggattcg     120
agtaggctca ggatctgctg aaggtcggag gagttagtcc ccgcaatcaa gagcctgtct     180
tcctgaagcc cttggtgata ttttgccact cagccaagaa tgaggatgca tccttcagat     240
tctctatgtc ccgaacctgg aacccatcca cgccagcttg cagccaaaac tccagagcat     300
ccttcacctt ggtggaaaaa aaaaaaaaaa aaaaaaaaaa aaaaaaaaaa aa              352

<210> SEQ ID NO 419
<211> LENGTH: 344
<212> TYPE: DNA
<213> ORGANISM: Homo sapiens

<400> SEQUENCE: 419
ctggacacca taatcccttt taagtggctg gatggtcaca cctctcccat tgacaagctg      60
ggttaagtca ataggttgac taggatcaac acgacccaaa tcaataagat actgcagtct     120
attgagactc aaaggcttat actggcgtct gaaactatgt ccttcgttaa acccgtattt     180
tgggattcgg atgtaaaatg gagtctggcc tccctcaaag cccaagcggg gccgggttcc     240
tctttgcctt tctcctttat ggcctctgcc acatttttcta cctcttctcc gacctcttgg     300
tcttctctcc ggtttcttgg agccgggatt cggctttaag ttgg                     344

<210> SEQ ID NO 420
<211> LENGTH: 935
<212> TYPE: DNA
<213> ORGANISM: Homo sapiens

<400> SEQUENCE: 420
cgaaagtcaa cgttaagggg ctcaggtgaa ccatgatgat gaccttctgt tgactttgaa      60
atattggctc ttgtgggtga caaaagccag acaagctgtg gctgtggtcc gattttaaga     120
cgaggttctc aaagatccaa aggagggaaa gggtattgga aacactgtgt atcatctgag     180
acacacgtgt cctcatgatc ttaaatgcct actttaaagc cacctaatac tgcccttcat     240
```

```
tgtggtcaga agagatttct acaaaagcac tcagaattct ggaggcagtt gtgattttgc      300
catgtggcag ttggtttgtg gagttgggca ggtgtgaaag ggtaaaactc cacttctgaa      360
tgctgcttct gccccctggg acccagcaca ttgttagacc atcttcttga ctgaaaattc      420
tctcctgatg ctgagccctg caccaccacc ttccttttcc taactatgaa ttgatggcaa      480
agtccactca aaacaaccag ttaagtgctc acgagagagt agtcaagcac ctccagaaag      540
aaaccgggtt tttgttcaca tagcaggaag tgactccctg ggtggtaatt tatcttggaa      600
acacaggtag attggcagaa aaacgggaac atgtaggtac cgcgatgttg gtgcatgtcc      660
attactttgg gataggcttt ctcagtcttt cctcaaatga tagttgagcc agttttccag      720
tggcaattct gagtgacttg cgcttgtctt atggtgtggt caagggacgt tcagaactac      780
ggaaaacttt tactgaaaca gcgaagcaga gtataccggc atgagaggga agatgaacac      840
tcacctatgt accactcttt gacaataaat atagtatttc tcaaaaaaaa aaaaaaaaa      900 agtaaaaaaa ctgaaatcgc aagtcaaaaa atcca                                 935

<210> SEQ ID NO 421
<211> LENGTH: 745
<212> TYPE: DNA
<213> ORGANISM: Homo sapiens

<400> SEQUENCE: 421
ggcttcgagc ggccgcccgg gcaggtccta gatgtcattt gggacccttc acaaccattt       60
tgaagccctg tttgagtccc tgggatatgt gagctgtttc tatgcataat ggatattcgg      120
ggttaacaac agtcccctgc ttggcttcta ttctgaatcc ttttctttca ccatggggtg      180
cctgaagggt ggctgatgca tatggtacaa tggcacccag tgtaaagcag ctacaattag      240
gagtggatgt gttctgtagc atcctattta aataagccta ttttatcctt tggcccgtca      300
actctgttat ctgctgcttg tactggtgcc tgtacttttc tgactctcat tgaccatatt      360
ccacgaccat ggttgtcatc cattacttga tcctacttta catgtctagt ctgtgtggtt      420
ggtggtgaat aggcttcttt ttacatggtg ctgccagccc agctaattaa tggtgcacgt      480
ggacttttag caagcgggct cactggaaga gactgaacct ggcatggaat tcctgaagat      540
gtttggggtt ttttttcttt ttaatcgaaa gttaacattg tctgaaaagt tttgttagaa      600
ctactgcgga acctcaaaat cagtagattt ggaagtgatt caaagctaaa cttttttcctt     660 ggccctcctt tgttctaat tgcttgcaag tgtaatacta ggatgtccaa gatgccagtt       720
tttgcttctt tgttagttgt cagac                                           745

<210> SEQ ID NO 422
<211> LENGTH: 764
<212> TYPE: DNA
<213> ORGANISM: Homo sapiens

<400> SEQUENCE: 422
gagttcagta gcaaagtcac acctgtccaa ttccctgagc tttgctcact cagctaatgg       60
gatggcaaag gtggtggtgc tttcatcttc aggcagaagc ctctgcccat cccctcaag      120 ggctgcaggc ccagttctca tgctgccctt gggtgggcat ctgttaacag aggagaacgt      180
ctgggtggcg gcagcagctt tgctctgagt gcctacaaag ctaatgcttg gtgctagaaa      240
catcatcatt attaaacttc agaaaagcag cagccatgtt cagtcaggct catgctgcct      300
cactgcttaa gtgcctgcag gagccgcctg ccaagctccc cttcctacac ctggcacact      360
ggggtctgca caaggctttg tcaaccaaag acagcttccc ccttttgatt gcctgtagac     420
```

| | |
|---|---|
| tttggagcca agaaacactc tgtgtgactc tacacacact tcaggtggtt tgtgcttcaa | 480 |
| agtcattgat gcaacttgaa aggaaacagt ttaatggtgg aaatgaacta ccatttataa | 540 |
| cttctgtttt tttattgaga aaatgattca cgaattccaa atcagattgc caggaagaaa | 600 |
| taggacgtga cggtactggg ccctgtgatt ctcccagccc ttgcagtccg ctaggtgaga | 660 |
| ggaaaagctc tttacttccg cccctggcag ggacttctgg gttatgggag aaaccagaga | 720 |
| tgggaatgag gaaaatatga actacagcag aagcccctgg gcag | 764 |

<210> SEQ ID NO 423
<211> LENGTH: 1041
<212> TYPE: DNA
<213> ORGANISM: Homo sapiens

<400> SEQUENCE: 423

| | |
|---|---|
| ctcagagagg ttgaaagatt tgcctacgaa agggacagtg atgaagctaa gctctagatc | 60 |
| caggatgtct gacttcaaat tgaaactccc aaagtaatga gtttggaagg gtggggtgtg | 120 |
| gcctttccag gatggggtc tttctgctc ccagcggata gtgaaacccc tgtctgcacc | 180 |
| tggttgggcg tgttgctttc ccaaaggttt ttttttttagg tccgtcgctg tcttgtggat | 240 |
| taggcattat tatctttact ttgtctccaa ataacctgga gaatggagag agtagtgacc | 300 |
| agctcagggc cacagtgcga tgaggaccat cttctcacct ctctaaatgc aggaagaaac | 360 |
| gcagagtaac gtggaagtgg tccacaccta ccgccagcac attgtgaatg acatgaaccc | 420 |
| cggcaacctg cacctgttca tcaatgccta caacaggtat tgggatgtag ttcagccaca | 480 |
| tcattgctat ttatgaggtg tcttctgtag atccgaaatg tgggacagat gagagggaga | 540 |
| gtataaaatg agcggaagag gcaggctctg agtttgagca aatagattaa taggacaggt | 600 |
| gtccccagga aggacacctg gcctgtaagc tggttcctgg cattcagctc gccttgcagg | 660 |
| gatctgaaca aacactccag accactgggg gtgcagacgt gagagggacg cagtcgcaca | 720 |
| ctcagagggt tgagagtaaa tatgtgtgcc cgctgctgac cttcacgaaa ggccaaatgt | 780 |
| aagaagagct aagtgagaga gcagcaaagc actcctggag gccggggata atccaggcag | 840 |
| gcttctggga gtttgtcatt ccaaggataa ggaggacctg aacatggcct ttgcctaagg | 900 |
| cgtggccctc tcaaccagca ctaggtgctt atctggagct cagctagggg aggagacagc | 960 |
| tcagggccat tggtgtcagc cagagactct gtaatcttcc agggagctcg ctcaacctgc | 1020 |
| tgagctcgct ctgccacgca c | 1041 |

<210> SEQ ID NO 424
<211> LENGTH: 1288
<212> TYPE: DNA
<213> ORGANISM: Homo sapiens

<400> SEQUENCE: 424

| | |
|---|---|
| ctaagaactg agacttgtga cacaaggcca acgacctaag attagcccag ggttgtagct | 60 |
| ggaagaccta caacccaagg atggaaggcc cctgtcacaa agcctaccta gatggataga | 120 |
| ggacccaagc gaaaaaggta tctcaagact aacggccgga atctggaggc ccatgaccca | 180 |
| gaacccagga aggatagaag cttgaagacc tggggaaatc ccaagatgag aaccctaaac | 240 |
| cctacctctt ttctattgtt tacacttctt actcttagat atttccagtt ctcctgttta | 300 |
| tctttaagcc tgattctttt gagatgtact ttttgatgtt gccggttacc tttagattga | 360 |
| cagtattatg cctgggccag tcttgagcca gctttaaatc acagcttta cctatttgtt | 420 |

-continued

```
aggctatagt gttttgtaaa cttctgtttc tattcacatc ttctccactt gagagagaca      480
ccaaaatcca gtcagtatct aatctggctt ttgttaactt ccctcaggag cagacattca      540
tataggtgat actgtatttc agtcctttct tttgacccca gaagccctag actgagaaga      600
taaaatggtc aggttgttgg ggaaaaaaaa gtgccaggct ctctagagaa aaatgtgaag      660
agatgctcca ggccaatgag aagaattaga caagaaatac acagatgtgc cagacttctg      720
agaagcacct gccagcaaca gcttccttct ttgagcttag tccatccctc atgaaaaatg      780
actgaccact gctgggcagc aggagggatg atgaccaact aattcccaaa ccccagtctc      840
attggtacca gccttgggga accacctaca cttgagccac aattggtttt gaagtgcatt      900
tacaagtttc tggcatcact accactactg attaaacaag aataagagaa cattttatca      960
tcatctgctt tattcacata aatgaagttg tgatgaataa atctgctttt atgcagacac     1020
aaggaattaa gtggcttcgt cattgtcctt ctacctcaaa gataatttat tccaaaagct     1080
aagataaatg gaagactctt gaacttgtga actgatgtga aatgcagaat ctcttttgag     1140
tctttgctgt ttggaagatt gaaaaatatt gttcagcatg ggtgaccacc agaaagtaat     1200
cttaagccat ctagatgtca caattgaaac aaactgggga gttggttgct attgtaaaat     1260
aaaatatact gttttgaaaa aaaaaaac                                        1288

<210> SEQ ID NO 425
<211> LENGTH: 446
<212> TYPE: DNA
<213> ORGANISM: Homo sapiens

<400> SEQUENCE: 425
ccacttaaag ggtgcctctg ccaactggtg gaatcatcgc cacttccagc accacgccaa       60
gcctaacatc ttccacaagg atcccgatgt gaacatgctg cacgtgtttg ttctgggcga      120
atggcagccc atcgagtacg gcaagaagaa gctgaaatac ctgccctaca atcaccagca      180
cgaatacttc ttcctgattg ggccgccgct gctcatcccc atgtatttcc agtaccagat      240
catcatgacc atgatcgtcc ataagaactg ggtggacctg gcctgggccg tcagctacta      300
catccggttc ttcatcacct acatccctt ctacggcatc ctgggagccc tccttttcct      360
caacttcatc aggttcctgg agagccactg gtttgtgtgg gtcacacaga tgaatcacat      420
cgtcatggag attgaccagg aggacc                                           446

<210> SEQ ID NO 426
<211> LENGTH: 874
<212> TYPE: DNA
<213> ORGANISM: Homo sapiens

<400> SEQUENCE: 426
tttttttttt tttttttttt tttttcaat taaagatttg atttattcaa gtatgtgaaa       60
acattctaca atggaaactt ttattaaatg ctgcatgtac tgtgctatgg accacgcaca      120
tacagccatg ctgtttcaga agacttgaaa tgccattgat agtttaaaaa ctctacaccc      180
gatggagaat cgaggaagac aatttaatgt ttcatctgaa tccagaggtg catcaaatta      240
aatgacagct ccacttggca ataatagct gttacttgat ggtatccaag aagaaatggt      300
tggtgatgga taaattcaga aatgcttccc caaggtggg tggtttttaa aaagttttca      360
ggtcacaacc cttgcagaaa acactgatgc ccaacacact gattcgcggt ccaggaaaca      420
cgggtcttcc aagttccaag gggctgggt tccccaacga tcaagttcct gtgctgtaat      480
caagagggtc ctttggactg gatagggagc acttgggagc tgtacaccat cagtcataat      540
```

```
ggatggcagt gtaaaagatg atccaaatga cctgagatgc tcctgaggag tggtgcacca    600
gacccaggag tgccactgta gggctgcttc tttgctttag tcatcacaca cacacacagc    660
tccagagcag caatggcctt tcctgtaaca ggaaaaaagc ctcctgctat tcccaagaac    720
cctcgtaatg gcaaaactcc ccaaatgaca cccaggacca cagcaatgat ctgtcggaac    780
cagtagatca catctaaaaa ttcatcctta tcctcccagg ccgcgtcgct ccgcagcacc    840
ttactccaga cggagacttt gagggccccg ttgg                                874
```

<210> SEQ ID NO 427
<211> LENGTH: 638
<212> TYPE: DNA
<213> ORGANISM: Homo sapiens

<400> SEQUENCE: 427

```
acttgtaatt agcacttggt gaaagctgga aggaagataa ataacactaa actatgctat     60 ttgattttc ttcttgaaag agtaaggttt acctgttaca ttttcaagtt aattcatgta    120
aaaaatgata gtgattttga tgtaatttat ctcttgtttg aatctgtcat tcaaaggcca    180
ataatttaag ttgctatcag ctgatattag tagctttgca accctgatag agtaaataaa    240
ttttatgggc gggtgccaaa tactgctgtg aatctatttg tatagtatcc atgaatgaat    300
ttatggaaat agatatttgt gcagctcaat ttatgcagag attaaatgac atcataatac    360
tggatgaaaa cttgcataga attctgatta aatagtgggt ctgtttcaca tgtgcagttt    420
gaagtattta ataaccact cctttcacag tttatttct tctcaagcgt tttcaagatc    480
tagcatgtgg attttaaaag atttgccctc attaacaaga ataacattta aaggagattg    540
tttcaaaata tttttgcaaa ttgagataag gacagaaaga ttgagaaaca ttgtatattt    600
tgcaaaaaca agatgtttgt agctgtttca gagagagt                           638
```

<210> SEQ ID NO 428
<211> LENGTH: 535
<212> TYPE: DNA
<213> ORGANISM: Homo sapiens

<400> SEQUENCE: 428

```
acaagatgat tcttcctcct caatttgaca gatcaaagaa gtatcccttg ctaattcaag     60
tgtatggtgg tccctgcagt cagagtgtaa ggtctgtatt tgctgttaat tggatatctt    120
atcttgcaag taaggaaggg atggtcattg ccttggtgga tggtcgagga acagctttcc    180
aaggtgacaa actcctctat gcagtgtatc gaaagctggg tgtttatgaa gttgaagacc    240
agattacagc tgtcagaaaa ttcatagaaa tgggtttcat tgatgaaaaa agaatagcca    300 tatgggctg gtcctatgga ggatacgttt catcactggc ccttgcatct ggaactggtc    360
ttttcaaatg tggtatagca gtggctccag tctccagctg gaatattac gcgtctgtct    420 acacagagag attcatgggt ctcccaacaa aggatgataa tcttgagcac tataagaatt    480
caactgtgat ggcaagagca gaatatttca gaaatgtaga ctatcttctc atcca         535
```

<210> SEQ ID NO 429
<211> LENGTH: 675
<212> TYPE: DNA
<213> ORGANISM: Homo sapiens

<400> SEQUENCE: 429

```
actattttca accctgagca ttaacactgc ataccaaggg ggggtgggtc aagaagctgg     60
```

| | |
|---|---|
| ttagatcgaa gcacaagcac aagccactga tattctctat gtgatcaggt ttttacaaaa | 120 |
| aaatacatag ttttcaataa ataatgctta attttacaac tttgatacag caatgtcata | 180 |
| caccgtttca acacactaca ctctgcatgc tagatagtct acgagaagac gaaactttgc | 240 |
| catgcatttt ctttcccccc tagtgctatc aaacacttca tcctccagcg cactgcctca | 300 |
| ggtagcttta ccttctctct gtttcacagc aataggccgt gcgctggcat gcaaactcta | 360 |
| aaaaaggtcc cccccacaaa ccactcagac ttctacacaa aagggttttt cagcttttct | 420 |
| gctcccaaac ctggagtggc taagaaagta agtttcatgt ggccttggaa aatacacact | 480 |
| tgttaacagt gtcatgctga aaactgctct aaaacatcag gtggttctgt cctggtggcc | 540 |
| gtcacgaagc attatgggat gccataacca ctaggagtcc caaaccggaa aaaataggcc | 600 |
| tccgttttaa aacagtcaat tcaaaaaagg tgtcacagaa caaatgcaaa agactcttaa | 660 |
| acccacaaca tatgt | 675 |

<210> SEQ ID NO 430
<211> LENGTH: 434
<212> TYPE: DNA
<213> ORGANISM: Homo sapiens

<400> SEQUENCE: 430

| | |
|---|---|
| acctctgcca gaagtccagc gagaggacct cacagtagag cacaggccac tccgggagtg | 60 |
| catcagaaga ttcatcctca tggaggaaga aggcttcaaa cgtgaatggg taggagaagt | 120 |
| gagccacctt gtccattgcc agggacttgg tggtgcaggt ctgtgttact cctgagagct | 180 |
| gctggaatgc tgggcttgac cagtgagcag ttggcaattc tacaaagaag tggacgtaga | 240 |
| gattgtcata ctcatagcct tgggctgaaa cgacctctcc atttacaaag agccggaggg | 300 |
| cacctgggac agtcatctca aagtcggtgc ctacgaggct gctgagatac tccttgtgcc | 360 |
| ggccataaag atccttgaac actcgccgtt cccgctcctc ctcctccggc tgtgcgtggg | 420 |
| gggaaacatt gtcg | 434 |

<210> SEQ ID NO 431
<211> LENGTH: 581
<212> TYPE: DNA
<213> ORGANISM: Homo sapiens

<400> SEQUENCE: 431

| | |
|---|---|
| acacaagcct ccagcccgac ccagcggcct aatgaaactc tggcaaccta tcctgggcgt | 60 |
| ggccacgagt atccagctcc aagcccaagt gaggcgggga gtcaacttcc ccatgattgc | 120 |
| caagtgacca agaccagaag cagggacgat taggctagtt ctgcggcaag gtgaactgga | 180 |
| gaccctgtct ctgccctcct tccctggcct gtcccacaga catcccgttg tttaacccac | 240 |
| tgcctttgca aggacctgct ctgtccactc caaatcaaag gatacttgca tccttcttac | 300 |
| acagactccc atctctctgc tcatagtggt cccaggctgc ccgagaaaaa gaaacttggg | 360 |
| tcagtagaag gctcattagt gtgaaggagt gagaggccag gccttcctgt gacataatgc | 420 |
| ttctatgctt gtttcctaaa cacttggtcc acacacaata cctgggcagg aagagagaac | 480 |
| caagcaccac tggatggctc tggagccagg ggacttctat gcacatacaa ccaacatcac | 540 |
| cccactctgc tcatctgtgc ctccaccctg aacagcagag t | 581 |

<210> SEQ ID NO 432
<211> LENGTH: 532
<212> TYPE: DNA
<213> ORGANISM: Homo sapiens

<400> SEQUENCE: 432

```
actccaactc aagtttacaa gttacacctt tgccacagcc ttggctaaat cttgaactag    60
tgcagaattc agctgtggta gagtgctgat cttagcatgc ttcgatgtgg catacttgtt   120
cttgacagtc atgtgctttg taagtccttg atttaccatg actacattct tagccagtg   180
ctgcataact ggaagaagag attcttcagt atatgacagg taatgttgta gagttggtgt   240
ccattcacca ttatccagaa ttttcagtgc taagcaaaaa gctcctgctg caatttgaga   300
aggaggaaag tgcaccatgt catagtccaa catagttagt tccatcaggt atttggccaa   360
agtatgttgc tcgacatcaa cctctccaat cttagatgct ctccgaagga agtgcaaagg   420
tagaggccga cccagaccaa agtttaaagc tcttagaatc ttcatttcca tctgtctgat   480
ttggtgctta gtataagtgt tgtcagtcac aaaagcaaag tcaccaattt ct           532
```

<210> SEQ ID NO 433
<211> LENGTH: 531
<212> TYPE: DNA
<213> ORGANISM: Homo sapiens

<400> SEQUENCE: 433

```
acttggtttt acagctcctt tgaaaactct gtgtttggaa tatctctaaa aacatagaaa    60
acactacagt ggtttagaaa ttactaattt tacttctaag tcattcataa accttgtcta   120
tgaaatgact tcttaaatat ttagttgata gactgctaca ggtaataggg acttagcaag   180
ctctttttata tgctaaagga gcatctatca gattaagtta gaacatttgc tgtcagccac   240
atattgagat gacactaggt gcaatagcag ggatagattt tgttggtgag tagtctcatg   300
ccttgagatc tgtggtggtc ttcaaaatgg tggccagcca gatcaaggat gtagtatctc   360
atagttccca ggtgatattt ttcttattag aaaaatatta taactcattt gttgtttgac   420
acttatagat tgaaatttcc taatttattc taaattttaa gtggttcttt ggttccagtg   480
ctttatgttg ttgttgtttt tggatggtgt tacatattat atgttctaga a             531
```

<210> SEQ ID NO 434
<211> LENGTH: 530
<212> TYPE: DNA
<213> ORGANISM: Homo sapiens

<400> SEQUENCE: 434

```
acaagagaaa acccctaaaa aaaggatggc tttagatgac aagctctacc agagagactt    60
agaagttgca ctagctttat cagtgaagga acttccaaca gtcaccacta atgtgcagaa   120
ctctcaagat aaaagcattg aaaaacatgg cagtagtaaa atagaaacaa tgaataagtc   180
tcctcatatc tctaattgca gtgtagccag tgattattta gatttggata agattactgt   240
ggaagatgat gttggtggtg ttcaagggaa agaaaagca gcatctaaag ctgcagcaca   300
gcagaggaag attcttctgg aaggcagtga tggtgatagt gctaatgaca ctgaaccaga   360
ctttgcacct ggtgaagatt ctgaggatga ttctgatttt tgtgagagtg aggataatga   420
cgaagacttc tctatgagaa aaagtaaagt taaagaaatt aaaaagaaag aagtgaaggt   480
aaaatcccca gtagaaaaga aagagaagaa atctaaatcc aaatgtaatg                530
```

<210> SEQ ID NO 435
<211> LENGTH: 677
<212> TYPE: DNA
<213> ORGANISM: Homo sapiens

<400> SEQUENCE: 435

```
accttatgat ctaattaata gatattagaa acagtagaaa gacaagttac acgtcaatgc      60
ccaatgacta gagtcaacat taaagagttg taatttaagt aatccaaact gacatctaat     120
tccaaaatca tttataaaat gtatttggct ttggaatcca caggacttca aacaagcaaa     180
gtttcactgc agatagtcac aaagatgcag atacactgaa atacttaaga gccttattaa     240
tgattttgt tattttggat cttctgtttt tttcttatta tggtccgaag cctccttaat      300
accaatttat cagacagaag catgtcatct tgttgttcaa gataatccag taaattttca     360
gtccattcaa gtgccgcttt atggctaata cgcttctctg gattcagttc tgttttcta     420
ctcttactgg aaggcttttg ctcagcagcc ttggtctggt cctcagcact ttcactgtca     480
gtcagcacct gacagcttga gtcactgctc cgagagtcga accactgatc aatattctca     540
atgtcaacat gttcacattc ttctgtgttc tgtaaaactg ttgctaaatt agctgctaaa     600
atggctcctt catcaatgtt catacctgaa ttctcttcat tgccagggaa aagttttttc     660
catgctttgg ttatggt                                                    677
```

<210> SEQ ID NO 436
<211> LENGTH: 573
<212> TYPE: DNA
<213> ORGANISM: Homo sapiens

<400> SEQUENCE: 436

```
acctcttagg gtgggagaaa tggtgaagag ttgttcctac aacttgctaa cctagtggac      60
agggtagtag attagcatca tccggataga tgtgaagagg acggctgttt ggataataat     120
taaggataaa atttggccag ttgacagatt ctgtttccag cagttttac agcaacagtg      180
gagtgcttca gtattgtgtt cctgtaaatt taattttgat ccgcaatcat ttggtataca     240
atgctgtttg aagttttgtc ctattggaaa agtcttgtgt tgcaggggtg cagttaagat     300
ctttgtgatg aggaatggga tgggctaatt ttttgccgtt tcttggaat tggggggcatg     360
gcaaatacag tagggtagtt tagttcttta cacagaacat gataaactac acctgttgat     420
gtcaccgtct gtcaatgaat attatagaag gtatgaaggt gtaattacca taataacaaa     480
acccctgtc tttagggctg accttttcgtc ctttgacctc ctcagcctcc attcccatct     540
tcgctcagac tgcaagtatg tttgtattaa tgt                                  573
```

<210> SEQ ID NO 437
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 437

```
acaattggta tccatatctt gttgaaattg taatgggaaa acaatatatt tcaatctcta      60
tgtagatagt gggttttgt tttcataata tattctttta gtttactgta tgagttttgc     120
aggactgcat aatagatcac cacaatcata acatcttagg accacagaca tttatgagat     180
catggcttct gtgggttaga agtatgctca tgtcttaact gggtcctctg ctcagtctta     240
tctggctgca atcaaggtgt cagctgggct gaattttcat ttggaatctt gactgggaaa     300
gagtctgctt ccaaggtcat gaagtttgct ggcaaaatgt atgttttat gacagtatga     360
ctgaaatccc aagctatctc ctgactttta gctgggtaat ctcaggccct aaatgttgcc     420
```

```
tacagttcct agaggctggt cacagttctt agccatgtgg atttcctcaa catggctgct      480
tgcttcatca agtcagcaag aatagcctgt catatcagtg tatatcaggc tcactcagga      540
taatttccct actgatgagc caaacactaa ctgattttag agcttaacta catctgcaaa      600
attcngttca ccagaggcaa gtcatattca gggaaggaga agtgt                      645

<210> SEQ ID NO 438
<211> LENGTH: 485
<212> TYPE: DNA
<213> ORGANISM: Homo sapiens

<400> SEQUENCE: 438
acagaattga gagacaagat tgcttgtaat ggagatgctt ctagctctca gataatacat       60
atttctgatg aaaatgaagg aaaagaaatg tgtgttctgc gaatgactcg agctagacgt      120
tcccaggtag aacagcagca gctcatcact gttgaaaagg ctttggcaat tctttctcag      180
cctacaccct cacttgttgt ggatcatgag cgattaaaaa atcttttgaa gactgttgtt      240
aaaaaaagtc aaaactacaa catatttcag ttggaaaatt tgtatgcagt aatcagccaa      300
tgtatttatc ggcatcgcaa ggaccatgat aaaacatcac ttattcagaa aatggagcaa      360
gaggtagaaa acttcagttg ttccagatga tgatgtcatg gtatcgagta ttctttatat      420
tcagttccta tttaagtcat ttttgtcatg tccgcctaat tgatgtagta tgaaaccctg      480
catct                                                                  485

<210> SEQ ID NO 439
<211> LENGTH: 533
<212> TYPE: DNA
<213> ORGANISM: Homo sapiens

<400> SEQUENCE: 439
acagcagttt cctcatccct gcagctgtgt ttgaacaggt catttaccat actgtcctcc       60
aggttcaaca gtatggctcc aaatgatgaa atttcattct gattttctgg ctgaagacta      120
ttctgtttgt gtatgtccac cacagttact ttatcccttc atctgtggat gggcagaatg      180
aaacatatat ggaaatgttc tgtgcaataa aaacagcagt ggtaacacag atgtaggctc      240
tgagtgtctc actggagact gaagtccaca gatatgcaac aaagcctttg tctccctgat      300
gtttttgcct cctgctggtc atgtgctttc acacatcaag agaggacatt taacatttga      360
gccacagtgt catttgctgt tgtctgatgg ttggttggca gagaatttga actggagatg      420
aactttatta tccaggacgc tgagagtata acatgcatga cagagctttt agagcactgt      480
gatgtaacat gtcaagcaga aatagggagc atgtttacag ccattctatg aaa            533

<210> SEQ ID NO 440
<211> LENGTH: 341
<212> TYPE: DNA
<213> ORGANISM: Homo sapiens

<400> SEQUENCE: 440
catggggtag gggggtcggg gattcattga attgtggttg gcaggagcaa gccctgctca       60
cactctcaca ctcgcaccca gaattgtcaa agatacagat tgtaaaaatc tacgatccct      120
cagtctcact cacaaaaaat aaaatctcat gtccccaacg aacccagagt cagacgacag      180
ctggagcatt ggcagggaca gtcagaaagg agacaagtga aaacggtcag atggacacag      240
gcggaggaga aaagacagag ggagagagac catcgggaac aatcagaggg gccgagacga      300
```

-continued

| tcagaaaagg gtcagcccga gacaggctga gccagagttt c | 341 |

<210> SEQ ID NO 441
<211> LENGTH: 572
<212> TYPE: DNA
<213> ORGANISM: Homo sapiens
<220> FEATURE:
<221> NAME/KEY: misc_feature
<222> LOCATION: (1)...(572)
<223> OTHER INFORMATION: n = A,T,C or G

<400> SEQUENCE: 441

| aagtttgggg ataatttatt atgcagcaag agataataca caggacttct canagcactt | 60 |
| aatatgttaa tataaatctc caanaaaaaa gatatacaat gaaacattcc tcttagttat | 120 |
| ctggccaagg anactttntt tttttganaa tattcttcaa aaagctgatc taatgatatg | 180 |
| gctctggtcc tacaattcca tgtaacttct aaccttgatt ttatctcatg agcaaatcat | 240 |
| ttatccttcc agaacctcaa cttttccctt ttacaaagta gaaataaacc atctgccttt | 300 |
| acataaatca ttaatacagc cctggatggg cagattctga gctattttg gctgggggt | 360 |
| gggaaatagc ctgtggaggt cctaaaaaga tctacgggc tcgagatggt tctctgcaag | 420 |
| gtagcaggtg ggctcaggc ccatttcagt ctttgttccc caggccattt ccacaaaatg | 480 |
| gtgagaaata gtgtcttctt ttagcttgct cataactcaa agatggggg catggacctg | 540 |
| ggcctttcta ggctagggca tgaacctcct cc | 572 |

<210> SEQ ID NO 442
<211> LENGTH: 379
<212> TYPE: DNA
<213> ORGANISM: Homo sapiens
<220> FEATURE:
<221> NAME/KEY: misc_feature
<222> LOCATION: (1)...(379)
<223> OTHER INFORMATION: n = A,T,C or G

<400> SEQUENCE: 442

| tcccagctgc actgcttaca cgtcttcctt cgtnttcacc taccccgagg ctgactcctt | 60 |
| ccccagntgt gcagctgccc accgcaaggg cagcagcagc aatgagcctt cctctgactc | 120 |
| gctcagctca cccacgctgc tggccctgtg aggggcagg gaaggggagg cagccggcac | 180 |
| ccacaagtgc cactgcccga gctggtgcat tacagagagg agaaacacat cttccctaga | 240 |
| gggttcctgt agacctaggg aggacctat ctgtgcgtga acacaccag gctgtgggcc | 300 |
| tcaaggactt gaaagcatcc atgtgtggac tcaagtcctt acctcttccg agatgtagc | 360 |
| aaaacgcatg gagtgtgta | 379 |

<210> SEQ ID NO 443
<211> LENGTH: 511
<212> TYPE: DNA
<213> ORGANISM: Homo sapiens
<220> FEATURE:
<221> NAME/KEY: misc_feature
<222> LOCATION: (1)...(511)
<223> OTHER INFORMATION: n = A,T,C or G

<400> SEQUENCE: 443

| acatgccccc aaaggctcgc ttcattgcta cgattctcta cttaaatcca cattcacagc | 60 |
| tattgcctca gaccctctgg aggaggggcc aggggttagc tggctttgaa tagcatgtag | 120 |
| agcacaggca gtgtggccac aaatgtcaca caggtgacca gggtgctata gatggtgttc | 180 |
| ctgttgactt gggcttctag tctctgctcc gtgtctgaca gtgccaagat catgctcccc | 240 |

```
tgctccagca agaagctggg catagccccg tctgctggtt ccaccaggcc tgggtgtgct    300
gcagacttta caagctgaac caccccagcc atttggctac aagtcttttc taggccatca    360
agctgctctc gtaagccttc tagacatgaa tggacttgcc tggaatgact aagctgctct    420
ttcaaggcag ctgaaaggac atcnacatct ctgtctctgg tcggggg gact acctgcctgt    480 gacccagagt cctgccctgg cccagcagca t                                    511
```

<210> SEQ ID NO 444
<211> LENGTH: 612
<212> TYPE: DNA
<213> ORGANISM: Homo sapiens
<220> FEATURE:
<221> NAME/KEY: misc_feature
<222> LOCATION: (1)...(612)
<223> OTHER INFORMATION: n = A,T,C or G

<400> SEQUENCE: 444

```
acaggaagaa ttctacagtt aatctatcac agtgttccag caaagcatat gttgaaaact    60
acagttttca atctaacatc taaattttaa aaagtagcat ttcagcaaca aacaagctca    120
gagaggctca tggcaaaagt gaaataacag aactattgct cagatgtctg caaagtcaag    180
ctgctgccct cagctccgcc cacttgaagg cttaggcaga cacgtaaggt ggcggtggct    240
ccttggcagc accattcaca gtggcatcat catacggagg tagcagcacc gtagtgtcat    300
tgctggtaac ataaaccagg acatcagagg agttcctacc attgatgtat cggtagcagt    360
tccaaacaca gctaatcaag taacccttaa aagtcaagat aatgctaata aacagaagaa    420
taataaggac caaacaggta ggattcactg acatgсасаtс atctctgtag ggaaaattag    480
gaggcagttg ccgtatgtat tcctgaatgg agtttggata ataagcaca gtgattgcaa    540 ccaacanctt cagggcaaag tcaaagatct ggtaacagaa gaatgggatg atccaggctg    600
cgcgttgctt gt                                                        612
```

<210> SEQ ID NO 445
<211> LENGTH: 708
<212> TYPE: DNA
<213> ORGANISM: Homo sapiens
<220> FEATURE:
<221> NAME/KEY: misc_feature
<222> LOCATION: (1)...(708)
<223> OTHER INFORMATION: n = A,T,C or G

<400> SEQUENCE: 445

```
accatcctgt tccaacagag ccattgccta ttcctaaatt gaatctgact gggtgtgccc    60
ctcctcggaa cacaacagta gaccttaata gtggaaacat cgatgtgcct cccaacatga    120
caagctgggc cagctttcat aatggtgtgg ctgctggcct gaagatagct cctgcctccc    180
agatcgactc agcttggatt gtttacaata agcccaagca tgctgagttg gccaatgagt    240
atgctggctt tctcatggct ctgggtttga tgggcacct taccaagctg gcgactctca    300
atatccatga ctacttgacc aagggccatg aaatgacaag cattggactg ctacttggtg    360
tttctgctgc aaaactaggc accatggata tgtctattac tcggcttgtt agcattcgca    420
ttcctgctct cttaccccca acgtccacag agttggatgt tcctcacaat gtccaagtgg    480
ctgcagtggt tggcattggc cttgtatatc aagggacagc tcacagacat actgcagaag    540
tcctgttggc tgagatagga cggcctcctg gtcctgaaat ggaatactgc actgacagag    600
agtcatactc cttagctgct ggcttggccc tgggcatggt ctncttgggg catggcagca    660
```

-continued atttgatagg tatgtntgat ctcaatgtgc ctgagcagct ctatcagt    708

<210> SEQ ID NO 446
<211> LENGTH: 612
<212> TYPE: DNA
<213> ORGANISM: Homo sapiens

<400> SEQUENCE: 446
acaagcaacg cgcagcctgg atcatcccat tcttctgtta ccagatcttt gactttgccc    60
tgaacatgtt ggttgcaatc actgtgctta tttatccaaa ctccattcag gaatacatac    120
ggcaactgcc tcctaatttt ccctacagag atgatgtcat gtcagtgaat cctacctgtt    180
tggtccttat tattcttctg tttattagca ttatcttgac ttttaagggt tacttgatta    240
gctgtgtttg gaactgctac cgatacatca atggtaggaa ctcctctgat gtcctggttt    300
atgttaccag caatgacact acggtgctgc taccccccgta tgatgatgcc actgtgaatg    360
gtgctgccaa ggagccaccg ccaccttacg tgtctgccta agccttcaag tgggcggagc    420
tgagggcagc agcttgactt tgcagacatc tgagcaatag ttctgttatt tcacttttgc    480
catgagcctc tctgagcttg tttgttgctg aaatgctact ttttaaaatt tagatgttag    540
attgaaaact gtagttttca acatatgctt tgctggaaca ctgtgataga ttaactgtag    600
aattcttcct gt    612

<210> SEQ ID NO 447
<211> LENGTH: 642
<212> TYPE: DNA
<213> ORGANISM: Homo sapiens

<400> SEQUENCE: 447
actgaaagaa ttaaagtcag aagtcttccc aaaacaaaaa gaactgccca cagagaaaat    60
cctttctgat acttttcatt gctaaaataa acaggcgggg aaatgtggaa aagaaattca    120
acaaaataat gtagcaccag aagaacaagt cctagatgat tcaagttcaa aaggtaagct    180
ccagcaatgt ggaagaggta aagaccaatg tagacaagct gacgaggaat atcttctttt    240
ttggttttct ggaagtagag ttcaggaaaa gcatgaagcc agtaagccag ctgtgatatg    300
tagaaaaact tcatttgaaa tgtcatcagg ttatggggat aagccctcca taagatagtt    360
gggtctgaga tgtagttttc agagatgaga atgaatgtgc cccaaacaca ggcaaaaagg    420
tagaacgcac taagctgacc agattcatta aacttgctgt gttttgtttt ggagaagtgc    480
attcgcctgt taattttatc caacatatac tcttgaatta cggcatgaat aattatcgcc    540
actagcatgt agaagaaaac agtagccaaa tctttgatgc catagtaata aagggacact    600
gattcagtag cttgttcttc tgttgctggg agggtgacat tg    642

<210> SEQ ID NO 448
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 448
accagaagac cttagaaaaa ggaggaaagg aggagaggca gataatttgg atgaattcct    60
caaagngttt gaaaatccag aggttcctag agaggaccag caacagcagc atcagcagcg    120
tgatgttatc gatgagccca ttattgaaga gccaagccgc ctccaggagt cagtgatgga    180

```
ggccagcaga acaaacatag atgagtcagc tatgcctcca ccaccacctc agggagttaa      240
gcgaaaagct ggacaaattg acccagagcc tgtgatgcct cctcagcagg tagagcagat      300
ggaaatacca cctgtagagc ttcccccaga agaacctcca aatatctgtc agctaatacc      360
agagttagaa cttctgccag aaaaagagaa ggag                                  394
```

<210> SEQ ID NO 449
<211> LENGTH: 494
<212> TYPE: DNA
<213> ORGANISM: Homo sapiens
<220> FEATURE:
<221> NAME/KEY: misc_feature
<222> LOCATION: (1)...(494)
<223> OTHER INFORMATION: n = A,T,C or G

<400> SEQUENCE: 449

```
acaaaaaaca caaggaatac aacccaatag aaaatagtcc tgggaatgtg gtcagaagca       60
aaggcntgag tgtctttctc aaccgtgcaa aagccgtgtt cttcccggga aaccaggaaa      120
aggatccgct actcaaaaac caagaattta aaggagtttc ttaaatttcg accttgtttc      180
tgaagctcac ttttcagtgc cattgatgtg agatgtgctg gagtggctat taacctttttt    240 ttcctaaaga ttattgttaa atagatattg tggtttgggg aagttgaatt ttttataggt      300
taaatgtcat tttagagatg gggagaggga ttatactgca ggcagcttca gccatgttgt      360
gaaactgata aaagcaactt agcaaggctt cttttcatta ttttttatgt ttcacttata      420
aagtcttagg taactagtag gatagaaaca ctgtgtcccg agagtaagga gagaagctac      480
tattgattag agcc                                                        494
```

<210> SEQ ID NO 450
<211> LENGTH: 547
<212> TYPE: DNA
<213> ORGANISM: Homo sapiens

<400> SEQUENCE: 450

```
actttgggct ccagacttca ctgtccttag gcattgaaac catcacctgg tttgcattct       60
tcatgactga ggttaactta aaacaaaaat ggtaggaaag cttttcctatg cttcgggtaa    120 gagacaaatt tgcttttgta gaattggtgg ctgagaaagg cagacagggc ctgattaaag      180 aagcatttg tcaccactag ccaccaagtt aagttgtgga acccaaaggt gacggccatg       240
gaaacgtaga tcatcagctc tgctaagtag ttaggggaag aaacatattc aaaccagtct      300
ccaaatggga tcctgtggtt acagtgaatg gccactcctg ctttattttt cctgagattg      360
ccgagaataa catggcactt atactgatgg gcagatgacc agatgaacat catcatccca      420
agaatatgga accaccgtgc ttgcatcaat agatttttcc ctgttatgta ggcattcctg      480
ccatccattg gcacttggct cagcacagtt aggccaacaa ggacataata gacaagtcca      540
aaacagt                                                                547
```

<210> SEQ ID NO 451
<211> LENGTH: 384
<212> TYPE: DNA
<213> ORGANISM: Homo sapiens
<220> FEATURE:
<221> NAME/KEY: misc_feature
<222> LOCATION: (1)...(384)
<223> OTHER INFORMATION: n = A,T,C or G

<400> SEQUENCE: 451

```
actacttnnt ggttaaaang ccactggtag agtcatctga ntgtaaacaa tgtccctgca      60
ctgctggaaa aatccactgg ctcccaagaa aagaaaatgg tctgaagcct ctgttgtggc     120
tctcacaact catctttccc taagtcatca agctccacat cactgaggtc aatgtcatcc     180
tccacgggaa gctcgccatc cctgccgtcc caaggctctc tctcaacgat ggtagggaaa     240
gccccgcctc ctacaggtgc cgtggagcca cgcccaaaag agagctccct gagaaactcg     300
ttgatgcctt gctcactgaa ggagcctttt agcagagcaa atttcatctt gcgtgcattg     360
atggcggcca tggcggggta ccca                                            384
```

<210> SEQ ID NO 452
<211> LENGTH: 381
<212> TYPE: DNA
<213> ORGANISM: Homo sapiens
<220> FEATURE:
<221> NAME/KEY: misc_feature
<222> LOCATION: (1)...(381)
<223> OTHER INFORMATION: n = A,T,C or G

<400> SEQUENCE: 452

```
actctaaagt tgccactctc acagggtca gtgatacca ctgaacctgg caggaacagt       60
cctgcagcca gaatctgcaa gcagcgcctg tatgcaacgt ttagggccaa aggctgtctg    120 gtgggttgt tcatcacagc ataatggcct agtaggtcaa ggatccaggg tgtgaggggc     180
tcaaagccag gaaaacgaat cctcaagtcc ttcagtagtc tgatgagaac tttaactgtg    240
gactgagaag cattttcctc gaaccagcgg gcatgtcgga tggctgctaa ngcactctgc    300
aatactttga tatccaaatg gagttctgga tccagttttc naagattggg tggcactgtt    360
gtaatganaa tcttcactgt a                                              381
```

<210> SEQ ID NO 453
<211> LENGTH: 455
<212> TYPE: DNA
<213> ORGANISM: Homo sapiens

<400> SEQUENCE: 453

```
actgtgctaa acagcctata gccaagtttt aaagagttac aggaacaact gctacacatt      60
caaagaacag gcattcactg cagcctcctg atttgacctg atgggaggga caggagaatg     120
agtcactctg ccaccacttt tcctgccttg gatttgtaga ggatttgttt tgctctaatt     180
tgtttttcct atatctgccc tactaaggta cacagtctgg gcactttgaa aatgttaaag    240 ttttttaacgt ttgactgaca gaagcagcac ttaaaggctt catgaatcta ttttccaaaa    300
aaagtatgct ttcagtaaaa catttttacca ttttatctaa ctatgcactg acattttgt    360 tcttcctgaa aagggatt atgctaacac tgtattttta atgtaaaaat atacgtgtag     420
agatatttta acttcctgag tgacttatac ctcaa                               455
```

<210> SEQ ID NO 454
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 454

```
acagagcanc tttacaagtt gtcacatttc tttataaatt ttttttaaagc tacagtttaa      60 tacaaaatga attgcggttt tattacatta ataacctttc acctcagggt tttatgaaga    120
```

```
ggaaagggtt ttatgcaaaa gaaagtgcta caattcctaa tcattttaga cactttagga     180
gggggtgaag ttgtatgata aagcagatat tttaattatt tgttatcttt ttgtattgca     240
agaaatttct tgctagtgaa tcaagaaaac atccagattg acagtctaaa atggctactg     300
gtattttagt taattcaaaa atgaaacttt tcagtgattc actttactaa cattctatttt    360 gagaaggctt attggtaaag ttt                                             383

<210> SEQ ID NO 455
<211> LENGTH: 383
<212> TYPE: DNA
<213> ORGANISM: Homo sapiens
<220> FEATURE:
<221> NAME/KEY: misc_feature
<222> LOCATION: (1)...(383)
<223> OTHER INFORMATION: n = A,T,C or G

<400> SEQUENCE: 455
actcctttan gacaaggaaa caggtatcag catgatggta gcagaaacct tatcaccaag      60
gtgcaggagc tgacttcttc caaagagttg tggttccggg cagcggtcat tgccgtgccc    120
attgctggag ggctgatttt agtgttgctt attatgttgg ccctgaggat gcttcgaagt    180
gaaaataaga ggctgcagga tcagcggcaa cagatgctct cccgtttgca ctacagcttt    240
cacggacacc attccaaaaa ggggcaggtt gcaagttag acttggaatg catggtgccg     300
gtcagtgggc acgagaactg ctgtctgacc tgtgataaaa tgagacaagc agacctcagc    360
aacgataaga tcctctcgct tgt                                             383

<210> SEQ ID NO 456
<211> LENGTH: 543
<212> TYPE: DNA
<213> ORGANISM: Homo sapiens
<220> FEATURE:
<221> NAME/KEY: misc_feature
<222> LOCATION: (1)...(543)
<223> OTHER INFORMATION: n = A,T,C or G

<400> SEQUENCE: 456
acaaacattt tacaaaaaag aacattacca atatcagtgg cagtaagggc aagctgaaga     60
atangtagac tgagttttccg ggcaatgtct gtcctcaaag acatccaaac tgcgttcagg   120
cagctgaaac aggcttcttt cccagtgaca agcatatgtg gtcagtaata caaacgatgg    180
taaatgaggc tactacatag gcccagttaa caaactcctc ttctcctcgg gtaggccatg    240
atacaagtgg aactcatcaa ataatttaaa cccaaggcga taacaacact atttcccatc    300
taaactcatt taagccttca caatgtcgca atggattcag ttacttgcaa acgatcccgg    360
gttgtcatac agatacttgt tttttacaca taacgctgtg ccatcccttc cttcactgcc    420
ccagtcaggt ttcctgttgt tggaccgaaa ggggatacat tttagaaatg cttccctcaa    480
gacagaagtg agaaagaaag gagaccctga ggccaggatc tattaaacct ggtgtgtgcg    540
caa                                                                   543

<210> SEQ ID NO 457
<211> LENGTH: 544
<212> TYPE: DNA
<213> ORGANISM: Homo sapiens
<220> FEATURE:
<221> NAME/KEY: misc_feature
<222> LOCATION: (1)...(544)
<223> OTHER INFORMATION: n = A,T,C or G
```

<400> SEQUENCE: 457

```
actggtgcca atattgncat ggtgagctcc tctctaatgt cttccagggc accaatatct      60
gcccatgtca cattagggac agtgacaaag ccttcccttt tggcagaggg ttggactgag     120
gatagagcaa caatgaaatc attcagttca atgcacagtc cttgcatctg ctcctctgag    180
agggatcttt ggtctcttag caaccccagc agcctttgta attcatcctg tgtttcagaa    240
gtgggctcag ttcccagcct ttcctcctgg actcctttag atggcaaatc ttccatttca    300
ggattttcct tctgctgttc ctgtagcttc attaagactc tattgactgc acacattgct    360
gcctctcggc acagtgccat gagatcagca ccaacaaagc ctggagttag gtgtgctaag    420
tgacagaaat caaaagcttg aggaagcctc agttttctgc acaatgtttg aagtattctt    480
tccctggatg cttcatctgg gatacctagg catatttctc ggtcgaacct tcccgcacgt    540
ctca                                                                  544
```

<210> SEQ ID NO 458
<211> LENGTH: 382
<212> TYPE: DNA
<213> ORGANISM: Homo sapiens
<220> FEATURE:
<221> NAME/KEY: misc_feature
<222> LOCATION: (1)...(382)
<223> OTHER INFORMATION: n = A,T,C or G

<400> SEQUENCE: 458

```
acctntaggc tcaacggcag aancttcacc acaaaagcga atgggcaca ccacagggag       60
aaaactggtt gtcctggatg tttgaaaagt tggtcgttgt catggtgtgt tacttcatcc    120
tatctatcat taactccatg gcacaaagtt atgccaaacg aatccagcag cggttgaact    180
cagaggagaa aactaaataa gtagagaaag ttttaaactg cagaaattgg agtggatggg    240
ttctgcctta aattggggagg actccaagcc gggaaggaaa attccctttt ccaacctgta   300
tcaatttta caactttttt cctgaaagca gtttagtcca tactttgcac tgacatactt    360
tttccttctg tgctaaggta ag                                              382
```

<210> SEQ ID NO 459
<211> LENGTH: 168
<212> TYPE: DNA
<213> ORGANISM: Homo sapiens

<400> SEQUENCE: 459

```
ctcgtactct agccaggcac gaaaccatga agtagcctga tccttcttag ccatcctggc      60
cgccttagcg gtagtaactt tgtgttatga atcacatgaa agcatggaat cttatgaact    120
taatcccttc attaacagga gaatgcaaa taccttcata tcccctca                  168
```

<210> SEQ ID NO 460
<211> LENGTH: 190
<212> TYPE: DNA
<213> ORGANISM: Homo sapiens
<220> FEATURE:
<221> NAME/KEY: misc_feature
<222> LOCATION: (1)...(190)
<223> OTHER INFORMATION: n = A,T,C or G

<400> SEQUENCE: 460

```
acanctgcta ccagggagcc gagagctgac tatcccagcc tcggctaatg tattctacgc      60
catggatgga gcttcacacg atttcctcct gcggcagcgg cgaaggtcct ctactgctac    120
acctggcgtc accagtggcc cgtctgcctc aggaactcct ccgagtgagg gaggaggggg    180
```

```
ctcctttccc                                                          190

<210> SEQ ID NO 461
<211> LENGTH: 495
<212> TYPE: DNA
<213> ORGANISM: Homo sapiens

<400> SEQUENCE: 461
acagacaggc ttctctgcta tcctccaggc agtgtaatag tcaaggaaaa gggcaacagt     60
attggatcat tccttagaca ctaatcagct ggggaaagag ttcattggca aaagtgtcct    120
cccaagaatg gtttacacca agcagagagg acatgtcact gaatgggaa agggaacccc    180 cgtatccaca gtcactgtaa gcatccagta ggcaggaaga tggctttggg cagtggctgg    240
atgaaagcag atttgagata cccagctccg gaacgaggtc atcttctaca ggttcttcct    300
tcactgagac aatgaattca gggtgatcat tctctgaggg gctgagaggt gcttcctcga    360
ttttcactac cacattagct tggctctctg tctcagaggg tatctctaag actaggggct    420
tggtatatat gtggtcaaaa cgaattagtt cattaatggc ttccagcttg gctgatgacg    480
tccccactga cagag                                                    495

<210> SEQ ID NO 462
<211> LENGTH: 493
<212> TYPE: DNA
<213> ORGANISM: Homo sapiens
<220> FEATURE:
<221> NAME/KEY: misc_feature
<222> LOCATION: (1)...(493)
<223> OTHER INFORMATION: n = A,T,C or G

<400> SEQUENCE: 462
acactgaaac ataaatccgc aagtcaccac acatacaaca cccggcagga aaaaacaaa     60 aacagggngt ttacatgatc cctgtaacag ccatggtctc aaactcagat gcttcctcca    120
tctgccaagt gtgttttgga tacagagcac atcgtggctt ctggggtcac actcagctta    180
ggctgtgggt ccacagagca ctcatctggc tgggctatgg tggtggtggc tctactcaag    240
aagcaaagca gttaccagca cattcaaaca gtgtattgaa catctttaa atatcaaagt    300 gagaaacaag aaggcaacat aataatgtta tcagaaagat gttaggaagt aaggacagct    360
gtgtaaagct tgaggctgaa aagtagcttg ccagcttcat ttctttggtt tcttgggtag    420
tgggcgccgg aacagcaaga tgtgaggttc tggttcatgg atcatataat ggacccatcc    480
ctgactctgc tga                                                      493

<210> SEQ ID NO 463
<211> LENGTH: 3681
<212> TYPE: DNA
<213> ORGANISM: Homo sapiens

<400> SEQUENCE: 463
tccgagctga ttacagacac caaggaagat gctgtaaaga gtcagcagcc acagccctgg     60
ctagctggcc ctgtgggcat ttattagtaa agttttaatg acaaaagctt tgagtcaaca    120
cacccgtggg taattaacct ggtcatcccc acctggaga gccatcctgc ccatgggtga    180
tcaaagaagg aacatctgca ggaacacctg atgaggctgc acccttggcg gaaagaacac    240
ctgacacagc tgaagcttg gtggaaaaaa cacctgatga ggctgcaccc ttggtggaaa    300
gaacacctga cacggctgaa agcttggtgg aaaaaacacc tgatgaggct gcatccttgg    360
```

```
tggagggaac atctgacaaa attcaatgtt tggagaaagc gacatctgga aagttcgaac    420
agtcagcaga agaaacacct agggaaatta cgagtcctgc aaaagaaaca tctgagaaat    480
ttacgtggcc agcaaaagga agacctagga agatcgcatg ggagaaaaaa gaagacacac    540
ctagggaaat tatgagtccc gcaaaagaaa catctgagaa atttacgtgg gcagcaaaag    600
gaagacctag gaagatcgca tgggagaaaa aagaaacacc tgtaaagact ggatgcgtgg    660
caagagtaac atctaataaa actaaagttt tggaaaaagg aagatctaag atgattgcat    720
gtcctacaaa agaatcatct acaaaagcaa gtgccaatga tcagaggttc ccatcagaat    780
ccaaacaaga ggaagatgaa gaatattctt gtgattctcg gagtctcttt gagagttctg    840
caaagattca agtgtgtata cctgagtcta tatcaaaaa agtaatggag ataaatagag    900
aagtagaaga gcctcctaag aagccatctg ccttcaagcc tgccattgaa atgcaaaact    960
ctgttccaaa taaagccttt gaattgaaga atgaacaaac attgagagca gatccgatgt   1020
tcccaccaga atccaaacaa aaggactatg aagaaaattc ttgggattct gagagtctct   1080
gtgagactgt ttcacagaag gatgtgtgtt tacccaaggc tacacatcaa aaagaaatag   1140
ataaaataaa tggaaaatta gaagagtctc ctaataaaga tggtcttctg aaggctacct   1200
gcggaatgaa agtttctatt ccaactaaag ccttagaatt gaaggacatg caaactttca   1260
aagcagagcc tccggggaag ccatctgcct tcgagcctgc cactgaaatg caaaagtctg   1320
tcccaaataa agccttggaa ttgaaaaatg aacaaacatt gagagcagat gagatactcc   1380
catcagaatc caaacaaaag gactatgaag aaagttcttg ggattctgag agtctctgtg   1440
agactgtttc acagaaggat gtgtgtttac ccaaggctrc rcatcaaaaa gaaatagata   1500
aaataaatgg aaaattagaa gggtctcctg ttaaagatgg tcttctgaag gctaactgcg   1560
gaatgaaagt ttctattcca actaaagcct tagaattgat ggacatgcaa actttcaaag   1620
cagagcctcc cgagaagcca tctgccttcg agcctgccat tgaaatgcaa aagtctgttc   1680
caaataaagc cttggaattg aagaatgaac aaacattgag agcagatgag atactcccat   1740
cagaatccaa acaaaaggac tatgaagaaa gttcttggga ttctgagagt ctctgtgaga   1800
ctgtttcaca gaaggatgtg tgtttaccca aggctrcrca tcaaaaagaa atagataaaa   1860
taaatggaaa attagaagag tctcctgata atgatggttt tctgaaggct ccctgcagaa   1920
tgaaagtttc tattccaact aaagccttag aattgatgga catgcaaact ttcaaagcag   1980
agcctcccga gaagccatct gccttcgagc ctgccattga atgcaaaag tctgttccaa   2040 ataaagcctt ggaattgaag aatgaacaaa cattgagagc agatcagatg ttcccttcag   2100
aatcaaaaca aaagaasgtt gaagaaaatt cttgggattc tgagagtctc cgtgagactg   2160
tttcacagaa ggatgtgtgt gtacccaagg ctacacatca aaaagaaatg gataaaataa   2220
gtggaaaatt agaagattca actagccttat caaaaatcttt ggatacagtt cattcttgtg   2280
aaagagcaag ggaacttcaa aaagatcact gtgaacaacg tacaggaaaa atggaacaaa   2340
tgaaaaagaa gttttgtgta ctgaaaaaga actgtcaga agcaaagaa ataaaatcac   2400 agttagagaa ccaaaaagtt aaatgggaac aagagctctg cagtgtgagg tttctcacac   2460
tcatgaaaat gaaaattatc tcttacatga aaattgcatg ttgaaaaagg aaattgccat   2520
gctaaaactg gaaatagcca cactgaaaca ccaataccag gaaaaggaaa ataaatactt   2580
tgaggacatt aagatttttaa aagaaaagaa tgctgaactt cagatgaccc taaaactgaa   2640
agaggaatca ttaactaaaa gggcatctca atatagtggg cagcttaaag ttctgatagc   2700
tgagaacaca atgctcactt ctaaattgaa ggaaaaacaa gacaaagaaa tactagaggc   2760
```

| | |
|---|---|
| agaaattgaa tcacaccatc ctagactggc ttctgctgta caagaccatg atcaaattgt | 2820 |
| gacatcaaga aaaagtcaag aacctgcttt ccacattgca ggagatgctt gtttgcaaag | 2880 |
| aaaaatgaat gttgatgtga gtagtacgat atataacaat gaggtgctcc atcaaccact | 2940 |
| ttctgaagct caaggaaat ccaaaagcct aaaaattaat ctcaattatg cmggagatgc | 3000 |
| tctaagagaa aatacattgg tttcagaaca tgcacaaaga gaccaacgtg aaacacagtg | 3060 |
| tcaaatgaag gaagctgaac acatgtatca aaacgaacaa gataatgtga acaaacacac | 3120 |
| tgaacagcag gagtctctag atcagaaatt atttcaacta caaagcaaaa atatgtggct | 3180 |
| tcaacagcaa ttagttcatg cacataagaa agctgacaac aaaagcaaga taacaattga | 3240 |
| tattcattt cttgagagga aaatgcaaca tcatctccta aaagagaaaa atgaggagat | 3300 |
| atttaattac aataaccatt taaaaaccg tatatatcaa tatgaaaaag agaaagcaga | 3360 |
| aacagaaaac tcatgagaga caagcagtaa gaaacttctt ttggagaaac aacagaccag | 3420 |
| atctttactc acaactcatg ctaggaggcc agtcctagca tcaccttatg ttgaaaatct | 3480 |
| taccaatagt ctgtgtcaac agaatactta ttttagaaga aaaattcatg atttcttcct | 3540 |
| gaagcctaca gacataaaat aacagtgtga agaattactt gttcacgaat tgcataaagc | 3600 |
| tgcacaggat tcccatctac cctgatgatg cagcagacat cattcaatcc aaccagaatc | 3660 |
| tcgctctgtc actcaggctg g | 3681 |

<210> SEQ ID NO 464
<211> LENGTH: 1424
<212> TYPE: DNA
<213> ORGANISM: Homo sapiens

<400> SEQUENCE: 464

| | |
|---|---|
| tccgagctga ttacagacac caaggaagat gctgtaaaga gtcagcagcc acagccctgg | 60 |
| ctagctggcc ctgtgggcat ttattagtaa agttttaatg acaaaagctt tgagtcaaca | 120 |
| cacccgtggg taattaacct ggtcatcccc accctggaga gccatcctgc ccatgggtga | 180 |
| tcaaagaagg aacatctgca ggaacacctg atgaggctgc acccttggcg gaaagaacac | 240 |
| ctgacacagc tgaaagcttg gtggaaaaaa cacctgatga ggctgcaccc ttggtggaaa | 300 |
| gaacacctga cacggctgaa agcttggtgg aaaaaacacc tgatgaggct gcatccttgg | 360 |
| tggagggaac atctgacaaa attcaatgtt tggagaaagc gacatctgga aagttcgaac | 420 |
| agtcagcaga agaaacacct agggaaatta cgagtcctgc aaaagaaaca tctgagaaat | 480 |
| ttacgtggcc agcaaaagga agacctagga agatcgcatg ggagaaaaaa gaagacacac | 540 |
| ctagggaaat tatgagtccc gcaaaagaaa catctgagaa atttacgtgg gcagcaaaag | 600 |
| gaagacctag gaagatcgca tgggagaaaa aagaaacacc tgtaaagact ggatgcgtgg | 660 |
| caagagtaac atctaataaa actaaagttt tggaaaaagg aagatctaag atgattgcat | 720 |
| gtcctacaaa agaatcatct acaaaagcaa gtgccaatga tcagaggttc ccatcagaat | 780 |
| ccaaacaaga ggaagatgaa gaatattctt gtgattctcg gagtctcttt gagagttctg | 840 |
| caaagattca agtgtgtata cctgagtcta tatcaaaa agtaatggag ataaatagag | 900 |
| aagtagaaga gcctcctaag aagccatctg ccttcaagcc tgccattgaa atgcaaaact | 960 |
| ctgttccaaa taaagccttt gaattgaaga tgaacaaac attgagagca gatccgatgt | 1020 |
| tcccaccaga atccaaacaa aaggactatg aagaaaattc ttgggattct gagagtctct | 1080 |
| gtgagactgt ttcacagaag gatgtgtgtt tacccaaggc tacacatcaa aaagaaatag | 1140 |

```
ataaaataaa tggaaaatta gaaggtaaga accgttttt atttaaaaat cagttgaccg   1200
aatatttctc taaactgatg aggagggata tcctctagta gctgaagaaa attacctcct   1260
aaatgcaaac catggaaaaa aagagaagtg caatggtcgt aagttgtatg tctcatcagg   1320
tgttggcaac agactatatt gagagtgctg aaaaggagct gaattattag tttgaattca   1380
agatattgca agacctgaga gaaaaaaaaa aaaaaaaaaa aaaa                    1424
```

<210> SEQ ID NO 465
<211> LENGTH: 674
<212> TYPE: DNA
<213> ORGANISM: Homo sapiens

<400> SEQUENCE: 465

```
attccgagct gattacagac accaaggaag atgctgtaaa gagtcagcag ccacagccct    60
ggctagctgg ccctgtgggc atttattagt aaagttttaa tgacaaaagc tttgagtcaa   120 cacaccgtg  ggtaattaac ctggtcatcc ccaccctgga gagccatcct gcccatgggt    180
gatcaaagaa ggaacatctg caggaacacc tgatgaggct gcacccttgg cggaaagaac    240
acctgacaca gctgaaagct tggtggaaaa acacctgat gaggctgcac ccttggtgga    300
aagaacacct gacacggctg aaagcttggt ggaaaaaaca cctgatgagg ctgcatcctt    360
ggtggaggga acatctgaca aaattcaatg tttggagaaa gcgacatctg gaaagttcga    420
acagtcagca gaagaaacac ctagggaaat tacgagtcct gcaaagaaa  catctgagaa    480 atttacgtgg ccagcaaaag gaagacctag gaagatcgca tgggagaaaa aagatgactc    540
agttaaggca aaaaaaaaaa aaaaaaaaaa aaaaaaaaaa aaaaaaaaaa aaaaaaaaaa    600
aaaaaaaaaa aaaaaaaaaa aaaaaaaaaa aaaaaaaaa  aaaaaaaaaa aaaaaaaaaa    660
aaaaaaaaaa aaaa                                                     674
```

<210> SEQ ID NO 466
<211> LENGTH: 1729
<212> TYPE: DNA
<213> ORGANISM: Homo sapiens
<220> FEATURE:
<221> NAME/KEY: unsure
<222> LOCATION: (11)
<223> OTHER INFORMATION: n=A,T,C or G
<221> NAME/KEY: unsure
<222> LOCATION: (1128)
<223> OTHER INFORMATION: n=A,T,C or G

<400> SEQUENCE: 466

```
gaaagttcga ncagtcagca gaagaaacac ctagggaaat tacgagtcct gcaaaagaaa    60
catctgagaa atttacgtgg ccagcaaaag gaagacctag gaagatcgca tgggagaaaa   120
aagaagacac acctagggaa attatgagtc ccgcaaaaga aacatctgag aaatttacgt   180
gggcagcaaa aggaagacct aggaagatcg catgggagaa aaaagaaaca cctgtaaaga   240
ctggatgcgt ggcaagagta acatctaata aaactaaagt tttggaaaaa ggaagatcta   300
agatgattgc atgtcctaca aaagaatcat ctacaaaagc aagtgccaat gatcagaggt   360
tcccatcaga atccaaacaa gaggaagatg aagaatattc ttgtgattct cggagtctct   420
ttgagagttc tgcaaagatt caagtgtgta tacctgagtc tatatatcaa aaagtaatgg   480
agataaatag agaagtagaa gagcctccta agaagccatc tgccttcaag cctgccattg   540
aaatgcaaaa ctctgttcca aataaagcct tgaattgaa  gaatgaacaa acattgagag   600
cagatccgat gttcccacca gaatccaaac aaaaggacta tgaagaaaat tcttgggatt   660
```

-continued

```
ctgagagtct ctgtgagact gtttcacaga aggatgtgtg tttacccaag gctacacatc      720
aaaaagaaat agataaaata aatggaaaat tagaagagtc tcctaataaa gatggtcttc      780
tgaaggctac ctgcggaatg aaagtttcta ttccaactaa agccttagaa ttgaaggaca      840
tgcaaacttt caaagcagag cctccgggga agccatctgc cttcgagcct gccactgaaa      900
tgcaaaagtc tgtcccaaat aaagccttgg aattgaaaaa tgaacaaaca ttgagagcag      960
atgagatact cccatcagaa tccaaacaaa aggactatga agaaaattct tgggatactg     1020
agagtctctg tgagactgtt tcacagaagg atgtgtgttt acccaaggct gcgcatcaaa     1080
aagaaataga taaataaat ggaaaattag aagggtctcc tggtaaanat ggtcttctga     1140
aggctaactg cggaatgaaa gtttctattc caactaaagc cttagaattg atggacatgc     1200
aaactttcaa agcagagcct cccgagaagc catctgcctt cgagcctgcc attgaaatgc     1260
aaaagtctgt tccaaataaa gccttggaat tgaagaatga acaaacattg agagcagatg     1320
agatactccc atcagaatcc aaacaaagg actatgaaga agttcttgg gattctgaga     1380 gtctctgtga gactgtttca cagaaggatg tgtgtttacc caaggctgcg catcaaaaag     1440
aaatagataa aataaatgga aaattagaag gtaagaaccg tttttattt aaaaatcatt     1500 tgaccaaata tttctctaaa ttgatgagga aggatatcct ctagtagctg aagaaaatta     1560
cctcctaaat gcaaaccatg gaaaaaaaga gaagtgcaat ggtcataagc tatgtgtctc     1620
atcaggcatt ggcaacagac tatattgtga gtgctgaaga ggagctgaat tactagttta     1680
aattcaagat attccaagac gtgaggaaaa tgagaaaaaa aaaaaaaaa                  1729
```

<210> SEQ ID NO 467
<211> LENGTH: 1337
<212> TYPE: DNA
<213> ORGANISM: Homo sapiens

<400> SEQUENCE: 467

```
aaaaagaaat agataaaata aatggaaaat tagaagggtc tcctgttaaa gatggtcttc       60
tgaaggctaa ctgcggaatg aaagtttcta ttccaactaa agccttagaa ttgatggaca      120
tgcaaacttt caaagcagag cctcccgaga agccatctgc cttcgagcct gccattgaaa      180
tgcaaaagtc tgttccaaat aaagccttgg aattgaagaa tgaacaaaca ttgagagcag      240
atgagatact cccatcagaa tccaaacaaa aggactatga agaaagttct tgggattctg      300
agagtctctg tgagactgtt tcacagaagg atgtgtgttt acccaaggct gcgcatcaaa      360
aagaaataga taaataaat ggaaaattag aagagtctcc tgataatgat ggttttctga      420
aggctccctg cagaatgaaa gtttctattc caactaaagc cttagaattg atggacatgc      480
aaactttcaa agcagagcct cccgagaagc catctgcctt cgagcctgcc attgaaatgc      540
aaaagtctgt tccaaataaa gccttggaat tgaagaatga acaaacattg agagcagatc      600
agatgttccc ttcagaatca aacaaaaga aggttgaaga aaattcttgg gattctgaga      660
gtctccgtga gactgtttca cagaaggatg tgtgtaccc aaggctaca catcaaaaag      720 aaatggataa aataagtgga aaattagaag attcaactag cctatcaaaa atcttggata      780
cagttcattc ttgtgaaaga gcaagggaac ttcaaaaaga tcactgtgaa caacgtacag      840
gaaaaatgga acaaatgaaa aagaagtttt gtgtactgaa aagaaactg tcagaagcaa      900 aagaaataaa atcacagtta gagaaccaaa aagttaaatg gaacaagag ctctgcagtg      960 tgagattgac tttaaaccaa gaagaagaga agagaagaaa tgccgatata ttaaatgaaa     1020
aaattaggga agaattagga agaatcgaag agcagcatag gaaagagtta gaagtgaaac     1080
```

```
aacaacttga acaggctctc agaatacaag atatagaatt gaagagtgta gaaagtaatt    1140
tgaatcaggt ttctcacact catgaaaatg aaaattatct cttacatgaa aattgcatgt    1200
tgaaaaagga aattgccatg ctaaaactgg aaatagccac actgaaacac caataccagg    1260
aaaaggaaaa taaatacttt gaggacatta agattttaaa agaaaagaat gctgaacttc    1320
agatgacccc tcgtgcc                                                   1337

<210> SEQ ID NO 468
<211> LENGTH: 2307
<212> TYPE: DNA
<213> ORGANISM: Homo sapiens

<400> SEQUENCE: 468
attgagagca gatgagatac tcccatcaga atccaaacaa aaggactatg aagaaagttc      60
ttgggattct gagagtctct gtgagactgt ttcacagaag gatgtgtgtt tacccaaggc     120
tacacatcaa aaagaaatag ataaaataaa tggaaaatta aagggtctc ctgttaaaga     180 tggtcttctg aaggctaact gcggaatgaa agtttctatt ccaactaaag ccttagaatt     240
gatggacatg caaactttca aagcagagcc tcccgagaag ccatctgcct tcgagcctgc     300
cattgaaatg caaaagtctg ttccaaataa agccttggaa ttgaagaatg aacaaacatt     360
gagagcagat gagatactcc catcagaatc caaacaaaag gactatgaag aaagttcttg     420
ggattctgag agtctctgtg agactgtttc acagaaggat gtgtttac ccaaggctac     480 acatcaaaaa gaaatagata aataaatgg aaaattagaa gagtctcctg ataatgatgg     540 tttttctgaag tctccctgca gaatgaaagt ttctattcca actaaagcct tagaattgat     600
ggacatgcaa actttcaaag cagagcctcc cgagaagcca tctgccttcg agcctgccat     660
tgaaatgcaa aagtctgttc caaataaagc cttggaattg aagaatgaac aaacattgag     720
agcagatcag atgttccctt cagaatcaaa acaaagaac gttgaagaaa attcttggga     780
ttctgagagt ctccgtgaga ctgtttcaca gaaggatgtg tgtgtaccca aggctacaca     840
tcaaaaagaa atggataaaa taagtggaaa attagaagat tcaactagcc tatcaaaaat     900
cttggataca gttcattctt gtgaaagagc aagggaactt caaaaagatc actgtgaaca     960
acgtacagga aaaatggaac aaatgaaaaa gaagttttgt gtactgaaaa agaaactgtc    1020
agaagcaaaa gaaataaaat cacagttaga gaaccaaaaa gttaaatggg aacaagagct    1080
ctgcagtgtg aggtttctca cactcatgaa aatgaaaatt atctcttaca tgaaaattgc    1140
atgttgaaaa aggaaattgc catgctaaaa ctggaaatag ccacactgaa acaccaatac    1200
caggaaaagg aaaataaata cttgaggac attaagattt taaagaaaa gaatgctgaa    1260 cttcagatga cccctaaact gaaagaggaa tcattaacta aagggcatc tcaatatagt    1320 gggcagctta aagttctgat agctgagaac acaatgctca cttctaaatt gaggaaaaa    1380 caagacaaag aaatactaga ggcagaaatt gaatcacacc atcctagact ggcttctgct    1440
gtacaagacc atgatcaaat tgtgacatca agaaaaagtc aagaacctgc tttccacatt    1500
gcaggagatg cttgtttgca aagaaaaatg aatgttgatg tgagtagtac gatatataac    1560
aatgaggtgc tccatcaacc actttctgaa gctcaaagga atccaaaag cctaaaaatt    1620 aatctcaatt atgcaggaga tgctctaaga gaaaatacat tggtttcaga acatgcacaa    1680
agagaccaac gtgaaacaca gtgtcaaatg aaggaagctg aacacatgta tcaaaacgaa    1740
caagataatg tgaacaaaca cactgaacag caggagtctc tagatcagaa attatttcaa    1800
```

-continued

```
ctacaaagca aaaatatgtg gcttcaacag caattagttc atgcacataa gaaagctgac    1860
aacaaaagca agataacaat tgatattcat tttcttgaga ggaaaatgca acatcatctc    1920
ctaaaagaga aaaatgagga gatatttaat tacaataacc atttaaaaaa ccgtatatat    1980
caatatgaaa aagagaaagc agaaacagaa aactcatgag agacaagcag taagaaactt    2040
cttttggaga acaacagac cagatcttta ctcacaactc atgctaggag gccagtccta    2100
gcatcacctt atgttgaaaa tcttaccaat agtctgtgtc aacagaatac ttattttaga    2160
agaaaaattc atgatttctt cctgaagcct acagacataa aataacagtg tgaagaatta    2220
cttgttcacg aattgcataa agctgcacag gattcccatc taccctgatg atgcagcaga    2280
catcattcaa tccaaccaga atctcgc                                        2307
```

<210> SEQ ID NO 469
<211> LENGTH: 650
<212> TYPE: PRT
<213> ORGANISM: Homo sapiens
<220> FEATURE:
<221> NAME/KEY: unsure
<222> LOCATION: (310)
<221> NAME/KEY: Xaa = Any Amino Acid<221> unsure
<222> LOCATION: (429)
<221> NAME/KEY: Xaa = Any Amino Acid<221> unsure
<222> LOCATION: (522)
<223> OTHER INFORMATION: Xaa = Any Amino Acid

<400> SEQUENCE: 469

```
Met Ser Pro Ala Lys Glu Thr Ser Glu Lys Phe Thr Trp Ala Ala Lys
              5                  10                  15

Gly Arg Pro Arg Lys Ile Ala Trp Glu Lys Lys Glu Thr Pro Val Lys
         20                  25                  30

Thr Gly Cys Val Ala Arg Val Thr Ser Asn Lys Thr Lys Val Leu Glu
     35                  40                  45

Lys Gly Arg Ser Lys Met Ile Ala Cys Pro Thr Lys Glu Ser Ser Thr
 50                  55                  60

Lys Ala Ser Ala Asn Asp Gln Arg Phe Pro Ser Glu Ser Lys Gln Glu
65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Pro Ser Ala Phe
        115                 120                 125

Lys Pro Ala Ile Glu Met Gln Asn Ser Val Pro Asn Lys Ala Phe Glu
    130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240
```

-continued

```
Pro Gly Lys Pro Ser Ala Phe Glu Pro Ala Thr Glu Met Gln Lys Ser
            245                 250                 255

Val Pro Asn Lys Ala Leu Glu Leu Lys Asn Glu Gln Thr Leu Arg Ala
        260                 265                 270

Asp Glu Ile Leu Pro Ser Glu Ser Lys Gln Lys Asp Tyr Glu Glu Ser
            275                 280                 285

Ser Trp Asp Ser Glu Ser Leu Cys Glu Thr Val Ser Gln Lys Asp Val
        290                 295                 300

Cys Leu Pro Lys Ala Xaa His Gln Lys Glu Ile Asp Lys Ile Asn Gly
305                 310                 315                 320

Lys Leu Glu Gly Ser Pro Val Lys Asp Gly Leu Leu Lys Ala Asn Cys
                325                 330                 335

Gly Met Lys Val Ser Ile Pro Thr Lys Ala Leu Glu Leu Met Asp Met
            340                 345                 350

Gln Thr Phe Lys Ala Glu Pro Pro Glu Lys Pro Ser Ala Phe Glu Pro
            355                 360                 365

Ala Ile Glu Met Gln Lys Ser Val Pro Asn Lys Ala Leu Glu Leu Lys
    370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Xaa His Gln Lys
            420                 425                 430

Glu Ile Asp Lys Ile Asn Gly Lys Leu Glu Glu Ser Pro Asp Asn Asp
            435                 440                 445

Gly Phe Leu Lys Ala Pro Cys Arg Met Lys Val Ser Ile Pro Thr Lys
    450                 455                 460

Ala Leu Glu Leu Met Asp Met Gln Thr Phe Lys Ala Glu Pro Pro Glu
465                 470                 475                 480

Lys Pro Ser Ala Phe Glu Pro Ala Ile Glu Met Gln Lys Ser Val Pro
                485                 490                 495

Asn Lys Ala Leu Glu Leu Lys Asn Glu Gln Thr Leu Arg Ala Asp Gln
            500                 505                 510

Met Phe Pro Ser Glu Ser Lys Gln Lys Xaa Val Glu Glu Asn Ser Trp
            515                 520                 525

Asp Ser Glu Ser Leu Arg Glu Thr Val Ser Gln Lys Asp Val Cys Val
        530                 535                 540

Pro Lys Ala Thr His Gln Lys Glu Met Asp Lys Ile Ser Gly Lys Leu
545                 550                 555                 560

Glu Asp Ser Thr Ser Leu Ser Lys Ile Leu Asp Thr Val His Ser Cys
                565                 570                 575

Glu Arg Ala Arg Glu Leu Gln Lys Asp His Cys Glu Gln Arg Thr Gly
            580                 585                 590

Lys Met Glu Gln Met Lys Lys Phe Cys Val Leu Lys Lys Lys Lys Leu
            595                 600                 605

Ser Glu Ala Lys Glu Ile Lys Ser Gln Leu Glu Asn Gln Lys Val Lys
        610                 615                 620

Trp Glu Gln Glu Leu Cys Ser Val Arg Phe Leu Thr Leu Met Lys Met
625                 630                 635                 640

Lys Ile Ile Ser Tyr Met Lys Ile Ala Cys
                645                 650
```

```
<210> SEQ ID NO 470
<211> LENGTH: 228
<212> TYPE: PRT
<213> ORGANISM: Homo sapiens

<400> SEQUENCE: 470

Met Ser Pro Ala Lys Glu Thr Ser Glu Lys Phe Thr Trp Ala Ala Lys
                 5                  10                  15

Gly Arg Pro Arg Lys Ile Ala Trp Glu Lys Glu Thr Pro Val Lys
                20                  25                  30

Thr Gly Cys Val Ala Arg Val Thr Ser Asn Lys Thr Lys Val Leu Glu
             35                  40                  45

Lys Gly Arg Ser Lys Met Ile Ala Cys Pro Thr Lys Glu Ser Ser Thr
 50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
                100                 105                 110

Glu Ile Asn Arg Glu Val Glu Glu Pro Pro Lys Lys Pro Ser Ala Phe
            115                 120                 125

Lys Pro Ala Ile Glu Met Gln Asn Ser Val Pro Asn Lys Ala Phe Glu
130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
                180                 185                 190

Gln Lys Glu Ile Asp Lys Ile Asn Gly Lys Leu Glu Gly Lys Asn Arg
            195                 200                 205

Phe Leu Phe Lys Asn Gln Leu Thr Glu Tyr Phe Ser Lys Leu Met Arg
        210                 215                 220

Arg Asp Ile Leu
225

<210> SEQ ID NO 471
<211> LENGTH: 154
<212> TYPE: PRT
<213> ORGANISM: Homo sapiens
<220> FEATURE:
<221> NAME/KEY: unsure
<222> LOCATION: (148)
<223> OTHER INFORMATION: Xaa = Any Amino Acid

<400> SEQUENCE: 471

Met Arg Leu His Pro Trp Arg Lys Glu His Leu Thr Gln Leu Lys Ala
                 5                  10                  15

Trp Trp Lys Lys His Leu Met Arg Leu His Pro Trp Lys Glu His
                20                  25                  30

Leu Thr Arg Leu Lys Ala Trp Trp Lys Lys His Leu Met Arg Leu His
             35                  40                  45

Pro Trp Trp Arg Glu His Leu Thr Lys Phe Asn Val Trp Arg Lys Arg
 50                  55                  60

His Leu Glu Ser Ser Asn Ser Gln Gln Lys His Leu Gly Lys Leu
 65                  70                  75                  80
```

```
Arg Val Leu Gln Lys Lys His Leu Arg Asn Leu Arg Gly Gln Gln Lys
                 85                  90                  95

Glu Asp Leu Gly Arg Ser His Gly Arg Lys Lys Met Thr Gln Leu Arg
            100                 105                 110

Gln Lys Lys Lys Lys Lys Lys Lys Lys Lys Lys Lys Lys Lys Lys Lys
            115                 120                 125

Lys Lys Lys Lys Lys Lys Lys Lys Lys Lys Lys Lys Lys Lys Lys Lys
        130                 135                 140

Lys Lys Lys Xaa Lys Lys Lys Lys Lys
145                 150

<210> SEQ ID NO 472
<211> LENGTH: 466
<212> TYPE: PRT
<213> ORGANISM: Homo sapiens
<220> FEATURE:
<221> NAME/KEY: unsure
<222> LOCATION: (329)
<223> OTHER INFORMATION: Xaa = Any Amino Acid

<400> SEQUENCE: 472

Met Ser Pro Ala Lys Glu Thr Ser Glu Lys Phe Thr Trp Ala Ala Lys
                  5                  10                  15

Gly Arg Pro Arg Lys Ile Ala Trp Glu Lys Lys Glu Thr Pro Val Lys
             20                  25                  30

Thr Gly Cys Val Ala Arg Val Thr Ser Asn Lys Thr Lys Val Leu Glu
         35                  40                  45

Lys Gly Arg Ser Lys Met Ile Ala Cys Pro Thr Lys Glu Ser Ser Thr
     50                  55                  60

Lys Ala Ser Ala Asn Asp Gln Arg Phe Pro Ser Glu Ser Lys Gln Glu
 65                  70                  75                  80

Glu Asp Glu Glu Tyr Ser Cys Asp Ser Arg Ser Leu Phe Glu Ser Ser
                 85                  90                  95

Ala Lys Ile Gln Val Cys Ile Pro Glu Ser Ile Tyr Gln Lys Val Met
            100                 105                 110

Glu Ile Asn Arg Glu Val Glu Glu Pro Pro Lys Lys Pro Ser Ala Phe
            115                 120                 125

Lys Pro Ala Ile Glu Met Gln Asn Ser Val Pro Asn Lys Ala Phe Glu
        130                 135                 140

Leu Lys Asn Glu Gln Thr Leu Arg Ala Asp Pro Met Phe Pro Pro Glu
145                 150                 155                 160

Ser Lys Gln Lys Asp Tyr Glu Glu Asn Ser Trp Asp Ser Glu Ser Leu
                165                 170                 175

Cys Glu Thr Val Ser Gln Lys Asp Val Cys Leu Pro Lys Ala Thr His
            180                 185                 190

Gln Lys Glu Ile Asp Lys Ile Asn Gly Lys Leu Glu Glu Ser Pro Asn
        195                 200                 205

Lys Asp Gly Leu Leu Lys Ala Thr Cys Gly Met Lys Val Ser Ile Pro
    210                 215                 220

Thr Lys Ala Leu Glu Leu Lys Asp Met Gln Thr Phe Lys Ala Glu Pro
225                 230                 235                 240

Pro Gly Lys Pro Ser Ala Phe Glu Pro Ala Thr Glu Met Gln Lys Ser
                245                 250                 255

Val Pro Asn Lys Ala Leu Glu Leu Lys Asn Glu Gln Thr Leu Arg Ala
            260                 265                 270

Asp Glu Ile Leu Pro Ser Glu Ser Lys Gln Lys Asp Tyr Glu Glu Asn
```

```
                275                 280                 285
Ser Trp Asp Thr Glu Ser Leu Cys Glu Thr Val Ser Gln Lys Asp Val
    290                 295                 300

Cys Leu Pro Lys Ala Ala His Gln Lys Glu Ile Asp Lys Ile Asn Gly
305                 310                 315                 320

Lys Leu Glu Gly Ser Pro Gly Lys Xaa Gly Leu Leu Lys Ala Asn Cys
                325                 330                 335

Gly Met Lys Val Ser Ile Pro Thr Lys Ala Leu Glu Leu Met Asp Met
                340                 345                 350

Gln Thr Phe Lys Ala Glu Pro Glu Lys Pro Ser Ala Phe Glu Pro
                355                 360                 365

Ala Ile Glu Met Gln Lys Ser Val Pro Asn Lys Ala Leu Glu Leu Lys
370                 375                 380

Asn Glu Gln Thr Leu Arg Ala Asp Glu Ile Leu Pro Ser Glu Ser Lys
385                 390                 395                 400

Gln Lys Asp Tyr Glu Glu Ser Ser Trp Asp Ser Glu Ser Leu Cys Glu
                405                 410                 415

Thr Val Ser Gln Lys Asp Val Cys Leu Pro Lys Ala Ala His Gln Lys
                420                 425                 430

Glu Ile Asp Lys Ile Asn Gly Lys Leu Glu Gly Lys Asn Arg Phe Leu
                435                 440                 445

Phe Lys Asn His Leu Thr Lys Tyr Phe Ser Lys Leu Met Arg Lys Asp
    450                 455                 460

Ile Leu
465

<210> SEQ ID NO 473
<211> LENGTH: 445
<212> TYPE: PRT
<213> ORGANISM: Homo sapiens

<400> SEQUENCE: 473

Lys Glu Ile Asp Lys Ile Asn Gly Lys Leu Glu Gly Ser Pro Val Lys
                5                   10                  15

Asp Gly Leu Leu Lys Ala Asn Cys Gly Met Lys Val Ser Ile Pro Thr
                20                  25                  30

Lys Ala Leu Glu Leu Met Asp Met Gln Thr Phe Lys Ala Glu Pro Pro
                35                  40                  45

Glu Lys Pro Ser Ala Phe Glu Pro Ala Ile Glu Met Gln Lys Ser Val
    50                  55                  60

Pro Asn Lys Ala Leu Glu Leu Lys Asn Glu Gln Thr Leu Arg Ala Asp
65                  70                  75                  80

Glu Ile Leu Pro Ser Glu Ser Lys Gln Lys Asp Tyr Glu Glu Ser Ser
                85                  90                  95

Trp Asp Ser Glu Ser Leu Cys Glu Thr Val Ser Gln Lys Asp Val Cys
                100                 105                 110

Leu Pro Lys Ala Ala His Gln Lys Glu Ile Asp Lys Ile Asn Gly Lys
            115                 120                 125

Leu Glu Glu Ser Pro Asp Asn Asp Gly Phe Leu Lys Ala Pro Cys Arg
130                 135                 140

Met Lys Val Ser Ile Pro Thr Lys Ala Leu Glu Leu Met Asp Met Gln
145                 150                 155                 160

Thr Phe Lys Ala Glu Pro Pro Glu Lys Pro Ser Ala Phe Glu Pro Ala
                165                 170                 175
```

```
Ile Glu Met Gln Lys Ser Val Pro Asn Lys Ala Leu Glu Leu Lys Asn
            180                 185                 190

Glu Gln Thr Leu Arg Ala Asp Gln Met Phe Pro Ser Glu Ser Lys Gln
            195                 200                 205

Lys Lys Val Glu Glu Asn Ser Trp Asp Ser Glu Ser Leu Arg Glu Thr
            210                 215                 220

Val Ser Gln Lys Asp Val Cys Val Pro Lys Ala Thr His Gln Lys Glu
225                 230                 235                 240

Met Asp Lys Ile Ser Gly Lys Leu Glu Asp Ser Thr Ser Leu Ser Lys
            245                 250                 255

Ile Leu Asp Thr Val His Ser Cys Glu Arg Ala Arg Glu Leu Gln Lys
            260                 265                 270

Asp His Cys Glu Gln Arg Thr Gly Lys Met Glu Gln Met Lys Lys Lys
            275                 280                 285

Phe Cys Val Leu Lys Lys Leu Ser Glu Ala Lys Glu Ile Lys Ser
            290                 295                 300

Gln Leu Glu Asn Gln Lys Val Lys Trp Glu Gln Glu Leu Cys Ser Val
305                 310                 315                 320

Arg Leu Thr Leu Asn Gln Glu Glu Glu Lys Arg Arg Asn Ala Asp Ile
            325                 330                 335

Leu Asn Glu Lys Ile Arg Glu Glu Leu Gly Arg Ile Glu Glu Gln His
            340                 345                 350

Arg Lys Glu Leu Glu Val Lys Gln Gln Leu Glu Gln Ala Leu Arg Ile
            355                 360                 365

Gln Asp Ile Glu Leu Lys Ser Val Glu Ser Asn Leu Asn Gln Val Ser
            370                 375                 380

His Thr His Glu Asn Glu Asn Tyr Leu Leu His Glu Asn Cys Met Leu
385                 390                 395                 400

Lys Lys Glu Ile Ala Met Leu Lys Leu Glu Ile Ala Thr Leu Lys His
            405                 410                 415

Gln Tyr Gln Glu Lys Glu Asn Lys Tyr Phe Glu Asp Ile Lys Ile Leu
            420                 425                 430

Lys Glu Lys Asn Ala Glu Leu Gln Met Thr Pro Arg Ala
            435                 440                 445

<210> SEQ ID NO 474
<211> LENGTH: 221
<212> TYPE: DNA
<213> ORGANISM: Homo sapiens
<220> FEATURE:
<221> NAME/KEY: misc_feature
<222> LOCATION: (1)...(221)
<223> OTHER INFORMATION: n = A,T,C or G

<400> SEQUENCE: 474
ggtccattcc tttcctcgcg tnggggtttc tctgtgtcag cgagcctcgg tacactgatt      60
tccgatcaaa agaatcatca tctttaacctt gacttttcag ggaattactg aactttcttc    120
tcagaagata gggcacagcc attgccttgg cctcacttga agggtctgca tttgggtcct    180
ctggtctctt gccaagtttc ccagccactc gagggagaaa t                        221
```

COMPOSITIONS FOR THE TREATMENT AND DIAGNOSIS OF BREAST CANCER AND METHODS FOR THEIR USE

CROSS-REFERENCE TO RELATED APPLICATIONS

This application is a continuation-in-part of U.S. application No. 09/389,681, filed on Sep. 2, 1999, which is a continuation-in-part of U.S. application No. 09/339,338, filed on Jun. 23, 1999, which is a continuation-in-part of U.S. application No. 09/285,480, filed on Apr. 2, 1999, which is a continuation-in-part of U.S. applicaton No. 09/222,575, filed Dec. 28, 1998, now U.S. Pat. No. 6,387,697.

TECHNICAL FIELD

The present invention relates generally to compositions and methods for the treatment of breast cancer. The invention is more particularly related to polypeptides comprising at least a portion of a protein that is preferentially expressed in breast tumor tissue and to polynucleotides encoding such polypeptides. Such polypeptides and polynucleotides may be in vaccines and pharmaceutical compositions for treatment of breast cancer.

BACKGROUND OF THE INVENTION

Breast cancer is a significant health problem for women in the United States and throughout the world. Although advances have been made in detection and treatment of the disease, breast cancer remains the second leading cause of cancer-related deaths in women, affecting more than 180,000 women in the United States each year. For women in North America, the life-time odds of getting breast cancer are one in eight.

No vaccine or other universally successful method for the prevention or treatment of breast cancer is currently available. Management of the disease currently relies on a combination of early diagnosis (through routine breast screening procedures) and aggressive treatment, which may include one or more of a variety of treatments such as surgery, radiotherapy, chemotherapy and hormone therapy. The course of treatment for a particular breast cancer is often selected based on a variety of prognostic parameters, including an analysis of specific tumor markers. See, e.g., Porter-Jordan and parameters, including an analysis of specific tumor markers. See, e.g., Porter-Jordan and Lippman, *Breast Cancer* 8:73–100 (1994). However, the use of established markers often leads to a result that is difficult to interpret, and the high mortality observed in breast cancer patients indicates that improvements are needed in the treatment, diagnosis and prevention of the disease.

Accordingly, there is a need in the art for improved methods for the treatment and diagnosis of breast cancer. The present invention fulfills these needs and further provides other related advantages.

SUMMARY OF THE INVENTION

The present invention provides compounds and methods for the treatment ad diagnosis of cancer, such as breast cancer. In one aspect, isolated polypeptides are provided comprising at least a portion of a breast tumor protein or a variant thereof. Certain portions and other variants are immunogenic, such that the ability of the variant to react with protein-specific antisera is not substantially diminished. With certain embodiments, the polypeptide comprises an amino acid sequence encoded by a polynucleotide selected from the group consisting of: (a) nucleotide sequences recited in SEQ ID NO: 1–61, 63–175, 178, 180, 182–313, 320–324, 342, 353, 366–368, 377, 382, 385, 389, 395, 397, 400, 408, 411, 413, 414, 416, 417, 419–423, 426, 427, 429, 431, 435–438, 441, 443–446, 450, 453, 454 and 463–468; (b) complements of said nucleotide sequences; and (c) variants of a sequence of (a) or (b). In specific embodiments, the inventive polypeptides comprise at least a portion of a tumor antigen that comprises an amino acid sequence selected from the group consisting of SEQ ID NO: 62, 176, 179, 181 and 459–473.

In related aspects, isolated polynucleotides encoding the above polypeptides, or a portion thereof (such as a portion encoding at least 15 contiguous amino acid residues of a breast tumor protein), are provided. In specific embodiments, such polynucleotides comprise a sequence selected from the group consisting of sequences provided in SEQ ID NO: 1–61, 63–175, 178, 180, 182–313, 320–324, 342, 353, 366–368, 377, 382, 385, 389, 395, 397, 400, 408, 411, 413, 414, 416, 417, 419–423, 426, 427, 429, 431, 435–438, 441, 443–446, 450, 453, 454 and 463–468 and variants thereof. The present invention further provides expression vectors comprising the above polynucleotides, together with host cells transformed or transfected with such expression vectors. In preferred embodiments, the host cells are selected from the group consisting of *E. coli,* yeast and mammalian cells.

In another aspect, the present invention provides fusion proteins comprising a first and a second inventive polypeptide or, alternatively, an inventive polypeptide and a known breast tumor antigen.

The present invention also provides pharmaceutical compositions comprising at least one of the above polypeptides, or a polynucleotide encoding such a polypeptide, and a physiologically acceptable carrier, together with vaccines. For prophylactic or therapeutic use, comprising at least one such polypeptide or polynucleotide in combination with an immunostimulant. Pharmaceutical compositions and vaccines comprising one or more of the above fusion proteins are also provided.

The present invention further provides pharmaceutical compositions that comprise: (a) an antibody or antigen-binding fragment thereof that specifically binds to a breast tumor protein, and (b) a physiologically acceptable carrier.

Within further aspects, the present invention provides pharmaceutical compositions comprising: (a) an antigen presenting cell that expresses a polypeptide as described above and (b) a pharmaceutically acceptable carrier or excipient. Antigen presenting cells include dentritic cells, macrophages, monocytes, fibroblasts and B cells.

Within related aspects, vaccines are provided that comprise: (a) an antigen presenting cell that expresses a polypeptide as described above and (b) an immunostimulant.

In yet another aspect, methods are provided for inhibiting the development of breast cancer in a patient, comprising administering an effective amount of at least one of the above pharmaceutical compositions and/or vaccines.

The present invention further provides, within other aspects, methods for removing tumor cells from a biological sample, comprising contacting a biological sample with T cells that specifically react with a breast tumor protein, wherein the step of contacting is performed under conditions and for a time sufficient to permit the removal of cells expressing the protein from the sample.

Within related aspects, methods are provided for inhibiting the development of a cancer in a patient, comprising administering to a patient a biological sample treated as described above.

Methods are further provided, within other aspects, for stimulating and/or expanding T cells specific for a breast tumor protein, comprising contacting T cells with one or more of: (i) a polypeptide as described above; (ii) a polynucleotide encoding such a polypeptide; and/or (iii) an antigen presenting cell that expresses such a polypeptide; under conditions and for a time sufficient to permit the stimulation and/or expansion of T cells. Isolated T cell populations comprising T cells prepared as described above are also provided.

Within further aspects, the present invention provides methods for inhibiting the development of a cancer a patient, comprising administering to a patient an effective amount of a T cell population as described above.

The present invention further provides methods for inhibiting the development of a cancer in a patient comprising the steps of: (a) incubating CD4$^+$ and/or CD8$^+$ T cells isolated from a patient with one or more of: (i) a polypeptide comprising at least an immunogenic portion of a breast tumor protein; (ii) a polynucleotide encoding such a polypeptide; and (iii) an antigen-presenting cell that expressed such a polypeptide; and (b) administering to the patient an effective amount of the proliferated T cells, and thereby inhibiting the development of a cancer in the patient. Proliferated cells may, but need not, be cloned prior to administration to the patient.

The polypeptides disclosed herein may be usefully employed in the diagnosis and monitoring of breast cancer. In one aspect of the present invention, methods are provided for detecting a cancer in a patient, comprising: (a) contacting a biological sample obtained from a patient with a binding agent that is capable of binding to one of the above polypeptides, and (b) detecting in the sample an amount of polypeptide that binds to the binding agent; and (c) comparing the amount of polypeptide with a predetermined cut-off value, and therefrom determining the presence or absence of a cancer in a patient. In preferred embodiments, the biding agent is an antibody, most preferably a monoclonal antibody. The cancer may be breast cancer.

In related aspects, methods are provided for monitoring the progression of a cancer in a patient, comprising: (a) contacting a biological sample obtained from a patient with a binding agent that is capable of binding to one of the above polypeptides; (b) detecting in the sample an amount of a polypeptide that binds to the binding agent; (c) repeating steps (a) and (b) using a biological sample obtained from the patient at a subsequent point in time; and (d) comparing the amounts of polypeptide detected in steps (b) and (c).

Within related aspects, the present invention provides antibodies, preferably monoclonal antibodies, that bind to the inventive polypeptides, as well as diagnostic kits comprising such antibodies, and methods of using such antibodies to inhibit the development of breast cancer.

The present invention further provides, within other aspects, methods for determining the presence or absence of a cancer in a patient, comprising the steps of: (a) contacting a biological sample obtained from a patient with an oligonucleotide that hybridizes to a polynucleotide that encodes a breast tumor protein: (b) detecting in the sample a level of a polynucleotide, preferably mRNA, that hybridizes to the oligonucleotide; and (c) comparing the level of polynucleotide that hybridizes to the oligonucleotide with a predetermined cut-off value, and therefrom determining the presence or absence of a cancer in the patient. Within certain embodiments, the amount of mRNA is detected via polymerase chain reaction using, for example, at least one oligonucleotide primer that hybridizes to a polynucleotide encoding a polypeptide as recited above, or a complement of such a polynucleotide. Within other embodiments, the amount of mRNA is detected using a hybridization technique, employing an oligonucleotide probe that hybridizes to a polynucleotide that encodes a polypeptide as recited above, or a complement of such a polynucleotide.

In related aspects, diagnostic kits comprising the above oligonucleotide probes or primers are provided.

These and other aspects of the present invention will become apparent upon reference to the following detailed description. All references disclosed herein are hereby incorporated by reference in their entirety as if each was incorporated individually.

BRIEF DESCRIPTION OF THE DRAWING AND SEQUENCE IDENTIFIERS

FIG. 1 shows the results of a Northern blot of the clone SYN18C6 (SEQ ID NO: 40).

SEQ ID NO: 1 is the determined cDNA sequence of JBP2.

SEQ ID NO: 2 is the determined cDNA sequence of JBP6.

SEQ ID NO: 3 is the determined cDNA sequence of JBP7.

SEQ ID NO: 4 is the determined cDNA sequence of JBP10.

SEQ ID NO: 5 is the determined cDNA sequence of JBP13.

SEQ ID NO: 6 is the determined cDNA sequence of JBP14.

SEQ ID NO: 7 is the determined cDNA sequence of JBP15.

SEQ ID NO: 8 is the determined cDNA sequence of JBP16.

SEQ ID NO: 9 is the determined cDNA sequence of JBP17.

SEQ ID NO: 10 is the determined cDNA sequence of JBP22.

SEQ ID NO: 11 is the determined cDNA sequence of JBP25.

SEQ ID NO: 12 is the determined cDNA sequence of JBP28.

SEQ ID NO: 13 is the determined cDNA sequence of JBP32.

SEQ ID NO: 14 is the determined cDNA sequence of JBP33.

SEQ ID NO: 15 is the determined cDNA sequence of JBP34.

SEQ ID NO: 16 is the determined cDNA sequence of JBP36.

SEQ ID NO: 17 is the determined cDNA sequence of JBP37.

SEQ ID NO: 18 is the determined cDNA sequence of JBP51.

SEQ ID NO: 19 is the determined cDNA sequence of JBPT1.

SEQ ID NO: 20 is the determined cDNA sequence of JBPT7.

SEQ ID NO: 21 is the determined cDNA sequence of JBPT11.

SEQ ID NO: 22 is the determined cDNA sequence of JBPT14.

SEQ ID NO: 23 is the determined cDNA sequence of JBPT18.

SEQ ID NO: 24 is the determined cDNA sequence of JBPT19.

SEQ ID NO: 25 is the determined cDNA sequence of JBPT20.

SEQ ID NO: 26 is the determined cDNA sequence of JBPT21.

SEQ ID NO: 27 is the determined cDNA sequence of JBPT22.

SEQ ID NO: 28 is the determined cDNA sequence of JBPT28.

SEQ ID NO: 29 is the determined cDNA sequence of JBPT29.

SEQ ID NO: 30 is the determined cDNA sequence of JBPT33.

SEQ ID NO: 31 is the determined cDNA sequence of JBPT37.

SEQ ID NO: 32 is the determined cDNA sequence of JBPT38.

SEQ ID NO: 33 is the determined cDNA sequence of JBPT47.

SEQ ID NO: 34 is the determined cDNA sequence of JBPT48.

SEQ ID NO: 35 is the determined cDNA sequence of JBPT50.

SEQ ID NO: 36 is the determined cDNA sequence of JBPT51.

SEQ ID NO: 37 is the determined cDNA sequence of JBPT52.

SEQ ID NO: 38 is the determined cDNA sequence of JBPT54.

SEQ ID NO: 39 is the determined cDNA sequence of SYN17F4.

SEQ ID NO: 40 is the determined cDNA sequence of SYN18C6.

SEQ ID NO: 41 is the determined cDNA sequence of SYN19A2.

SEQ ID NO: 42 is the determined cDNA sequence of SYN19C8.

SEQ ID NO: 43 is the determined cDNA sequence of SYN20A12.

SEQ ID NO: 44 is the determined cDNA sequence of SYN20G6.

SEQ ID NO: 45 is the determined cDNA sequence of SYN20G6-2.

SEQ ID NO: 46 is the determined cDNA sequence of SYN21B9.

SEQ ID NO: 47 is the determined cDNA sequence of SYN21B9-2.

SEQ ID NO: 48 is the determined cDNA sequence of SYN21C10.

SEQ ID NO: 49 is the determined cDNA sequence of SYN21G10.

SEQ ID NO: 50 is the determined cDNA sequence of SYN21G10-2.

SEQ ID NO: 51 is the determined cDNA sequence of SYN21G11.

SEQ ID NO: 52 is the determined cDNA sequence of SYN21G11-2.

SEQ ID NO: 53 is the determined cDNA sequence of SYN21H8.

SEQ ID NO: 54 is the determined cDNA sequence of SYN22A10.

SEQ ID NO: 55 is the determined cDNA sequence of SYN22A10-2.

SEQ ID NO: 56 is the determined cDNA sequence of SYN22A12.

SEQ ID NO: 57 is the determined cDNA sequence of SYN22A2.

SEQ ID NO: 58 is the determined cDNA sequence of SYN22B4.

SEQ ID NO: 59 is the determined cDNA sequence of SYN22C2.

SEQ ID NO: 60 is the determined cDNA sequence of SYN22E10.

SEQ ID NO: 61 is the determined cDNA sequence of SYN22F2.

SEQ ID NO: 62 is a predicted amino acid sequence for SYN18C6.

SEQ ID NO: 63 is the determined cDNA sequence of B723P.

SEQ ID NO: 64 is the determined cDNA sequence of B724P.

SEQ ID NO: 65 is the determined cDNA sequence of B770P.

SEQ ID NO: 66 is the determined cDNA sequence of B716P.

SEQ ID NO: 67 is the determined cDNA sequence of B725P.

SEQ ID NO: 68 is the determined cDNA sequence of B717P.

SEQ ID NO: 69 is the determined cDNA sequence of B771P.

SEQ ID NO: 70 is the determined cDNA sequence of B722P.

SEQ ID NO: 71 is the determined cDNA sequence of B726P.

SEQ ID NO: 72 is the determined cDNA sequence of B727P.

SEQ ID NO: 73 is the determined cDNA sequence of B728P.

SEQ ID NO: 74–87 are the determined cDNA sequences of isolated clones which show homology to known sequences.

SEQ ID NO: 88 is the determined cDNA sequence of 13053.

SEQ ID NO: 89 is the determined cDNA sequence of 13057.

SEQ ID NO: 90 is the determined cDNA sequence of 13059.

SEQ ID NO: 91 is the determined cDNA sequence of 13065.

SEQ ID NO: 92 is the determined cDNA sequence of 13067.

SEQ ID NO: 93 is the determined cDNA sequence of 13068.

SEQ ID NO: 94 is the determined cDNA sequence of 13071.

SEQ ID NO: 95 is the determined cDNA sequence of 13072.

SEQ ID NO: 96 is the determined cDNA sequence of 13073.

SEQ ID NO: 97 is the determined cDNA sequence of 13075.

SEQ ID NO: 98 is the determined cDNA sequence of 13078.
SEQ ID NO: 99 is the determined cDNA sequence of 13079.
SEQ ID NO: 100 is the determined cDNA sequence of 13081.
SEQ ID NO: 101 is the determined cDNA sequence of 13082.
SEQ ID NO: 102 is the determined cDNA sequence of 13092.
SEQ ID NO: 103 is the determined cDNA sequence of 13097.
SEQ ID NO: 104 is the determined cDNA sequence of 13101.
SEQ ID NO: 105 is the determined cDNA sequence of 13102.
SEQ ID NO: 106 is the determined cDNA sequence of 13119.
SEQ ID NO: 107 is the determined cDNA sequence of 13131.
SEQ ID NO: 108 is the determined cDNA sequence of 13133.
SEQ ID NO: 109 is the determined cDNA sequence of 13135.
SEQ ID NO: 110 is the determined cDNA sequence of 13139.
SEQ ID NO: 111 is the determined cDNA sequence of 13140.
SEQ ID NO: 112 is the determined cDNA sequence of 13146.
SEQ ID NO: 113 is the determined cDNA sequence of 13147.
SEQ ID NO: 114 is the determined cDNA sequence of 13148.
SEQ ID NO: 115 is the determined cDNA sequence of 13149.
SEQ ID NO: 116 is the determined cDNA sequence of 13151.
SEQ ID NO: 117 is the determined cDNA sequence of 13051
SEQ ID NO: 118 is the determined cDNA sequence of 13052
SEQ ID NO: 119 is the determined cDNA sequence of 13055
SEQ ID NO: 120 is the determined cDNA sequence of 13058
SEQ ID NO: 121 is the determined cDNA sequence of 13062
SEQ ID NO: 122 is the determined cDNA sequence of 13064
SEQ ID NO: 123 is the determined cDNA sequence of 13080
SEQ ID NO: 124 is the determined cDNA sequence of 13093
SEQ ID NO: 125 is the determined cDNA sequence of 13094
SEQ ID NO: 126 is the determined cDNA sequence of 13095
SEQ ID NO: 127 is the determined cDNA sequence of 13096
SEQ ID NO: 128 is the determined cDNA sequence of 13099
SEQ ID NO: 129 is the determined cDNA sequence of 13100
SEQ ID NO: 130 is the determined cDNA sequence of 13103
SEQ ID NO: 131 is the determined cDNA sequence of 13106
SEQ ID NO: 132 is the determined cDNA sequence of 13107
SEQ ID NO: 133 is the determined cDNA sequence of 13108
SEQ ID NO: 134 is the determined cDNA sequence of 13121
SEQ ID NO: 135 is the determined cDNA sequence of 13126
SEQ ID NO: 136 is the determined cDNA sequence of 13129
SEQ ID NO: 137 is the determined cDNA sequence of 13130
SEQ ID NO: 138 is the determined cDNA sequence of 13134
SEQ ID NO: 139 is the determined cDNA sequence of 13141
SEQ ID NO: 140 is the determined cDNA sequence of 13142
SEQ ID NO: 141 is the determined cDNA sequence of 14376
SEQ ID NO: 142 is the determined cDNA sequence of 14377
SEQ ID NO: 143 is the determined cDNA sequence of 14383
SEQ ID NO; 144 is the determined cDNA sequence of 14384
SEQ ID NO: 145 is the determined cDNA sequence of 14387
SEQ ID NO: 146 is the determined cDNA sequence of 14392
SEQ ID NO: 147 is the determined cDNA sequence of 14394
SEQ ID NO: 148 is the determined cDNA sequence of 14398
SEQ ID NO: 149 is the determined cDNA sequence of 14401
SEQ ID NO: 150 is the determined cDNA sequence of 14402
SEQ ID NO: 151 is the determined cDNA sequence of 14405
SEQ ID NO: 152 is the determined cDNA sequence of 14409
SEQ ID NO: 153 is the determined cDNA sequence of 14412
SEQ ID NO: 154 is the determined cDNA sequence of 14414
SEQ ID NO: 155 is the determined cDNA sequence of 14415
SEQ ID NO: 156 is the determined cDNA sequence of 14416
SEQ ID NO: 157 is the determined cDNA sequence of 14419
SEQ ID NO: 158 is the determined cDNA sequence of 14426
SEQ ID NO: 159 is the determined cDNA sequence of 14427

SEQ ID NO: 160 is the determined cDNA sequence of 14375

SEQ ID NO: 161 is the determined cDNA sequence of 14378

SEQ ID NO: 162 is the determined cDNA sequence of 14379

SEQ ID NO: 163 is the determined cDNA sequence of 14380

SEQ ID NO: 164 is the determined cDNA sequence of 14381

SEQ ID NO: 165 is the determined cDNA sequence of 14382

SEQ ID NO: 166 is the determined cDNA sequence of 14388

SEQ ID NO: 167 is the determined cDNA sequence of 14399

SEQ ID NO: 168 is the determined cDNA sequence of 14406

SEQ ID NO: 169 is the determined cDNA sequence of 14407

SEQ ID NO: 170 is the determined cDNA sequence of 14408

SEQ ID NO: 171 is the determined cDNA sequence of 14417

SEQ ID NO: 172 is the determined cDNA sequence of 14418

SEQ ID NO: 173 is the determined cDNA sequence of 14423

SEQ ID NO: 174 is the determined cDNA sequence of 14424

SEQ ID NO: 175 is the determined cDNA sequence of B726P-20

SEQ ID NO: 176 is the determined cDNA sequence of B726P-20

SEQ ID NO: 177 is a PCR primer

SEQ ID NO: 178 is the determined cDNA sequence of B726P-74

SEQ ID NO: 179 is the predicted amino acid sequence of B726P-74

SEQ ID NO: 180 is the determined cDNA sequence of B726P-79

SEQ ID NO: 181 is the predicted amino acid sequence of B726P-79

SEQ ID NO: 182 is the determined cDNA sequence of 19439.1, showing homology to the mammaglobin gene SEQ ID NO: 183 is the determined cDNA sequence of 19407.1, showing homology to the human keratin gene SEQ ID NO: 184 is the determined cDNA sequence of 19428.1, showing homology to human chromosome 17 clone SEQ ID NO: 185 is the determined cDNA sequence of B808P (19408), showing no significant homology to any known gene SEQ ID NO: 186 is the determined cDNA sequence of 19460.1, showing no significant homology to any known gene SEQ ID NO: 187 is the determined cDNA sequence of 19419.1, showing homology to Ig kappa light chain SEQ ID NO: 188 is the determined cDNA sequence of 19411.1, showing homology to human alpha-1 collagen SEQ ID NO: 189 is the determined cDNA sequence of 19420.1 showing homology to mus musculus proteinase-3

SEQ ID NO: 190 is the determined cDNA sequence of 19432.1, showing homology to human high motility group box SEQ ID NO: 191 is the determined cDNA sequence of 19412.1, showing homology to the human plasminogen activator gene SEQ ID NO: 192 is the determined cDNA sequence of 19415.1, showing homology to mitogen activated protein kinase SEQ ID NO: 193 is the determined cDNA sequence of 19409.1, showing homology to the chrondroitin sulfate proteoglycan protein SEQ ID NO: 194 is the determined cDNA sequence of 19406.1, showing no significant homology to any known gene SEQ ID NO: 195 is the determined cDNA sequence of 19421.1, showing homology to human fibronectin SEQ ID NO: 196 is the determined cDNA sequence of 19426.1, showing homology to the retinoic acid receptor responder 3

SEQ ID NO: 197 is the determined cDNA sequence of 19425.1 showing homology to MyD88 mRNA SEQ ID NO: 198 is the determined cDNA sequence of 19424.1, showing homology to peptide transporter (TAP-1) mRNA SEQ ID NO: 199 is the determined cDNA sequence of 19429.1, showing no significant homology to any known gene SEQ ID NO: 200 is the determined cDNA sequence of 19435.1, showing homology to human polymorphic epithelial mucin SEQ ID NO: 201 is the determined cDNA sequence of B813P (19434.1), showing homology to human GATA-3 transcription factor SEQ ID NO: 202 is the determined cDNA sequence of 19461.1, showing homology to the human AP-2 gene SEQ ID NO: 203 is the determined cDNA sequence of 19450.1, showing homology to DNA binding regulatory factor SEQ ID NO: 204 is the determined cDNA sequence of 1945.1, showing homology to Na/H exchange regulatory co-factor SEQ ID NO: 205 is the determined cDNA sequence of 19462.1, showing no significant homology to any known gene SEQ ID NO: 206 is the determined cDNA sequence of 19455.1, showing homology to human mRNA for histone HAS.Z SEQ ID NO: 207 is the determined cDNA sequence of 19459.1, showing homology to PAC clone 179N16

SEQ ID NO: 208 is the determined cDNA sequence of 19464.1, showing no significant homology to any known gene SEQ ID NO: 209 is the determined cDNA sequence of 19414.1, showing homology to lipophilin B SEQ ID NO: 210 is the determined cDNA sequence of 19413.1, showing homology to chromosome 17 clone hRPK.209_J_20

SEQ ID NO: 211 is the determined cDNA sequence of 19416.1, showing no significant homology to any known gene SEQ ID NO: 212 is the determined cDNA sequence of 19437.1, showing homology to human clone 24976 mRNA SEQ ID NO: 213 is the determined cDNA sequence of 19449.1, showing homology to mouse DNA for PG-M core protein SEQ ID NO: 214 is the determined cDNA sequence of 19446.1, showing no significant homology to any known gene SEQ ID NO: 215 is the determined cDNA sequence of 19452.1, showing no significant homology to any known gene SEQ ID NO: 216 is the determined cDNA sequence of 19483.1, showing no significant homology to any known gene SEQ ID NO: 217 is the determined cDNA sequence of 19526.1, showing homology to human lipophilin C SEQ ID NO: 218 is the determined cDNA sequence of 19484.1, showing homology to the secreted cement gland protein XAG-2.

SEQ ID NO: 219 is the determined cDNA sequence of 19470.1, showing no significant homology to any known gene SEQ ID NO: 220 is the determined cDNA sequence of 19469.1, showing homology to the human HLA-DM gene SEQ ID NO: 221 is the determined cDNA sequence of 19482.1, showing homology to the human pS2 protein gene SEQ ID NO: 222 is the determined cDNA sequence of B805P (19468.1), showing no significant homology to any known gene SEQ ID NO: 223 is the determined cDNA sequence of 19467.1, showing homology to human thrombospondin mRNA SEQ ID NO: 224 is the determined cDNA sequence of 19498.1, showing homology to the CDC2 gene involved in cell cycle control SEQ ID NO: 225 is the determined cDNA sequence of 19506.1 showing homology to human cDNA for TREB protein SEQ ID NO: 226 is the determined cDNA sequence of B806P (19505.1), showing no significant homology to any known gene SEQ ID NO: 227 is the determined cDNA sequence of 19486.1, showing homology to type I epidermal keratin SEQ ID NO: 228 is the determined cDNA sequence of 19510.1, showing homology to glucose transporter for glycoprotein SEQ ID NO: 229 is the determined cDNA sequence of 19512.1, showing homology to the human lysyl hydroxylase gene SEQ ID NO: 230 is the determined cDNA sequence of 19511.1, showing homology to human palimotoyl-protein thioesterase SEQ ID NO: 231 is the determined cDNA sequence of 19508.1, showing homology to human alpha enolase SEQ ID NO: 232 is the determined cDNA sequence of B807P (19509.1), showing no significant homology to any known gene SEQ ID NO: 233 is the determined cDNA sequence of B809P (19520.1), showing homology to clone 102D24 on chromosome 11q13.31

SEQ ID NO: 234 is the determined cDNA sequence of 19507.1, showing homology toprosome beta-subunit SEQ ID NO: 235 is the determined cDNA sequence of 19525.1, showing homology to human pro-urokinase precursor SEQ ID NO: 236 is the determined cDNA sequence of 19513.1, showing no significant homology to any known gene SEQ ID NO: 237 is the determined cDNA sequence of 19517.1, showing homology to human PAC 128M19 clone SEQ ID NO: 238 is the determined cDNA sequence of 19564.1, showing homology to human cytochrome P450-IIB SEQ ID NO: 239 is the determined cDNA sequence of 19553.1, showing homology to human GABA-A receptor pi subunit SEQ ID NO: 240 is the determined cDNA sequence of B811P (19575.1), showing no significant homology to any known gene SEQ ID NO: 241 is the determined cDNA sequence of B810P (19560.1), showing no significant homology to any known gene SEQ ID NO: 242 is the determined cDNA sequence of 19588.1, showing homology to aortic carboxypetidase-like protein SEQ ID NO: 243 is the determined cDNA sequence of 19551.1, showing homology to human BCL-1 gene SEQ ID NO: 244 is the determined cDNA sequence of 19567.1, showing homology to human proteasome-related mRNA SEQ ID NO: 245 is the determined cDNA sequence of B803P (19583.1), showing no significant homology to any known gene SEQ ID NO: 246 is the determined cDNA sequence of B812P (19587.1), showing no significant homology to any known gene SEQ ID NO: 247 is the determined cDNA sequence of B802P (19392.2), showing homology to human chromosome 17

SEQ ID NO: 248 is the determined cDNA sequence of 19393.2, showing homology to human nicein B2 chain SEQ ID NO: 249 is the determined cDNA sequence of 19398.2, human MHC class II DQ alpha mRNA SEQ ID NO: 250 is the determined cDNA sequence of B804P (19399.2), showing homology to human Xp22 BAC GSHB-184P14

SEQ ID NO: 251 is the determined cDNA sequence of 19401.2, showing homology to human ikB kinase-b gene SEQ ID NO: 252 is the determined cDNA sequence of 20266, showing no significant homology to any known gene SEQ ID NO: 253 is the determined cDNA sequence of B826P (20270), showing no significant homology to any known gene SEQ ID NO: 254 is the determined cDNA sequence of 20274, showing no significant homology to any known gene SEQ ID NO: 255 is the determined cDNA sequence of 20276, showing no significant homology to any known gene SEQ ID NO: 256 is the determined cDNA sequence of 20277, showing no significant homology to any known gene SEQ ID NO: 257 is the determined cDNA sequence of B823P (20280), showing no significant homology to any known gene SEQ ID NO: 258 is the determined cDNA sequence of B821P (20281), showing no significant homology to any known gene SEQ ID NO: 259 is the determined cDNA sequence of B824P (20294), showing no significant homology to any known gene SEQ ID NO: 260 is the determined cDNA sequence of 20303, showing no significant homology to any known gene SEQ ID NO: 261 is the determined cDNA sequence of B820P (20310), showing no significant homology to any known gene SEQ ID NO: 262 is the determined cDNA sequence of B825P (20336), showing no significant homology to any known gene SEQ ID NO: 263 is the determined cDNA sequence of B827P (20341), showing no significant homology to any known gene SEQ ID NO: 264 is the determined cDNA sequence of 20941, showing no significant homology to any known gene SEQ ID NO: 265 is the determined cDNA sequence of 20954, showing no significant homology to any known gene SEQ ID NO: 266 is the determined cDNA sequence of 20961, showing no significant homology to any known gene SEQ ID NO: 267 is the determined cDNA sequence of 20965, showing no significant homology to any known gene SEQ ID NO: 268 is the determined cDNA sequence of 20965, showing no significant homology to any known gene SEQ ID NO: 269 is the determined cDNA sequence of 20261, showing homology to Human p120 catenin SEQ ID NO: 270 is the determined cDNA sequence of B822P (20262), showing homology to Human membrane glycoprotein 4F2

SEQ ID NO: 271 is the determined cDNA sequence of 20265, showing homology to Human Na, K-ATPase Alpha 1

SEQ ID NO: 272 is the determined cDNA sequence of 20267, showing homology to Human heart HS 90, partial cds SEQ ID NO: 273 is the determined cDNA sequence of 20268, showing homology to Human mRNA GPI-anchored protein p137

SEQ ID NO: 274 is the determined cDNA sequence of 20271, showing homology to Human cleavage stimulation factor 77 kDa subunit SEQ ID NO: 275 is the determined cDNA sequence of 20272, showing homology to Human p190-B SEQ ID NO: 276 is the determined cDNA sequence of 20273, showing homology to Human ribophorin SEQ ID NO: 277 is the determined cDNA sequence of 20278, showing homology to Human ornithine amino transferase SEQ ID NO: 278 is the determined cDNA sequence of 20279, showing homology to Human S-adenosylmethionine synthetase SEQ ID NO: 279 is the determined cDNA sequence of 20293, showing homology to Human x inactivation transcript SEQ ID NO: 280 is the determined cDNA sequence of 20300, showing homology to Human cytochrome p450

SEQ ID NO: 281 is the determined cDNA sequence of 20305, showing homology to Human elongation factor-1 alpha SEQ ID NO: 282 is the determined cDNA sequence of 20306, showing homology to Human epithelial ets protein SEQ ID NO: 283 is the determined cDNA sequence of 20307, showing homology to Human signal transducer mRNA SEQ ID NO: 284 is the determined cDNA sequence of 20313, showing homology to Human GABA-A receptor pi subunit mRNA SEQ ID NO: 285 is the determined cDNA sequence of 20317, showing homology to Human tyrosine phosphatase SEQ ID NO: 286 is the determined cDNA sequence of 20318, showing homology to Human cathepsine B proteinase SEQ ID NO: 287 is the determined cDNA sequence of 20320, showing homology to Human 2-phosphopyruvate-hydratase-alpha-enolase SEQ ID NO: 288 is the determined cDNA sequence of 20321, showing homology to Human E-cadherin SEQ ID NO: 289 is the determined cDNA sequence of 20322, showing homology to Human hsp86

SEQ ID NO: 290 is the determined cDNA sequence of B828P (20326), showing homology to Human x inactivation transcript SEQ ID NO: 291 is the determined cDNA sequence of 20333, showing homology to Human chromatin regulator, SMARCA5

SEQ ID NO: 292 is the determined cDNA sequence of 20335, showing homology to Human sphingolipid activator protein 1

SEQ ID NO: 293 is the determined cDNA sequence of 20337, showing homology to Human hepatocyte growth factor activator inhibitor type 2

SEQ ID NO: 294 is the determined cDNA sequence of 20338, showing homology to Human cell adhesion molecule CD44

SEQ ID NO: 295 is the determined cDNA sequence of 20340, showing homology to Human nuclear factor (erythroid-derived)-like 1

SEQ ID NO: 296 is the determined cDNA sequence of 20938, showing homology to Human vinculin mRNA SEQ ID NO: 297 is the determined cDNA sequence of 20939, showing homology to Human elongation factor EF-1-alpha SEQ ID NO: 298 is the determined cDNA sequence of 20940, showing homology to Human nestin gene SEQ ID NO: 299 is the determined cDNA sequence of 20942, showing homology to Human pancreatic ribonuclease SEQ ID NO: 300 is the determined cDNA sequence of 20943, showing homology to Human transcobalamin I SEQ ID NO: 301 is the determined cDNA sequence of 20944, showing homology to Human beta-tubulin SEQ ID NO: 302 is the determined cDNA sequence of 20946, showing homology to Human HS1 protein SEQ ID NO: 303 is the determined cDNA sequence of 20947, showing homology to Human cathepsin B SEQ ID NO: 304 is the determined cDNA sequence of 20948, showing homology to Human testis enhanced gene transcript SEQ ID NO: 305 is the determined cDNA sequence of 20949, showing homology to Human elongation factor EF-1-alpha SEQ ID NO: 306 is the determined cDNA sequence of 20950, showing homology to Human ADP-ribosylation factor 3

SEQ ID NO: 307 is the determined cDNA sequence of 20951, showing homology to Human IFP53 or WRS for tryptophanyl-tRNA synthetase SEQ ID NO: 308 is the determined cDNA sequence of 20952, showing homology to Human cyclin-dependent protein kinase SEQ ID NO: 308 is the determined cDNA sequence of 20957, showing homology to Human alpha-tubulin sioform 1

SEQ ID NO: 309 is the determined cDNA sequence of 20959, showing homology to Human tyrosine phosphatase-61bp deletion SEQ ID NO: 310 is the determined cDNA sequence of 20966, showing homology to Human tyrosine phosphatase SEQ ID NO: 311 is the determined cDNA sequence of B830P (20976), showing homology to Human nuclear factor NF 45

SEQ ID NO: 312 is the determined cDNA sequence of B829P (20977), showing homology to Human delta-6 fatty acid desaturase SEQ ID NO: 313 is the determined cDNA sequence of 20978, showing homology to Human nuclear aconitase SEQ ID NO: 314 is the determined cDNA sequence of 19465, showing no significant homology to any known gene.

SEQ ID NO: 315 is the determined cDNA sequence of clone 23176.

SEQ ID NO: 316 is the determined cDNA sequence of clone 23140.

SEQ ID NO: 317 is the determined cDNA sequence of clone 23166.

SEQ ID NO: 318 is the determined cDNA sequence of clone 23167.

SEQ ID NO: 319 is the determined cDNA sequence of clone 23177.

SEQ ID NO: 320 is the determined cDNA sequence of clone 23217.

SEQ ID NO: 321 is the determined cDNA sequence of clone 23169.

SEQ ID NO: 322 is the determined cDNA sequence of clone 23160.

SEQ ID NO: 323 is the determined cDNA sequence of clone 23182.

SEQ ID NO: 324 is the determined cDNA sequence of clone 23232.

SEQ ID NO: 325 is the determined cDNA sequence of clone 23203.

SEQ ID NO: 326 is the determined cDNA sequence of clone 23198.

SEQ ID NO: 327 is the determined cDNA sequence of clone 23224.

SEQ ID NO: 328 is the determined cDNA sequence of clone 23142.

SEQ ID NO: 329 is the determined cDNA sequence of clone 23138.

SEQ ID NO: 330 is the determined cDNA sequence of clone 23147.

SEQ ID NO: 331 is the determined cDNA sequence of clone 23148.

SEQ ID NO: 332 is the determined cDNA sequence of clone 23149.

SEQ ID NO: 333 is the determined cDNA sequence of clone 23172.

SEQ ID NO: 334 is the determined cDNA sequence of clone 23158.

SEQ ID NO: 335 is the determined cDNA sequence of clone 23156.

SEQ ID NO: 336 is the determined cDNA sequence of clone 23221.

SEQ ID NO: 337 is the determined cDNA sequence of clone 23223.

SEQ ID NO: 338 is the determined cDNA sequence of clone 23155.

SEQ ID NO: 339 is the determined cDNA sequence of clone 23225.

SEQ ID NO: 340 is the determined cDNA sequence of clone 23226.

SEQ ID NO: 341 is the determined cDNA sequence of clone 23228.

SEQ ID NO: 342 is the determined cDNA sequence of clone 23229.

SEQ ID NO: 343 is the determined cDNA sequence of clone 23231.

SEQ ID NO: 344 is the determined cDNA sequence of clone 23154.

SEQ ID NO: 345 is the determined cDNA sequence of clone 23157.

SEQ ID NO: 346 is the determined cDNA sequence of clone 23153.

SEQ ID NO: 347 is the determined cDNA sequence of clone 23159.

SEQ ID NO: 348 is the determined cDNA sequence of clone 23152.

SEQ ID NO: 349 is the determined cDNA sequence of clone 23161.

SEQ ID NO: 350 is the determined cDNA sequence of clone 23162.

SEQ ID NO: 351 is the determined cDNA sequence of clone 23163.

SEQ ID NO: 352 is the determined cDNA sequence of clone 23164.

SEQ ID NO: 353 is the determined cDNA sequence of clone 23165.

SEQ ID NO: 354 is the determined cDNA sequence of clone 23151.

SEQ ID NO: 355 is the determined cDNA sequence of clone 23150.

SEQ ID NO: 356 is the determined cDNA sequence of clone 23168.

SEQ ID NO: 357 is the determined cDNA sequence of clone 23146.

SEQ ID NO: 358 is the determined cDNA sequence of clone 23170.

SEQ ID NO: 359 is the determined cDNA sequence of clone 23171.

SEQ ID NO: 360 is the determined cDNA sequence of clone 23145.

SEQ ID NO: 361 is the determined cDNA sequence of clone 23174.

SEQ ID NO: 362 is the determined cDNA sequence of clone 23175.

SEQ ID NO: 363 is the determined cDNA sequence of clone 23144.

SEQ ID NO: 364 is the determined cDNA sequence of clone 23178.

SEQ ID NO: 365 is the determined cDNA sequence of clone 23179.

SEQ ID NO: 366 is the determined cDNA sequence of clone 23180.

SEQ ID NO: 367 is the determined cDNA sequence of clone 23181.

SEQ ID NO: 368 is the determined cDNA sequence of clone 23143.
SEQ ID NO: 369 is the determined cDNA sequence of clone 23183.
SEQ ID NO: 370 is the determined cDNA sequence of clone 23184.
SEQ ID NO: 371 is the determined cDNA sequence of clone 23185.
SEQ ID NO: 372 is the determined cDNA sequence of clone 23186.
SEQ ID NO: 373 is the determined cDNA sequence of clone 23187.
SEQ ID NO: 374 is the determined cDNA sequence of clone 23190.
SEQ ID NO: 375 is the determined cDNA sequence of clone 23189.
SEQ ID NO: 376 is the determined cDNA sequence of clone 23202.
SEQ ID NO: 378 is the determined cDNA sequence of clone 23191.
SEQ ID NO: 379 is the determined cDNA sequence of clone 23188.
SEQ ID NO: 380 is the determined cDNA sequence of clone 23194.
SEQ ID NO: 381 is the determined cDNA sequence of clone 23196.
SEQ ID NO: 382 is the determined cDNA sequence of clone 23195.
SEQ ID NO: 383 is the determined cDNA sequence of clone 23193.
SEQ ID NO: 384 is the determined cDNA sequence of clone 23199.
SEQ ID NO: 385 is the determined cDNA sequence of clone 23200.
SEQ ID NO: 386 is the determined cDNA sequence of clone 23192.
SEQ ID NO: 387 is the determined cDNA sequence of clone 23201.
SEQ ID NO: 388 is the determined cDNA sequence of clone 23141.
SEQ ID NO: 389 is the determined cDNA sequence of clone 23139.
SEQ ID NO: 390 is the determined cDNA sequence of clone 23204.
SEQ ID NO: 391 is the determined cDNA sequence of clone 23205.
SEQ ID NO: 392 is the determined cDNA sequence of clone 23206.
SEQ ID NO: 393 is the determined cDNA sequence of clone 23207.
SEQ ID NO: 394 is the determined cDNA sequence of clone 23208.
SEQ ID NO: 395 is the determined cDNA sequence of clone 23209.
SEQ ID NO: 396 is the determined cDNA sequence of clone 23210.
SEQ ID NO: 397 is the determined cDNA sequence of clone 23211.
SEQ ID NO: 398 is the determined cDNA sequence of clone 23212.
SEQ ID NO: 399 is the determined cDNA sequence of clone 23214.
SEQ ID NO: 400 is the determined cDNA sequence of clone 23215.
SEQ ID NO: 401 is the determined cDNA sequence of clone 23216.
SEQ ID NO: 402 is the determined cDNA sequence of clone 23137.
SEQ ID NO: 403 is the determined cDNA sequence of clone 23218.
SEQ ID NO: 404 is the determined cDNA sequence of clone 23220.
SEQ ID NO: 405 is the determined cDNA sequence of clone 19462.
SEQ ID NO: 406 is the determined cDNA sequence of clone 19430.
SEQ ID NO: 407 is the determined cDNA sequence of clone 19407.
SEQ ID NO: 408 is the determined cDNA sequence of clone 19448.
SEQ ID NO: 409 is the determined cDNA sequence of clone 19447.
SEQ ID NO: 410 is the determined cDNA sequence of clone 19426.
SEQ ID NO: 411 is the determined cDNA sequence of clone 19441.
SEQ ID NO: 412 is the determined cDNA sequence of clone 19454.
SEQ ID NO: 413 is the determined cDNA sequence of clone 19463.
SEQ ID NO: 414 is the determined cDNA sequence of clone 19419.
SEQ ID NO: 415 is the determined cDNA sequence of clone 19434.
SEQ ID NO: 416 is the determined extended cDNA sequence of B820P.
SEQ ID NO: 417 is the determined extended cDNA sequence of B821P.
SEQ ID NO: 418 is the determined extended cDNA sequence of B822P.
SEQ ID NO: 419 is the determined extended cDNA sequence of B823P.
SEQ ID NO: 420 is the determined extended cDNA sequence of B824P.
SEQ ID NO: 421 is the determined extended cDNA sequence of B825P.
SEQ ID NO: 422 is the determined extended cDNA sequence of B826P.
SEQ ID NO: 423 is the determined extended cDNA sequence of B827P.
SEQ ID NO: 424 is the determined extended cDNA sequence of B828P.
SEQ ID NO: 425 is the determined extended cDNA sequence of B829P.
SEQ ID NO: 426 is the determined extended cDNA sequence of B830P.
SEQ ID NO: 427 is the determined cDNA sequence of clone 266B4.
SEQ ID NO: 428 is the determined cDNA sequence of clone 22892.
SEQ ID NO: 429 is the determined cDNA sequence of clone 266G3.
SEQ ID NO: 430 is the determined cDNA sequence of clone 22890.

SEQ ID NO: 431 is the determined cDNA sequence of clone 264B4.

SEQ ID NO: 432 is the determined cDNA sequence of clone 22883.

SEQ ID NO: 433 is the determined cDNA sequence of clone 22882.

SEQ ID NO: 434 is the determined cDNA sequence of clone 22880.

SEQ ID NO: 435 is the determined cDNA sequence of clone 263G1.

SEQ ID NO: 436 is the determined cDNA sequence of clone 263G6.

SEQ ID NO: 437 is the determined cDNA sequence of clone 262B2.

SEQ ID NO: 438 is the determined cDNA sequence of clone 262B6.

SEQ ID NO: 439 is the determined cDNA sequence of clone 22869.

SEQ ID NO: 440 is the determined cDNA sequence of clone 21374.

SEQ ID NO: 441 is the determined cDNA sequence of clone 21362.

SEQ ID NO: 442 is the determined cDNA sequence of clone 21349.

SEQ ID NO: 443 is the determined cDNA sequence of clone 21309.

SEQ ID NO: 444 is the determined cDNA sequence of clone 21097.

SEQ ID NO: 445 is the determined cDNA sequence of clone 21096.

SEQ ID NO: 446 is the determined cDNA sequence of clone 21094.

SEQ ID NO: 447 is the determined cDNA sequence of clone 21093.

SEQ ID NO: 448 is the determined cDNA sequence of clone 21091.

SEQ ID NO: 449 is the determined cDNA sequence of clone 21089.

SEQ ID NO: 450 is the determined cDNA sequence of clone 21087.

SEQ ID NO: 451 is the determined cDNA sequence of clone 21085.

SEQ ID NO: 452 is the determined cDNA sequence of clone 21084.

SEQ ID NO: 453 is a first partial cDNA sequence of clone 2BT1-40.

SEQ ID NO: 454 is a second partial cDNA sequence of clone 2BT1-40.

SEQ ID NO: 455 is the determined cDNA sequence of clone 21063.

SEQ ID NO: 456 is the determined cDNA sequence of clone 21062.

SEQ ID NO: 457 is the determined cDNA sequence of clone 21060.

SEQ ID NO: 458 is the determined cDNA sequence of clone 21053.

SEQ ID NO: 459 is the determined cDNA sequence of clone 21050.

SEQ ID NO: 460 is the determined cDNA sequence of clone 21036.

SEQ ID NO: 461 is the determined cDNA sequence of clone 21037.

SEQ ID NO: 462 is the determined cDNA sequence of clone 21048.

SEQ ID NO: 463 is a consensus DNA sequence of B726P (referred to as B726P-spliced_seq_B726P).

SEQ ID NO: 464 is the determined cDNA sequence of a second splice form of B726P (referred to as 27490.seq_B726P).

SEQ ID NO: 465 is the determined cDNA sequence of a third splice form of B726P (referred to as 27068.seq_B726P).

SEQ ID NO: 466 is the determined cDNA sequence of a second splice form of B726P (referred to as 23113.seq_B726P).

SEQ ID NO: 467 is the determined cDNA sequence of a second splice form of B726P (referred to as 23103.seq_B726P).

SEQ ID NO: 468 is the determined cDNA sequence of a second splice form of B726P (referred to as 19310.seq_B726P).

SEQ ID NO: 469 is the predicted amino acid sequence encoded by the upstream ORF of SEQ ID NO: 463.

SEQ ID NO: 470 is the predicted amino acid sequence encoded by SEQ ID NO: 464.

SEQ ID NO: 471 is the predicted amino acid sequence encoded by SEQ ID NO: 465.

SEQ ID NO: 472 is the predicted amino acid sequence encoded by SEQ ID NO: 466.

SEQ ID NO: 473 is the predicted amino acid sequence encoded by SEQ ID NO: 467.

DETAILED DESCRIPTION OF THE INVENTION

As noted above, the present invention is generally directed to compositions and methods for the therapy and diagnosis of cancer, such as breast cancer. The compositions described herein may include breast tumor polypeptides, polynucleotides encoding such polypeptides, binding agents such as antibodies, antigen presenting cells (APCs) and/or immune system cells (e.g., T cells). Polypeptides of the present invention generally comprise at least a portion (such as an immunogenic portion) of a breast tumor protein or a variant thereof. A "breast tumor protein" is a protein that is expressed in breast tumor cells at a level that is at least two fold, and preferably at least five fold, greater than the level of expression in a normal tissue, as determined using a representative assay provided herein. Certain breast tumor proteins are tumor proteins that react detectably (within an immunoassay, such as an ELISA or Western blot) with antisera of a patient afflicted with breast cancer. Polynucleotides of the subject invention generally comprise a DNA or RNA sequence that encodes all or a portion of such a polypeptide, or that is complementary to such a sequence. Antibodies are generally immune system proteins, or antigen-binding fragments thereof, that are capable of binding to a polypeptide as described above. Antigen presenting cells include dendritic cells, macrophages, monocytes, fibroblasts and B-cells that express a polypeptide as described above. T cells that may be employed within such compositions are generally T cells that are specific for a polypeptide as described above.

The present invention is based on the discovery of human breast tumor proteins. Sequences of polynucleotides encoding specific tumor proteins are provided in SEQ ID NOS:1–175, 178, 180 and 182–468.

Breast Tumor Protein Polynucleotides

Any polynucleotide that encodes a breast tumor protein or a portion or other variant thereof as described herein is encompassed by the present invention. Preferred polynucleotides comprise at least 15 consecutive nucleotides, preferably at least 30 consecutive nucleotides and more preferably at least 45 consecutive nucleotides, that encode a portion of a breast tumor protein. More preferably, a polynucleotide encodes an immunogenic portion of a breast tumor protein. Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes a breast tumor protein or a portion thereof) or may comprise a variant of such a sequence. Polynucleotide variants may contain one or more substitutions, additions, deletions and/or insertions such that the immunogenicity of the encoded polypeptide is not diminished, relative to a native tumor protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native breast tumor protein or a portion thereof. The term "variants" also encompasses homologous genes of xenogenic origin.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) *CABIOS* 5:151–153; Myers, E. W. and Muller W. (1988) *CABIOS* 4:11–17; Robinson, E. D. (1971) *Comb. Theor* 11:105; Santou, N. Nes, M. (1987) *Mol. Biol. Evol.* 4:406–425; Sneath, P. H. A. and Sokal, R. R. (1973) *Numerical Taxonomy—the Principles and Practice of Numerical Taxonomy*, Freeman Press, San Francisco, Calif.; Wilbur, W. J. and Lipman D. J. (1983) *Proc. Natl. Acad., Sci. USA* 80:726–730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native breast tumor protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, a polynucleotide may be identified, as described in more detail below, by screening a microarray of cDNAs for tumor-associated expression (i.e., expression that is at least five fold greater in a breast tumor than in normal tissue, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein, such as breast tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., a breast tumor cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A laboratory Manual*, Cold Spring Harbor Laboratories, Cold Spring Harbor, N.Y., 1989). Hybridizing colonies or plaques are selected and expanded, and the DNA is isolated for further analysis. cDNA clones may be analyzed to determined the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primes are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Another such technique is known as "rapid amplification of cDNA ends" or RACE. This technique involves the use of an internal primer and an external primer, which hybridizes to a polyA region or vector sequence, to identify sequences that are 5' and 3' of a known sequence. Additional techniques include capture PCR (Lagerstrom et al., *PCR Methods Applic.* 1:111–19, 1991) and walking PCR (Parker et al., *Nucl. Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length DNA sequences may also be obtained by analysis of genomic fragments.

Certain nucleic acid sequences of cDNA molecules encoding portions of breast tumor proteins are provided in SEQ ID NO: 1–175, 178, 180 and 182–468. The isolation of these sequences is described in detail below.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a breast tumor protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g. by transfecting antigen-presenting cells, such as dendritic cells, with a cDNA construct encoding a breast tumor polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a tumor protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl-, methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). The polynucleotides may also be administered as naked plasmid vectors. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Breast Tumor Polypeptides

Within the context of the present invention, polypeptides may comprise at least an immunogenic portion of a breast tumor protein or a variant thereof, as described herein. As noted above, a "breast tumor protein" is a protein that is expressed by breast tumor cells. Proteins that are breast tumor proteins also react detectably within an immunoassay (such as an ELISA) with antisera from a patient with breast cancer. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of a protein that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of a breast tumor protein or a variant thereof. Certain preferred immunogenic portions include peptides in which an N-terminal leader sequence and/or transmembrane domain have been deleted. Other preferred immunogenic portions may contain a small N- and/or C-terminal deletion (e.g., 1–30 amino acids, preferably 5–15 amino acids), relative to the mature protein.

Immunogenic portions may generally be identified using well known techniques, such as those summarized in Paul, *Fundamental Immunology*, 3rd ed., 243–247 (Raven Press, 1993) and references cited therein. Such techniques include screening polypeptides for the ability to react with antigen-specific antibodies, antisera and/or T-cell lines or clones. As used herein, antisera and antibodies are "antigen-specific" if they specifically bind to an antigen (i.e., they react with the protein in an ELISA or other immunoassay, and do not react detectably with unrelated proteins). Such antisera and antibodies may be prepared as described herein, and using well known techniques. An immunogenic portion of a native breast tumor protein is a portion that reacts with such antisera and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length polypeptide. Such screens may generally be performed using methods well known to those of ordinary skill in the art, such as those described in Harlow and Lane, *Antibodies: A Laboratory Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native breast tumor protein. A polypeptide "variant," as used herein, is a polypeptide that differs from a native breast tumor protein in one or more substitutions, deletions, additions and/or insertions, such that the immunogenicity of the polypeptide is not substantially diminished. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity (determined as described above) to the identified polypeptides.

Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast, higher eukaryotic and plant cells. Preferably, the host cells employed are *E. coli,* yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as perkin Elmer/Applied BioSystems Division (Foster City, Calif.), and may be operated according to the manufacturer's instructions.

Within certain specific embodiments, a polypeptide may be a fusion protein that comprises multiple polypeptides as described herein, or that comprises at least one polypeptide as described herein and an unrelated sequence, such as a known tumor protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors. (1) their ability to adopt a flexible extended confirmation; (2) their inability to adopt a secondary structure that could interact with functional epitopes on the first and second polypeptides; and (3) the lack of hydrophobic or charged residues that might react with the polypeptides functional epitopes. Preferred peptide linker sequences contain Gly, Asn and Ser residues. Other near neutral amino acids, such as Thr and Ala may also be used in the linker sequence. Amino acid sequences which may be usefully employed as liners include those disclosed in Maratea et al., *Gene* 40:39–46, 1985; Murphy et al., *Proc. Natl. Acad. Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is cable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 18 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see Biotechnology 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to a breast tumor protein. As used herein, an antibody, or antigen-binding fragment thereof, is said to "specifically bind" to a breast tumor protein if it reacts at a detectable level (within, for example, an ELISA) with a breast tumor protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a cancer, such as breast cancer, using the representative assays provided herein. In other words, antibodies or other binding agents that bind to a breast tumor protein will generate a signal indicating the presence of a cancer in at least about 20% of patients with the disease, and will generate a negative signal indicating the absence of the disease in at least about 90% of individuals without the cancer. To determine whether a binding magnet satisfies this requirement, biological samples (e.g., blood, sera, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria, however, those of ordinary skill in the art will recognize that binding agents may be used in combination to improve sensitivity.

Any agent that satisfies the above requirements may be a binding agent. For example, a binding agent may be a ribosome, with our without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngenic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and dervatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diphtheria toxin, cholera toxin, gelonin. Pseudomonas exotoxin, Shigelia toxin, and pokeweed antiviral protein.

A therapeutic agent may be coupled (e.g., covalently bonded) to a suitable monoclonal antibody either directly or indirectly (e.g., via a linker group), A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups of oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.) by serum complement-mediated hydrolysis (e.g., U.S. Pat. No. 4,671,958, to Rodwell et al.), and acid-catalyzed hydrolysis (e.g., U.S. Pat. No. 4,569,789, to Blatter et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

T Cells

Immunotherapeutic compositions may also, or alternatively, comprise T cells specific for a breast tumor protein. Such cells may generally be prepared in vitro or ex vivo, using standard procedures. For example, T cells may be isolated from bone marrow, peripheral blood, or a fraction of bone marrow or peripheral blood of a patient, using a commercially available cell separation system, such as the ISOLEX™ system, available from Nexell Therapeutics Inc., Irvine, Calif. (see also U.S. Pat. No. 5,240,856; U.S. Pat. No. 5,215,926; WO 89/06280; WO 91/16116 and WO 92/07243). Alternatively, T cells may be derived from related or unrelated humans, non-human mammals, cell lines or cultures.

T cells may be stimulated with a breast tumor polypeptide, polynucleotide encoding a breast tumor polypeptide and/or an antigen presenting cell (APC) that expresses such a polypeptide. Such stimulation is performed under conditions and for a time sufficient to permit the generation of T cells that are specific for the polypeptide. Preferably, a breast tumor polypeptide or polynucleotide is present within a delivery vehicle, such as a microsphere, to facilitate the generation of specific T cells.

T cells are considered to be specific for a breast tumor polypeptide if the T cells kill target cells coated with the polypeptide or expressing a gene encoding the polypeptide. T cell specifically may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated in DNA). Contact with a breast tumor polypeptide (100 ng/ml–100 μg/ml, preferably 200 ng/ml–25 μg/ml) for 3–7 days should result in at least a two fold increase in proliferation of the T cells. Contact as described above for 2–3 hours should result in activation of the T cells, as measured using standard cytokine assays in which a two fold increase in the level of cytokine release (e.g., TNF or IFN-γ) is indicative of T cell activation (see Coligan et al., Current Protocols in Immunology, vol. 1, Wiley Interscience (Greene 1998)). T cells that have been activated in response to a breast tumor polypeptide, polynucleotide or polypeptide-expressing APC may be $CD4^-$ and/or $CD8^+$. Breast tumor protein-specific T cells may be expanded using standard techniques. Within preferred embodiments, the T cells are derived from either a patient or a related, or unrelated, donor and are administered to the patient following stimulation and expansion.

For therapeutic purposes, $CD4^+$ or $CD8^+$ T cells that proliferate in response to a breast tumor polypeptide, polynucleotide or APC can be expanded in number either in vitro or in vivo. Proliferation of such T cells in vitro may be accomplished in a variety of ways. For example, the T cells can be re-exposed to a breast tumor polypeptide, or a short peptide corresponding to an immunogenic portion of such a polypeptide, with or without the addition of T cell growth factors, such as interleukin-2, and/or stimulator cells that synthesize a breast tumor polypeptide. Alternatively, one or more T cells that proliferate in the presence of a breast tumor protein can be expanded in number by cloning. Methods for cloning cells are well known in the art, and include limiting dilution.

Pharmaceutical Compositions and Vaccines

Within certain aspects, polypeptides, polynucleotides, T cells and/or binding agents disclosed herein may be incorporated into pharmaceutical compositions or immunogenic compositions (i.e., vaccines). Pharmaceutical compositions comprise one or more such compounds and a physiologically acceptable carrier. Vaccines may comprise one or more such compounds and an immunostimulant. An immunostimulant may be any substance that enhances an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacterial and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a baceterium (such as Bacillus-Calmette-Guerrin) that expresses an immunogenic portion of the polypeptide on its cell surface or secretes such an epitope. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *Proc. Natl. Acad. Sci. USA* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434; 1991; Kolls et al., *Proc. Natl. Acad. Sci. USA* 91:215–219, 1994; Kass-Eisler et al., *Proc. Natl. Acad. Sci. USA* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperiotoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included: Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine; acylated sugars; cationically or anioncially derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, TNF-α, IL-2 and IL-12) tend to favor the induction of cell mediated immune responses to an administered antigen. In contrast, high levels of Th2-type cytokines (e.g., IL-4, IL-5, Il-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytolines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt, MPL adjuvants are available from Ribi ImmunoChem Research Inc. (Hamilton, Mont.) (see U.S. Pat. Nos. 4,436,727; 4,877,611, 4,866,034 and 4,912,094). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL, and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formation (i.e., a formulation such as a capsule, sponge or gel (composed of polysaccharides, for example, that effects a slow release of compound following administration). Such formulations may generally be prepared using well known technology and administered by, for example, oral, rectal or subcutaneous implantation, or by implantation to the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable, preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, microphages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites visible in vitro), their ability to take up, process and present antigens with high efficiency, and their ability to activate nerve T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be different into dendritic cells by adding to the culture medium combinations of GM-CSF, IL-3, TNFα; CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity of antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD11) and constimulatory molecules (e.g., CD40, CD80, CD86 and 4-1BB).

APCs may generally be transfected with a polynucleotide encoding a breast tumor protein (or portion or other variant thereof) such that the breast tumor polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the breast tumor polypeptide. DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as breast cancer. Within such methods, pharmaceutical compositions and vaccines are typically administered to a patient. As used herein, a "patient" refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. A cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immune response-modifying agents (such a polypeptides and polynucleotides disclosed herein).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T cells as discussed above, T lymphocytes (such as CD8$^-$ cytotoxic T lymphocytes and CD4$^-$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned expressed and transferred into other vectors or effector cells for adoptive immunotherapy. The polypeptides provided herein may also be generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage, monocyte, fibroblast or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into antigen presenting cells taken from a patient and clonally propagated ex vivo for transplant back into the same patient. Transfected cells may be reintroduced into the patient using any means known in the art, preferably in sterile form by intravenous, intracavitary, intraperiotoneal or intratumor administration.

Routes and frequency of administration of the therapeutic compositions disclosed herein, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration) or orally. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune respone that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges form about 100 $\mu$g to 5 mg per kg of host. Suitable dose sizes will vary with the size of the patient, but will typically range from 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to a breast tumor protein generally correlate with an improved clinical outcome. Such immune responses may generally be evaluated using standard proliferation, cytotoxicity or cytokine assays, which may be performed using samples obtained from a patient before and after treatment.

Methods for Detecting Cancer

In general, a cancer may be detected in a patient based on the presence of one or more breast tumor proteins and/or polynucleotides encoding such proteins in a biological sample (for example, blood, sera, urine and/or tumor biopsies) obtained from the patient. In other words, such proteins may be used as markers to indicate the presence or absence of a cancer as breast cancer. In addition, such proteins may be useful for the detection of other cancers. The binding agents provided herein generally permit detection of the level of antigen that binds to the agent in the biological sample. Polynucleotide primers and probes may be used to detect the level of mRNA encoding a tumor protein, which is also indicative of the presence or absence of a cancer. In general, a breast tumor sequence should be present at a level that is at least three fold higher in tumor tissue than in normal tissue.

There are a variety of assay formats known to those of ordinary skill in the art for using a binding agent to direct polypeptide markers in a sample. See, e.g., Harlow and Lane, *Antibodies: A Laboratory Manual,* Cold Spring Harbor Laboratory, 1988. In general, the presence or absence of a cancer in a patient may be determined by (a) contacting a biological sample obtained from a patient with a binding agent; (b) detecting in the sample level of polypeptide that binds to the binding agent, and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length breast tumor proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 $\mu$g, and preferably about 100 ng to about 1 $\mu$g, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent then remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with breast cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradioagraphic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as breast cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof.

Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those or ordinary skill in the art that the above protocols may be readily modified to use breast tumor polypeptides to detect antibodies that bind to such polypeptides in a biological sample. The detection of such breast tumor protein specific antibodies may correlate with the presence of a cancer.

A cancer may also, or alternatively, be detected based on the presence of T cells that specifically react with a breast tumor protein in a biological sample. Within certain methods, a biological sample comprising CD4$^-$ and/or CD8$^+$ T cells isolated from a patient is incubated with a breast tumor polypeptide, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with polypeptide (e.g., 5–25 $\mu$g/ml). It may be desirable to incubate another aliquot of a T cell sample in the absence of breast tumor polypeptide to serve as a control. For CD4$^+$ T cells, activation is preferably detected by evaluating proliferation of the T cells. For CD8$^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding a breast tumor protein in a biological sample. For example, at least two oligonucleotide primers may be employed in a polymerase chain reaction (PCR) based assay to amplify a portion of a breast tumor cDNA derived from a biological sample, wherein at least one of the oligonucleotide primers is specific for (i.e., hybridizes to) a polynucleotide encoding the breast tumor protein. The amplified cDNA is then separated and detected using techniques well known in the art, such as gel electrophoresis. Similarly, oligonucleotide probes that specifically hybridize to a polynucleotide encoding a breast tumor protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding a breast tumor protein that is at least 10 nucleotides, and preferably at least 20 nucleotides, in length. Preferably, oligonucleotide primers and/or probes will hybridize to a polynucleotide encoding a polypeptide disclosed herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence recited in SEQ ID NOS:1–175, 178, 180 and 182–468. Techniques for both PCR based assays and hybridization assays are well known in the art (see, for example, Mullis et al., *Cold Spring Harbor Symp. Quant. Biol.*, 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample, such as biopsy tissue, and is reverse transcribed to produce cDNA molecules. PCR amplification using at least one specific primer generates a cDNA molecule which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, the disclosed compositions may be used as markers for the progression of cancer. In this embodiment, assays as described above for the diagnosis of a cancer may be performed over time, and the change in the level of reactive polypeptide(s) or polynucleotide evaluated. For example, the assays may be performed every 24–72 hours for a period of 6 months to 1 year, and thereafter performed as needed. In general, a cancer is progressing in those patients in whom the level of polypeptide or polynucleotide detected increases over time. In contrast, the cancer is not progressing when the level of reactive polypeptide or polynucleotide either remains constant or decreases with time.

Certain in vivo diagnostic assays may be performed directly on a tumor. One such assay involves contacting tumor cells with a binding agent. The bound binding agent may then be detected directly or indirectly via a receptor group. Such binding agents may also be used in histological applications. Alternatively, polynucleotide probes may be used within such applications.

As noted above, to improve sensitivity, multiple breast tumor protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to a breast tumor protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding a breast tumor protein in a biological sample. Such kits generally comprise at least one oligonucleotide probe or primer, as described above, that hybridizes to a polynucleotide encoding a breast tumor protein. Such an oligonucleotide may be used, for example, within a PCR or hybridization assay. Additional components that may be present within such kits include a second oligonucleotide and/or a diagnostic reagent or container to facilitate the detection of a polynucleotide encoding a breast tumor protein.

The following Examples are offered by way of illustration and not by way of limitation.

EXAMPLES

Example 1

Isolation and Characterization of Breast Tumor Polypeptides

This Example describes the isolation of breast tumor polypeptides from a breast tumor cDNA library.

A cDNA subtraction library containing cDNA from breast tumor subtracted with normal breast cDNA was constructed as follows. Total RNA was extracted from primary tissues using Trizol reagent (Gibco BRL Life Technologies, Gaithersburg, Md.) as described by the manufacturer. The polyA+ RNA was purified using an oligo(dT) cellulose column according to standard protocols. First standard cDNA was synthesized using the primer supplied in a Clontech PCR-Select cDNA Subtraction Kit (Contech, Palo Alto, Calif.). The driver DNA consisted of cDNAs from two normal breast tissues with the tester cDNA being from three primary breast tumors. Double-stranded cDNA was synthesized for both tester and driver, and digested with a combination of endonucleases (MluI, MscI, PvuII, SalI and StuI) which recognize six base pairs DNA. This modification increased the average cDNA size dramatically compared with cDNAs generated according to the protocol of Clontech (Palo Alto, Calif.). The digested tester cDNAs were ligated to two different adaptors and the subtraction was performed according to Clontech's protocol. The subtracted cDNAs were subjected to two rounds of PCR amplification, following the manufacturer's protocol. The resulting PCR products were subcloned into the TA cloning vector, pCRII (Invitrogen, San Diego, Calif.) and transformed into ElectroMax *E. coli* DH108 cells (Gibco BRL Life, Technologies) by electroporation. DNA was isolated from independent clones and sequenced using a Perkin Elmer/Applied Biosystems Division (Foster City, Calif.). Automated Sequencer Model 373A.

Sixty-three distinct cDNA clones were found in the subtracted breast tumor-specific cDNA library. The determined one strand (5' or 3') cDNA sequences for the clones are provided in SEQ ID NO: 1–61, 72 and 73, respectively. Comparison of these cDNA sequences with known sequences in the gene bank using the EMBL and GenBank databases (Release 97) revealed no significant homologies to the sequences provided on SEQ ID NO: 14, 21, 22, 27, 29, 30, 32, 38, 44, 45, 53, 72 and 73. The sequences of SEQ ID NO: 1, 3, 16, 17, 34, 48, 57, 60 and 61 were found to represent known human genes. The sequences of SEQ ID NO: 2, 4, 23, 39 and 50 were found to show some similarity to previously identified non-human genes. The remaining clones (SEQ ID NO: 5–13, 15, 18–20, 24–26, 28, 31, 33, 35–37, 40–43, 46, 47, 49, 51, 52, 54–56, 58 and 59) were found to show at least some degree of homology to previously identified expressed sequence tags (ESTs).

To determine mRNA expression levels of the isolated cDNA clones, cDNA clones from the breast subtraction described above were randomly picked and colony PCR amplified. Their mRNA expression levels in breast tumor, normal breast and various other normal tissues were determined using microarray technology (Synteni, Palo Alto, Calif.). Briefly, the PCR amplification products were arrayed onto slides in an array format, with each product occupying a unique location in the array. mRNA was extracted from the tissue sample to be tested, reverse transcribed, and fluorescent-labeled cDNA probes were generated. The microarrays were probed with the labeled cDNA probes, the slides scanned and fluorescence intensity was measured. Data was analyzed using Synteni provided GEMTOOLS Software. Of the seventeen cDNA clones examined, those of SEQ ID NO: 40, 46, 59 and 73 were found to be over-expressed in breast tumor and expressed at low levels in all normal tissues tested (breast, PBMC, colon, fetal tissue, salivary gland, bone marrow, lung, pancreas, large intestine, spinal cord, adrenal gland, kidney, pancreas, liver, stomach, skeletal muscle, heart, small intestine, skin, brain and human mammary epithelial cells). The clones of SEQ ID NO: 41 and 48 were found to be over-expressed in breast tumor and expressed at low levels in all other tissues tested, with the exception of bone marrow. The clones of SEQ ID NO: 42 was found to be over-expressed in breast tumor and expressed at low levels in all other tissues tested except bone marrow and spinal cord. The clone of SEQ ID NO: 43 was found to be over-expressed in breast tumor and expressed at low levels in all other tissues tested with the exception of spinal cord, heart and small intestine. The clone of SEQ ID NO: 51 was found to be over-expressed in breast tumor and expressed at low levels in all other tissues tested with the exception of large intestine. The clone of SEQ ID NO: 54 was found to be over-expressed in breast tumor and expressed at low levels in all other tissues tested with the exception of PBMC, stomach and small intestine. The clone of SEQ ID NO: 56 was found to be over-expressed in breast tumor and expressed at low levels in all other tissues tested with the exception of large and small intestine, human mammary epithelia cells and SCID mouse-passaged breast tumor. The clone of SEQ ID NO: 60 was found to be over-expressed in breast tumor and expressed at low levels in all other tissues tested with the exception of spinal cord and heart. The clone of SEQ ID NO: 61 was found to be over-expressed in breast tumor and expressed at low levels in all other tissues tested with the exception of small intestine. The clone of SEQ ID NO: 72 was found to be over-expressed in breast tumor and expressed at low levels in all other tissues tested with the exception of colon and salivary gland.

The results of a Northern blot analysis of the clone of SYN18C6 (SEQ ID NO: 40) are shown in FIG. 1. A predicted protein sequence encoded by SYN18C6 is provided in SEQ ID NO: 62.

Additional cDNA clones that are over-expressed in breast tumor tissue were isolated from breast cDNA subtraction libraries as follows. Breast subtraction libraries were prepared, as described above, by PCR-based subtraction employing pools of breast tumor cDNA as the tester and pools of either normal breast cDNA or cDNA from other normal tissues as the driver. cDNA clones from breast subtraction were randomly picked and colony PCR amplified and their mRNA expression levels in breast tumor, normal breast and various other normal tissues were determined using the microarray technology described above. Twenty-four distinct cDNA clones were found to be over-expressed in breast tumor and expressed at low levels in all normal tissues tested (breast, brain, liver, pancreas, lung, salivary gland, stomach, colon, kidney, bone marrow, skeletal muscle, PBMC, heart, small intestine, adrenal gland, spinal cord, large intestine and skin). The determined partial cDNA sequences for these clones are provided in SEQ ID NO: 63–87. Comparison of the sequences of SEQ ID NO: 74–87 with those in the gene bank as described above, revealed homology to previously identified human genes. No significant homologies were found to the sequences of SEQ ID NO: 63–73.

Three DNA isoforms for the clone B726P (partial sequence provided in SEQ ID NO: 71) were isolated as follows. A radioactive probe was synthesized from B726P by excising B726P DNA from a pT7Blue vector (Novagen) by a BamHI/XbaI restriction digest and using the resulting DNA as the template in a single-stranded PCR in the presence of [α-32P]dCTP. The sequence of the primer employed for this PCR is provided in SEQ ID NO: 177. The resulting radioactive probe was used to probe a directional cDNA library and a random-primed cDNA library made using RNA isolated from breast tumors. Eighty-five clones were identified, excised, purified and sequenced. Of these 85 clones, three were found to each contain a significant open reading frame. The determined cDNA sequence of the isoform B726P-20 is provided in SEQ ID NO: 175, with the corresponding predicted amino acid sequence being provided in SEQ ID NO: 176. The determined cDNA sequence of the isoform B726P-74 is provided in SEQ ID NO: 178, with the corresponding predicted amino acid sequence being provided in SEQ ID NO: 179. The determined cDNA sequence of the isoform B726P-79 is provided in SEQ ID NO: 180, with the corresponding predicted amino acid sequence being provided in SEQ ID NO: 181.

Efforts to obtain a full-length clone of B726P using standard techniques led to the isolation of five additional clones that represent additional 5' sequence of B726P. These clones appear to be alternative splice forms of the same gene. The determined cDNA sequences of these clones are provided in SEQ ID NO:464–468, with the predicted amino acid sequences encoded by SEQ ID NO:464–467 being provided in SEQ ID NO:470–473, respectively. Using standard computer techniques, a 3,681 bp consensus DNA sequence (SEQ ID NO:463) was created that contains two large open reading frames. The downstream ORF encodes the predicted amino acid sequence of SEQ ID NO: 176. The predicted amino acid sequence encoded by the upstream ORF is provided in SEQ ID NO:469.

Further isolation of individual clones that are over-expressed in breast tumor tissue was conducted using cDNA subtraction library techniques described above. In particular, a cDNA subtraction library containing cDNA from breast tumors subtracted with five other normal human tissue cDNAs (brain, liver, PBMC, pancreas and normal breast) was utilized in this screening. From the original subtraction, one hundred seventy seven clones were selected to be further characterized by DNA sequencing and microarray analysis. Microarray analysis demonstrated that the sequences in SEQ ID NO: 182–251 were 2 or more fold over-expressed in human breast tumor tissues over normal human tissues. No significant homologies were found for nineteen of these clones, including, SEQ ID NO: 185, 186, 194, 199, 205, 208, 211, 214–216, 219, 222, 226, 232, 236, 240, 241, 245 and 246, with the exception of some previously identified expressed sequence tags (ESTs). The remaining clones share some homology to previously identified genes, specifically SEQ ID NO: 181–184, 187–193, 195–198, 200–204, 206, 207, 209, 210, 212, 213, 217, 218, 220, 221, 223–225, 227–231, 233–235, 237–239, 242–244 and 247–251.

Of the seventy clones showing over-expression in breast tumor tissues, fifteen demonstrated particularly good expression levels in breast tumor over normal human tissues. The following eleven clones did not show any significant homology to any known genes. Clone 19463.1 (SEQ ID NO: 185) was over-expressed in the majority of breast tumors and also in the SCID breast tumors tested (refer to Example 2), additionally, over-expression was found in a majority of normal breast tissues. Clone 19483.1, (SEQ ID NO: 216) was over-expressed in a few breast tumors, with no over-expression in any normal tissue tested. Clone 19470.1 (SEQ ID NO: 219) was found to be slightly over-expressed in some breast tumors. Clone 19468.1 (SEQ ID NO: 222) was found to be slightly over-expressed in the majority of breast tumors tested. Clone 19505.1 (SEQ ID NO: 226) was found to be slightly over-expressed in 50% of breast tumors, as well as in SCID tumor tissues, with some degree of over-expression in found in normal breast. Clone 1509.1 (SEQ ID NO: 232) was found to be over-expressed in very few breast tumors, but with a certain degree of over-expression in metastatic breast tumor tissues, as well as no significant over-expression found in normal tissues. Clone 19513.1 (SEQ ID NO: 236) was shown to be slightly over-expressed in few breast tumors, with no significant over-expression levels found in normal tissues. Clone 19575.1 (SEQ ID NO: 240) showed low level over-expression in some breast tumors and also in normal breast. Clone 19560.1 (SEQ ID NO: 241) was over-expressed in 50% of breast tumors tested, as well as in some normal breast tissues. Clone 19583.1 (SEQ ID NO: 245) was slightly over-expressed in some breast tumors, with very low levels of over-expression found in normal tissues. Clones 19587.1 (SEQ ID NO: 246) showed low level over-expression in some breast tumors and no significant over-expression in normal tissues.

Clone 19520.1 (SEQ ID NO: 233), showing homology to clone 102D24 on chromosome 11q13.31, was found to be over-expressed in breast tumors and in SCID tumors. Clone 19517.1 (SEQ ID NO: 237), showing homology to human PAC 128M19 clone, was found to be slightly over-expressed in the majority of breast tumors tested. Clone 19392 2 (SEQ ID NO: 247), showing homology to human chromosome 17, was shown to be over-expressed in 50% of breast tumors tested. Clone 19399.2 (SEQ ID NO: 250), showing homology to human Xp22 BAC GSHB-184P14, was shown to be slightly over-expressed in a limited number of breast tumors tested.

In subsequent studies, 64 individual clones were isolated from a subtracted cDNA library containing cDNA from a pool of breast tumors subtracted with cDNA from five normal tissues (brain, liver, PBMC, pancreas and normal breast). The subtracted cDNA library was prepared as described above with the following modification. A combination of five six-base cutters (MluI, MscI, PvuII, SalI and StuI) was used to digest the cDNA instead of RsaI. This resulted in an increase in the average insert size from 300 bp to 600 bp. The 64 isolated clones were colony PCR amplified and their mRNA expression levels in breast tumor tissue, normal breast and various other normal tissues were examined by microarray technology as described above. The determined cDNA sequences of 11 clones which were found to be over-expressed in breast tumor tissue are provided in SEQ ID NO: 405–414. Comparison of these sequences to those in the public database, as outlined above, revealed homologies between the sequences of SEQ ID NO: 408, 411, 413 and 414 and previously isolated ESTs. The sequences of SEQ ID NO: 405–407, 409, 410, 412 and 415 were found to show some homology to previously identified sequences.

In further studies, a subtracted cDNA library was prepared from cDNA from metastatic breast tumors subtracted with a pool of cDNA from five normal tissues (breast, brain, lung, pancreas and PBMC) using the PCR-subtraction protocol of Clontech, described above. The determined cDNA sequences of 90 clones isolated from this library are provided in SEQ ID NO: 315–404. Comparison of these sequences with those in public database, as described above, revealed no significant homologies to the sequence of SEQ ID NO: 366. The sequences of SEQ ID NO: 320–324, 342, 353, 367, 368, 377, 382, 385, 389, 395, 397 and 400 were found to show some homology to previously isolated ESTs. The remaining sequences were found to show homology to previously identified gene sequences.

In yet further studies, a subtracted cDNA library (referred to as 2BT) was prepared from cDNA from breast tumors subtracted with a pool of cDNA from six normal tissues (liver, brain, stomach, small intestine, kidney and heart) using the PCR-subtraction protocol of Clontech, described above. cDNA clones isolated from this subtraction were subjected to DNA microarray analysis as described above and the resulting data subjected to four modified Gemtools analyses. The first analysis compared 28 breast tumors with 28 non-breast normal tissues. A mean over-expression of at least 2.1 fold was used as a selection cut-off. The second analysis compared 6 metastatic breast tumors with 29 non-breast normal tissues. A mean over-expression of at least 2.5 fold was used as a cut-off. The third and fourth analyses compared 2 early SCID mouse-passaged with 2 late SCID mouse-passaged tumors. A mean over-expression in the early or late passaged tumors of 2.0 fold or greater was used as a cut-off. In addition, a visual analysis was performed on the microarray data for the 2BT clones. The determined cDNA sequences of 13 clones identified in the visual analysis are provided in SEQ ID NO: 427–439. The determined cDNA sequences of 22 clones identified using the modified Gemtools analysis are provided in SEQ ID NO: 440–462, wherein SEQ ID NO: 453 and 454 represent two partial, non-overlapping, sequences of the same clone.

Comparison of the clone sequences of SEQ ID NO: 436 and 437 (referred to as 263G6 and 262B2) with those in the public databases, as described above, revealed no significant homologies to previously identified sequences. The sequences of SEQ ID NO: 427, 429, 431, 435, 438, 441, 443, 444, 445, 446, 450, 453 and 454 (referred to as 266B4, 266G3, 264B4, 263G1, 262B6, 2BT2-34, 2BT1-77, 2BT1-62, 2BT1-60,61, 2-BT1-59, 2BT1-52 and 2BT1-40, respectively) showed some homology to previously isolated expressed sequences tags (ESTs). The sequences of SEQ ID NO: 428, 430, 432, 433, 434, 439, 440, 442, 447, 448, 449, 451, 452 and 455–462 (referred to as clones 22892, 22890, 22883, 22882, 22880, 22869, 21374, 21349, 21093, 21091, 21089, 21085, 21084, 21063, 21062, 21060, 21053, 21050, 21036, 21037 and 21048, respectively), showed some homology to gene sequences previously identified in humans.

Example 2

Isolation and Characterization of Breast Tumor Polypeptides Obtained by PCR-Based Subtraction Using SCID-Passaged Tumor RNA Human breast tumor antigens were obtained by PCR-based subtraction using SCID mouse passaged breast tumor RNA as follows. Human breast tumor was implanted in SCID mice and harvested on the first or sixth serial passage as described in patent application Ser. No. 08/556,659 filed Nov. 13, 1995, U.S. Pat. No. 5,986,170. Genes found to be differently expressed between early and late passage SCID tumor may be stage specific and therefore useful in therapeutic and diagnostic applications. Total RNA was prepared from snap frozen SCID passaged human breast tumor from both the first and sixth passage.

PCR-based subtraction was performed essentially as described above. In the first subtraction (referred to as T9), RNA from first passage tumor was subtracted from sixth passage tumor RNA to identify more aggressive, later passage-specific antigens. Of the 64 clones isolated and sequenced from this subtraction, no significant homologies were found to 30 of these clones, hereinafter referred to as: 13053, 13057, 13059, 13065, 13067, 10368, 13071–13073, 13075, 13078, 13079, 13081, 13082, 13092, 13097, 13101, 13102, 13131, 13133, 13119, 13135, 13139, 13140, 13146–13149, and 13151, with the exception of some previously identified expressed sequence tags (ESTs). The determined cDNA sequences for the clones are provided in SEQ ID NO: 88–116, respectively. The isolated cDNA sequences of SEQ ID NO: 117–140 showed homology to known genes.

In a second PCR-based subtraction, RNA from sixth passage tumor was subtracted from first passage tumor RNA to identify antigens down-regulated over multiple passages. Of the 36 clones isolated and sequenced, no significant homologies were found to nineteen of these clones, hereinafter referred to as: 14376, 14377, 14383, 14384, 14387, 14392, 14394, 13498, 14401, 14402, 14405, 14409, 14412, 14414–14416, 14419, 14426, and 14427, with the exception of some previously identified expressed sequence tags (ESTs). The determined cDNA sequences for these clones are provided in SEQ ID NO: 141–159, respectively. The isolated cDNA sequences of SEQ ID NO: 160–174 were found to show homology to previously known genes.

Further analysis of human breast tumor antigens through PCR-based subtraction using first and sixth passage SCID tumor RNA was performed. Sixty three clones were found to be differentially expressed by a two or more fold margin, as determined by microarray analysis, i.e., higher expression in early passage tumor over late passage tumor, or vice versa. Seventeen of these clones showed no significant homology to any known genes, although some degree of homology with previously identified expressed sequence tags (ESTs) was found, hereinafter referred to as 20266, 20270, 20274, 20276, 20277, 20280, 20281, 20294, 20303, 20310, 20336, 20341, 20941, 20954, 20961, 20965 and 20975 (SEQ ID NO: 252–268, respectively). The remaining clones were found to share some degree of homology to known genes, which are identified in the Brief Description of the Drawings and Sequence Identifiers section above, hereinafter referred to as 20261, 20262, 20265, 20267, 20268, 20271, 20272, 20273, 20278, 20279, 20293, 20300, 20305, 20306, 20307, 20313, 20317, 20318, 20320, 20321, 20322, 20326, 20333, 20335, 20337, 20338, 20340, 20938, 20939, 20940, 20942, 20943, 20944, 20946, 20947, 20948, 20949, 20950, 20951, 20952, 20957, 20959, 20966, 20976, 20977 and 20978. The determined cDNA sequences for these clones are provided in SEQ ID NO: 269–313, respectively.

The clones 20310, 20281, 20262, 20280, 20303, 20336, 20270, 20341, 20326 and 20977 (also referred to as B820P, B821P, B822P, B823P, B824P, B825P, B826P, B827P, B828P and B829P, respectively) were selected for further analysis based on the results obtained with microarray analysis. Specifically, microarray data analysis indicated at least two- to three-fold overexpression of these clones in breast tumor RNA compared to normal tissues tested. Subsequent studies led to the determination of the complete insert sequence for the clones B820P, B821P, B822P, B823P, B824P, B825P, B826P, B827P, B828P and B829P. These extended cDNA sequences are provided in SEQ ID NO: 416–426, respectively.

Example 3

Synthesis of Polypeptides

Polypeptides may be synthesized on an Perkin Elmer/Applied Biosystems Division 430A peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugation, binding to an immobilized surface, or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0%–60% acetonitrile (containing 0.1% TFA) in water (containing 0.1% TFA) may be used to elute the peptides. Following lyophilization of the pure fractions, the peptides may be characterized using electrospray or other types of mass spectrometry and by amino acid analysis.

From the foregoing, it will be appreciated that, although specific embodiments of the invention have been described herein for the purposes of illustration, various modifications may be made without deviating from the spirit and scope of the invention.

What is claimed is:

1. An isolated polypeptide comprising SEQ ID NO:469.

2. A composition comprising a polypeptide according to claim 1, in combination with a physiologically acceptable carrier.

3. An isolated polypeptide according to claim 1, wherein the polypeptide comprises an amino acid sequence that is encoded by a polynucleotide of SEQ ID NO:463.

4. An immunogenic composition comprising a physiologically acceptable carrier and a polypeptide, wherein the polypeptide comprises SEQ ID NO:469.

5. An immunogenic composition according to claim 4, wherein the non-specific immune response enhancer is an adjuvant.

6. An immunogenic composition according to claim 4, wherein the immunostimulant induces a predominantly Type I response.

7. A fusion protein comprising at least one polypeptide, wherein the polypeptide comprises SEQ ID NO:469.

8. A fusion protein according to claim 7, wherein the fusion protein comprises an expression enhancer that increases expression of the fusion protein in a host cell transfected with a polynucleotide encoding the fusion protein.

9. A fusion protein according to claim 7, wherein the fusion protein comprises a T helper epitope that is not present within the polypeptide.

10. A fusion protein according to claim 7, wherein the fusion protein comprises an affinity tag.

11. A composition comprising a fusion protein according to claim 7, in combination with a physiologically acceptable carrier.

12. An immunogenic composition comprising a fusion protein according to claim 7, in combination with a non-specific immune response enhancer.

13. An immunogenic composition according to claim 12, wherein the non-specific immune response enhancer is an adjuvant.

14. An immunogenic composition according to claim 12, wherein the non-specific immune response enhancer induces a predominantly Type I response.

* * * * *

UNITED STATES PATENT AND TRADEMARK OFFICE
CERTIFICATE OF CORRECTION

PATENT NO.     : 6,579,973 B1
DATED          : June 17, 2003
INVENTOR(S)    : Yuqiu Jiang et al.

It is certified that error appears in the above-identified patent and that said Letters Patent is hereby corrected as shown below:

Title page,
Item [76], Inventors, "Jiang Yuqiu" should read as -- Yuqiu Jiang --.
Item [56], References Cited, add the following:
U.S. PATENT DOCUMENTS:
-- 5,891,857     4/06/99          Holt et al. --.
FOREIGN PATENT DOCUMENTS:
-- WO 01/47959      07/05/01
   WO 01/37779      05/31/01
   WO 00/60076      10/12/00
   WO 00/73801      12/07/00
   WO 00/43420      07/27/00
   WO 00/08210      02/17/00
   WO 98/21331      05/22/98 --.
OTHER PUBLICATIONS,
-- GenBank Accession Number AF269087, March 28, 2001.
   GenBank Accession Number AAK27325, March 28, 2001.
   GenBank Accession Number AC069200, May 24, 2000.
   Sulston et al., "Toward a complete human genome sequence," *Genome Research 8* (11) :1097-1108, 1998. --.

Signed and Sealed this

Fifteenth Day of November, 2005

JON W. DUDAS
*Director of the United States Patent and Trademark Office*